US011028095B2

(12) United States Patent
Khan

(10) Patent No.: US 11,028,095 B2
(45) Date of Patent: Jun. 8, 2021

(54) SPIRO-LACTAM AND BIS-SPIRO-LACTAM NMDA RECEPTOR MODULATORS AND USES THEREOF

(71) Applicant: Aptinyx Inc., Evanston, IL (US)

(72) Inventor: M. Amin Khan, Evanston, IL (US)

(73) Assignee: Aptinyx Inc., Evanston, IL (US)

( * ) Notice: Subject to any disclaimer, the term of this patent is extended or adjusted under 35 U.S.C. 154(b) by 312 days.

(21) Appl. No.: 16/321,906

(22) PCT Filed: Aug. 1, 2017

(86) PCT No.: PCT/US2017/044861
§ 371 (c)(1),
(2) Date: Jan. 30, 2019

(87) PCT Pub. No.: WO2018/026792
PCT Pub. Date: Feb. 8, 2018

(65) Prior Publication Data
US 2020/0181159 A1 Jun. 11, 2020

Related U.S. Application Data

(60) Provisional application No. 62/369,534, filed on Aug. 1, 2016.

(51) Int. Cl.
| | | |
|---|---|---|
| *C07D 487/10* | (2006.01) | |
| *C07D 487/20* | (2006.01) | |
| *A61P 25/00* | (2006.01) | |
| *A61P 25/06* | (2006.01) | |
| *A61P 25/22* | (2006.01) | |
| *A61P 25/28* | (2006.01) | |
| *A61P 25/24* | (2006.01) | |

(52) U.S. Cl.
CPC ............ *C07D 487/20* (2013.01); *A61P 25/24* (2018.01); *A61P 25/28* (2018.01); *C07D 487/10* (2013.01)

(58) Field of Classification Search
CPC ..... C07D 487/10; C07D 487/20; A61P 25/00; A61P 25/06; A61P 25/22; A61P 25/24; A61P 25/28
See application file for complete search history.

(56) References Cited

U.S. PATENT DOCUMENTS

| | | |
|---|---|---|
| 4,904,681 A | 2/1990 | Cordi et al. |
| 4,959,493 A | 9/1990 | Ohfume et al. |
| 5,061,721 A | 10/1991 | Cordi et al. |
| 5,086,072 A | 2/1992 | Trullas et al. |
| 5,166,136 A | 11/1992 | Ward et al. |
| 5,168,103 A | 12/1992 | Kinney et al. |
| 5,350,769 A | 9/1994 | Kasai et al. |
| 5,523,323 A | 6/1996 | Maccecchini |
| 5,605,911 A | 2/1997 | Olney et al. |
| 5,648,259 A | 7/1997 | Mallet et al. |
| 5,741,778 A | 4/1998 | Martin et al. |
| 5,763,393 A | 6/1998 | Moskal et al. |
| 5,804,550 A | 9/1998 | Bourguignon |
| 5,902,815 A | 5/1999 | Olney et al. |
| 5,952,389 A | 9/1999 | Fogel |
| 5,959,075 A | 9/1999 | Lok et al. |
| 6,007,841 A | 12/1999 | Caruso |
| 6,025,471 A | 2/2000 | Deghenghi |
| 6,107,271 A | 8/2000 | Moskal et al. |
| 6,147,230 A | 11/2000 | Shimamoto et al. |
| 6,197,820 B1 | 3/2001 | Sontheimer et al. |
| 6,521,414 B2 | 2/2003 | Melcher et al. |
| 6,541,453 B2 | 4/2003 | Oldham et al. |
| 6,635,270 B2 | 10/2003 | Hong et al. |
| 6,667,317 B2 | 12/2003 | Chenard et al. |
| 6,821,985 B2 | 11/2004 | Chenard et al. |
| 6,828,318 B2 | 12/2004 | Snape et al. |
| 7,273,889 B2 | 9/2007 | Mermelstein et al. |
| 7,884,080 B2 | 2/2011 | Aslanian et al. |
| 8,097,634 B2 | 1/2012 | Ackermann et al. |
| 8,492,340 B2 | 7/2013 | Moskal |
| 9,504,670 B2 | 11/2016 | Lowe, III et al. |
| 9,512,133 B2 | 12/2016 | Khan et al. |
| 9,512,134 B2 | 12/2016 | Lowe, III et al. |
| 9,579,304 B2 | 2/2017 | Lowe, III et al. |
| 9,708,335 B2 | 7/2017 | Lowe, III et al. |
| 9,738,650 B2 | 8/2017 | Lowe, III et al. |
| 9,758,525 B2 | 9/2017 | Lowe, III et al. |
| 9,802,946 B2 | 10/2017 | Khan et al. |
| 9,828,384 B2 | 11/2017 | Lowe, III et al. |
| 9,925,169 B2 | 3/2018 | Khan |

(Continued)

FOREIGN PATENT DOCUMENTS

| | | |
|---|---|---|
| CN | 101066945 A | 11/2007 |
| CN | 101125817 A | 2/2008 |

(Continued)

OTHER PUBLICATIONS

Abbott AV et al., 'The Formalin Test: Scoring Properties of the First and Second Phases of the Pain Response in Rats,' Pain, Jan. 1995 (Jan. 1995), 60(1):91-102.
Abramets, II, 'Neurophysiological and Neurochemical Aspects of the Effects of Antidepressants and Mood Stabilizers,' Neurophysiol, Jan. 2008 (Jan. 2008), 40(1):64-78.
Alonso E et al., 'Spiro-Beta-Lactams as Beta-Turn Mimetics. Design, Synthesis, and NMR Conformational Analysis,' J Org Chem, Sep. 21, 2001 (Sep. 21, 2001), 66(19):6333-8.
Anonymous, Database Accession No. 1031928-30-9, Database Registry [Online] Chemical Abstracts Service, Columbus, Ohio, US; Jul. 1, 2008 (Jul. 1, 2008), XP002668992.
Anonymous, Database Accession No. 1053605-89-2, Database Registry [Online] Chemical Abstracts Service, Columbus, Ohio, US; Sep. 28, 2008 (Sep. 28, 2008), XP002668993.

(Continued)

*Primary Examiner* — Laura L Stockton
(74) *Attorney, Agent, or Firm* — Goodwin Procter LLP

(57) ABSTRACT

Disclosed are compounds having potency in the modulation of NMDA receptor activity. Such compounds can be used in the treatment of conditions such as depression and related disorders. Orally delivered formulations and other pharmaceutically acceptable delivery forms of the compounds, including intravenous formulations, are also disclosed.

20 Claims, 2 Drawing Sheets

(56) References Cited

U.S. PATENT DOCUMENTS

| | | | |
|---|---|---|---|
| 9,932,347 | B2 | 4/2018 | Khan |
| 10,052,308 | B2 | 8/2018 | Lowe, III et al. |
| 10,150,769 | B2 | 12/2018 | Khan |
| 10,195,179 | B2 | 2/2019 | Khan |
| 10,196,401 | B2 | 2/2019 | Khan |
| 2002/0103335 | A1 | 8/2002 | Oldham et al. |
| 2003/0022253 | A1 | 1/2003 | Moskal |
| 2003/0064921 | A1 | 4/2003 | Millhauser et al. |
| 2003/0175734 | A1 | 9/2003 | Kroes et al. |
| 2005/0037433 | A1 | 2/2005 | Nakanishi et al. |
| 2005/0118286 | A1 | 6/2005 | Suffin et al. |
| 2006/0063707 | A1 | 3/2006 | Baudry et al. |
| 2006/0241046 | A1 | 10/2006 | Olivera et al. |
| 2007/0087404 | A1 | 4/2007 | Stahl et al. |
| 2007/0208001 | A1 | 9/2007 | Zhuo et al. |
| 2009/0221544 | A1 | 9/2009 | Stein et al. |
| 2010/0102616 | A1 | 4/2010 | Yamasaki et al. |
| 2011/0306586 | A1 | 12/2011 | Khan et al. |
| 2012/0295852 | A1 | 11/2012 | Moskal |
| 2013/0005662 | A1 | 1/2013 | Moskal |
| 2013/0035292 | A1 | 2/2013 | Moskal et al. |
| 2013/0053325 | A1 | 2/2013 | Moskal et al. |
| 2013/0310323 | A1 | 11/2013 | Moskal |
| 2013/0316954 | A1 | 11/2013 | Moskal |
| 2014/0107037 | A1 | 4/2014 | Moskal |
| 2015/0051262 | A1 | 2/2015 | Khan et al. |
| 2015/0105364 | A1 | 4/2015 | Khan et al. |
| 2015/0336969 | A1 | 11/2015 | Khan et al. |
| 2015/0368252 | A1 | 12/2015 | Lowe, III et al. |
| 2015/0368253 | A1 | 12/2015 | Lowe, III et al. |
| 2015/0368254 | A1 | 12/2015 | Lowe, III et al. |
| 2015/0376195 | A1 | 12/2015 | Lowe, III et al. |
| 2016/0122359 | A1 | 5/2016 | Lowe, III et al. |
| 2016/0289240 | A1 | 10/2016 | Lowe, III et al. |
| 2016/0368926 | A1 | 12/2016 | Lowe, III et al. |
| 2017/0231956 | A1 | 8/2017 | Lowe, III et al. |
| 2017/0333395 | A1 | 11/2017 | Khan |
| 2017/0334922 | A1 | 11/2017 | Khan |
| 2018/0092879 | A1 | 4/2018 | Khan |
| 2018/0093994 | A1 | 4/2018 | Khan |
| 2018/0127430 | A1 | 5/2018 | Lowe, III et al. |
| 2018/0155354 | A1 | 6/2018 | Lowe, III et al. |
| 2018/0179217 | A1 | 6/2018 | Lowe, III et al. |
| 2018/0179218 | A1 | 6/2018 | Lowe, III et al. |
| 2018/0215767 | A1 | 8/2018 | Lowe, III et al. |
| 2018/0244680 | A1 | 8/2018 | Lowe, III et al. |
| 2018/0250267 | A1 | 9/2018 | Lowe, III et al. |
| 2018/0291023 | A1 | 10/2018 | Khan |
| 2019/0077807 | A1 | 3/2019 | Khan et al. |
| 2019/0161442 | A1 | 5/2019 | Khan |
| 2019/0175588 | A1 | 6/2019 | Khan |
| 2019/0177334 | A1 | 6/2019 | Khan |
| 2019/0194200 | A1 | 6/2019 | Khan |

FOREIGN PATENT DOCUMENTS

| | | |
|---|---|---|
| CN | 103974712 A | 8/2014 |
| CN | 104321071 A | 1/2015 |
| EP | 0180398 A1 | 5/1986 |
| EP | 2542254 A1 | 1/2013 |
| EP | 2771021 | 5/2013 |
| JP | 2013519683 A | 5/2013 |
| JP | 2014520072 A | 8/2014 |
| RU | 2039035 C1 | 7/1995 |
| WO | WO-1996/032105 A1 | 10/1996 |
| WO | WO-1997/043306 A1 | 11/1997 |
| WO | WO-1999/024584 A1 | 5/1999 |
| WO | WO-1999/051985 A1 | 10/1999 |
| WO | WO-2000/028090 A2 | 5/2000 |
| WO | WO-2001/36685 A2 | 5/2001 |
| WO | WO-2001/96606 A2 | 12/2001 |
| WO | WO-2001/98367 A2 | 12/2001 |
| WO | WO-2002/47535 A2 | 6/2002 |
| WO | WO-2002/072609 A2 | 9/2002 |
| WO | WO-2003/010540 A1 | 2/2003 |
| WO | WO-2004/005293 A2 | 1/2004 |
| WO | WO-2005/020973 A2 | 3/2005 |
| WO | WO-2005/035535 A1 | 4/2005 |
| WO | WO-2007/088041 A1 | 8/2007 |
| WO | WO-2007/103719 A2 | 9/2007 |
| WO | WO-2009/039390 A2 | 3/2009 |
| WO | WO-2009/105718 A1 | 8/2009 |
| WO | WO-2009/156396 A1 | 12/2009 |
| WO | WO-2010/015545 A1 | 2/2010 |
| WO | WO-2010/018213 A2 | 2/2010 |
| WO | WO-2010/033757 A1 | 3/2010 |
| WO | WO-2010/065709 A2 | 6/2010 |
| WO | WO-2010/102616 A1 | 9/2010 |
| WO | WO-2011/003064 A2 | 1/2011 |
| WO | WO-2011/044089 A2 | 4/2011 |
| WO | WO-2011/100585 A1 | 8/2011 |
| WO | WO-2012/021712 A1 | 2/2012 |
| WO | WO-2012/149389 A2 | 11/2012 |
| WO | WO-2013/001448 A1 | 1/2013 |
| WO | WO-2013/014448 A1 | 1/2013 |
| WO | WO-2013/063120 A2 | 5/2013 |
| WO | WO-2014/011590 A2 | 1/2014 |
| WO | WO-2014/120783 A1 | 8/2014 |
| WO | WO-2014/120784 A1 | 8/2014 |
| WO | WO-2014/120789 A1 | 8/2014 |
| WO | WO-2014/120800 A1 | 8/2014 |
| WO | WO-2014120786 A1 | 8/2014 |
| WO | WO-2017/201283 A1 | 11/2017 |
| WO | WO-2017/201285 A1 | 11/2017 |
| WO | WO-2018/026763 A1 | 2/2018 |
| WO | WO-2018/026779 A1 | 2/2018 |
| WO | WO-2018/026782 A1 | 2/2018 |
| WO | WO-2018/026792 A1 | 2/2018 |
| WO | WO-2018/026798 A1 | 2/2018 |

OTHER PUBLICATIONS

Anonymous, NCBI Submission NM_000149, 'Homo sapiens Fucosyltransferase 3 (galactoside 3(4)-L-fucosyltransferase, Lewis Blood Group)(FUT3), Transcript Variant 1, mRNA,' 1990 (1990), Retrieved from the internet; <<URL:http://www.ncbi.nlm.nih.gov/nuccore/148277008>>, pp. 1-5.

Anonymous, NCBI Submission NM_001276, 'Homo sapiens Chitinase 3-like 1 (cartilage glycoprotein-39)(CHI3L1), mRNA,' 1989 (1989), Retrieved from the internet; <URL:http://www.ncbi.nlm.nih.gov/nuccore/144226250>, pp. 1-5.

Anonymous, NCBI Submission NM_030979.1, 'Homo sapiens poly(A) Binding Protein, Cytoplasmic 3 (PABPC3), mRNA,' 2003 (2003), Retrieved from the internet; <URL:http://www.ncbi.nlm.nih.gov/nuccore/13569957>, pp. 1.

Anonymous, NCBI Submission NM_173216, 'Homo sapiens ST6 beta-galactosamide alpha-2,6-sialyltransferase 1 (ST6GAL1), transcript variant 1, mRNA,' 1989 (1989), Retrieved from the internet; <URL:http://www.ncbi.nlm.nih.gov/nuccore/27765090>, pp. 1-5.

Bennett GJ and Xie Y-K, 'A Peripheral Mononeuropathy in Rat That Produces Disorders of Pain Sensation Like Those Seen in Man,' Pain, Apr. 1988 (Apr. 1988), 33(1):87-107.

Bittermann H and Gmeiner P, 'Chirospecific Synthesis of Spirocyclic beta-Lactams and Their Characterization as Potent Type II beta-Turn Inducing Peptide Mimetics,' J Org Chem, Jan. 6, 2006 (Jan. 6, 2006), 71(1):97-102.

Bittermann H et al., 'A Highly Practical RCM Approach Towards a Molecular Building Kit of Spirocyclic Reverse Turn Mimics,' Chem Eur J, Aug. 16, 2006 (Aug. 16, 2006), 12(24):6315-22.

Burch RM et al., 'GLYX-13, An NMDA Receptor Glycine Site Functional Partial Agonist, Does Not Elicit Psychotomimetic Side Effects in Normal Human Volunteers at Doses Expected to be Therapeutic in Treatment-Resistant Major Depressive Disorder,' NCDEU, Jun. 16, 2010 (Jun. 16, 2010), Naurex, Inc., Evanston, IL (Publ), pp. 1 (Poster #unknown).

Burgdorf JS et al., 'Neurobiology of 50-kHz Ultrasonic Vocalizations in Rats: Electrode, Lesion, and Pharmacology Studies,' Behav Brain Res, Mar. 19, 2007 (Mar. 19, 2007) (ePub), 182(2):274-83.

Burgdorf JS et al., 'The Antidepressant and Anxiolytic Properties of GLYX-13: A Novel NMDA Receptor Glycine Site Functional Partial Agonist,' ACNP 2010 Meeting, Dec. 6, 2010 (Dec. 6, 2010), pp. 1 (Poster #198).

(56) References Cited

OTHER PUBLICATIONS

Burgdorf JS et al., 'The Effects of Selective Breeding for Differential Rates of 50-kHz Ultrasonic Vocalizations on Emotional Behavior in Rats,' Dev Psychobiol, Jan. 2009 (Jan. 2009), 51(1):34-46.

Burgdorf JS et al., 'The N-Methyl-D-Aspartate Receptor Modulator GLYX-13 Enhances Learning and Memory, in Young Adult and Learning Impaired Aging Rats,' Neurobiol Aging, May 14, 2009 (May 14, 2009) (ePub), 32(4):698-706.

Burgdorf JS et al., 'Uncovering the Molecular Basis of Positive Affect Using Rough-and-Tumble Play in Rats: A Role for the NMDA Receptor and Implications for Depression,' Neuroscience, Jul. 14, 2010, (Jul. 14, 2010) (ePub), 168(3):769-77.

Burgdorf JS et al., 'Uncovering the Molecular Basis of Positive Affect Using Rough-and-Tumble Play in Rats: A Role for the NMDA Receptor and Implications for Depression,' Neuroscience 38th Annual Meeting, Washington DC, Nov. 17, 2008 (Nov. 17, 2008), pp. 1-2 (Poster #393.1/UU11) [Electronically available Sep. 2008].

Careri M et al., 'Pentcopper(II) 12-Metallacrown-4 Complexes with alpha- and beta-Aminohydroxamic Acids in Aqueous Solution: A Reinvestigation,' J Inorg Chem, Jan. 15, 2003 (Jan. 15, 2003), 93(3-4):174-80.

Coates C et al., 'Product Class 9: Beta-Lactams,' *Science of Synthesis*, Georg Thieme Verlag KG, Stuttgart, DE (Pub), 2000 (2000), 21:609-46.

Cremonesi G et al., 'Enantiomerically Pure Polyheterocyclic Spiro-beta-Lactams from trans-4-Hydroxy-L-proline,' J Org Chem, Mar. 19, 2010 (Mar. 19, 2010), 75(6):2010-7.

Dalla Croce P and La Rosa C, 'Stereoselective Synthesis of N-Phenylsulfonyl Substituted Spiro-beta-Lactams,' Tetrahedron: Asymmetry, Mar. 26, 1999 (Mar. 26, 1999), 10(6):1193-9.

Dalla Croce P et al., 'Reaction of Mesoionic Compounds Deriving from Cyclic N-Acyl-alpha-amino Acids with N-(Phenylmethylene)benzenesulfonamide,' Tetrahedron, Jan. 1, 1999 (Jan. 1, 1999), 55(1):201-10.

Del Pozo C et al., 'Diastereo- and Enantioselective Synthesis of Novel beta-Lactam-Containing 1,4-Benzodiazepines Through a Ketene-Imine Cycloaddition Reaction,' Eur J Org Chem, Jan. 19, 2004 (Jan. 19, 2004), 2004(3):535-45.

Duman RS, 'Pathophysiology of Depression: The Concept of Synaptic Plasticity,' Eur Psychiatry, Jul. 2002 (Jul. 2002), 17(Suppl 3):306-10.

Erick M Carreira and Lisbet Kvaerno, Classics in Stereoselective Synthesis, (1st ed. 2009), Wiley-Vch Verlag GmbH & Co. KGaA, Weinham, DE (Publ), pp. 19-102 ISBN: 978-3-527-32452-1.

European Patent Office, Supplementary European Search Report (Form 1503) for EP 09 81 5233 (Fink D), completed at Munich DE on Feb. 8, 2012 (Feb. 8, 2012) pp. 1-3.

European Patent Office, Supplementary European Search Report (Form 1503) for EP 10 82 2514 (Fink D), completed at Munich DE on Feb. 1, 2013 (Feb. 1, 2013) pp. 1-2.

Export Data for 3 hydroxy 2 5 sulfonyl oxo2 5 diazaspiro, Apr. 22, 2016, Feb. 3, 2016, Jan. 30, 2016 and Mar. 26, 2015.

Forni A, 'Two Diastereoisomers of 2-(Benzenesulfonyl)-5-benzoyl-1-oxo-3-phenyl-2,5-diazaspiro[3.4]octan-7-yl acetate,' Acta Crystallographica Sec C: Crystal Structure Commun, Sep. 1998 (Sep. 1998), C54(9):1320-2.

Foster AC and Fagg GE, 'Neurobiology: Taking Apart NMDA Receptors,' Nature, Oct. 1, 1987 (Oct. 1, 1987), 329(6138):395-6.

Golik U, 'Synthesis of Malonimide Derivatives as Potential Penicillin Analogs,' J Heterocycl Chem, Feb. 1972 (Feb. 1972), 9(1):21-4.

Grigg R et al., 'X=Y-ZH Systems as Potential 1,3-Dipoles. Part 46. Cascade 1,3-Dipolar Cycloaddition Reactions of Cephalosporin Imines,' Tetrahedron, Nov. 1995 (Nov. 1995), 51(48):13347-56.

Haring R et al., 'Binding Studies and Photoaffinity Labeling Identify Two Classes of Phencyclidine Receptors in Rat Brain,' Biochemistry, Sep. 8, 1987 (Sep. 8, 1987), 26(18):5854-61.

Haring R et al., 'Glycine-Like Modulation of N-Methyl-D-Aspartate Receptors by a Monoclonal Antibody that Enhances Long-Term Potentiation,' J Neurochem, Jul. 1991 (Jul. 1991), 57(1):323-32.

Haring R et al., 'Identification of Polypeptides of the Phencyclidine Receptor of Rat Hippocampus by Photoaffinity Labeling with [H3]Azidophencyclidine,' Biochemistry, Feb. 11, 1986 (Feb. 11, 1986), 25(3):612-20.

Haring R et al., 'Multiple Mode of Binding of Phencyclidines: High Affinity Association Between Phencyclidine Receptors in Rat Brain and a Monovalent Ion-Sensitive Polypeptide,' Biochem Biophys Res Commun, Jan. 30, 1987 (Jan. 30, 1987), 142(2):501-10.

Holderbach R et al., 'Enhanced Long-Term Synaptic Depression in an Animal Model of Depression,' Biol Psychiatry, Dec. 4, 2006 (Dec. 4, 2006) (ePub), 62(1):92-100.

International Search Report and Written Opinion for International Application No. PCT/US2017/033323, dated Jul. 17, 2017, 12 pages.

International Search Report and Written Opinion for International Application No. PCT/US2017/033326, dated Jul. 10, 2017, 12 pages.

International Search Report and Written Opinion for International Application No. PCT/US2017/044813, dated Oct. 19, 2017, 13 pages.

International Search Report and Written Opinion for International Application No. PCT/US2017/044838, dated Oct. 19, 2017, 11 pages.

International Search Report and Written Opinion for International Application No. PCT/US2017/044841, dated Oct. 23, 2017, 11 pages.

International Search Report and Written Opinion for International Application No. PCT/US2017/044861, dated Oct. 19, 2017, 11 pages.

International Search Report and Written Opinion for International Application No. PCT/US2017/044871, dated Oct. 19, 2017, 13 pages.

International Searching Authority, International Search Report (ISA/210) for Application No. PCT/US08/77045, (Young LW), completed on Mar. 28, 2009 (Mar. 28, 2009) and dated Apr. 29, 2009 (dated Apr. 29, 2009), pp. 1-3.

International Searching Authority, International Search Report (ISA/210) for Application No. PCT/US09/57401, (Young LW), completed Dec. 6, 2009 (Dec. 6, 2009) and dated Dec. 24, 2009 (dated Dec. 24, 2009), pp. 1-2.

International Searching Authority, International Search Report (ISA/210) for Application No. PCT/US09/66536, (Kang YJ), completed Aug. 9, 2010 (Aug. 9, 2010) and dated Aug. 8, 2010 (dated Aug. 9, 2010), pp. 1-5.

International Searching Authority, International Search Report (ISA/210) for Application No. PCT/US2014/013619, (Wolf C), completed Mar. 6, 2014 (Mar. 6, 2014) and dated Mar. 20, 2014 (dated Mar. 20, 2014), pp. 1-3.

International Searching Authority, International Search Report (ISA/210) for Application No. PCT/US2014/013621, (Wolf C), completed Feb. 27, 2014 (Feb. 27, 2014) and dated Mar. 13, 2014 (dated Mar. 13, 2014), pp. 1-2.

International Searching Authority, International Search Report (ISA/210) for Application No. PCT/US2014/013623, (Wolf C), completed Mar. 3, 2014 (Mar. 3, 2014) and dated Mar. 13, 2014 (dated Mar. 13, 2014), pp. 1-3.

International Searching Authority, International Search Report (ISA/210) for Application No. PCT/US2014/013626, (Rudolf M), completed Mar. 10, 2014 (Mar. 10, 2014) and dated Mar. 18, 2014 (dated Mar. 18, 2014), pp. 1-4.

International Searching Authority, International Search Report (ISA/210) for Application No. PCT/US2014/013639, (Wolf C), completed Feb. 28, 2014 (Feb. 28, 2014) and dated Mar. 13, 2014 (dated Mar. 13, 2014), pp. 1-3.

International Searching Authority, Written Opinion of Application No. PCT/US2008/077045 (ISA/237), (Young LW), completed Mar. 28, 2009 (Mar. 28, 2009) and dated Mar. 24, 2010 (dated Mar. 24, 2010), pp. 1-8.

(56) References Cited

OTHER PUBLICATIONS

International Searching Authority, Written Opinion of Application No. PCT/US2009/057401 (ISA/237), (Young LW), completed Dec. 6, 2009 (Dec. 6, 2009) and dated Mar. 22, 2011 (dated Mar. 22, 2011), pp. 1-6.

International Searching Authority, Written Opinion of Application No. PCT/US2009/066536 (ISA/237), (Kang YJ), completed Aug. 9, 2010 (Aug. 9, 2010) and dated Jun. 7, 2011 (dated Jun. 7, 2011), pp. 1-8.

International Searching Authority, Written Opinion of Application No. PCT/US2014/013619 (ISA/237), (Wolf C), completed Mar. 6, 2014 (Mar. 6, 2014) and dated Aug. 4, 2015 (dated Aug. 4, 2015), pp. 1-4.

International Searching Authority, Written Opinion of Application No. PCT/US2014/013621 (ISA/237), (Wolf C), completed Feb. 27, 2014 (Feb. 27, 2014) and dated Aug. 4, 2015 (dated Aug. 4, 2015), pp. 1-6.

International Searching Authority, Written Opinion of Application No. PCT/US2014/013623 (ISA/237), (Wolf C), completed Mar. 3, 2014 (Mar. 6, 2014) and dated Aug. 4, 2015 (dated Aug. 4, 2015), pp. 1-4.

International Searching Authority, Written Opinion of Application No. PCT/US2014/013626 (ISA/237), (Rudolf M, completed Mar. 10, 2014 (Mar. 10, 2014) and dated Aug. 4, 2015 (dated Aug. 4, 2015), pp. 1-6.

International Searching Authority, Written Opinion of Application No. PCT/US2014/013639 (ISA/237), (Wolf C), completed Feb. 28, 2014 (Feb. 28, 2014) and dated Aug. 4, 2015 (dated Aug. 4, 2015), pp. 1-4.

Johnson JA et al., 'The Preparation of a Double Metallahelicate Containing 28 Copper Atoms,' Angew Chem Int Ed Engl, Feb. 3, 2003 (Feb. 3, 2003), 42(5):546-9.

Johnson KM and Jones SM, 'Neuropharmacolgy of Phencyclidine: Basic Mechanisms and Therapeutic Potential,' Annu Rev Pharmacol Toxicol, 1990 (1990), 30:707-50.

Khasanov AB et al., 'Novel Asymmetric Approach to Proline-Derived Spiro-beta-Lactams,' J Org Chem., Aug. 20, 2004 (Aug. 20, 2004), 69(17):5766-9.

Kloog Y et al., 'Kinetic Characterization of the Phencyclidine-N-Methyl-d-asparate Receptor Interaction: Evidence for a Steric Blockade of the Channel,' Biochemistry, Feb. 9, 1988 (Feb. 9, 1988), 27(3):843-8.

Kloog Y et al., 'Mode of Binding of [3H]dibenzocycloalkenimine (MK-801) to the N-methyl-D-Aspartate (NMDA) Receptor and its Therapeutic Implication,' FEBS Letts, Mar. 28, 1988 (Mar. 28, 1988), 230(1-2):167-70.

Koller M and Urwyler S, 'Novel N-Methyl-D-aspartate Receptor Antagonists: A Review of Compounds Patented Since 2006,' Expert Opin Ther Pat, Nov. 8, 2010 (Nov. 8, 2010) (epub), 20(12):1683-702.

Kroes RA et al., 'Development of a Novel Glycobiologic Therapy for Glioblastoma,' Neuro-oncol, Oct. 2006 (Oct. 2006), 8(4):397-8, (Abstract #CB-14).

Kroes RA et al., 'Development of a Novel Glycobiology-Based Therapeutic for Glioblastoma,' J Neurochem, Nov. 10, 2006 (Nov. 10, 2006), 99(Suppl. 1):17 (Abstract #50).

Krystall JH et al., 'NMDA Agonists and Antagonists as Probes of Glutamatergic Dysfunction and Pharmacotherapies in Neuropsychiatric Disorders,' Harvard Rev Psychiatry, Sep.-Oct. 1999 (Sep.-Oct. 1999), 7(3):125-43.

Leander JD et al., 'Lack of Ketamine-Like Discriminative Effects of GLYX-13: A Novel NMDA Receptor Glycine Site Functional Partial Agonist with Antidepressant-Like Preclinical Effects,' ACNP 49th Annual Meeting, Dec. 2010 (Dec. 2010), Miami Beach, FL, Naurex, Inc., Evanston, IL (Pub) (Poster #218).

Li G-Q et al., 'N-Heterocyclic Carbene Catalyzed Ring Expansion of 4-Formyl-beta-lactams: Synthesis of Succinimide Derivatives,' Org Lett, Aug. 9, 2007 (Aug. 9, 2007) (ePub), 9(18):3519-21.

Lynch G et al., 'Synaptic Pasticity in Early Aging,' Ageing Res Rev, Aug. 28, 2006 (Aug. 28, 2006) (ePub), 5(3):255-80.

Macias A et al., 'Diastereoselective [2+2]-Cycloaddition Reactions of Unsymmetrical Cyclic Ketenes with Imines: Synthesis of Modified Prolines and Theoretical Study of the Reaction Mechanism,' J Org Chem, Oct. 1, 2004 (Oct. 1, 2004) Sep. 10, 2005 (Sep. 10, 2005)(ePub), 69(21):7004-12.

Macias A et al., 'Unusual Rearrangement of Spiro-beta-Lactams to 1,4-diazabicyclo[4,4,0]decanes and 1,4-diazabicyclo[4,3,0]nonanes. Synthesis of Conformationally Restricted Sigma-Receptor Ligands,' Tetrahedron Lett, Jun. 2004 (Jun. 2004), 45(24):4657-60.

Marcias A et al., 'Synthesis of Enantiopure Pyrrolidine-Derived Peptidomimetics and Oligo-beta-Peptides via Nucleophilic Ring-Opening of beta-Lactams,' J Org Chem, Sep. 29, 2006 (Sep. 29, 2006), 71(20):7721-30.

Mayer ML and Miller RJ, 'Excitatory Amino Acid Receptors, Second Messengers and Regulation of Intracellular Ca2+ in Mammalian Neurons,' Trends Pharmacol Sci, Jun. 1990 (Jun. 1990), 11(6):254-60.

McLeod MN et al., 'Chromium Potentiation of Antidepressant Pharmacotherapy for Dysthymic Disorder in 5 Patients,' J Clin Psychiatry, Apr. 1999 (Apr. 1999), 60(4):237-40.

Mishra H et al., 'Three-Dimensional Quantitative Structure-Activity Relationship and Comparative Molecular Field Analysis of Dipeptide Hydroxamic Acid Helicobacter pylori Urease Inhibitors,' Antimicrob Agents Chemother, Aug. 2002 (Aug. 2002), 46(8):2613-8.

Monahan JB et al., 'D-Cycloserine, a Positive Modulator of the N-Methyl-d-Asparate Receptor, Enhances Performance of Learning in Rats,' Pharmacol Biochem Behav, Nov. 1989 (Nov. 1989), 34(3):649-53.

Moskal JR and Burgdorf JS, 'The Antidepressant and Anxiolytic Properties of GLYX-13: A Novel NMDA Receptor Glycine Site Functional Partial Agonist,' ACNP 29th Annual Meeting, Dec. 7, 2009 (Dec. 7, 2009), Hollywood, FL, Naurex, Inc. Evanston, IL (Pub) (Poster #059).

Moskal JR and Schaffner AE, 'Monoclonal Antibodies to the Dentate Gyrus: Immunocytochemical Characterization and Flow Cytometric Analysis of Hippocampal Neurons Bearing a Unique Cell-Surface Antigen,' J Neurosci, Jul. 1986 (Jul. 1986), 6(7):2045-53.

Moskal JR et al., 'A Novel Approach to Unlocking the Therapeutic Potential of the NMDA Receptor,' Vital Signs e-Magazine, Sep. 2010 (Sep. 2010), pp. 1-2.

Moskal JR et al., 'GLYX-13: A Monoclonal Antibody-Derived Peptide that Acts as an N-Methyl-D-Aspartate Receptor Modulator,' Neuropharmacol, Jul. 26, 2005 (Jul. 26, 2005) (ePub), 49(7):1077-87.

Moskal JR et al., 'The Use of Antibody Engineering to Create Novel Drugs that Target N-Methyl-D-Aspartate Receptors,' Curr Drug Targets, Sep. 2001 (Sep. 2001), 2(3):331-45.

Moskal JR, 'The Anti-depressant and Anxiolytic Properties of GLYX-13: A Glycine-site Functional Partial Agonist (GFPA), a Novel Mechanism for Modulating NMDA,' ACNP 48th Annual Meeting, Dec. 7, 2009 (Dec. 7, 2009), Hollywood, FL, pp. 1-2 (Abstract).

Myers SM and Johnson CP, 'Management of Children with Autism Spectrum Disorders,' Pediatrics, Oct. 29, 2007 (Oct. 29, 2007) (ePub), 120(5):1162-82.

Narahashi T et al., 'Mechanisms of Action of Cognitive Enhancers on Neuroreceptors,' Biol Pharm Bull, Nov. 2004 (Nov. 2004), 27(11):1701-6.

Overman LE and Osawa T, 'A Convenient Synthesis of 4-Unsubstituted beta-Lactams,' J Am Chem Soc, Mar. 1985 (Mar. 1985), 107(6):1698-701.

Parac-Vogt TN et al., 'Pentacopper(II) Complexes of alpha-Aminohydroxamic Acids: Uranyl-Induced Conversion of a 12-Metallacrown-4 to a 15-Metallacrown-5,' J Inorg Biochem, Nov. 21, 2004 (Nov. 21, 2004) (ePub), 99(2):497-504.

Patani et al., "Bioisosterism: A Rational Approach in Drug Design," Chem. Rev., Jan. 1, 1997, 96(8):3147-3176.

Pittenger C et al., 'The NMDA Receptor as a Therapeutic Target in Major Depressive Disorder,' CNS Neurol Disord Targets, Apr. 2007 (Apr. 2007), 6(2):101-15.

(56) References Cited

OTHER PUBLICATIONS

Raghavan B et al., 'Allosteric Modulation of the Dopamine D2 Receptor by Pro-Leu-Gly-NH2 Peptidomimetics Constrained in Either a Polyproline II Helix or a Type II beta-Turn Conformation,' J Med Chem, Apr. 9, 2009 (Apr. 9, 2009), 52(7):2043-51.

Ransom RW and Stec NL, 'Cooperative Modulation of [3H]MK-801 Binding to the N-Methyl-d-Asparate Receptor-Ion Channel Complex by I-Glumate, Glycine, and Polyamines,' J Neurochem, Sep. 1988 (Sep. 1988), 51(3):830-6.

Rasmusson GH et al., '6-Substituted Penicillin Derivatives,' Tetrahedron Lett, 1973 (1973), 14(2):145-8.

Rautio J et al., 'Prodrugs: Design and Clinical Applications,' Nat Rev Drug Discov, Mar. 2008 (Mar. 2008), 7(3):255-70.

Schell MJ, 'The N-methyl D-aspartate Receptor Glycine Site and D-serine Metabolism: An Evolutionary Perspective,' Philos Trans R Soc Lond B Biol Sci, Jun. 29, 2004 (Jun. 29, 2004), 359(1446):943-64.

Shankar GM and Walsh DM, 'Alzheimer's Disease: Synaptic Dysfunction and A-beta,' Mol Neurodegener, Nov. 23, 2009 (Nov. 23, 2009), 4:48-61.

Siemion IZ et al., 'Conformational Preferences of the Sequential Fragments of the Hinge Region of the Human IgA1 Immunoglobulin Molecule,' Biophys Chem, Aug. 1988 (Aug. 1988), 31(1-2):35-44.

Simplicio AL et a;., 'Prodrugs for Amines,' Molecules, Mar. 2008 (Mar. 2008), 13(3):519-47.

Singapore Search Report and Written Opinion Issued for corresponding Singapore application No. 11201505860X, dated Apr. 18, 2016.

Singapore Search Report and Written Opinion Issued for corresponding Singapore application No. 11201505862T, dated Apr. 18, 2016.

Singapore Search Report and Written Opinion Issued for corresponding Singapore application No. 11201505934X, dated Apr. 27, 2016.

Singapore Search Report and Written Opinion Issued for corresponding Singapore application No. 11201505937S, dated May 5, 2016.

Singapore Search Report and Written Opinion Issued for corresponding Singapore application No. 11201505942Y, dated Mar. 22, 2016.

Stanton PK et al., 'Inhibition of the Production and Maintenance of Long-Term Potentiation in Rat Hippocampal Slices by a Monoclonal Antibody,' Proc Natl Acad Sci USA, Mar. 1987 (Mar. 1987), 84(6):1684-8.

Stanton PK et al., 'Neuroprotection by a Novel NMDAR Functional Glycine Site Partial Agonist, GLYX-13,' Neuroreport, Aug. 26, 2009 (Aug. 26, 2009), 20(13):1193-7.

Tanwar MK et al., 'Gene Expression Microarray Analysis Reveals YLK-40 to be a Potential Serum Marker for Malignant Character in Human Glioma,' Cancer Res, Aug. 1, 2002 (Aug. 1, 2002), 62(15):4364-8.

Thompson LT et al., 'Hippocampus-Dependent Learning Facilitated by a Monoclonal Antibody or D-Cycloserine,' Nature, Oct. 15, 1992 (Oct. 15, 1992), 359(6396):638-41.

Turturro A et al., 'Growth Curves and Survival Characteristics of the Animals Used in the Biomarkers of Aging Program,' J Gerentol A Biol Sci Med Sci, Nov. 1999 (Nov. 1999), 54A(11):B492-B501.

Various, *The NMDA Receptor*, (2nd ed. 1994), GL Collingridge and JC Watkins Eds., Oxford. University Press, Inc., New York, New York US (Publ), pp. 1-479 ISBN: 0-19-262371-0.

Wood PL et al., 'Antinociceptive Action of GLYX-13: An N-Methyl-D-aspartate Receptor Glycine Site Partial Agonist,' Neuroreport, Jul. 2, 2008 (Jul. 2, 2008), 19(10):1061-3.

Wood PL, 'The NMDA Receptor Complex: A Long and Winding Road to Therapeutics,' IDrugs, Mar. 2005 (Mar. 2005), 8(3):229-35.

Wood SG et al., 'Tetrapeptide Inhibitors of the IgA1 Proteinases from Type I Neisseria gonorrhoeae,' J Med Chem, Oct. 1989 (Oct. 1989), 32(10):2407-11.

Zhang X-L et al., 'A NMDA Receptor Glycine Site Partial Agonist, GLYX-13, Simultaneously Enhances LTP and Reduces LTD at Schaffer Collateral-CA1 Synapses in Hippocampus,' Neuropharmacology, Aug. 29, 2008 (Aug. 29, 2008), 55(7):1238-50.

| | |
|---|---|
| Empirical formula | $C_{12}H_{19}N_3O_2$ |
| Formula weight | 237.30 |
| Temperature | 294(2) K |
| Wavelength | 0.71073 Å |
| Crystal system | Orthorhombic |
| Space group | $P2_12_12_1$ |
| Unit cell dimensions | a = 8.6170(5) Å    α = 90°. |
| | b = 11.0510(16) Å    β = 90°. |
| | c = 27.4310(6) Å    γ = 90°. |
| Volume | 2612.2(4) Å$^3$ |
| Z | 8 |
| Density (calculated) | 1.207 Mg/m$^3$ |
| Absorption coefficient | 0.084 mm$^{-1}$ |
| F(000) | 1024 |
| Crystal size | 0.420 x 0.300 x 0.230 mm$^3$ |
| θ range for data collection | 2.367 to 28.295°. |
| Index ranges | -11<=h<=11, -14<=k<=14, -36<=l<=36 |
| Reflections collected | 30540 |
| Independent reflections | 6343 [R(int) = 0.0445] |
| Completeness to θ = 25.242° | 99.9 % |
| Refinement method | Full-matrix least-squares on F$^2$ |
| Data / restraints / parameters | 6343 / 0 / 327 |
| Goodness-of-fit on F$^2$ | 1.070 |
| Final R indices [I>2σ(I)] | R1 = 0.0611, wR2 = 0.1583 |
| R indices (all data) | R1 = 0.0700, wR2 = 0.1648 |
| Absolute structure parameter | 0.2(4) |
| Largest diff. peak and hole | 0.424 and -0.227 e.Å$^{-3}$ |
| Measurement | Bruker Smart Apex CCD diffractometer |
| Software Used | SHELXTL-PLUS |

Figure 1

| | |
|---|---|
| Empirical formula | $C_{12}H_{19}N_3O_2$ |
| Formula weight | 237.30 |
| Temperature | 294(2) K |
| Wavelength | 0.71073 Å |
| Crystal system | Orthorhombic |
| Space group | $P2_12_12_1$ |
| Unit cell dimensions | a = 8.6158(5) Å  α= 90°. |
| | b = 11.0530(7) Å  β= 90°. |
| | c = 27.4300(17) Å  γ = 90°. |
| Volume | 2612.2(3) Å$^3$ |
| Z | 8 |
| Density (calculated) | 1.207 Mg/m$^3$ |
| Absorption coefficient | 0.084 mm$^{-1}$ |
| F(000) | 1024 |
| Crystal size | 0.400 x 0.300 x 0.280 mm$^3$ |
| θ range for data collection | 2.367 to 28.332°. |
| Index ranges | -11<=h<=11, -14<=k<=14, -35<=l<=35 |
| Reflections collected | 30944 |
| Independent reflections | 6350 [R(int) = 0.0280] |
| Completeness to θ = 25.242° | 99.9 % |
| Refinement method | Full-matrix least-squares on F$^2$ |
| Data / restraints / parameters | 6350 / 0 / 327 |
| Goodness-of-fit on F$^2$ | 1.080 |
| Final R indices [I>2σ(I)] | R1 = 0.0655, wR2 = 0.1666 |
| R indices (all data) | R1 = 0.0748, wR2 = 0.1737 |
| Absolute structure parameter | -0.3(3) |
| Largest diff. peak and hole | 0.457 and -0.243 e.Å$^{-3}$ |
| Measurement | Bruker Smart Apex CCD diffractometer |
| Software Used | SHELXTL-PLUS |

Figure 2

SPIRO-LACTAM AND BIS-SPIRO-LACTAM NMDA RECEPTOR MODULATORS AND USES THEREOF

CROSS REFERENCE TO RELATED APPLICATIONS

This application is a national stage application under 35 U.S.C. § 371 of International Application No. PCT/US2017/044861, filed on Aug. 1, 2017, which application claims priority to and the benefit of U.S. Provisional Patent Application No. 62/369,534, filed on Aug. 1, 2016; the contents of each of which are hereby incorporated by reference herein in their entirety.

BACKGROUND

An N-methyl-d-aspartate ("NMDA") receptor is a post-synaptic, ionotropic receptor that is responsive to, inter alia, the excitatory amino acids glutamate and glycine and the synthetic compound NMDA. The NMDA receptor controls the flow of both divalent and monovalent ions into the postsynaptic neural cell through a receptor associated channel (Foster et al., Nature 1987, 329:395-396; Mayer et al., Trends in Pharmacol. Sci. 1990, 11:254-260). The NMDA receptor has been implicated during development in specifying neuronal architecture and synaptic connectivity, and may be involved in experience-dependent synaptic modifications. In addition, NMDA receptors are also thought to be involved in long term potentiation and central nervous system disorders.

The NMDA receptor plays a major role in the synaptic plasticity that underlies many higher cognitive functions, such as memory acquisition, retention and learning, as well as in certain cognitive pathways and in the perception of pain (Collingridge et al., The NMDA Receptor, Oxford University Press, 1994). In addition, certain properties of NMDA receptors suggest that they may be involved in the information-processing in the brain that underlies consciousness itself.

The NMDA receptor has drawn particular interest since it appears to be involved in a broad spectrum of CNS disorders. For instance, during brain ischemia caused by stroke or traumatic injury, excessive amounts of the excitatory amino acid glutamate are released from damaged or oxygen deprived neurons. This excess glutamate binds to the NMDA receptors which opens their ligand-gated ion channels; in turn the calcium influx produces a high level of intracellular calcium which activates a biochemical cascade resulting in protein degradation and cell death. This phenomenon, known as excitotoxicity, is also thought to be responsible for the neurological damage associated with other disorders ranging from hypoglycemia and cardiac arrest to epilepsy. In addition, there are preliminary reports indicating similar involvement in the chronic neurodegeneration of Huntington's, Parkinson's and Parkinson's related conditions such as dyskinesia and L-dopa induced dyskinesia and Alzheimer's diseases. Activation of the NMDA receptor has been shown to be responsible for post-stroke convulsions, and, in certain models of epilepsy, activation of the NMDA receptor has been shown to be necessary for the generation of seizures. Neuropsychiatric involvement of the NMDA receptor has also been recognized since blockage of the NMDA receptor $Ca^{++}$ channel by the animal anesthetic PCP (phencyclidine) produces a psychotic state in humans similar to schizophrenia (reviewed in Johnson, K. and Jones, S., 1990). Further, NMDA receptors have also been implicated in certain types of spatial learning.

The NMDA receptor is believed to consist of several protein chains embedded in the postsynaptic membrane. The first two types of subunits discovered so far form a large extracellular region, which probably contains most of the allosteric binding sites, several transmembrane regions looped and folded so as to form a pore or channel, which is permeable to $Ca^{++}$, and a carboxyl terminal region. The opening and closing of the channel is regulated by the binding of various ligands to domains (allosteric sites) of the protein residing on the extracellular surface. The binding of the ligands is thought to affect a conformational change in the overall structure of the protein which is ultimately reflected in the channel opening, partially opening, partially closing, or closing.

A need continues to exist in the art for novel and more specific and/or potent compounds that are capable of modulating NMDA receptors, and provide pharmaceutical benefits. In addition, a need continues to exist in the medical arts for orally deliverable forms of such compounds.

SUMMARY

The present disclosure includes compounds that can be NMDA modulators. More specifically, the present disclosure provides a compound having the formula:

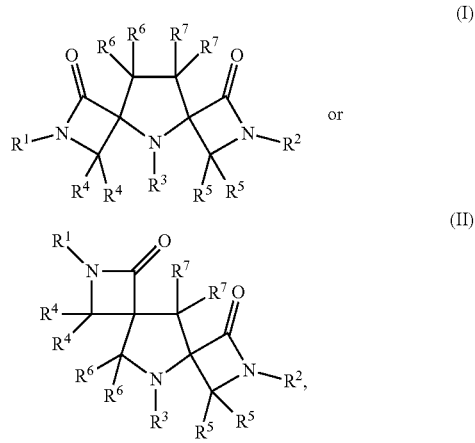

or a pharmaceutically acceptable salt, a stereoisomer, and/or an N-oxide thereof, wherein:

$R^1$ and $R^2$ are independently selected from the group consisting of hydrogen, —$C_1$-$C_6$alkyl, —C(O)—$C_1$-$C_6$alkyl, —C(O)—O—$C_1$-$C_6$alkyl, and —O—$CH_2$-phenyl;

$R^3$ is selected from the group consisting of hydrogen, —$C_1$-$C_6$alkyl, —C(O)—$R^{31}$, and —C(O)—O—$R^{32}$;

$R^{31}$ is selected from the group consisting of hydrogen, —$C_1$-$C_6$alkyl; —$C_1$-$C_6$haloalkyl, —$C_3$-$C_6$cycloalkyl, and phenyl;

$R^{32}$ is selected from the group consisting of hydrogen, —$C_1$-$C_6$alkyl; —$C_1$-$C_6$haloalkyl, —$C_3$-$C_6$cycloalkyl, and phenyl;

wherein any aforementioned $C_1$-$C_6$alkyl, independently for each occurrence, is optionally substituted by one, two or three substituents each independently selected from —C(O)$NR^aR^b$, —$NR^aR^b$, hydroxyl, —SH, phenyl, —O—$CH_2$-phenyl, and halogen; and any aforementioned phenyl, independently for each occurrence, is optionally substituted by one, two or three substituents each independently selected from —C(O)NR$^a$R$^b$, —NR$^a$R$^b$, —C$_1$-C$_3$alkoxy, hydroxyl, and halogen;

R$^a$ and R$^b$ are each independently for each occurrence selected from the group consisting of hydrogen, —C(O)—O—CH$_2$-phenyl, and —C$_1$-C$_3$alkyl; or R$^a$ and R$^b$ taken together with the nitrogen to which they are attached form a 4-6 membered heterocyclic ring;

R$^4$, R$^5$, R$^6$ and R$^7$ are each independently selected from the group consisting of hydrogen, halogen, hydroxyl, phenyl, amido, amino, C$_{1-4}$alkyl, C$_{2-4}$alkenyl, —NH—C(O)—C$_{1-6}$alkyl, —NH—C(O)—C$_{1-6}$alkylene-phenyl, —NH—C(O)—O—C$_{1-6}$alkyl, and —NH—C(O)—O—C$_{1-6}$alkylene-phenyl; wherein C$_{1-4}$alkyl, C$_{1-6}$alkylene, C$_{2-4}$alkenyl, C$_{1-4}$alkoxy, and phenyl are optionally substituted by one or more substituents selected from R$^P$;

two R$^5$s taken together form an oxo moiety; or wherein for the compound of Formula I, R$^6$ and R$^7$ taken together with the adjacent carbons to which they are attached form a 3-membered carbocyclic ring which is optionally substituted by one or two substituents independently selected from the group consisting of halogen, hydroxyl, —C$_1$-C$_3$alkyl, —C$_1$-C$_3$alkoxy, —C(O)NR$^a$R$^b$, and —NR$^a$R$^b$; and R$^P$ is selected, independently for each occurrence, from the group consisting of carboxy, hydroxyl, halogen, amino, phenyl, C$_{1-6}$alkoxy, and C$_{1-6}$alkyl optionally substituted by one or more substituents independently selected from the group consisting of halogen, hydroxyl and amino.

Also provided herein are pharmaceutically acceptable compositions comprising a disclosed compound, and a pharmaceutically acceptable excipient. Such compositions can be suitable for administration to a patient orally, parenterally, topically, intravaginally, intrarectally, sublingually, ocularly, transdermally, or nasally.

In some aspects, compounds described herein bind to NMDA receptors expressing certain NR2 subtypes. In some aspects, the compounds described herein bind to one NR2 subtype and not another.

In another aspect, a method of treating a condition selected from the group consisting of autism, anxiety, depression, bipolar disorder, attention deficit disorder, attention deficit hyperactivity disorder (ADHD), schizophrenia, a psychotic disorder, a psychotic symptom, social withdrawal, obsessive-compulsive disorder, phobia, post-traumatic stress syndrome, a behavior disorder, an impulse control disorder, a substance abuse disorder, a sleep disorder, a memory disorder, a learning disorder, urinary incontinence, multiple system atrophy, progressive supra-nuclear palsy, Friedrich's ataxia, Down's syndrome, fragile X syndrome, tuberous sclerosis, olivio-ponto-cerebellar atrophy, Rett syndrome, cerebral palsy, drug-induced optic neuritis, ischemic retinopathy, diabetic retinopathy, glaucoma, dementia, AIDS dementia, Alzheimer's disease, Huntington's chorea, spasticity, myoclonus, muscle spasm, Tourette's syndrome, epilepsy, cerebral ischemia, stroke, a brain tumor, traumatic brain injury, cardiac arrest, myelopathy, spinal cord injury, peripheral neuropathy, fibromyalgia, acute neuropathic pain, and chronic neuropathic pain, in a patient in need thereof is provided. Such methods may comprise administering to the patient a pharmaceutically effective amount of a disclosed compound or pharmaceutically acceptable salts, stereoisomers, N-oxides, and hydrates thereof.

In some embodiments, a method of this disclosure includes treating depression. For example, depression may include one or more of major depressive disorder, dysthymic disorder, psychotic depression, postpartum depression, seasonal affective disorder, bipolar disorder, mood disorder, or depression caused by a chronic medical condition. In certain embodiments, a method of this disclosure may treat schizophrenia. Such schizophrenia may be, for example, paranoid type schizophrenia, disorganized type schizophrenia, catatonic type schizophrenia, undifferentiated type schizophrenia, residual type schizophrenia, post-schizophrenic depression, or simple schizophrenia.

BRIEF DESCRIPTION OF THE DRAWINGS

FIG. 1 consists of crystal data and structure refinement for the single crystal X-ray structure of Compound AD.

FIG. 2 consists of crystal data and structure refinement for the single crystal X-ray structure of Compound AF.

DETAILED DESCRIPTION

This disclosure is generally directed to compounds that are capable of modulating NMDA receptors, for example, NMDA receptor antagonists, agonists, or partial agonists, and compositions and/or methods of using the disclosed compounds. It should be appreciated that the disclosed compounds may modulate other protein targets and/or specific NMDA receptor subtype.

The term "alkyl," as used herein, refers to a saturated straight-chain or branched hydrocarbon, such as a straight-chain or branched group of 1-6, 1-4, or 1-3 carbon atoms, referred to herein as C$_1$-C$_6$ alkyl, C$_1$-C$_4$ alkyl, and C$_1$-C$_3$ alkyl, respectively. For example, "C$_1$-C$_6$ alkyl" refers to a straight-chain or branched saturated hydrocarbon containing 1-6 carbon atoms. Examples of a C$_1$-C$_6$ alkyl group include, but are not limited to, methyl, ethyl, propyl, butyl, pentyl, hexyl, isopropyl, isobutyl, sec-butyl, tert-butyl, isopentyl, and neopentyl. In another example, "C$_1$-C$_4$ alkyl" refers to a straight-chain or branched saturated hydrocarbon containing 1-4 carbon atoms. Examples of a C$_1$-C$_4$ alkyl group include, but are not limited to, methyl, ethyl, propyl, butyl, isopropyl, isobutyl, sec-butyl and tert-butyl. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 3-methyl-2-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl.

The term "alkylene" as used herein refers to the diradical of an alkyl group.

The term "alkenyl" as used herein refers to an unsaturated straight or branched hydrocarbon having at least one carbon-carbon double bond, such as a straight or branched group of 2-6 or 3-4 carbon atoms, referred to herein for example as C$_2$-C$_6$alkenyl, and C$_3$-C$_4$ alkenyl, respectively. Exemplary alkenyl groups include, but are not limited to, vinyl, allyl, butenyl, pentenyl, etc.

The term "alkoxy," as used herein, refers to an alkyl group attached to an oxygen atom (alkyl-O—). Alkoxy groups can have 1-6 or 2-6 carbon atoms and are referred to herein as C$_1$-C$_6$ alkoxy and C$_2$-C$_6$ alkoxy, respectively. Exemplary alkoxy groups include, but are not limited to, methoxy, ethoxy, propyloxy, isopropoxy, and tert-butoxy.

The term "haloalkyl" as used herein refers to an alkyl group, in which one or more hydrogen atoms of the alkyl group are replaced with one or more independently selected halogens. A haloalkyl group can have 1 to 10 carbon atoms (i.e., $C_1$-$C_{10}$ haloalkyl group), for example, 1 to 6 carbon atoms (i.e., $C_1$-$C_6$ haloalkyl group). Examples of haloalkyl groups include —$CF_3$, —$C_2F_5$, —$CHF_2$, —$CH_2F$, —$CCl_3$, —$CHCl_2$, —$CH_2Cl$, —$CH_2CH_2Cl$, —$CHFCH_2Cl$, and —$C_2Cl_5$. Perhaloalkyl groups, i.e., alkyl groups where all of the hydrogen atoms are replaced with halogen atoms (e.g., —$CF_3$ and —$C_2F_5$), are included within the definition of "haloalkyl."

The term "carbonyl," as used herein, refers to the radical —C(O)— or C=O.

The term "cyano," as used herein, refers to the radical —CN.

The phrase, "carbocyclic ring," as used herein, refers to a hydrocarbon ring system in which all the ring atoms are carbon. Exemplary carbocyclic rings including cycloalkyls and phenyl.

The term "cycloalkyl," as used herein, refers to a monocyclic saturated or partially unsaturated hydrocarbon ring (carbocyclic) system, for example, where each ring is either completely saturated or contains one or more units of unsaturation, but where no ring is aromatic. A cycloalkyl can have 3-6 or 4-6 carbon atoms in its ring system, referred to herein as $C_3$-$C_6$ cycloalkyl or $C_4$-$C_6$ cycloalkyl, respectively. Exemplary cycloalkyl groups include, but are not limited to, cyclohexyl, cyclohexenyl, cyclopentyl, cyclopentenyl, cyclobutyl, and cyclopropyl.

The terms "halo" and "halogen," as used herein, refer to fluoro (F), chloro (Cl), bromo (Br), and/or iodo (I).

The term "heteroatom," as used herein, refers to an atom of any element other than carbon or hydrogen and includes, for example, nitrogen (N), oxygen (O), silicon (Si), sulfur (S), phosphorus (P), and selenium (Se).

The term "heterocycloalkyl," "heterocyclic ring," or "heterocycle," as used herein, is art-recognized and refer to saturated or partially unsaturated 3- to 8-membered ring structures, whose ring system include one, two or three heteroatoms, such as nitrogen, oxygen, and/or sulfur. A heterocycloalkyl can be fused to one or more phenyl, partially unsaturated, or saturated rings. Examples of heterocycloalkyls include, but are not limited to, pyrrolidinyl, piperidinyl, morpholinyl, thiomorpholinyl, and piperazinyl.

The term "heteroaryl," as used herein, refers to a monocyclic aromatic 5- to 8-membered ring system containing one or more heteroatoms, for example, one to three heteroatoms, such as nitrogen, oxygen, and sulfur. Where possible, a heteroaryl can be linked to the adjacent radical though carbon or nitrogen. Examples of heteroaryls include, but are not limited to, furan, thiophene, pyrrole, thiazole, oxazole, isothiazole, isoxazole, imidazole, pyrazole, triazole, pyridine, and pyrimidine.

The terms "hydroxy" and "hydroxyl," as used herein, refer to the radical —OH.

The term "oxo," as used herein, refers to the radical =O (double bonded oxygen).

The term "amino acid," as used herein, includes any one of the following alpha amino acids: isoleucine, alanine, leucine, asparagine, lysine, aspartate, methionine, cysteine, phenylalanine, glutamate, threonine, glutamine, tryptophan, glycine, valine, proline, arginine, serine, histidine, and tyrosine. An amino acid also can include other art-recognized amino acids such as beta amino acids.

The term "compound," as used herein, refers to the compound itself and its pharmaceutically acceptable salts, hydrates, esters and N-oxides including its various stereoisomers and its isotopically-labelled forms, unless otherwise understood from the context of the description or expressly limited to one particular form of the compound, i.e., the compound itself, a specific stereoisomer and/or isotopically-labelled compound, or a pharmaceutically acceptable salt, a hydrate, an ester, or an N-oxide thereof. It should be understood that a compound can refer to a pharmaceutically acceptable salt, or a hydrate, an ester or an N-oxide of a stereoisomer of the compound and/or an isotopically-labelled compound.

The term "moiety," as used herein, refers to a portion of a compound or molecule.

The compounds of the disclosure can contain one or more chiral centers and/or double bonds and therefore, can exist as stereoisomers, such as geometric isomers, and enantiomers or diastereomers. The term "stereoisomers," when used herein, consists of all geometric isomers, enantiomers and/or diastereomers of the compound. For example, when a compound is shown with specific chiral center(s), the compound depicted without such chirality at that and other chiral centers of the compound are within the scope of the present disclosure, i.e., the compound depicted in two-dimensions with "flat" or "straight" bonds rather than in three dimensions, for example, with solid or dashed wedge bonds. Stereospecific compounds may be designated by the symbols "R" or "S," depending on the configuration of substituents around the stereogenic carbon atom. The present disclosure encompasses all the various stereoisomers of these compounds and mixtures thereof. Mixtures of enantiomers or diastereomers can be designated "(±)" in nomenclature, but a skilled artisan will recognize that a structure can denote a chiral center implicitly. It is understood that graphical depictions of chemical structures, e.g., generic chemical structures, encompass all stereoisomeric forms of the specified compounds, unless indicated otherwise.

Individual enantiomers and diastereomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns, or (4) kinetic resolution using stereoselective chemical or enzymatic reagents. Racemic mixtures also can be resolved into their component enantiomers by well-known methods, such as chiral-phase gas chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations. See, for example, Carreira and Kvaerno, *Classics in Stereoselective Synthesis*, Wiley-VCH: Weinheim, 2009.

Geometric isomers, resulting from the arrangement of substituents around a carbon-carbon double bond or arrangement of substituents around a cycloalkyl or heterocycloalkyl, can also exist in the compounds of the present disclosure. The symbol ═══ denotes a bond that may be a single, double or triple bond as described herein. Substituents around a carbon-carbon double bond are designated as being in the "Z" or "E" configuration, where the terms "Z" and "E"

are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The disclosure also embraces isotopically-labeled compounds which are identical to those compounds recited herein, except that one or more atoms are replaced by an atom having an atomic mass or mass number different from the atomic mass or mass number usually found in nature. Examples of isotopes that can be incorporated into compounds described herein include isotopes of hydrogen, carbon, nitrogen, oxygen, phosphorus, fluorine and chlorine, such as $^2$H ("D"), $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. For example, a compound described herein can have one or more H atoms replaced with deuterium.

Certain isotopically-labeled compounds (e.g., those labeled with $^3$H and $^{14}$C) can be useful in compound and/or substrate tissue distribution assays. Tritiated (i.e., $^3$H) and carbon-14 (i.e., $^{14}$C) isotopes can be particularly preferred for their ease of preparation and detectability. Further, substitution with heavier isotopes such as deuterium (i.e., $^2$H) can afford certain therapeutic advantages resulting from greater metabolic stability (e.g., increased in vivo half-life or reduced dosage requirements) and hence can be preferred in some circumstances. Isotopically-labeled compounds can generally be prepared by following procedures analogous to those disclosed herein, for example, in the Examples section, by substituting an isotopically-labeled reagent for a non-isotopically-labeled reagent.

The phrases "pharmaceutically acceptable" and "pharmacologically acceptable," as used herein, refer to compounds, molecular entities, compositions, materials, and/or dosage forms that do not produce an adverse, allergic or other untoward reaction when administered to an animal, or a human, as appropriate. For human administration, preparations should meet sterility, pyrogenicity, general safety and purity standards as required by FDA Office of Biologics standards.

The phrases "pharmaceutically acceptable carrier" and "pharmaceutically acceptable excipient," as used herein, refer to any and all solvents, dispersion media, coatings, isotonic and absorption delaying agents, and the like, that are compatible with pharmaceutical administration. Pharmaceutical acceptable carriers can include phosphate buffered saline solution, water, emulsions (e.g., such as an oil/water or water/oil emulsions), and various types of wetting agents. The compositions also can include stabilizers and preservatives.

The phrase "pharmaceutical composition," as used herein, refers to a composition comprising at least one compound as disclosed herein formulated together with one or more pharmaceutically acceptable carriers. The pharmaceutical compositions can also contain other active compounds providing supplemental, additional, or enhanced therapeutic functions.

The terms "individual," "patient," and "subject," as used herein, are used interchangeably and include any animal, including mammals, preferably mice, rats, other rodents, rabbits, dogs, cats, swine, cattle, sheep, horses, or primates, and more preferably, humans. The compounds described in the disclosure can be administered to a mammal, such as a human, but can also be administered to other mammals such as an animal in need of veterinary treatment, for example, domestic animals (e.g., dogs, cats, and the like), farm animals (e.g., cows, sheep, pigs, horses, and the like) and laboratory animals (e.g., rats, mice, guinea pigs, and the like). The mammal treated in the methods described in the disclosure is preferably a mammal in which treatment, for example, of pain or depression, is desired.

The term "treating," as used herein, includes any effect, for example, lessening, reducing, modulating, ameliorating, or eliminating, that results in the improvement of the condition, disease, disorder, and the like, including one or more symptoms thereof. Treating can be curing, improving, or at least partially ameliorating the disorder.

The term "disorder" refers to and is used interchangeably with, the terms "disease," "condition," or "illness," unless otherwise indicated.

The term "modulation," as used herein, refers to and includes antagonism (e.g., inhibition), agonism, partial antagonism, and/or partial agonism.

The phrase "therapeutically effective amount," as used herein, refers to the amount of a compound (e.g., a disclosed compound) that will elicit the biological or medical response of a tissue, system, animal or human that is being sought by the researcher, veterinarian, medical doctor or other clinician. The compounds described in the disclosure can be administered in therapeutically effective amounts to treat a disease. A therapeutically effective amount of a compound can be the quantity required to achieve a desired therapeutic and/or prophylactic effect, such as an amount which results in lessening of a symptom of a disease such as depression.

As used herein, the term "pharmaceutically acceptable salt" refers to any salt of an acidic or a basic group that may be present in a compound of the present disclosure, which salt is compatible with pharmaceutical administration. As is known to those of skill in the art, "salts" of the compounds of the present disclosure may be derived from inorganic or organic acids and bases.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present disclosure compounded with a suitable cation such as Na$^+$, NH$_4$$^+$, and NW$_4$$^+$ (where W can be a C$_{1-4}$ alkyl group), and the like. For therapeutic use, salts of the compounds of the present disclosure can be pharmaceutically acceptable. However, salts of acids and bases that are non-pharmaceutically acceptable may also find use, for example, in the preparation or purification of a pharmaceutically acceptable compound.

Compounds included in the present compositions that are basic in nature are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions, including but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts.

Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

Compounds included in the present compositions that include a basic or acidic moiety can also form pharmaceutically acceptable salts with various amino acids. The compounds of the disclosure can contain both acidic and basic groups; for example, one amino and one carboxylic acid group. In such a case, the compound can exist as an acid addition salt, a zwitterion, or a base salt.

The compounds disclosed herein can exist in a solvated form as well as an unsolvated form with pharmaceutically acceptable solvents such as water, ethanol, and the like, and it is intended that the disclosure embrace both solvated and unsolvated forms. In some embodiments, the compound is amorphous. In certain embodiments, the compound is a single polymorph. In various embodiments, the compound is a mixture of polymorphs. In particular embodiments, the compound is in a crystalline form.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al, Nature Reviews Drug Discovery 2008, 7, 255). For example, if a compound described herein or a pharmaceutically acceptable salt, hydrate or solvate of the compound contains a carboxylic acid functional group, a prodrug can comprise an ester formed by the replacement of the hydrogen atom of the acid group with a group such as $(C_1-C_8)$alkyl, $(C_2-C_{12})$ alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$alkyl.

Similarly, if a compound described herein contains an alcohol functional group, a prodrug can be formed by the replacement of the hydrogen atom of the alcohol group with a group such as $(C_1-C_6)$alkanoyloxymethyl, 1-($(C_1-C_6)$alkanoyloxy)ethyl, 1-methyl-1-($(C_1-C_6)$alkanoyloxy)ethyl $(C_1-C_6)$alkoxycarbonyloxymethyl, N-$(C_1-C_6)$alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl, where each α-aminoacyl group is independently selected from the naturally occurring L-amino acids, P(O)(OH)$_2$, —P(O)(O$(C_1-C_6)$alkyl)$_2$ or glycosyl (the radical resulting from the removal of a hydroxyl group of the hemiacetal form of a carbohydrate).

If a compound described herein incorporates an amine functional group, a prodrug can be formed, for example, by creation of an amide or carbamate, an N-acyloxyakyl derivative, an (oxodioxolenyl) methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplicio, et al., *Molecules* 2008, 13, 519 and references therein.

Unless defined otherwise, all technical and scientific terms used herein have the same meaning as commonly understood by one of ordinary skill in the art to which this disclosure pertains.

Throughout the description, where compositions and kits are described as having, including, or comprising specific components, or where processes and methods are described as having, including, or comprising specific steps, it is contemplated that, additionally, there are compositions and kits of the present disclosure that consist essentially of, or consist of, the recited components, and that there are processes and methods according to the present disclosure that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present disclosure, whether explicit or implicit herein. For example, where reference is made to a particular compound, that compound can be used in various embodiments of compositions of the present disclosure and/or in methods of the present disclosure, unless otherwise understood from the context. In other words, within this application, embodiments have been described and depicted in a way that enables a clear and concise application to be written and drawn, but it is intended and will be appreciated that embodiments can be variously combined or separated without parting from the present teachings and disclosure(s). For example, it will be appreciated that all features described and depicted herein can be applicable to all aspects of the disclosure(s) described and depicted herein.

The articles "a" and "an" are used in this disclosure to refer to one or more than one (i.e., to at least one) of the grammatical object of the article, unless the context is inappropriate. By way of example, "an element" means one element or more than one element.

The term "and/or" is used in this disclosure to mean either "and" or "or" unless indicated otherwise.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present disclosure also include the specific quantitative value itself, unless specifically stated otherwise. As used herein, the term "about" refers to a ±10% variation from the nominal value unless otherwise indicated or inferred.

Where a percentage is provided with respect to an amount of a component or material in a composition, the percentage should be understood to be a percentage based on weight, unless otherwise stated or understood from the context.

Where a molecular weight is provided and not an absolute value, for example, of a polymer, then the molecular weight should be understood to be an average molecule weight, unless otherwise stated or understood from the context.

It should be understood that the order of steps or order for performing certain actions is immaterial so long as the present disclosure remain operable. Moreover, two or more steps or actions can be conducted simultaneously.

At various places in the present specification, substituents are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Additional examples include that the phrase "optionally substituted with 1-5 substituents" is specifically intended to individually disclose a chemical group that can include 0, 1, 2, 3, 4, 5, 0-5, 0-4, 0-3, 0-2, 0-1, 1-5, 1-4, 1-3, 1-2, 2-5, 2-4, 2-3, 3-5, 3-4, and 4-5 substituents.

The use of any and all examples, or exemplary language herein, for example, "such as" or "including," is intended merely to illustrate better the present disclosure and does not pose a limitation on the scope of the disclosure unless claimed. No language in the specification should be construed as indicating any non-claimed element as essential to the practice of the present disclosure.

Further, if a variable is not accompanied by a definition, then the variable is defined as found elsewhere in the disclosure unless understood to be different from the context. In addition, the definition of each variable and/or substituent, for example, $C_1$-$C_6$ alkyl, $R^2$, $R^b$, w and the like, when it occurs more than once in any structure or compound, can be independent of its definition elsewhere in the same structure or compound.

Definitions of the variables and/or substituents in formulae and/or compounds herein encompass multiple chemical groups. The present disclosure includes embodiments where, for example, i) the definition of a variable and/or substituent is a single chemical group selected from those chemical groups set forth herein, ii) the definition is a collection of two or more of the chemical groups selected from those set forth herein, and iii) the compound is defined by a combination of variables and/or substituents in which the variables and/or substituents are defined by (i) or (ii).

Various aspects of the disclosure are set forth herein under headings and/or in sections for clarity; however, it is understood that all aspects, embodiments, or features of the disclosure described in one particular section are not to be limited to that particular section but rather can apply to any aspect, embodiment, or feature of the present disclosure.

Compounds

Disclosed compounds include a compound having Formula I or Formula II:

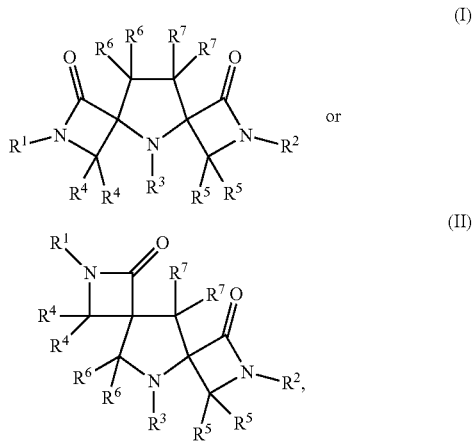

or a pharmaceutically acceptable salt, a stereoisomer, and/or an N-oxide thereof, wherein:

$R^1$ and $R^2$ are independently selected from the group consisting of hydrogen, —$C_1$-$C_6$alkyl, —C(O)—O—$C_1$-$C_6$alkyl, and —O—$CH_2$-phenyl;

$R^3$ is selected from the group consisting of hydrogen, —$C_1$-$C_6$alkyl, —C(O)—$R^{31}$, and —C(O)—O—$R^{32}$;

$R^{31}$ is selected from the group consisting of hydrogen, —$C_1$-$C_6$alkyl; —$C_1$-$C_6$haloalkyl, —$C_3$-$C_6$cycloalkyl, and phenyl;

$R^{32}$ is selected from the group consisting of hydrogen, —$C_1$-$C_6$alkyl; —$C_1$-$C_6$haloalkyl, —$C_3$-$C_6$cycloalkyl, and phenyl;

wherein any aforementioned $C_1$-$C_6$alkyl, independently for each occurrence, can be optionally substituted by one, two or three substituents each independently selected from —C(O)$NR^aR^b$, —$NR^aR^b$, hydroxyl, —SH, phenyl, —O—$CH_2$-phenyl, and halogen; and any aforementioned phenyl, independently for each occurrence, can be optionally substituted by one, two or three substituents each independently selected from —C(O)$NR^aR^b$, —$NR^aR^b$, —$C_1$-$C_3$alkoxy, hydroxyl, and halogen;

$R^a$ and $R^b$ are each independently for each occurrence selected from the group consisting of hydrogen, —C(O)—O—$CH_2$-phenyl, and —$C_1$-$C_3$alkyl; or $R^a$ and $R^b$ taken together with the nitrogen to which they are attached form a 4-6 membered heterocyclic ring;

$R^4$, $R^5$, $R^6$ and $R^7$ are each independently selected from the group consisting of hydrogen, halogen, hydroxyl, phenyl, amido, amino, $C_{1-4}$alkyl, $C_{2-4}$alkenyl, —NH—C(O)—$C_{1-6}$alkyl, —NH—C(O)—$C_{1-6}$alkylene-phenyl, —NH—C(O)—O—$C_{1-6}$alkyl, and —NH—C(O)—O—$C_{1-6}$alkylene-phenyl; wherein $C_{1-4}$alkyl, $C_{1-6}$alkylene, $C_{2-4}$alkenyl, $C_{1-4}$alkoxy, and phenyl are optionally substituted by one or more substituents selected from $R^P$;

two $R^5$s taken together form an oxo moiety; or wherein for the compound of Formula I, $R^6$ and $R^7$ taken together with the adjacent carbons to which they are attached form a 3-membered carbocyclic ring which can be optionally substituted by one or two substituents independently selected from the group consisting of halogen, hydroxyl, —$C_1$-$C_3$alkyl, —$C_1$-$C_3$alkoxy, —C(O)NR$^a$R$^b$, and —NR$^a$R$^b$; and $R^P$ is selected, independently for each occurrence, from the group consisting of carboxy, hydroxyl, halogen, amino, phenyl, $C_{1-6}$alkoxy, and $C_{1-6}$alkyl optionally substituted by one or more substituents independently selected from the group consisting of halogen, hydroxyl and amino.

In certain embodiments, $R^1$ and $R^2$ can be hydrogen. In certain embodiments, $R^1$ and $R^2$ can be —O—CH$_2$-phenyl.

In certain embodiments, $R^1$ and $R^2$ can be —$C_1$-$C_6$alkyl each independently and optionally substituted by one, two or three substituents independently selected from the group consisting of —C(O)NR$^a$R$^b$, hydroxyl, —SH, and halogen. For example, $R^1$ and $R^2$ can be independently selected from the group consisting of:

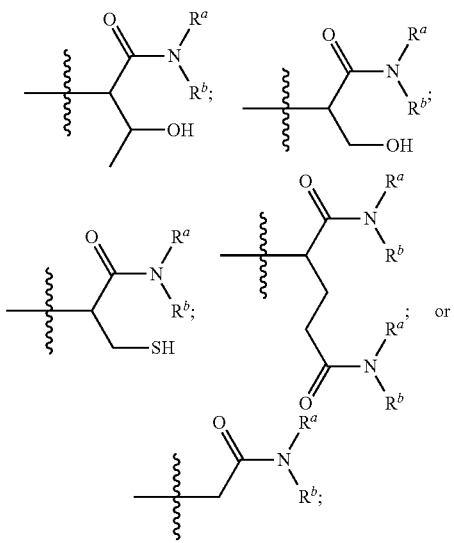

wherein:

$R^a$ and $R^b$ are each independently selected for each occurrence from the group consisting of hydrogen and —$C_1$-$C_3$alkyl.

In some embodiments, $R^3$ can be hydrogen. In certain embodiments, $R^3$ can be —$C_1$-$C_6$alkyl. For example, $R^3$ can be methyl, isobutyl, or —CH$_2$-phenyl.

In certain embodiments, $R^3$ can be —C(O)—$C_1$-$C_6$alkyl. For example, $R^3$ can be —C(O)— isopropyl. In some embodiments, $R^3$ can be —C(O)—O—$C_1$-$C_6$alkyl. For example, $R^3$ can be —C(O)—O-tert-butyl.

In some embodiments, $R^4$, $R^5$, $R^6$, and $R^7$ can be hydrogen. In other embodiments, one, two, three or four of $R^6$ and $R^7$, independently, can be fluoro.

In certain embodiments, $R^1$, $R^2$, and $R^3$ independently can be an amino acid or a derivative of an amino acid, for example, an alpha "amino amide" represented by H$_2$N—CH(amino acid side chain)-C(O)NH$_2$. In certain embodiments, the nitrogen atom of the amino group of the amino acid or the amino acid derivative is a ring nitrogen in a chemical formula described herein. In such embodiments, the carboxylic acid of the amino acid or the amide group of an amino amide (amino acid derivative) is not within the ring structure, i.e., not a ring atom. In certain embodiments, the carboxylic acid group of the amino acid or the amino acid derivative forms an amide bond with a ring nitrogen in a chemical formula disclosed herein, thereby providing an amino amide, where the amino group of the amino amide is not within the ring structure, i.e., not a ring atom. In certain embodiments, $R^1$, $R^2$, and $R^3$ independently can be an alpha amino acid, an alpha amino acid derivative, and/or another amino acid or amino acid derivative such as a beta amino acid or a beta amino acid derivative, for example, a beta amino amide.

For example, disclosed compounds can include a compound having Formula III or Formula IV:

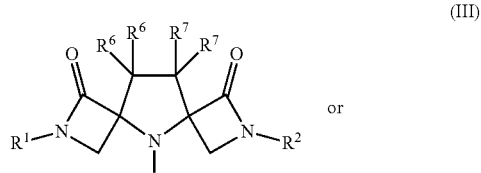

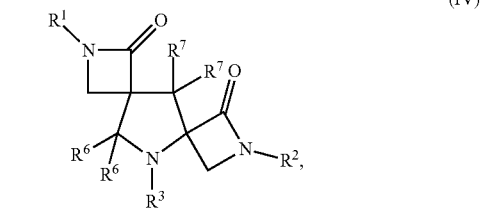

or a pharmaceutically acceptable salt, a stereoisomer, and/or an N-oxide thereof, wherein:

$R^1$ and $R^2$ are independently selected from the group consisting of hydrogen, —$C_1$-$C_6$alkyl, —C(O)—$C_1$-$C_6$alkyl, —C(O)—O—$C_1$-$C_6$alkyl, and —O—CH$_2$-phenyl;

$R^3$ is selected from the group consisting of hydrogen, —$C_1$-$C_6$alkyl, —C(O)—$R^{31}$, and —C(O)—O—$R^{32}$;

$R^{31}$ is selected from the group consisting of hydrogen, —$C_1$-$C_6$alkyl; —$C_1$-$C_6$haloalkyl, —$C_3$-$C_6$cycloalkyl, and phenyl;

$R^{32}$ is selected from the group consisting of hydrogen, —$C_1$-$C_6$alkyl; —$C_1$-$C_6$haloalkyl, —$C_3$-$C_6$cycloalkyl, and phenyl;

wherein any aforementioned $C_1$-$C_6$alkyl, independently for each occurrence, can be optionally substituted by one, two or three substituents each independently selected from —C(O)NR$^a$R$^b$, —NR$^a$R$^b$, hydroxyl, —SH, phenyl, —O—CH$_2$-phenyl, and halogen; and any aforementioned phenyl, independently for each occurrence, can be optionally substituted by one, two or three substituents each independently selected from —C(O)NR$^a$R$^b$, —NR$^a$R$^b$, —$C_1$-$C_3$alkoxy, hydroxyl, and halogen; and $R^a$ and $R^b$ are each independently for each occurrence selected from the group consisting of hydrogen, —C(O)—O—CH$_2$-phenyl, and —C$_1$-C$_3$alkyl; or $R^a$ and $R^b$ taken together with the nitrogen to which they are attached form a 4-6 membered heterocyclic ring;

$R^6$ and $R^7$ are each independently selected from the group consisting of hydrogen, halogen, hydroxyl, phenyl, amido, amino, C$_{1-4}$alkyl, C$_{2-4}$alkenyl, —NH—C(O)—C$_{1-6}$alkyl, —NH—C(O)—C$_{1-6}$alkylene-phenyl, —NH—C(O)—O—C$_{1-6}$alkyl, and —NH—C(O)—O—C$_{1-6}$alkylene-phenyl; wherein C$_{1-4}$alkyl, C$_{1-6}$alkylene, C$_{2-4}$alkenyl, C$_{1-4}$alkoxy, and phenyl are optionally substituted by one or more substituents selected from $R^P$; or wherein for the compound of Formula III, $R^6$ and $R^7$ taken together with the adjacent carbons to which they are attached form a 3-membered carbocyclic ring which can be optionally substituted by one or two substituents independently selected from the group consisting of halogen, hydroxyl, —C$_1$-C$_3$alkyl, —C$_1$-C$_3$alkoxy, —C(O)NR$^a$R$^b$, and —NR$^a$R$^b$; and $R^P$ is selected, independently for each occurrence, from the group consisting of carboxy, hydroxyl, halogen, amino, phenyl, C$_{1-6}$alkoxy, and C$_{1-6}$alkyl optionally substituted by one or more substituents independently selected from the group consisting of halogen, hydroxyl and amino.

In certain embodiments, $R^6$ and $R^7$ can be hydrogen. In some embodiments, one, two, three or four of $R^6$ and $R^7$ can be fluoro.

In certain embodiments, disclosed compounds can include a compound having Formula V or Formula VI:

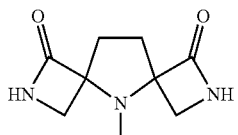

(V)

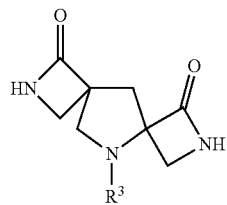

(VI)

or a pharmaceutically acceptable salt, a stereoisomer, and/or an N-oxide thereof, wherein:

$R^3$ is selected from the group consisting of hydrogen, —C$_1$-C$_6$alkyl, —C(O)—R$^{31}$, and —C(O)—O—R$^{32}$;

$R^{31}$ is selected from the group consisting of hydrogen, —C$_1$-C$_6$alkyl; —C$_1$-C$_6$haloalkyl, —C$_3$-C$_6$cycloalkyl, and phenyl;

$R^{32}$ is selected from the group consisting of hydrogen, —C$_1$-C$_6$alkyl; —C$_1$-C$_6$haloalkyl, —C$_3$-C$_6$cycloalkyl, and phenyl;

wherein any aforementioned C$_1$-C$_6$alkyl, independently for each occurrence, can be optionally substituted by one, two or three substituents each independently selected from —C(O)NR$^a$R$^b$, —NR$^a$R$^b$, hydroxyl, —SH, phenyl, —O—CH$_2$-phenyl, and halogen; and any aforementioned phenyl, independently for each occurrence, can be optionally substituted by one, two or three substituents each independently selected from —C(O)NR$^a$R$^b$, —NR$^a$R$^b$, —C$_1$-C$_3$alkoxy, hydroxyl, and halogen; and $R^a$ and $R^b$ are each independently for each occurrence selected from the group consisting of hydrogen, —C(O)—O—CH$_2$-phenyl, and —C$_1$-C$_3$alkyl; or $R^a$ and $R^b$ taken together with the nitrogen to which they are attached form a 4-6 membered heterocyclic ring.

Disclosed compounds include a compound having Formula VI or Formula VII:

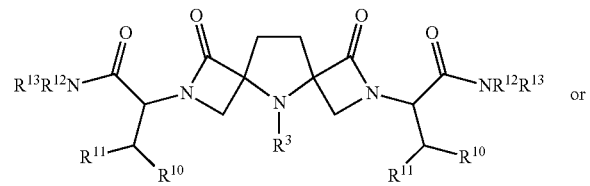

(VI)

or

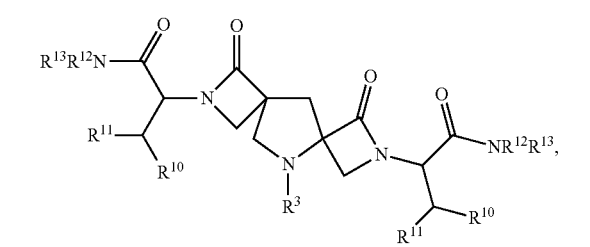

(VII)

or a pharmaceutically acceptable salt, a stereoisomer, and/or an N-oxide thereof, wherein:

$R^3$ is selected from the group consisting of hydrogen, —C$_1$-C$_6$alkyl, —C(O)—R$^{31}$, and —C(O)—O—R$^{32}$;

$R^{31}$ is selected from the group consisting of hydrogen, —C$_1$-C$_6$alkyl; C$_1$-C$_6$haloalkyl, —C$_3$-C$_6$cycloalkyl, and phenyl;

$R^{32}$ is selected from the group consisting of hydrogen, —C$_1$-C$_6$alkyl; C$_1$-C$_6$haloalkyl, —C$_3$-C$_6$cycloalkyl, and phenyl;

$R^{10}$ and $R^{11}$ for each occurrence are independently selected from the group consisting of hydrogen, halogen, —OH, —C$_1$-C$_6$alkyl, —C$_1$-C$_6$alkoxy, —CO$_2$H, or —NR'R', wherein R' for each occurrence is independently selected from hydrogen and, —C$_1$-C$_6$ alkyl; and $R^{12}$ and $R^{13}$ for each occurrence are independently selected from the group consisting of hydrogen and —C$_1$-C$_6$ alkyl; or $R_{13}$ and $R_{12}$ together with the nitrogen to which they are bound form a 4-6 membered heterocycle; and wherein C$_1$-C$_6$ alkyl is optionally for each occurrence substituted by one, two, or three substituents each selected from the group consisting of halogen, hydroxyl, and amino.

In certain embodiments, $R^{12}$ and $R^{13}$ can be hydrogen.

In some embodiments, $R^{11}$ can be OH.

In some embodiments, $R^{10}$ can be methyl.

For example, a disclosed compound can be selected from the group consisting of:

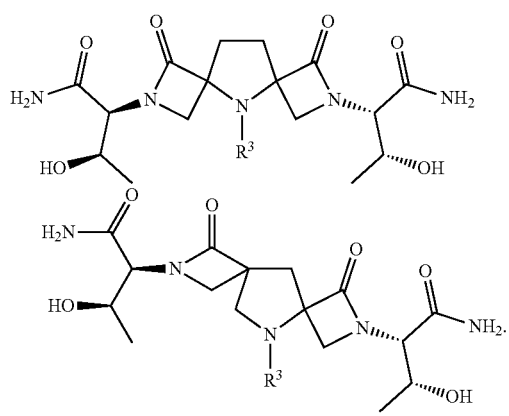

In some embodiments, $R^3$ can be hydrogen. In certain embodiments, $R^3$ can be —$C_1$-$C_6$alkyl. For example, $R^3$ can be methyl, isobutyl, or —$CH_2$-phenyl.

In certain embodiments, $R^3$ can be —C(O)—$C_1$-$C_6$alkyl. For example, $R^3$ can be —C(O)—isopropyl. In some embodiments, $R^3$ can be —C(O)—O—$C_1$-$C_6$alkyl. For example, $R^3$ can be —C(O)—O-tert-butyl.

Disclosed compounds can include a compound having Formula IX or Formula X:

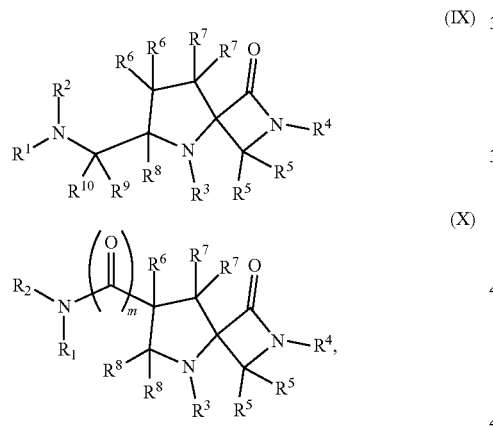

or a pharmaceutically acceptable salt, a stereoisomer, and/or an N-oxide thereof, wherein:

- $R^1$ and $R^2$ are independently selected from the group consisting of hydrogen, —$C_1$-$C_6$alkyl, —C(O)—$C_1$-$C_6$alkyl, and —C(O)—O—$C_1$-$C_6$alkyl; or $R^1$ and $R^2$ taken together with the nitrogen to which they are attached form a 4-6 membered heterocyclic ring;
- $R^3$ is selected from the group consisting of hydrogen, —$C_1$-$C_6$alkyl, —C(O)—$R^{31}$, and —C(O)—O—$R^{32}$;
- $R^{31}$ is selected from the group consisting of hydrogen, —$C_1$-$C_6$alkyl; —$C_1$-$C_6$haloalkyl, —$C_3$-$C_6$cycloalkyl, and phenyl;
- $R^{32}$ is selected from the group consisting of hydrogen, —$C_1$-$C_6$alkyl; —$C_1$-$C_6$haloalkyl, —$C_3$-$C_6$cycloalkyl, and phenyl;
- $R^4$ selected from the group consisting of hydrogen, —$C_1$-$C_6$alkyl, —C(O)—$C_1$-$C_6$alkyl, —C(O)—O—$C_1$-$C_6$alkyl, and —O—$CH_2$-phenyl;
- wherein any aforementioned $C_1$-$C_6$alkyl, independently for each occurrence, can be optionally substituted by one, two or three substituents each independently selected from —C(O)$NR^aR^b$, —$NR^aR^b$, hydroxyl, —SH, phenyl, —O—$CH_2$-phenyl, and halogen; and any aforementioned phenyl, independently for each occurrence, can be optionally substituted by one, two or three substituents each independently selected from —C(O)$NR^aR^b$, —$NR^aR^b$, —$C_1$-$C_3$alkoxy, hydroxyl, and halogen;
- $R^a$ and $R^b$ are each independently for each occurrence selected from the group consisting of hydrogen, —C(O)—O—$CH_2$-phenyl, and —$C_1$-$C_3$alkyl; or $R^a$ and $R^b$ taken together with the nitrogen to which they are attached form a 4-6 membered heterocyclic ring;
- $R^5$, $R^6$, $R^7$ and $R^8$ are each independently selected from the group consisting of hydrogen, halogen, hydroxyl, phenyl, amido, amino, $C_{1-4}$alkyl, $C_{2-4}$alkenyl, —NH—C(O)—$C_{1-6}$alkyl, —NH—C(O)—$C_{1-6}$alkylene-phenyl, —NH—C(O)—O—$C_{1-6}$alkyl, and —NH—C(O)—O—$C_{1-6}$alkylene-phenyl; wherein $C_{1-4}$alkyl, $C_{1-4}$alkoxy, and phenyl are optionally substituted by one or more substituents selected from $R^P$; or
- $R^6$ and $R^7$ taken together with the adjacent carbons to which they are attached form a 3-membered carbocyclic ring which can be optionally substituted by one or two substituents independently selected from the group consisting of halogen, hydroxyl, —$C_1$-$C_3$alkyl, —$C_1$-$C_3$alkoxy, —C(O)$NR^aR^b$, and —$NR^aR^b$; and
- $R^P$ is selected, independently for each occurrence, from the group consisting of carboxy, hydroxyl, halogen, amino, phenyl, $C_{1-6}$alkoxy, and $C_{1-3}$alkyl optionally substituted by one or more substituents independently selected from the group consisting of halogen, hydroxyl and amino;
- $R^9$ and $R^{10}$ are each independently selected from the group consisting of hydrogen and —$C_1$-$C_3$alkyl, or $R^9$ and $R^{10}$ taken together form an oxo moiety; and
- m is 0 or 1.

In certain embodiments, $R^1$ and $R^2$ can be hydrogen.

In some embodiments, $R^1$ can be hydrogen and $R^2$ is —$C_1$-$C_6$alkyl can be optionally substituted by one, two or three substituents independently selected from the group consisting of —C(O)$NR^aR^b$, hydroxyl, —SH, and halogen. For example, $R^2$ can be selected from the group consisting of:

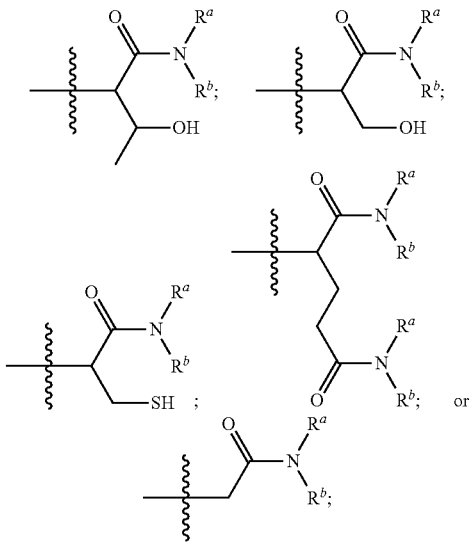

wherein:

$R^a$ and $R^b$ are each independently selected for each occurrence from the group consisting of hydrogen and —$C_1$-$C_6$alkyl.

In some embodiments, $R^3$ can be hydrogen. In certain embodiments, $R^3$ can be —$C_1$-$C_6$alkyl. For example, $R^3$ can be methyl, isobutyl, or —$CH_2$-phenyl.

In certain embodiments, $R^3$ can be —C(O)—$C_1$-$C_6$alkyl. For example, $R^3$ can be —C(O)-isopropyl. In some embodiments, $R^3$ can be —C(O)—O—$C_1$-$C_6$alkyl. For example, $R^3$ can be —C(O)—O-tert-butyl.

In some embodiments, $R^4$, $R^5$, $R^6$, and $R^7$ can be hydrogen. In certain embodiments, one, two, or three of $R^6$ and $R^7$, independently, can be fluoro.

For example, disclosed compounds can include a compound having Formula XI:

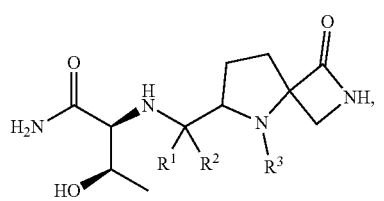

(XI)

or a pharmaceutically acceptable salt, a stereoisomer, and/or an N-oxide thereof, wherein:

$R^1$ and $R^2$ are each independently selected from the group consisting of hydrogen and —$C_1$-$C_3$alkyl, or $R^1$ and $R^2$ taken together form an oxo moiety;

$R^3$ is selected from the group consisting of hydrogen, —$C_1$-$C_6$alkyl, —C(O)—$R^{31}$, and —C(O)—O—$R^{32}$;

$R^{31}$ is selected from the group consisting of hydrogen, —$C_1$-$C_6$alkyl; —$C_1$-$C_6$haloalkyl, —$C_3$-$C_6$cycloalkyl, and phenyl;

$R^{32}$ is selected from the group consisting of hydrogen, —$C_1$-$C_6$alkyl; —$C_1$-$C_6$haloalkyl, —$C_3$-$C_6$cycloalkyl, and phenyl;

wherein any aforementioned $C_1$-$C_6$alkyl can be optionally substituted by one, two or three substituents each independently selected from —C(O)$NR^aR^b$, —$NR^aR^b$, hydroxyl, phenyl, and halogen; and any aforementioned phenyl can be optionally substituted by one, two or three substituents each independently selected from —C(O)$NR^aR^b$, —$NR^aR^b$, —$C_1$-$C_3$alkoxy, hydroxyl, and halogen; and $R^a$ and $R^b$ are each independently for each occurrence selected from the group consisting of hydrogen, —C(O)—O—$CH_2$-phenyl, and —$C_1$-$C_3$alkyl; or $R^a$ and $R^b$ taken together with the nitrogen to which they are attached form a 4-6 membered heterocyclic ring.

In certain embodiments, a disclosed compound is selected from the compounds delineated in the Examples, and includes pharmaceutically acceptable salts, stereoisomers, and/or N-oxides thereof.

The compounds of the present disclosure and formulations thereof may have a plurality of chiral centers. Each chiral center may be independently R, S, or any mixture of R and S. For example, in some embodiments, a chiral center may have an R:S ratio of between about 100:0 and about 50:50 ("racemate"), between about 100:0 and about 75:25, between about 100:0 and about 85:15, between about 100:0 and about 90:10, between about 100:0 and about 95:5, between about 100:0 and about 98:2, between about 100:0 and about 99:1, between about 0:100 and 50:50, between about 0:100 and about 25:75, between about 0:100 and about 15:85, between about 0:100 and about 10:90, between about 0:100 and about 5:95, between about 0:100 and about 2:98, between about 0:100 and about 1:99, between about 75:25 and 25:75, and about 50:50. Formulations of the disclosed compounds comprising a greater ratio of one or more isomers (i.e., R and/or S) may possess enhanced therapeutic characteristic relative to racemic formulations of a disclosed compounds or mixture of compounds. In some instances, chemical formulas contain the descriptor "-I-" or "-(S)-" that is further attached to solid wedge or dashed wedge. This descriptor is intended to show a methine carbon (CH) that is attached to three other substituents and has either the indicated R or S configuration.

Disclosed compounds may provide for efficient cation channel opening at the NMDA receptor, e.g. may bind or associate with the glutamate site or glycine site or other modulatory site of the NMDA receptor to assist in opening the cation channel. The disclosed compounds may be used to regulate (turn on or turn off) the NMDA receptor through action as an agonist or antagonist.

The compounds described herein, in some embodiments, may bind to a specific NMDA receptor subtypes. For example, a disclosed compound may bind to one NMDA subtype and not another. In certain embodiments, a disclosed compound may bind to one, or more than one NMDA subtype, and/or may have substantially less (or substantial no) binding activity to certain other NMDA subtypes. For example, in some embodiments, a disclosed compound (e.g., compound A) binds to NR2A with substantially no binding to NR2D. In some embodiments, a disclosed compound (e.g., compound B) binds to NR2B and NR2D with substantially lower binding to NR2A and NR2C.

The compounds as described herein may bind to NMDA receptors. A disclosed compound may bind to the NMDA receptor resulting in agonist-like activity (facilitation) over a certain dosing range and/or may bind to the NMDA receptor resulting in antagonist-like activity (inhibition) over a certain dosing range. In some embodiments, a disclosed compound may possess a potency that is 10-fold or greater than the activity of existing NMDA receptor modulators.

The disclosed compounds may exhibit a high therapeutic index. The therapeutic index, as used herein, refers to the ratio of the dose that produces a toxicity in 50% of the population (i.e., $TD_{50}$) to the minimum effective dose for 50% of the population (i.e., $ED_{50}$). Thus, the therapeutic index=$(TD_{50}):(ED_{50})$. In some embodiments, a disclosed compound may have a therapeutic index of at least about 10:1, at least about 50:1, at least about 100:1, at least about 200:1, at least about 500:1, or at least about 1000:1.

Compositions

In other aspects of the disclosure, a pharmaceutical formulation or a pharmaceutical composition including a disclosed compound and a pharmaceutically acceptable excipient are provided. In some embodiments, a pharmaceutical composition includes a racemic mixture or a varied stereoisomeric mixture of one or more of the disclosed compounds.

A formulation can be prepared in any of a variety of forms for use such as for administering an active agent to a patient, who may be in need thereof, as are known in the pharmaceutical arts. For example, the pharmaceutical compositions of the present disclosure can be formulated for administration in solid or liquid form, including those adapted for the following: (1) oral administration, for example, drenches (aqueous or non-aqueous solutions or suspensions), tablets (e.g., those targeted for buccal, sublingual, and/or systemic absorption), boluses, powders, granules, and pastes for application to the tongue; (2) parenteral administration by, for example, subcutaneous, intramuscular, intraperitoneal, intravenous or epidural injection as, for example, a sterile solution or suspension, or sustained-release formulation; (3) topical administration, for example, as a cream, ointment, or a controlled-release patch or spray applied to the skin; (4) intravaginal or intrarectal administration, for example, as a pessary, cream or foam; (5) sublingual administration; (6) ocular administration; (7) transdermal administration; or (8) nasal administration.

For example, pharmaceutical compositions of the disclosure can be suitable for delivery to the eye, i.e., ocularly. Related methods can include administering a pharmaceutically effective amount of a disclosed compound or a pharmaceutical composition including a disclosed compound to a patient in need thereof, for example, to an eye of the patient, where administering can be topically, subconjunctivally, subtenonly, intravitreally, retrobulbarly, peribulbarly, intracomerally, and/or systemically.

Amounts of a disclosed compound as described herein in a formulation may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier.

The specification for the dosage unit forms are dictated by and directly dependent on (a) the unique characteristics of the compound selected and the particular therapeutic effect to be achieved, and (b) the limitations inherent in the art of compounding such an active compound for the treatment of sensitivity in individuals.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin.

The compounds can be administered in a time release formulation, for example in a composition which includes a slow release polymer. The compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are generally known to those skilled in the art.

Sterile injectable solutions can be prepared by incorporating the compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In some embodiments, a compound can be formulated with one or more additional compounds that enhance the solubility of the compound.

Methods

Methods of the disclosure for treating a condition in a patient in need thereof generally include administering a therapeutically effective amount of a compound described herein or a composition including such a compound. In some embodiments, the condition may be a mental condition. For example, a mental illness may be treated. In another aspect, a nervous system condition may be treated. For example, a condition that affects the central nervous system, the peripheral nervous system, and/or the eye may be treated. In some embodiments, neurodegenerative diseases may be treated.

In some embodiments, the methods include administering a compound to treat patients suffering from autism, anxiety, depression, bipolar disorder, attention deficit disorder, attention deficit hyperactivity disorder (ADHD), schizophrenia, a psychotic disorder, a psychotic symptom, social withdrawal, obsessive-compulsive disorder (OCD), phobia, post-traumatic stress syndrome, a behavior disorder, an impulse control disorder, a substance abuse disorder (e.g., a withdrawal symptom, opiate addiction, nicotine addiction, and ethanol addition), a sleep disorder, a memory disorder (e.g., a deficit, loss, or reduced ability to make new memories), a learning disorder, urinary incontinence, multiple system atrophy, progressive supra-nuclear palsy, Friedrich's ataxia, Down's syndrome, fragile X syndrome, tuberous sclerosis, olivio-ponto-cerebellar atrophy, cerebral palsy, drug-induced optic neuritis, ischemic retinopathy, diabetic retinopathy, glaucoma, dementia, AIDS dementia, Alzheimer's disease, Huntington's chorea, spasticity, myoclonus, muscle spasm, infantile spasm, Tourette's syndrome, epilepsy, cerebral ischemia, stroke, a brain tumor, traumatic brain injury, cardiac arrest, myelopathy, spinal cord injury, peripheral neuropathy, acute neuropathic pain, and chronic neuropathic pain.

In some embodiments, methods of treating a memory disorder associated with aging, schizophrenia, special learning disorders, seizures, post-stroke convulsions, brain ischemia, hypoglycemia, cardiac arrest, epilepsy, Lewy body dementia, migraine, AIDS dementia, Huntington's chorea, Parkinson's disease, early stage Alzheimer's disease, and Alzheimer's disease are provided.

In certain embodiments, methods for treating schizophrenia are provided. For example, paranoid type schizophrenia, disorganized type schizophrenia (i.e., hebephrenic schizophrenia), catatonic type schizophrenia, undifferentiated type schizophrenia, residual type schizophrenia, post-schizophrenic depression, and simple schizophrenia may be treated using the methods and compositions disclosed herein. Psychotic disorders such as schizoaffective disorders, delusional disorders, brief psychotic disorders, shared psychotic disorders, and psychotic disorders with delusions or hallucinations may also be treated using the compositions disclosed herein.

Paranoid schizophrenia may be characterized where delusions or auditory hallucinations are present, but thought disorder, disorganized behavior, or affective flattening are not. Delusions may be persecutory and/or grandiose, but in addition to these, other themes such as jealousy, religiosity, or somatization may also be present. Disorganized type schizophrenia may be characterized where thought disorder and flat affect are present together. Catatonic type schizophrenia may be characterized where the patient may be almost immobile or exhibit agitated, purposeless movement. Symptoms can include catatonic stupor and waxy flexibility. Undifferentiated type schizophrenia may be characterized where psychotic symptoms are present but the criteria for paranoid, disorganized, or catatonic types have not been met. Residual type schizophrenia may be characterized where positive symptoms are present at a low intensity only. Post-schizophrenic depression may be characterized where a depressive episode arises in the aftermath of a schizophrenic illness where some low-level schizophrenic symptoms may still be present. Simple schizophrenia may be characterized by insidious and progressive development of prominent negative symptoms with no history of psychotic episodes.

In some embodiments, methods are provided for treating psychotic symptoms that may be present in other mental disorders, including, but not limited to, bipolar disorder, borderline personality disorder, drug intoxication, and drug-induced psychosis. In some embodiments, methods for treating delusions (e.g., "non-bizarre") that may be present in, for example, delusional disorder are provided.

In various embodiments, methods for treating social withdrawal in conditions including, but not limited to, social anxiety disorder, avoidant personality disorder, and schizotypal personality disorder.

In some embodiments, the disclosure provides methods for treating a neurodevelopmental disorder related to synaptic dysfunction in a patient in need thereof, where the methods generally include administering to the patient a therapeutically effective amount of a disclosed compound, or a pharmaceutical composition including a disclosed compound. In certain embodiments, the neurodevelopmental disorder related to synaptic dysfunction can be Rett syndrome also known as cerebroatrophic hyperammonemia, MECP2 duplication syndrome (e.g., a MECP2 disorder), CDKL5 syndrome, fragile X syndrome (e.g., a FMR1 disorder), tuberous sclerosis (e.g., a TSC1 disorder and/or a TSC2 disorder), neurofibromatosis (e.g., a NF1 disorder), Angelman syndrome (e.g., a UBE3A disorder), the PTEN hamartoma tumor syndrome, Phelan-McDermid syndrome (e.g., a SHANK3 disorder), or infantile spasms. In particular embodiments, the neurodevelopmental disorder can be caused by mutations in the neuroligin (e.g., a NLGN3 disorder and/or a NLGN2 disorder) and/or the neurexin (e.g., a NRXN1 disorder).

In some embodiments, methods are provided for treating neuropathic pain. The neuropathic pain can be acute or chronic. In some cases, the neuropathic pain can be associated with a condition such as herpes, HIV, traumatic nerve injury, stroke, post-ischemia, chronic back pain, post-herpetic neuralgia, fibromyalgia, reflex sympathetic dystrophy, complex regional pain syndrome, spinal cord injury, sciatica, phantom limb pain, diabetic neuropathy such as diabetic peripheral neuropathy ("DPN"), and cancer chemotherapeutic-induced neuropathic pain. In certain embodiments, methods for enhancing pain relief and for providing analgesia to a patient are also provided.

Further methods include a method of treating autism and/or an autism spectrum disorder in a patient need thereof, comprising administering an effective amount of a compound to the patient. In some embodiments, a method for reducing the symptoms of autism in a patient in need thereof comprises administering an effective amount of a disclosed compound to the patient. For example, upon administration, the compound may decrease the incidence of one or more symptoms of autism such as eye contact avoidance, failure to socialize, attention deficit, poor mood, hyperactivity, abnormal sound sensitivity, inappropriate speech, disrupted sleep, and perseveration. Such decreased incidence may be measured relative to the incidence in the untreated individual or an untreated individual(s).

Also provided herein is a method of modulating an autism target gene expression in a cell comprising contacting a cell with an effective amount of a compound described herein. The autism gene expression may be for example, selected from ABAT, APOE, CHRNA4, GABRA5, GFAP, GRIN2A, PDYN, and PENK. In certain embodiments, a method of modulating synaptic plasticity in a patient suffering from a synaptic plasticity related disorder is provided, comprising administering to the patient an effective amount of a compound.

In some embodiments, a method of treating Alzheimer's disease, or e.g., treatment of memory loss that e.g., accompanies early stage Alzheimer's disease, in a patient in need thereof is provided, comprising administering a compound. Also provided herein is a method of modulating an Alzheimer's amyloid protein (e.g., beta amyloid peptide, e.g. the isoform $A\beta_{1-42}$), in-vitro or in-vivo (e.g. in a cell) comprising contacting the protein with an effective amount of a compound is disclosed. For example, in some embodiments, a compound may block the ability of such amyloid protein to inhibit long-term potentiation in hippocampal slices as well as apoptotic neuronal cell death. In some embodiments, a disclosed compound may provide neuroprotective properties to a Alzheimer's patient in need thereof, for example, may provide a therapeutic effect on later stage Alzheimer's—associated neuronal cell death.

In certain embodiments, the disclosed methods include treating a psychosis or a pseudobulbar affect ("PBA") that is induced by another condition such as a stroke, amyotrophic lateral sclerosis (ALS or Lou Gehrig's disease), multiple sclerosis, traumatic brain injury, Alzheimer's disease, dementia, and/or Parkinson's disease. Such methods, as with other methods of the disclosure, include administration of a pharmaceutically effective amount of a disclosed compound to a patient in need thereof.

In certain embodiments, a method of treating depression includes administering a therapeutically effective amount of a compound described herein. In some embodiments, the treatment may relieve depression or a symptom of depression without affecting behavior or motor coordination and without inducing or promoting seizure activity. Exemplary depression conditions that are expected to be treated according to this aspect include, but are not limited to, major depressive disorder, dysthymic disorder, psychotic depression, postpartum depression, premenstrual syndrome, premenstrual dysphoric disorder, seasonal affective disorder (SAD), bipolar disorder (or manic depressive disorder), mood disorder, and depressions caused by chronic medical conditions such as cancer or chronic pain, chemotherapy, chronic stress, and post traumatic stress disorders. In addition, patients suffering from any form of depression often experience anxiety. Various symptoms associated with anxiety include fear, panic, heart palpitations, shortness of breath, fatigue, nausea, and headaches among others. Anxiety or any of the symptoms thereof may be treated by administering a compound as described herein.

Also provided herein are methods of treating a condition in treatment-resistant patients, e.g., patients suffering from a mental or central nervous system condition that does not, and/or has not, responded to adequate courses of at least one, or at least two, other compounds or therapeutics. For example, provided herein is a method of treating depression in a treatment resistant patient, comprising a) optionally identifying the patient as treatment resistant and b) administering an effective dose of a compound to said patient.

In some embodiments, a compound described herein may be used for acute care of a patient. For example, a compound may be administered to a patient to treat a particular episode (e.g., a severe episode) of a condition disclosed herein.

Also provided herein are combination therapies comprising a compound of the disclosure in combination with one or more other active agents. For example, a compound may be combined with one or more antidepressants, such as tricyclic antidepressants, MAO-I's, SSRI's, and double and triple uptake inhibitors and/or anxiolytic drugs. Exemplary drugs that may be used in combination with a compound include Anafranil, Adapin, Aventyl, Elavil, Norpramin, Pamelor, Pertofrane, Sinequan, Surmontil, Tofranil, Vivactil, Parnate, Nardil, Marplan, Celexa, Lexapro, Luvox, Paxil, Prozac, Zoloft, Wellbutrin, Effexor, Remeron, Cymbalta, Desyrel (trazodone), and Ludiomill. In another example, a compound may be combined with an antipsychotic medication. Non-limiting examples of antipsychotics include butyrophenones, phenothiazines, thioxanthenes, clozapine, olanzapine, risperidone, quetiapine, ziprasidone, amisulpride, asenapine, paliperidone, iloperidone, zotepine, sertindole, lurasidone, and aripiprazole. It should be understood that combinations of a compound and one or more of the above therapeutics may be used for treatment of any suitable condition and are not limited to use as antidepressants or antipsychotics.

EXAMPLES

The following examples are provided for illustrative purposes only, and are not intended to limit the scope of the disclosure.

The following abbreviations may be used herein and have the indicated definitions: Ac is acetyl (—C(O)CH$_3$), AIDS is acquired immune deficiency syndrome, Boc and BOC are tert-butoxycarbonyl, Boc$_2$O is di-tert-butyl dicarbonate, Bn is benzyl, BOM-Cl is benzyloxymethyl chloride, CAN is ceric ammonium nitrate, Cbz is carboxybenzyl, DCM is dichloromethane, DIAD is diisopropyl azodicarboxylate, DIPEA is N,N-diisopropylethylamine, DMAP is 4-dimethylaminopyridine, DMF is N,N-dimethylformamide, DMSO is dimethyl sulfoxide, EDC and EDCI are 1-ethyl-3-(3-dimethylaminopropyl)carbodiimide hydrochloride, ESI is electrospray ionization, EtOAc is ethyl acetate, Gly is glycine, h is hour, HATU is 2-(7-aza-1H-benzotriazole-1-yl)-1,1,3,3-tetramethyluronium hexafluorophosphate, HIV is human immunodeficiency virus, HPLC is high performance liquid chromatography, LCMS is liquid chromatography/mass spectrometry, LiHMDS is lithium hexamethyldisilazane, NMDAR is N-methyl-d-apartate receptor, NMR is nuclear magnetic resonance, Pd/C is palladium on carbon, PMB is para-methoxybenzyl, RT is room temperature (e.g., from about 20° C. to about 25° C.), TEA is rimethylamine, TLC is thin layer chromatography, TFA is trifluoroacetic acid, THF is tetrahydrofuran, TPP is triphenylphosphine, LDA is lithium diisopropylamide, TBSC1 is tert-butyldimethylsilyl chloride, TBAF is tetra-n-butylammonium fluoride, TsCl is tosyl chloride or p-toluenesulfonyl chloride, IBCF is isobutyl chloroformate, NMM is N-methylmorpholine, and DMP is Dess-Martin periodinane.

A. Synthesis of Compounds

Synthesis of AA-1, AA-2 & AA-3:

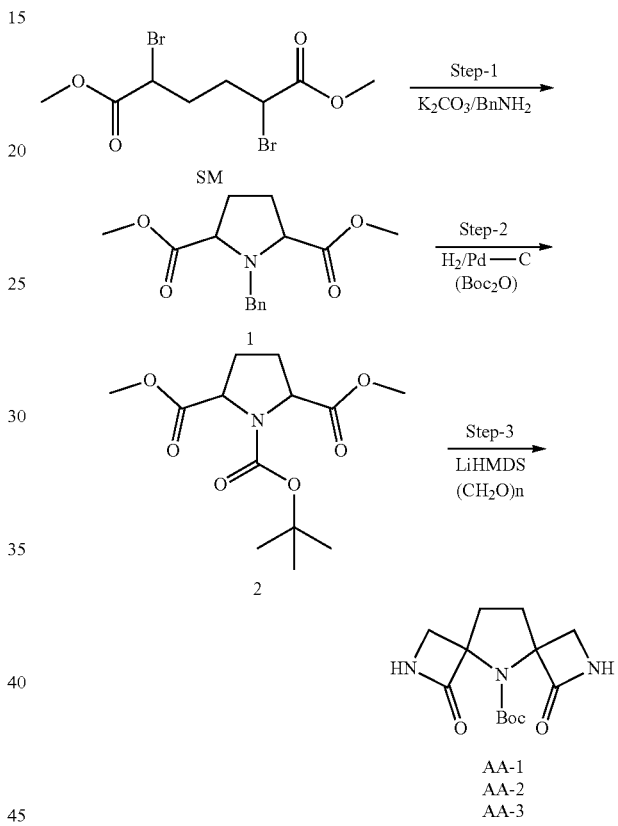

Synthesis of dimethyl
1-benzylpyrrolidine-2,5-dicarboxylate (1)

To a stirring solution of dimethyl 2,5-dibromohexanedioate (SM) (50 g, 0.15 mol) in toluene:water (150 mL, 2:1) were added benzyl amine (16 mL, 0.15 mol) and K$_2$CO$_3$ (24 g, 0.18 mol) at room temperature. The reaction mixture was heated to reflux at 110° C. and stirred for 4 h. After consumption of the starting material (by TLC), reaction mixture was cooled to room temperature and extracted with diethyl ether (2×50 mL). Separated organic layer was dried over anhydrous Na$_2$SO$_4$ and concentrated under reduced pressure to obtain compound 1-mixture (39 g, 93%) as liquid. This material was purified by silica gel column chromatography eluting with 20% EtOAc/n-hexane to afford compound 1-F1 (10 g), compound 1-F2 (13 g) and compound 1-F1 and F2 as a mixture (16 g) as liquid. $^1$H NMR (500 MHz, CDCl$_3$): δ 7.32-7.17 (m, 5H), 3.89 (s, 2H), 3.55 (s, 6H), 3.45-3.38 (m, 2H), 2.08-1.99 (m, 4H). LCMS (m/z): 278.2 [M$^+$+1].

Synthesis of 1-(tert-butyl) 2,5-dimethyl pyrrolidine-1,2,5-tricarboxylate (2)

To a stirring solution of compound 1-mixture (10 g, 0.036 mol) in methanol (100 mL) were added Boc-anhydride (12.4 mL, 0.054 mol) and 50% wet 10% Pd/C (5 g) at RT under nitrogen atmosphere and stirred for 16 h under $H_2$ atmosphere. After consumption of the starting material (by TLC), the reaction mixture was filtered through a pad of celite and the filtrate was concentrated under reduced pressure. The crude material was purified by silica gel column chromatography eluting with 10% MeOH/DCM to afford compound 2-mixture (10 g, 96%) as white solid. $^1$H NMR (400 MHz, DMSO-$d_6$): δ 4.28-4.19 (m, 2H), 3.65 (s, 3H), 3.63 (s, 3H), 2.25-2.13 (m, 2H), 1.96-1.86 (m, 2H), 1.34 (s, 9H). LCMS (ESI): m/z 188.1 [(M$^+$+1)-Boc].

Synthesis of tert-butyl 1,7-dioxo-2,5,8-triazadispiro [3.1.36.24]undecane-5-carboxylate (AA)

To a stirring solution of compound 2-mixture (10 g, 0.034 mol) in THF (30 mL) were added paraformaldehyde (2 g, 0.069 mol) and LiHMDS (1.0M in THF) (174 mL, 0.174 mol) at −50° C. under nitrogen atmosphere. The reaction mixture was brought to RT and stirred for 16 h. After consumption of the starting material (by TLC), the reaction was quenched with ice water (100 mL) and extracted with EtOAc (3×100 mL) and 10% MeOH/DCM (2×50 mL). The combined organic layer was dried over $Na_2SO_4$ and concentrated to obtain crude compound which was purified by column chromatography by eluting 10% MeOH/DCM to afford racemic AA (2 g, 20%) as white solid. Racemic AA (700 mg) was further purified by preparative HPLC to obtain 200 mg of enantiomer mixture F1 and 190 mg of AA-3 as white solid. 200 mg of enantiomer mixture F1 was further resolved by chiral HPLC preparative purification to afford 62 mg of AA-1 and 60 mg of AA-2.

AA-1: $^1$H NMR (400 MHz, DMSO-$d_6$): δ 7.93 (br d, J=19.6 Hz, 2H), 3.47-3.34 (m, 2H), 3.19 (dd, J=4.8, 16.8 Hz, 2H), 2.17-1.96 (m, 4H), 1.38 (s, 9H). LCMS (ESI): m/z 282.2 [M$^+$+1]. HPLC: 99.76%. Chiral HPLC: 99.36%.

AA-2: $^1$H NMR (400 MHz, DMSO-$d_6$): δ 7.93 (br d, J=19.6 Hz, 2H), 3.46-3.34 (m, 2H), 3.19 (dd, J=4.8, 16.8 Hz, 2H), 2.14-1.99 (m, 4H), 1.38 (s, 9H). LCMS (ESI): m/z 282.2 [M$^+$+1]. HPLC: 99.68%. Chiral HPLC: 100.00%

AA-3: $^1$H NMR (400 MHz, DMSO-$d_6$): δ 7.94-7.82 (m, 2H), 3.58 (d, J=4.9 Hz, 1H), 3.41 (d, J=5.0 Hz, 1H), 3.17 (d, J=5.1 Hz, 1H), 3.11 (d, J=4.9 Hz, 1H), 2.18-2.08 (m, 4H), 1.38 (s, 9H). LCMS (ESI): m/z 282.2 [M$^+$+1]. HPLC: 99.69%. Chiral HPLC: 100.00%.

Synthesis of AB-1, AB-2 & AB-3:

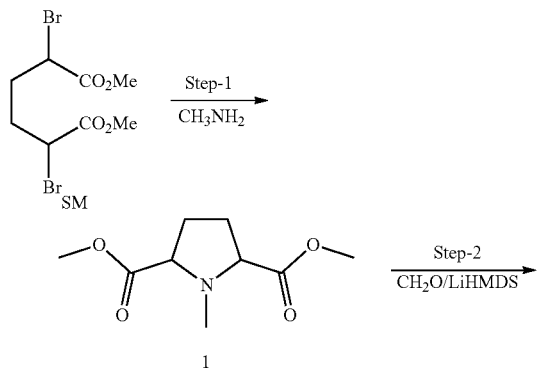

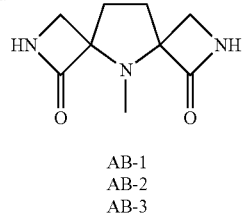

AB-1
AB-2
AB-3

Synthesis of dimethyl 1-methylpyrrolidine-2,5-dicarboxylate (1)

To a stirred solution of dimethyl 2, 5-dibromohexanedioate (SM) (20 g, 60.2 mmol) in THF (80 mL) was added methylamine (2M solution in THF) (90 mL, 180.7 mmol) slowly at 0° C. under nitrogen atmosphere and then stirred for 30 min. The reaction mixture was allowed to RT and continued stirring for 16 h. After consumption of the starting material (by TLC), reaction mixture was filtered and the filtrate was evaporated under reduced pressure. Obtained crude mixture was purified by column chromatography by eluting 20% EtOAC/n-hexane to afford compound 1 (8 g, 60%) as pure syrup. $^1$H-NMR: (500 MHz, CDCl$_3$): δ 3.76 (s, 6H), 3.23 (br s, 2H), 2.56 (s, 3H), 2.19-2.08 (m, 4H). LCMS (m/z): 202.1 [M$^+$+1].

Synthesis of 5-methyl-2,5,8-triazadispiro[3.1.36.24] undecane-1,7-dione (AB)

To a stirred solution of compound 1 (3 g, 14.9 mmol) in THF (30 mL) was added para formaldehyde (1 g, 35.7 mmol) and stirred at RT for 5 min. The reaction mixture was cooled to −70° C., LiHMDS (1 M solution in THF) (90 mL, 89.4 mmol) was added and stirred at RT for 1 h. Then, the reaction mixture was warmed to RT and stirred for 16 h. After consumption of the starting material (by TLC), quenched with water (50 mL) and extracted with EtOAc (2×100 mL). Combined organic layer was washed with water (10 mL) followed by brine solution (20 mL). The organic layer was dried over $Na_2SO_4$ and concentrated to obtain crude compound which was purified by column chromatography by eluting 5% MeOH/DCM to afford racemic AB (1 g, 34%) as off white solid. Racemic mixture AB (1 g) was further purified by preparative HPLC to obtain 350 mg of enatiomeric mixture-Ft and 115 mg of AB-3 as white solid. 350 mg of enatiomeric mixture-F1 was further resolved by chiral HPLC preparative purification to afford 100 mg of AB-1 and 100 mg of AB-2.

AB-1: $^1$H NMR (500 MHz, DMSO-$d_6$): δ 7.87 (br s, 2H), 3.33 (d, J=6.1 Hz, 2H), 3.04 (d, J=6.1 Hz, 2H), 2.29 (s, 3H), 2.08-1.99 (m, 4H). LCMS (ESI): m/z 196.2 [M$^+$+1]. HPLC: 99.32%. Chiral HPLC: 99.16%.

AB-2: $^1$H NMR (500 MHz, DMSO-$d_6$): δ 7.87 (br s, 2H), 3.33 (d, J=5.8 Hz, 2H), 3.04 (d, J=6.1 Hz, 2H), 2.28 (s, 3H), 2.07-1.99 (m, 4H). LCMS (ESI): m/z 196.2 [M$^+$+1]. HPLC: 99.36%. Chiral HPLC: 99.21%

AB-3: $^1$H NMR (400 MHz, DMSO-$d_6$): δ 7.84 (br s, 2H), 3.32 (d, J=5.7 Hz, 2H), 2.98 (d, J=5.7 Hz, 2H), 2.32 (s, 3H), 2.14-1.99 (m, 4H). LCMS (ESI): m/z 196.2 [M$^+$+1]. HPLC: 96.44%. Chiral HPLC: 96.69%

Synthesis of AC-1, AC-2 & AC-3:

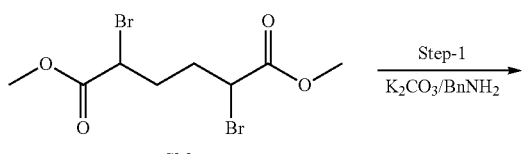

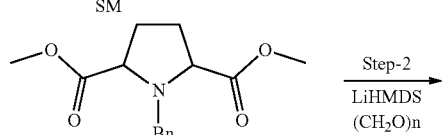

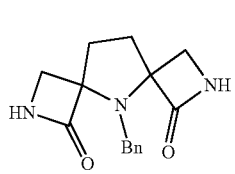

AC-1
AC-2
AC-3

Synthesis of dimethyl
1-benzylpyrrolidine-2,5-dicarboxylate (1)

To a stirring solution of dimethyl 2,5-dibromohexanedioate (SM) (50 g, 0.15 mol) in toluene:water (150 mL, 2:1) were added benzyl amine (16 mL, 0.15 mol) and $K_2CO_3$ (24 g, 0.18 mol) at room temperature. The reaction mixture was heated to reflux at 110° C. and stirred for 4 h. After consumption of the starting material (by TLC), reaction mixture was cooled to room temperature and extracted with diethyl ether (2×50 mL). Separated organic layer was dried over anhydrous $Na_2SO_4$ and concentrated under reduced pressure to obtain compound 1-mixture (39 g, 93%) as liquid. This material was purified by silica gel column chromatography eluting with 20% EtOAc/n-hexane to afford compound 1-F1 (10 g), compound 1-F2 (13 g) and compound 1-F1&F2 (16 g) as liquid. $^1$H NMR (500 MHz, CDCl$_3$): δ 7.32-7.17 (m, 5H), 3.89 (s, 2H), 3.55 (s, 6H), 3.45-3.38 (m, 2H), 2.08-1.99 (m, 4H). LCMS (m/z): 278.2 [M$^+$+1]

Synthesis of 5-benzyl-2,5,8-triazadispiro[3.1.36.24]undecane-1,7-dione (AC)

To a stirring solution of compound 1 (10 g, 0.036 mol) in THF (100 mL) were added paraformaldehyde (2.16 g, 0.072 mol) and LiHMDS (1.0M in THF) (180 mL, 0.18 mol) at −70° C. under nitrogen atmosphere. The reaction mixture was brought to RT and stirred for 16 h. After consumption of the starting material (by TLC), the reaction was quenched with ice water (100 mL) and extracted with EtOAc (2×100 mL) and 10% MeOH/DCM (2×50 mL). The combined organic layer was dried over $Na_2SO_4$ and concentrated to obtain crude compound which was purified by column chromatography by eluting 5% MeOH/DCM to afford AC as a racemic (2 g, 20%) as white solid. Racemic AC (1 g) was purified by preparative HPLC to obtain 150 mg of enantiomeric mixture F1 and 12 mg of AC-3 as white solid. 150 mg of enantiomeric mixture F1 was further resolved by chiral HPLC preparative purification to afford 50 mg of AC-1 and 46 mg of AC-2.

AC-1: $^1$H NMR (400 MHz, DMSO-d$_6$): δ 7.82 (s, 2H), 7.36 (d, J=7.0 Hz, 2H), 7.31-7.18 (m, 3H), 3.93-3.72 (m, 2H), 3.06-2.92 (m, 4H), 2.13-2.04 (m, 4H). LCMS (ESI): m/z 271.9 [M$^+$+1]. HPLC: 99.18%. Chiral HPLC: 99.83%.

AC-2: $^1$H NMR (400 MHz, DMSO-d$_6$): δ 7.82 (s, 2H), 7.40-7.33 (m, 2H), 7.32-7.18 (m, 3H), 3.93-3.73 (m, 2H), 3.05-2.94 (m, 4H), 2.09 (br d, J=2.7 Hz, 4H). LCMS (ESI): m/z 271.9 [M$^+$+1]. HPLC: 99.55%. Chiral HPLC: 100.00%.

AC-3: $^1$H NMR (400 MHz, DMSO-d$_6$): δ 7.69 (s, 2H), 7.37-7.17 (m, 5H), 3.91 (s, 2H), 3.11-3.01 (m, 4H), 2.24-2.13 (m, 2H), 2.13-2.02 (m, 2H). LCMS (ESI): m/z 271.9 [M$^+$+1]. HPLC: 92.75%. Chiral HPLC: 100.00%.

Synthesis of AD, AE and AF:

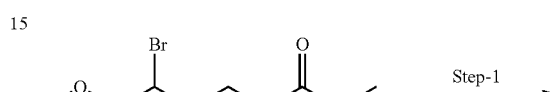
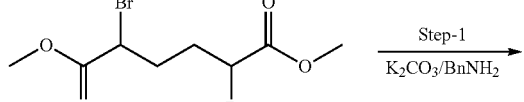
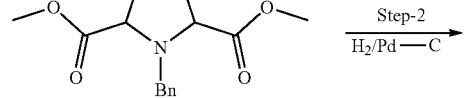
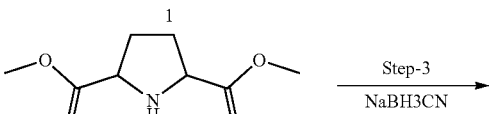
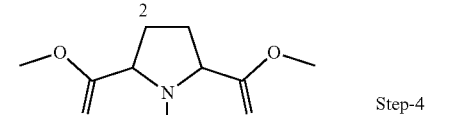
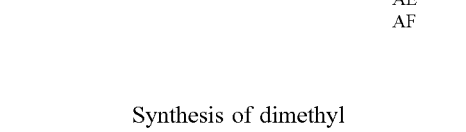
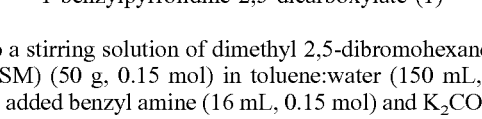
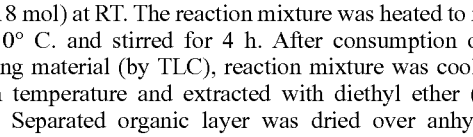

AD
AE
AF

Synthesis of dimethyl
1-benzylpyrrolidine-2,5-dicarboxylate (1)

To a stirring solution of dimethyl 2,5-dibromohexanedioate (SM) (50 g, 0.15 mol) in toluene:water (150 mL, 2:1) were added benzyl amine (16 mL, 0.15 mol) and $K_2CO_3$ (24 g, 0.18 mol) at RT. The reaction mixture was heated to reflux at 110° C. and stirred for 4 h. After consumption of the starting material (by TLC), reaction mixture was cooled to room temperature and extracted with diethyl ether (2×50 mL). Separated organic layer was dried over anhydrous $Na_2SO_4$ and concentrated under reduced pressure to obtain compound 1-mixture (39 g, 93%) as liquid. This material was purified by silica gel column chromatography eluting with 20% EtOAc/n-hexane to afford compound 1-F1 (10 g), compound 1-F2 (13 g) and compound 1-F1&F2 as a mixture (16 g) as liquid.

$^1$H NMR (500 MHz, CDCl$_3$): δ 7.32-7.17 (m, 5H), 3.89 (s, 2H), 3.55 (s, 6H), 3.45-3.38 (m, 2H), 2.08-1.99 (m, 4H). LCMS (m/z): 278.2 [M$^+$+1].

Synthesis of dimethyl pyrrolidine-2,5-dicarboxylate (2)

To a stirring solution of compound 1 (15 g, 0.054 mol, mixture) in methanol (100 mL) was added Pd/C (50% wet) (6 g) at RT and stirred for 16 h under H$_2$ atmosphere (balloon pressure). After consumption of the starting material (by TLC), the reaction mixture was filtered through a pad of celite and the pad was washed with MeOH (200 mL). Obtained filtrate was concentrated under reduced pressure. Crude material was triturated with methanol and ether to afford compound 2 (8 g, 79%) as white solid.

$^1$H NMR (400 MHz, DMSO-d$_6$): δ 9.24-8.86 (m, 1H), 4.32 (br s, 2H), 3.73 (s, 6H), 2.28-2.18 (m, 2H), 2.06-1.96 (m, 2H). LCMS (m/z): 188.1 [M$^+$+1].

Synthesis of dimethyl 1-isobutylpyrrolidine-2, 5-dicarboxylate (3)

To a stirring solution of compound 2 (3.9 g, 0.021 mol) in methanol (25 mL) were added isobutyraldehyde (2.2 g, 0.031 mol) and sodium cyanoborohydride (2.6 g, 0.041 mol) at 0° C. under nitrogen atmosphere. The reaction mixture was stirred at RT for 4 h. After consumption of the starting material (by TLC), reaction mixture was quenched with ice water (1 mL) and concentrated under reduced pressure. Crude material was diluted with water (100 mL) and extracted with EtOAc (2×25 mL). Separated organic layer was dried over anhydrous Na$_2$SO$_4$ and concentrated under reduced pressure to afford crude compound which was purified by column chromatography by eluting 15% EtOAc/n-hexane to obtain compound 3 (3.5 g, 72%) as liquid.

$^1$H NMR (400 MHz, DMSO-d$_6$): δ 3.60 (s, 6H), 3.31 (s, 2H), 2.39 (d, J=7.4 Hz, 2H), 2.08-1.99 (m, 2H), 1.95-1.85 (m, 2H), 1.51-1.39 (m, 1H), 0.81 (s, 3H), 0.79 (s, 3H). LCMS (m/z): 244.3 [M$^+$+1].

Synthesis of 5-isobutyl-2,5,8-triazadispiro [3.1.36.24]undecane-1,7-dione (AD, AE, AF)

To a stirring solution of compound 3 (4.5 g, 0.018 mol) in THF (60 mL) were added paraformaldehyde (1.1 g, 0.037 mol) and LiHMDS (1.0M in THF) (111 mL, 0.111 mol) at −50° C. under nitrogen atmosphere and stirred for 1 h. Then, reaction mixture was brought to RT and stirred for 16 h. After consumption of the starting material (by TLC), the reaction was quenched with ice water (25 mL) at 0° C. and extracted with EtOAc (3×25 mL). The combined organic layer was dried over Na$_2$SO$_4$ and concentrated to obtain crude compound which was purified by column chromatography by eluting 10% MeOH/DCM to afford racemic product (1.6 g). This product was further purified by reverse phase HPLC to obtain 470 mg of one fraction (having AD and AF) and 270 mg of another fraction (AE) as white solids. The fraction having (470 mg, AD and AF) was further purified by chiral preparative HPLC to obtain 110 mg of AD and 130 mg of AF.

AD: $^1$H NMR (400 MHz, DMSO-d$_6$): δ 7.83 (s, 2H), 3.26 (d, J=5.9 Hz, 2H), 3.08 (d, J=5.9 Hz, 2H), 2.47 (d, J=6.7 Hz, 1H), 2.34 (dd, J=8.5, 13.4 Hz, 1H), 2.08-2.01 (m, 4H), 1.72-1.61 (m, 1H), 0.84 (d, J=1.8 Hz, 3H), 0.82 (d, J=1.9 Hz, 3H). LCMS (ESI): m/z 238.0 [M$^+$+1]; HPLC: 99.41%. Chiral HPLC: 99.87%. Column: CHIRALPAK IC (250*4.6 mm, 5 μm), Mobile Phase A: 0.1% DEA in MeOH, Mobile Phase B: DCM:MeOH (50:50); A:B 75:25; Flow rate: 1.0 mL/min; Retention time: 9.344.

AE: $^1$H NMR (400 MHz, DMSO-d$_6$): δ 7.79 (s, 2H), 3.22 (d, J=5.6 Hz, 2H), 3.03 (d, J=5.6 Hz, 2H), 2.45 (d, J=7.5 Hz, 2H), 2.16-2.10 (m, 2H), 2.05-1.97 (m, 2H), 1.68-1.57 (m, 1H), 0.83 (s, 3H), 0.82 (s, 3H). LCMS (ESI): m/z 238.3 [M$^+$+1]. HPLC: 99.15%. Chiral HPLC: 100.00%. Column: CHIRALPAK IC (250*4.6 mm, 5 μm); Mobile Phase A: 0.1% DEA in MeOH; Mobile Phase B: DCM:MeOH (50: 50); A:B 75:25; Flow rate: 1.0 mL/min; Retention time: 11.861.

AF: $^1$H NMR (400 MHz, DMSO-d$_6$): δ 7.83 (s, 2H), 3.26 (d, J=5.8 Hz, 2H), 3.08 (d, J=5.9 Hz, 2H), 2.47 (d, J=6.8 Hz, 1H), 2.34 (dd, J=8.5, 13.3 Hz, 1H), 2.08-2.01 (m, 4H), 1.72-1.61 (m, 1H), 0.84 (d, J=1.8 Hz, 3H), 0.82 (d, J=2.0 Hz, 3H). LCMS (ESI): m/z 237.9 [M$^+$+1]. HPLC: 99.39%. Chiral HPLC: 100.00%. Column: CHIRALPAK IC (250*4.6 mm, 5 μm); Mobile Phase: A:0.1% DEA in MeOH; Mobile Phase: B:DCM:MeOH (50:50); A:B::75:25; Flow rate: 1.0 mL/min; Retention time: 10.005.

Recrystallization of AD:

100 mg of AD was taken into a 5 mL vial and dissolved in 1.5 mL of IPA. Resultant solution was left at room temperature for slow evaporation of the solvent. After 48 h crystal formation was observed which were used for single crystal X-ray analysis.

The results of the crystal X-ray diffraction analysis are shown in FIG. 1. FIG. 1 shows data for the crystal structure, and shows that the crystals are orthorhombic and have a P2$_1$2$_1$2$_1$ space group. Analysis of the single crystal diffraction data shows that the absolute configuration of each of the two chiral carbons at the spiro centers of AD is (S), as determined by the PLATON technique (A. L. Spek, *J. Appl. Cryst.*, 36, 7-13 (2003)).

Based on these results, the absolute stereochemistry of Compound AD is shown in the structure below:

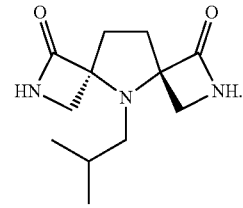 [SMILES: CC(C)CN1[C@@]2(CC[C@@]13CNC3=O)CNC2=O]

Recrystallization of AF:

50 mg of AF was taken into a 5 mL vial and dissolved in 1.5 mL of IPA. Resultant solution was left at room temperature for slow evaporation of the solvent. After 48 h crystal formation was observed which were used for single crystal X-ray analysis.

The results of the crystal X-ray diffraction analysis are shown in FIG. 2. FIG. 2 shows data for the crystal structure, and shows that the crystals are orthorhombic and have a P2$_1$2$_1$2$_1$ space group. Analysis of the single crystal diffraction data shows that the absolute configuration of each of the two chiral carbons at the spiro centers of AF is (R), as determined by the PLATON technique (A. L. Spek, *J. Appl. Cryst.*, 36, 7-13 (2003)).

Based on these results, the absolute stereochemistry of Compound AF is shown in the structure below:

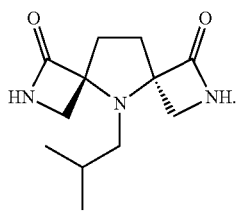 [SMILES: CC(C)CN1[C@]2(CC[C@]13CNC3=O)CNC2=O]

Synthesis of AG, AH & AI:

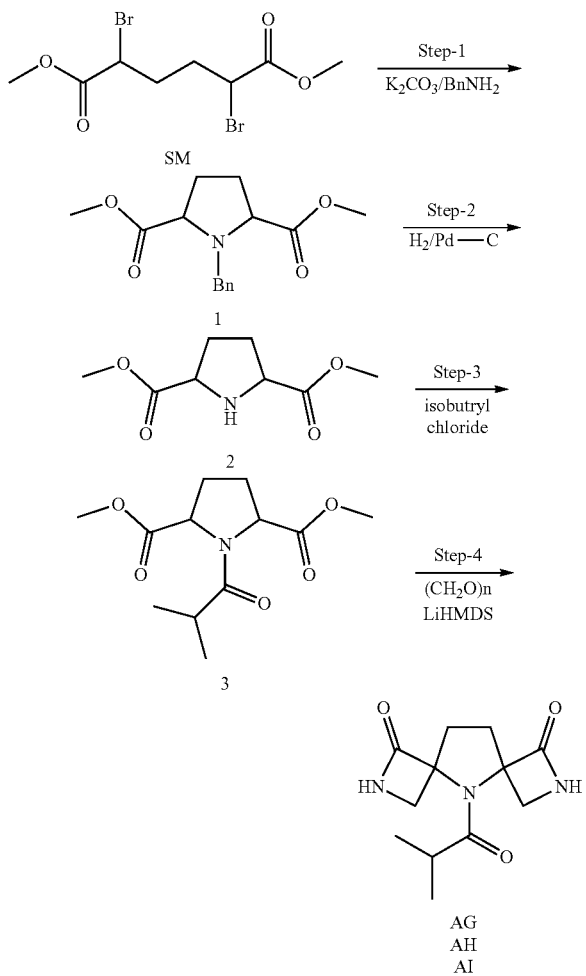

Synthesis of dimethyl 1-benzylpyrrolidine-2,5-dicarboxylate (1)

To a stirring solution of dimethyl 2,5-dibromohexanedioate (SM) (30 g, 0.091 mol) in toluene:water (90 mL, 2:1) were added benzyl amine (9.8 mL, 0.091 mol) and $K_2CO_3$ (15 g, 0.108 mol) at room temperature. The reaction mixture was heated to reflux at 90° C. and stirred for 16 h. After consumption of the starting material (by TLC), reaction mixture was cooled to room temperature and extracted with EtOAc (2×50 mL). Separated organic layer was dried over anhydrous $Na_2SO_4$ and concentrated under reduced pressure to obtain crude which was purified by silica gel column chromatography eluting with 20% EtOAc/n-Hexane to afford compound 1 (19.6 g, 78%) as liquid. $^1$H NMR (500 MHz, $CDCl_3$): δ 7.32-7.17 (m, 5H), 3.89 (s, 2H), 3.55 (s, 6H), 3.45-3.38 (m, 2H), 2.08-1.99 (m, 4H). LCMS (m/z): 278.2 [M$^+$+1].

Synthesis of dimethyl pyrrolidine-2,5-dicarboxylate (2)

To a stirring solution of compound 1 (50 g, 0.180 mol) in methanol (500 mL) was added Pd/C (50% wet) (25 g) at RT and stirred for 16 h under $H_2$ atmosphere (balloon pressure). After consumption of the starting material (by TLC), the reaction mixture was filtered through a pad of celite and the pad was washed with MeOH (500 mL). Obtained filtrate was concentrated under reduced pressure. Crude material was triturated with methanol and ether to afford compound 2 (30 g, 89%) as white solid. $^1$H NMR (400 MHz, DMSO-$d_6$): δ 9.24-8.86 (m, 1H), 4.32 (br s, 2H), 3.73 (s, 6H), 2.28-2.18 (m, 2H), 2.06-1.96 (m, 2H). LCMS (m/z): 188.1 [M$^+$+1].

Synthesis of dimethyl 1-isobutyrylpyrrolidine-2,5-dicarboxylate (3)

To a stirring solution of compound 2 (15 g, 0.080 mol) in DCM (150 mL) were added $Et_3N$ (22.3 mL, 0.160 mol) and Isobutyryl chloride (10 mL, 0.096 mol) at 0° C. under nitrogen atmosphere. The reaction mixture was then stirred at RT for 5 h. After consumption of the starting material (by TLC), reaction mixture was diluted with water (100 mL) and extracted with DCM (2×200 mL). Separated organic layer was dried over anhydrous $Na_2SO_4$ and concentrated under reduced pressure to afford crude compound which was purified by column chromatography by eluting 40% EtOAc/n-Hexane to obtain compound 3 (13.7 g, 66%) as a liquid. $^1$H NMR (400 MHz, DMSO-$d_6$): δ 4.77 (t, J=5.3 Hz, 1H), 4.32-4.26 (m, 1H), 3.68 (s, 3H), 3.59 (s, 3H), 2.70-2.59 (m, 1H), 2.25-2.15 (m, 3H), 1.84-1.72 (m, 1H), 0.98 (s, 3H), 0.97 (s, 3H). LCMS (m/z): 258.2 [M$^+$+1].

Synthesis of 5-isobutyryl-2,5,8-triazadispiro [3.1.36.24]undecane-1,7-dione (AG, AH, AI)

To a stirring solution of compound 3 (13.7 g, 0.053 mol) in THF (200 mL) were added paraformaldehyde (3.2 g, 0.106 mol) and LiHMDS (1.0M in THF) (320 mL, 0.319 mol) at −50° C. under nitrogen atmosphere and stirred for 1 h. Then, reaction mixture was brought to RT and stirred for 16 h. After consumption of the starting material (by TLC), the reaction was quenched with ice water (50 mL) at 0° C. and extracted with EtOAc (3×50 mL) and 2% MeOH/DCM mixture (3×100 mL). The combined organic layer was dried over $Na_2SO_4$ and concentrated to obtain crude compound which was triturated with EtOAc and methanol to afford racemic product (2 g). This product was further purified by reverse phase HPLC to obtain 305 mg of Fraction-1 and 450 mg of Fraction-2 AI as white solids. 305 mg of Fraction-1 was further purified by chiral preparative HPLC to obtain 85 mg of Fraction-1 AG and 75 mg of Fraction-2 AH.

AG: $^1$H NMR (500 MHz, DMSO-$d_6$): δ 8.33 (s, 1H), 7.83 (s, 1H), 3.47 (d, J=6.1 Hz, 1H), 3.40 (d, J=4.6 Hz, 1H), 3.27 (br s, 1H), 3.09 (d, J=4.6 Hz, 1H), 2.46-2.42 (m, 1H), 2.24-2.10 (m, 2H), 2.07-1.97 (m, 2H), 1.02 (d, J=6.7 Hz, 3H), 0.97 (d, J=6.4 Hz, 3H). LCMS (ESI): m/z 252.2 [M$^+$+1]. HPLC: 99.25%. Chiral HPLC: 100%.

AH: ¹H NMR (500 MHz, DMSO-d₆): δ 8.32 (s, 1H), 7.83 (s, 1H), 3.47 (d, J=6.1 Hz, 1H), 3.40 (d, J=4.3 Hz, 1H), 3.27 (br s, 1H), 3.09 (d, J=4.6 Hz, 1H), 2.46-2.42 (m, 1H), 2.23-2.11 (m, 2H), 2.07-1.97 (m, 2H), 1.02 (d, J=6.7 Hz, 3H), 0.97 (d, J=6.4 Hz, 3H). LCMS (ESI): m/z 252.2 [M⁺+1]. HPLC: 99.69%. Chiral HPLC: 98.65%.

AI: ¹H NMR (500 MHz, DMSO-d₆): δ 8.29 (s, 1H), 7.81 (s, 1H), 3.58 (d, J=4.3 Hz, 1H), 3.43 (d, J=6.4 Hz, 1H), 3.36 (d, J=6.4 Hz, 1H), 3.05 (d, J=4.3 Hz, 1H), 2.48 (s, 1H), 2.26-2.17 (m, 2H), 2.17-2.09 (m, 2H), 1.07 (d, J=6.4 Hz, 3H), 0.97 (d, J=6.4 Hz, 3H). LCMS (ESI): m/z 252.2 [M⁺+1]. HPLC: 98.90%. Chiral HPLC: 100%.

Synthesis of AJ & AK:

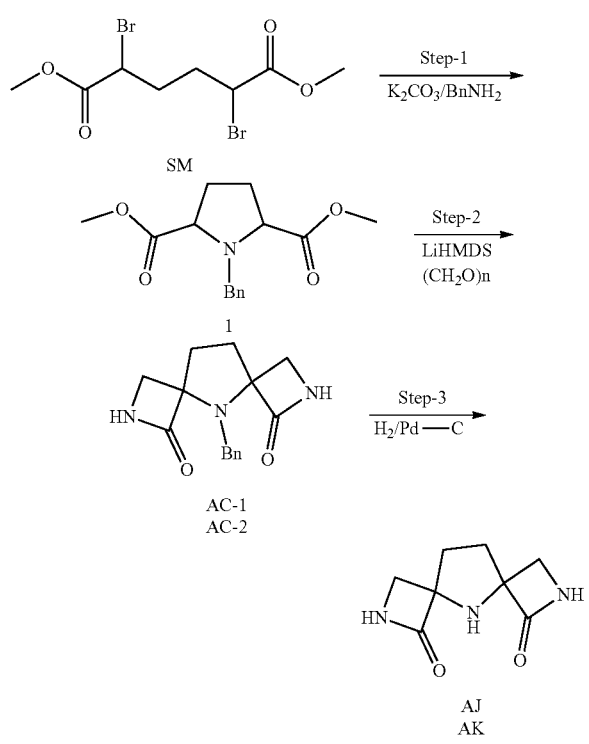

Synthesis of 2,5,8-triazadispiro[3.1.36.24]undecane-1,7-dione (AJ)

To a stirring solution of compound AC-1 (200 mg, 0.73 mmol) in methanol (20 mL) was added Pd(OH)₂ (200 mg) at RT and stirred for 16 h under H₂ atmosphere (balloon pressure). After consumption of the starting material (by TLC), the reaction mixture was filtered through a pad of celite and the pad was washed with MeOH (50 mL). Obtained filtrate was concentrated under reduced pressure. Crude material was triturated with methanol and ether to afford AJ (135 mg, 66%) as white solid. ¹H NMR (400 MHz, DMSO-d₆): δ 7.73 (br s, 2H), 3.94 (s, 1H), 3.20 (d, J=5.3 Hz, 2H), 3.10 (d, J=5.3 Hz, 2H), 2.01-1.98 (m, 4H). LCMS (ESI): m/z 182.19 [M⁺+1]. HPLC: 99.51%. Chiral HPLC: 100%.

Synthesis of 2,5,8-triazadispiro[3.1.36.24]undecane-1,7-dione (AK)

To a stirring solution of compound AC-2 (300 mg, 1.11 mmol) in methanol (30 mL) was added Pd(OH)₂ (300 mg) at RT and stirred for 16 h under H₂ atmosphere (balloon pressure). After consumption of the starting material (by TLC), the reaction mixture was filtered through a pad of celite and the pad was washed with MeOH (50 mL). Obtained filtrate was concentrated under reduced pressure. Crude material was triturated with methanol and ethyl acetate and purified by column chromatography by eluting 10% MeOH/DCM to afford AK (110 mg, 55%) as white solid. ¹H NMR (400 MHz, DMSO-d₆): δ 7.73 (s, 2H), 3.94 (s, 1H), 3.20 (d, J=5.3 Hz, 2H), 3.10 (d, J=5.3 Hz, 2H), 2.03-1.96 (m, 4H). LCMS (ESI): m/z 182.19 [M⁺+1]. HPLC: 99.55%. Chiral HPLC: 100%.

Synthesis of AL-1 & AL-2:

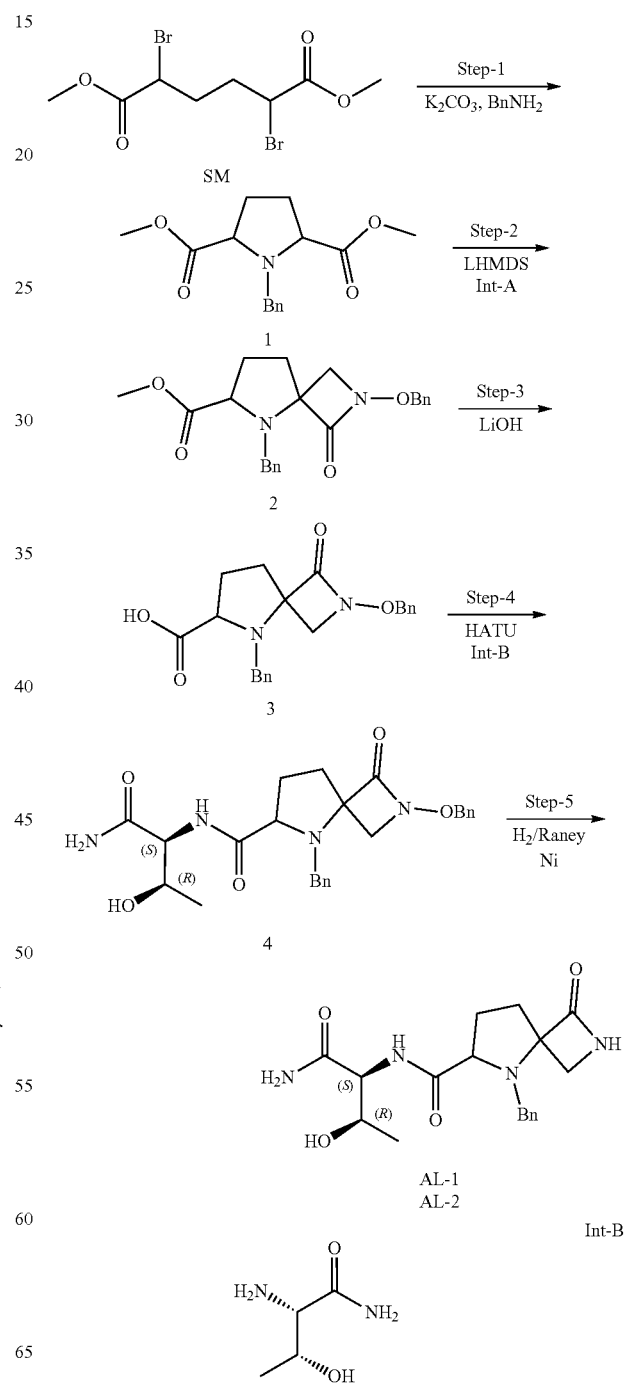

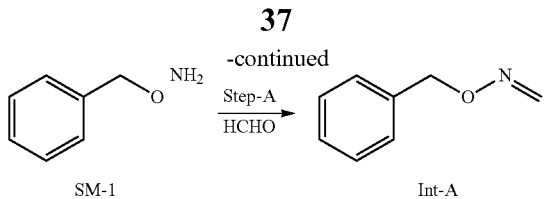

Synthesis of dimethyl 1-benzylpyrrolidine-2,5-dicarboxylate (1)

A mixture of dimethyl 2,5-dibromohexanedioate (SM) (20 g, 60.2 mmol), $K_2CO_3$ (10 g, 72.28 mmol) and benzylamine (6.56 mL, 60.24 mmol) in toluene:water (60 mL, 2:1) were heated to 110° C. and stirred at for 16 h under nitrogen atmosphere. After completion of the reaction, reaction mixture was cooled to RT, organic layer was separated and aqueous layer was extracted with hexane (2×50 mL). Combined organic layer was washed with brine solution, dried over anhydrous $Na_2SO_4$ and concentrated under reduced pressure. Obtained crude material was purified by column chromatography eluting with 20% EtOAc/Hexane to afford compound 1 (12 g, 72%) as yellow oil. $^1$H-NMR: (500 MHz, $CDCl_3$): δ 7.34-7.23 (m, 5H), 3.99 (s, 2H), 3.59 (s, 6H), 3.53-3.51 (m, 2H), 2.10-2.08 (m, 4H). LCMS (ESI): m/z 278.2 [M$^+$+1].

Synthesis of methyl 5-benzyl-2-(benzyloxy)-1-oxo-2,5-diazaspiro[3.4]octane-6-carboxylate (2)

To a stirring solution of compound 2 (5 g, 18.05 mmol) in THF (5 mL) was added LiHMDS (1M in THF) (21.6 mL, 21.66 mmol) drop wise at −70° C. under nitrogen atmosphere. After being stirred for 30 min, a solution of Int-A (2.44 g, 18.05 mmol) in THF (5 mL) was added. The reaction mixture was stirred at −78° C. for 2 h and then slowly raised the temperature to RT over a period of 1 h. After consumption of the starting material (by TLC), the reaction was quenched with aqueous $NH_4Cl$ solution (50 mL) and extracted with EtOAc (2×100 mL). Separated organic layer was dried over $Na_2SO_4$ and concentrated under reduced pressure. Obtained crude material was purified by column chromatography eluting with 10% EtOAc/hexane to afford compound 2 (2.5 g, 36%) as thick syrup. $^1$H NMR (400 MHz, $CDCl_3$): δ 7.51-7.46 (m, 2H), 7.43-7.37 (m, 3H), 7.32-7.26 (m, 5H), 5.11-5.02 (m, 2H), 4.01 (dd, J=11.4, 1.3 Hz, 1H), 3.82 (d, J=12.8 Hz, 1H), 3.68 (s, 3H), 3.55-3.45 (m, 2H), 3.38 (d, J=11.4 Hz, 1H), 2.34-2.24 (m, 1H), 2.18-2.08 (m, 1H), 1.97-1.91 (m, 1H), 1.76-1.71 (m, 1H). LCMS (ESI): m/z 381.3 [M$^+$+1].

Synthesis of methyl 5-benzyl-2-(benzyloxy)-1-oxo-2,5-diazaspiro[3.4]octane-6-carboxylate (3)

To a stirring solution of compound 2 (2.2 g, 5.78 mmol) in MeOH:THF:$H_2O$ (15 mL, 1:1:1) was added LiOH.$H_2O$ (364 mg, 8.68 mmol) at 0° C. and then slowly raised the temperature to RT over a period of 1 h. The reaction mixture was stirred at RT for 1 h. After consumption of the starting material (by TLC), volatiles were removed under reduced pressure to afford compound 3 (2.1 g, 99%) as white solid. $^1$H NMR (500 MHz, DMSO-$d_6$): δ 7.45-7.29 (m, 5H), 7.28-7.19 (m, 5H), 4.95-4.89 (m, 2H), 4.10 (d, J=13.5 Hz, 1H), 3.90 (d, J=11.2 Hz, 1H), 3.38-3.33 (m, 1H), 3.21-3.16 (m, 1H), 3.05-3.03 (m, 1H), 2.16-2.11 (m, 1H), 1.86-1.80 (m, 1H), 1.68-1.58 (m, 2H). LCMS (ESI): m/z 367.3 [M$^+$+1].

Synthesis of N-((2S,3R)-1-amino-3-hydroxy-1-oxobutan-2-yl)-5-benzyl-2-(benzyloxy)-1-oxo-2,5-diazaspiro[3.4]octane-6-carboxamide (4)

To a solution of compound 3 (2.1 g, 5.73 mmol) in DMF (20 mL) was added HATU (2.6 g, 6.88 mmol) at 0° C. under nitrogen atmosphere and stirred for 10 minutes. Then, Int-B (677 mg, 5.73 mmol) followed by DIPEA (2.1 mL, 11.47 mmol) were added. The reaction mixture was brought to RT and stirred for 8 h. After consumption of the starting material (by TLC), the reaction mixture was diluted with water (100 mL) and extracted with EtOAc (3×100 mL). Combined organic layer was washed with 1N HCl solution (50 mL), saturated $NaHCO_3$ solution (50 mL) and brine solution (50 mL). Organic layer was dried over anhydrous $Na_2SO_4$ and concentrated under reduced pressure to afford crude compound which was purified by column chromatography by eluting 4% MeOH/DCM to obtain compound 4 and HATU-Urea mixture. Again the mixture was diluted in DCM (250 mL) and washed with 1N HCl solution (50 mL), saturated $NaHCO_3$ solution (50 mL) and brine solution (50 mL). Organic layer was dried over anhydrous $Na_2SO_4$ and concentrated under reduced pressure to afford pure compound 4 (1.5 g, 49%) as white solid. $^1$H NMR (400 MHz, DMSO-$d_6$): δ 7.58 (br d, J=8.8 Hz, 1H), 7.52-0.27 (m, 11H), 7.11 (br s, 1H), 5.17-4.96 (m, 3H), 4.25-4.22 (m, 0.5H), 4.11-4.00 (m, 2H), 3.92-3.86 (m, 1.5H), 3.54 (br d, J=11.4 Hz, 1H), 3.24-3.15 (m, 2H), 2.24-1.76 (m, 4H), 1.03 (dd, J=11.4, 6.3 Hz, 3H). LCMS (m/z): 467.4 [M$^+$+1].

Synthesis of N-((2S,3R)-1-amino-3-hydroxy-1-oxobutan-2-yl)-5-benzyl-1-oxo-2,5-diazaspiro[3.4]octane-6-carboxamide (AL)

To a stirring solution of compound 4 (1 g, 2.14 mmol) in methanol (15 mL) was added Raney Ni (1 g) at RT and stirred for 4 h under $H_2$ atmosphere. After consumption of the starting material (by TLC), the reaction mixture was filtered through a pad of celite and the pad was washed with MeOH (50 mL). Obtained filtrate was concentrated under reduced pressure to afford racemic AL (750 mg, 97%) as off white solid. Racemic AL (350 mg) was purified by prep HPLC to obtain AL-1 (130 mg) and AL-2 (120 mg) as white solids.

AL-1: $^1$H NMR (400 MHz, DMSO-$d_6$): δ 7.66 (d, J=8.9 Hz, 1H), 7.54 (s, 1H), 7.48-7.39 (m, 3H), 7.35-7.25 (m, 3H), 7.11 (br s, 1H), 5.06 (d, J=5.6 Hz, 1H), 4.24 (dd, J=8.9, 2.9 Hz, 1H), 4.14-4.05 (m, 2H), 3.57 (d, J=12.5 Hz, 1H), 3.35 (d, J=12.2 Hz, 1H), 3.30-3.25 (m, 1H), 3.05 (d, J=6.5 Hz, 1H), 2.22-2.06 (m, 2H), 2.05-1.94 (m, 1H), 1.84-1.75 (m, 1H), 1.07 (d, J=6.3 Hz, 3H). LCMS (ESI): m/z 361.3 [M$^+$+1]. HPLC: 99.42%. Chiral HPLC: 100%.

AL-2: $^1$H NMR (500 MHz, DMSO-$d_6$): δ 7.65 (d, J=9.0 Hz, 1H), 7.54 (s, 1H), 7.39-7.27 (m, 6H), 7.10 (s, 1H), 5.15 (s, 1H), 4.14-4.08 (m, 2H), 3.97 (d, J=12.5 Hz, 1H), 3.57 (d, J=12.5 Hz, 1H), 3.42 (d, J=12.5 Hz, 1H), 3.31-3.28 (m, 1H), 3.03 (d, J=6.5 Hz, 1H), 2.26-2.20 (m, 1H), 2.07-1.99 (m, 2H), 1.82-1.77 (m, 1H), 1.02 (d, J=6.0 Hz, 3H). LCMS (ESI): m/z 361.3 [M$^+$+1]. HPLC: 98.43%. Chiral HPLC: 100%.

Preparation of Int-A:

Synthesis of formaldehyde O-benzyl oxime (Int-A):

To a stirring solution of O-benzylhydroxylamine (SM1) (5 g, 40.65 mmol) and aqueous NaOH solution (1.5 mL) in benzene (25 mL) was added 37% formaldehyde solution (3.3 mL, 40.65 mmol) at RT then stirred for 1 h. After consumption of the starting material (by TLC), the reaction mixture was extracted with EtOAc (2×100 mL). Separated organic layer was washed with brine solution, dried over $Na_2SO_4$ and concentrated under reduced pressure to afford Int-A (5 g, 91%) as pale yellow liquid. $^1$H NMR (400 MHz, $CDCl_3$): δ 7.38-7.28 (m, 5H), 7.08 (d, J=8.3 Hz, 1H), 6.46 (d, J=8.2 Hz, 1H), 5.12 (s, 2H).

Synthesis of AM & AN:

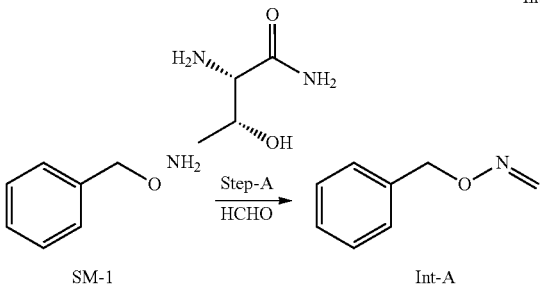

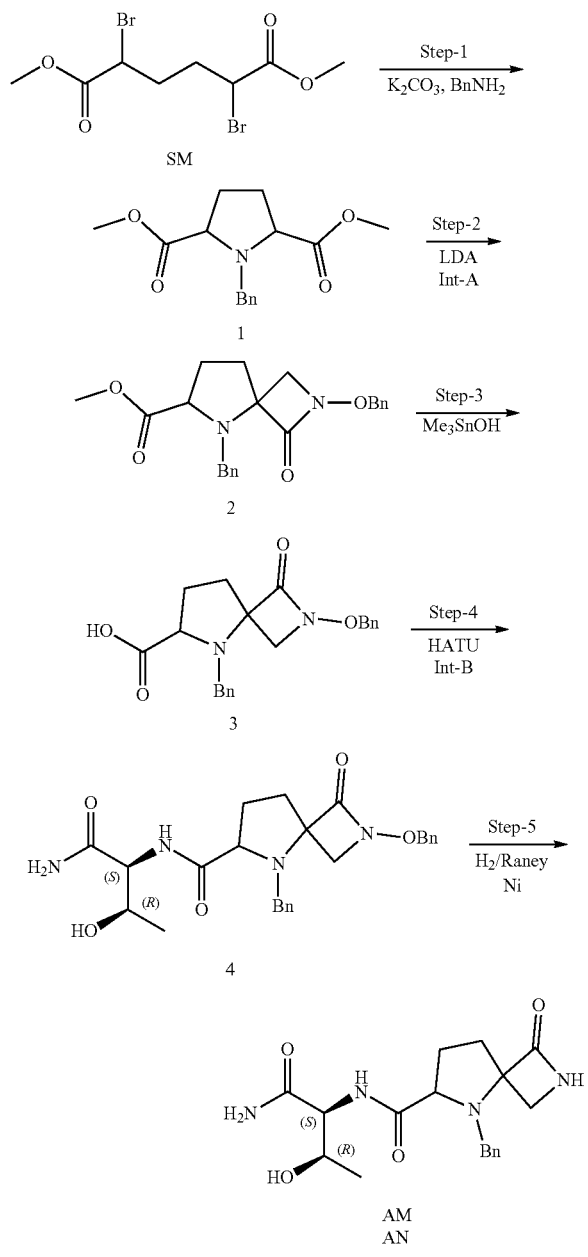

Synthesis of dimethyl 1-benzylpyrrolidine-2,5-dicarboxylate (1)

To a solution of dimethyl 2, 5-dibromohexanedioate (SM) (100 g, 0.301 mol) in toluene:water (300 mL, 2:1) were added $K_2CO_3$ (50 g, 0.361 mol) and benzylamine (32.23 g, 0.301 mol). Resultant reaction mixture was heated to 100° C. and stirred at for 16 h under nitrogen atmosphere. After completion of the reaction, reaction mixture was cooled to RT, diluted with EtOAc (200 mL). After stirring for 10 minutes, organic layer was separated and washed with brine solution. Combined organic layer was dried over anhydrous $Na_2SO_4$ and concentrated under reduced pressure. Obtained crude material was purified by column chromatography eluting with 20% EtOAc/Hexane to afford meso compound 1 (45 g, 54%) as brown syrup. 25 g of racemic compound 1 was also isolated. $^1$H NMR (500 MHz, $CDCl_3$): δ 7.36-7.20 (m, 5H), 3.92 (s, 2H), 3.58 (s, 6H), 3.48-3.41 (m, 2H), 2.11-2.02 (m, 4H). LCMS (ESI): m/z 277.9 [M$^+$+1].

Synthesis of methyl 5-benzyl-2-(benzyloxy)-1-oxo-2,5-diazaspiro[3.4]octane-6-carboxylate (2)

A solution of meso compound 1 (10 g, 36.10 mmol) in THF (80 mL) was added to a freshly prepared LDA solution (1.3 eq.) drop wise at −78° C. under nitrogen atmosphere. After being stirred at −78° C. for 1 h, a solution of Int-A (4.87 g, 36.10 mmol) in THF (20 mL) was added. The reaction mixture was stirred at −78° C. for 3 h and then slowly raised the temperature to RT. After consumption of the starting material (by TLC), the reaction was quenched with aqueous $NH_4Cl$ solution (100 mL) and extracted with EtOAc (3×100 mL). Separated organic layer was washed with brine solution, dried over $Na_2SO_4$ and concentrated under reduced pressure. Obtained crude material was purified by column chromatography eluting with 30% EtOAc/Hexane to afford compound 2 (2.9 g, Crude) as brown syrup. Another 10 g batch was performed to obtain 2.9 g of compound 2 as product. Both batches were combined and purified by reverse phase preparative HPLC to obtain compound-2-FI (1.6 g) and compound-2-F2 (1 g).

Compound-2-FI: $^1$H NMR (500 MHz, $CDCl_3$) δ 7.52-7.46 (m, 2H), 7.40 (br dd, J=2.0, 4.6 Hz, 3H), 7.34-7.21 (m, 5H), 5.12-5.00 (m, 2H), 4.01 (br d, J=11.3 Hz, 1H), 3.79 (d, J=12.7 Hz, 1H), 3.68 (s, 3H), 3.54-3.29 (m, 3H), 2.31-2.22 (m, 1H), 2.13-2.07 (m, 1H), 1.97-1.87 (m, 1H), 1.78-1.72 (m, 1H). LCMS (ESI): m/z 381.4 [M$^+$+1]. HPLC: 99.21%.

Compound-2-F2: $^1$H NMR (500 MHz, $CDCl_3$): δ 7.40-7.31 (m, 4H), 7.30-7.19 (m, 6H), 4.96-4.82 (m, 2H), 3.90 (d, J=14.2 Hz, 1H), 3.67 (d, J=14.2 Hz, 1H), 3.51 (s, 3H), 3.49 (dd, J=3.6, 7.4 Hz, 1H), 3.35 (d, J=4.6 Hz, 1H), 3.13 (d, J=4.6 Hz, 1H), 2.53-2.45 (m, 1H), 2.06-1.88 (m, 3H). LCMS (ESI): m/z 381.4 [M$^+$+1]. HPLC: 98.04%.

Synthesis of 5-benzyl-2-(benzyloxy)-1-oxo-2,5-diazaspiro[3.4]octane-6-carboxylic acid (3)

To a stirring solution of compound 2-F2 (1.8 g, 4.73 mmol) in dichloroethane (20 mL) was added Me$_3$SnOH (4.26 g, 23.6 mmol) under nitrogen atmosphere. Resultant reaction mixture was heated to 90-100° C. and stirred for 48 h. After consumption of the starting material (by TLC), volatiles were removed under reduced pressure to afford compound 3 (6 g, Crude) as syrup, which was taken to next step without any further purification. LCMS (ESI): m/z 367.3 [M$^+$+1].

Synthesis of N-((2S,3R)-1-amino-3-hydroxy-1-oxobutan-2-yl)-5-benzyl-2-(benzyloxy)-1-oxo-2,5-diazaspiro[3.4]octane-6-carboxamide (4)

To a solution of compound 3 (1.5 g, 4.09 mmol) in DMF (15 mL) was added HATU (1.86 g, 4.91 mmol) at 0-5° C. under nitrogen atmosphere. After stirring for 5 minutes, Int-B (532 mg, 4.51 mmol) followed by DIPEA (1.5 mL, 8.19 mmol) were added. The reaction mixture was brought to RT and stirred for 16 h. After consumption of the starting material (by TLC), the reaction mixture was diluted with water (50 mL) and extracted with EtOAc (3×100 mL). Combined organic layer was washed with 1N HCl solution and brine solution. Organic layer was dried over anhydrous Na$_2$SO$_4$ and concentrated under reduced pressure to afford crude compound which was purified by column chromatography by eluting 3% MeOH/DCM to obtain compound 4 (800 mg, 42%) as brown solid. $^1$H NMR (400 MHz, DMSO-d$_6$): δ 7.70-7.57 (m, 1H), 7.38-7.29 (m, 6H), 7.27-7.16 (m, 3H), 7.09-7.01 (m, 1H), 6.77 (s, 1H), 4.76-4.65 (m, 1H), 4.06-3.98 (m, 2H), 3.92-3.83 (m, 2H), 3.80-3.67 (m, 3H), 3.50-3.32 (m, 2H), 3.29-3.24 (m, 1H), 2.15-1.92 (m, 3H), 1.79-1.70 (m, 1H), 1.00-0.82 (m, 3H). LCMS (m/z): 467.4 [M$^+$+1].

Synthesis of N-((2S,3R)-1-amino-3-hydroxy-1-oxobutan-2-yl)-5-benzyl-1-oxo-2,5-diazaspiro[3.4]octane-6-carboxamide (AM, AN)

To a stirring solution of compound 4 (700 mg, 1.50 mmol) in methanol (10 mL) was added Raney Ni (1.4 g) under nitrogen atmosphere. Reaction mixture was de-gassed and then stirred for 16 h under H$_2$ atmosphere (balloon pressure). Crude HPLC and LCMS showed the presence of product and intermediate (N—OH product). Again Raney Ni (1 g) was added to reaction mixture and stirred for 8 h. After consumption of the starting material (by TLC), the reaction mixture was filtered through a pad of celite and the pad was washed with MeOH (50 mL). Obtained filtrate was concentrated under reduced pressure. Obtained crude material was submitted preparative HPLC purification (normal and reverse phase purification) to afford racemic AM (100 mg, 18%) and AN (90 mg, 17%) as white solids.

AM: $^1$H NMR (400 MHz, DMSO-d$_6$): δ 7.78 (s, 1H), 7.73 (br d, J=8.0 Hz, 1H), 7.37 (dd, J=1.6, 7.7 Hz, 2H), 7.25-7.16 (m, 3H), 7.03 (br s, 1H), 6.74 (br s, 1H), 4.89 (br d, J=4.5 Hz, 1H), 4.00-3.94 (m, 2H), 3.93-3.80 (m, 2H), 3.61 (d, J=5.8 Hz, 1H), 3.38 (dd, J=2.5, 9.4 Hz, 1H), 2.99 (d, J=5.8 Hz, 1H), 2.23-1.96 (m, 3H), 1.80-1.70 (m, 1H), 0.99 (d, J=6.1 Hz, 3H). LCMS (ESI): m/z 361.3 [M$^+$+1]. HPLC: 99.36%. Chiral HPLC: 99.82%.

AN: $^1$H NMR (400 MHz, DMSO-d$_6$): δ 7.81 (s, 1H), 7.68 (d, J=8.9 Hz, 1H), 7.38-7.32 (m, 2H), 7.29-7.17 (m, 3H), 7.07 (br d, J=13.6 Hz, 2H), 4.93 (d, J=4.4 Hz, 1H), 4.00 (dd, J=3.3, 8.9 Hz, 1H), 3.93-3.78 (m, 3H), 3.59 (d, J=5.9 Hz, 1H), 3.44 (dd, J=2.9, 8.8 Hz, 1H), 3.03 (d, J=5.9 Hz, 1H), 2.22-2.09 (m, 2H), 2.06-1.96 (m, 1H), 1.81-1.75 (m, 1H), 0.87 (d, J=6.3 Hz, 3H). LCMS (ESI): m/z 381.4 [M$^+$+1]. HPLC: 99.72%. Chiral HPLC: 100.00%.

Preparation of Int-A:

Synthesis of formaldehyde O-benzyl oxime (Int-A):

To a stirring solution of O-benzyl hydroxylamine (SM1) (5 g, 40.65 mmol) and aqueous NaOH solution (1.5 mL) in benzene (25 mL) was added 37% formaldehyde solution (3.3 mL, 40.65 mmol) at RT then stirred for 1 h. After consumption of the starting material (by TLC), the reaction mixture was extracted with EtOAc (2×100 mL). Separated organic layer was washed with brine solution, dried over Na$_2$SO$_4$ and concentrated under reduced pressure to afford Int-A (5 g, 91%) as pale yellow liquid. $^1$H NMR (400 MHz, CDCl$_3$): δ 7.38-7.28 (m, 5H), 7.08 (d, J=8.3 Hz, 1H), 6.46 (d, J=8.2 Hz, 1H), 5.12 (s, 2H).

Synthesis of AO & AP:

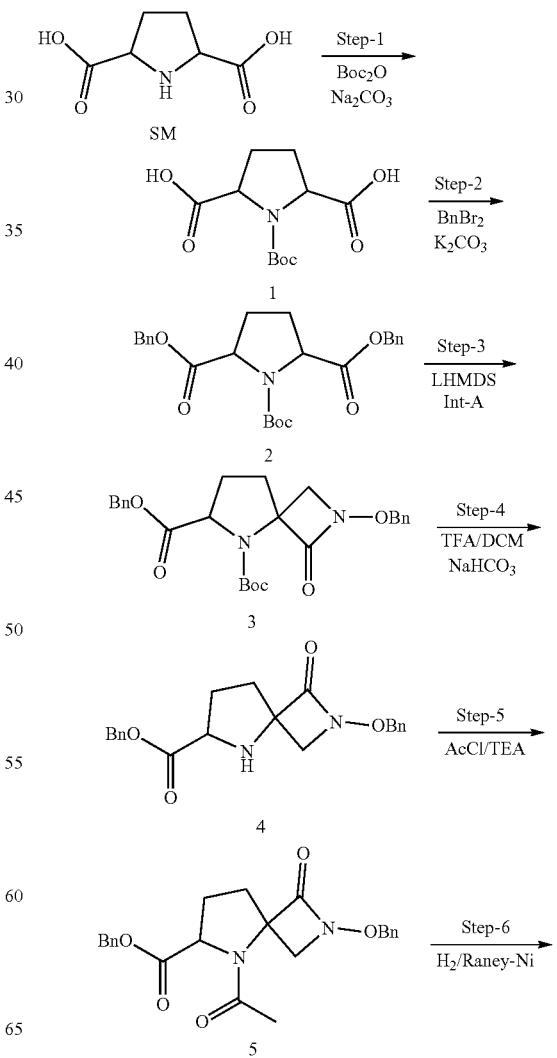

-continued

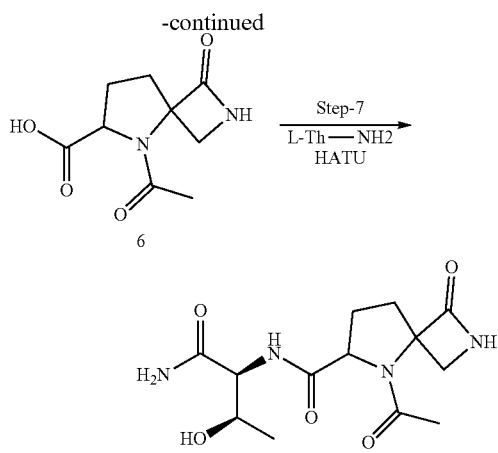

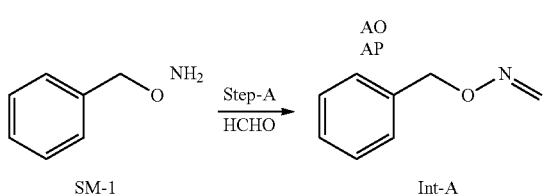

Synthesis of 1-(tert-butoxycarbonyl)pyrrolidine-2,5-dicarboxylic acid (1)

Pyrrolidine-2, 5-dicarboxylic acid (SM) (20 g, 125.7 mmol) was diluted with 1,4-dioxane:$H_2O$ (400 mL, 1:1), and was added $Boc_2O$ (41.1 g, 188.67 mmol) and $Na_2CO_3$ (53.3 g, 503.1 mmol)) at 10° C. to 15° C. Reaction mixture stirred at RT for 16 hours. After completion of the reaction, reaction mixture was diluted with water (200 mL) and washed with $Et_2O$ (200 mL). Aqueous layer acidified using 1N HCl and extracted with EtOAc (200 mL×2). Combined organic layer was washed with brine solution, dried over anhydrous $Na_2SO_4$ and concentrated under reduced pressure to afford compound 1 (23 g, 70%) as white solid. $^1H$ NMR (500 MHz, DMSO-$d_6$): δ 12.92-12.21 (br s, 2H), 4.24-4.12 (m, 2H), 2.27-2.11 (m, 2H), 1.97-1.84 (m, 2H), 1.36 (s, 9H).

Synthesis of 2,5-dibenzyl 1-(tert-butyl) pyrrolidine-1,2,5-tricarboxylate (2)

To a stirring solution of compound 1 (23 g, 88.80 mmol) in acetonitrile (300 mL) was added $K_2CO_3$ (36.23 g, 266.4 mmol) and benzylbromide (23 mL, 195.3 mmol). Reaction mixture stirred at RT for 24 hours. After completion of reaction by TLC, the reaction mixture was filtered through celite and bed washed with EtOAc (200 mL). Clear filtrate was concentrated to get colorless oil which on purification by column chromatography afford compound 2 (37 g, 95%) as colorless oil. $^1H$ NMR (500 MHz, $CDCl_3$): δ 7.39-7.25 (m, 10H), 5.24 (d, J=12.7 Hz, 1H), 5.15-5.06 (m, 3H), 4.49 (br dd, J=4.6, 6.9 Hz, 1H), 4.35 (br t, J=6.4 Hz, 1H), 2.28-2.08 (m, 4H), 1.34 (s, 9H). LCMS (m/z): 340.0 [$M^+$-Boc].

Synthesis of 6-benzyl 5-(tert-butyl) 2-(benzyloxy)-1-oxo-2,5-diazaspiro[3.4]octane-5,6-dicarboxylate (3)

To a stirring solution of compound 2 (19 g, 43.28 mmol) in THF (120 mL) was added LiHMDS (1M in THF) (65 mL, 64.92 mmol) drop wise at −70° C. under nitrogen atmosphere. After being stirred for 30 min, a solution of Int-A (7.01 g, 51.93 mmol) in THF (70 mL) was added. The reaction mixture was stirred at −78° C. for 2 h and then slowly raised the temperature to RT over a period of 16 h. After consumption of the starting material (by TLC), the reaction was quenched with aqueous $NH_4Cl$ solution (50 mL) and extracted with EtOAc (2×200 mL). Separated organic layer was dried over $Na_2SO_4$ and concentrated under reduced pressure. Obtained crude material was purified by column chromatography eluting with 30% EtOAc/Hexane to afford compound 3 (11 g, 54%) as thick syrup. $^1H$ NMR (400 MHz, DMSO-$d_6$): δ 7.47-7.30 (m, 10H), 5.23-5.12 (m, 2H), 4.95-4.86 (m, 2H), 4.29 (br d, J=6.3 Hz, 1H), 4.10-3.99 (m, 1H), 3.58 (d, J=10.7 Hz, 1H), 2.35-2.18 (m, 2H), 2.16-2.05 (m, 1H), 1.99-1.91 (s, 1H), 1.34 (s, 9H). LCMS (m/z): 467.6 [$M^+$+1].

Synthesis of benzyl 2-(benzyloxy)-1-oxo-2,5-diazaspiro[3.4]octane-6-carboxylate (4)

To a solution of compound 3 (10 g, 21.45 mmol) in DCM (100 mL) was added TFA (16.5 mL, 214.59 mmol) drop wise at 0° C. under nitrogen atmosphere. The reaction mixture brought to RT over a period of 1 h and then stirred at RT for 16 h. After consumption of the starting material (by TLC), volatiles were evaporated under reduced pressure to obtain 12 g of product crude brown syrup. Another 11 g batch was performed to obtain 13 g of crude brown syrup and both batches were combined. Obtained crude 25 g of TFA salt product was dissolved in EtOAc (500 mL) and washed with saturated $NaHCO_3$ solution. Aqueous layer was separated and again extracted with EtOAc (100 mL). Combined organic layer was washed with brine solution, dried over $Na_2SO_4$ and concentrated under reduced pressure. Obtained crude material was purified by column chromatography eluting with 3% MeOH/DCM to afford compound 4 (15 g, 78%) as brown syrup. $^1H$ NMR (500 MHz, DMSO-$d_6$): δ 7.44-7.30 (m, 10H), 5.17 (s, 2H), 4.92-4.85 (m, 2H), 3.64 (d, J=9.5 Hz, 1H), 3.60-3.57 (m, 2H), 3.39 (d, J=9.8 Hz, 1H), 1.98-1.79 (m, 4H). LCMS (m/z): 367.4 [$M^+$+1]. HPLC: 96.27%.

Synthesis of benzyl 5-acetyl-2-(benzyloxy)-1-oxo-2,5-diazaspiro[3.4]octane-6-carboxylate (5)

To a stirring solution of compound 4 (4 g, 10.9 mmol) in DCM (80 mL) were added TEA (3.83 mL, 27.3 mmol), acetyl chloride (1.28 g, 16.3 mmol) at 0-5° C. under nitrogen atmosphere and stirred for 5 min. The reaction mixture brought to RT and then stirred for 5 h. After consumption of the starting material (by TLC), volatiles were removed under reduced pressure. Crude material was diluted with EtOAc (300 mL) and washed with water (80 mL), 2N HCl solution and brine solution. Organic layer was dried over anhydrous $Na_2SO_4$, filtered and concentrated under reduced pressure. Obtained crude material was purified by silica gel column chromatography eluting 50% EtOAc/Hexane to afford compound 5 (4 g, 90%) as brown syrup. $^1H$ NMR (500 MHz, DMSO-$d_6$): δ 7.45-7.41 (m, 2H), 7.40-7.31 (m, 8H), 5.19 (d, J=12.7 Hz, 1H), 5.08-5.03 (m, 1H), 4.96-4.88 (m, 2H), 4.59 (d, J=6.7 Hz, 1H), 3.98 (d, J=10.4 Hz, 1H), 3.49 (d, J=10.4 Hz, 1H), 2.34-2.18 (m, 2H), 2.13-2.02 (m, 2H), 1.99 (s, 3H). LCMS (m/z): 409.1 [$M^+$+1]. HPLC: 98.91%.

Synthesis of 5-acetyl-1-oxo-2,5-diazaspiro[3.4]octane-6-carboxylic acid (6)

To a stirring solution of compound 5 (4 g, 9.80 mmol) in methanol (100 mL) was added Raney Ni (10 g) at RT and stirred for 16 h under H₂ atmosphere (balloon pressure). Crude LCMS showed the presence of hydroxyl amine intermediate. Again H₂ atmosphere balloon was changed and continued stirring for 24 h. After consumption of the starting material (by TLC), the reaction mixture was filtered through a pad of celite and the pad was washed with warm MeOH (300 mL). Obtained filtrate was concentrated under reduced pressure to afford crude solid, which was washed with Et₂O (100 mL) and dried under vacuum to obtain compound 6 (2 g, 96%) as off white solid. $^1$H NMR (400 MHz, D₂O): δ 4.61 (br d, J=4.1 Hz, 1H), 3.94 (br d, J=12.2 Hz, 1H), 3.45-3.34 (m, 1H), 2.51 (br d, J=7.8 Hz, 2H), 2.31 (br d, J=12.7 Hz, 2H), 2.19 (s, 3H). LCMS (ESI): m/z 211.0 [M⁺−1].

Synthesis of 5-acetyl-N-((2S,3R)-1-amino-3-hydroxy-1-oxobutan-2-yl)-1-oxo-2,5-diazaspiro[3.4]octane-6-carboxamide (AO, AP)

To a solution of compound 6 (2 g, 9.43 mmol) in DMF (10 mL) were added HATU (4.3 g, 11.3 mmol) at RT under nitrogen atmosphere and stirred for 5 minutes. Then, L-Th-NH₂ (1.33 g, 11.3 mmol) and DIPEA (2.6 mL, 14.1 mmol) were added and continued stirring at RT for 16 h. After consumption of the starting material (by TLC), the reaction mixture was quenched with ice (5 g) and stirred for 10 minutes. Volatiles were removed under reduced pressure. Obtained crude material was purified by column chromatography by eluting 5-8% MeOH/DCM to obtain two products, which were further purified by chiral phase preparative HPLC to obtain AO (550 mg, 19%) and AP (700 mg, 24%) as white solids.

AO: $^1$H NMR (400 MHz, DMSO-d₆): δ 7.58 (s, 1H), 7.28 (s, 1H), 7.14 (br d, J=4.5 Hz, 1H), 7.05 (s, 1H), 4.73 (d, J=4.0 Hz, 1H), 4.43 (d, J=5.8 Hz, 1H), 4.08 (dd, J=3.6, 8.7 Hz, 1H), 4.04-3.95 (m, 1H), 3.68 (br d, J=11.7 Hz, 1H), 3.15-3.08 (m, 1H), 2.41-2.28 (m, 2H), 2.20-2.07 (m, 1H), 2.03 (s, 3H), 2.00-1.94 (m, 1H), 1.03 (d, J=6.4 Hz, 3H). LCMS (ESI): m/z 313.2 [M⁺+1]. HPLC: 98.84%. Chiral HPLC: 100.00%.

AP: $^1$H NMR (400 MHz, DMSO-d₆): δ 7.63 (s, 1H), 7.32 (br d, J=7.7 Hz, 1H), 7.14 (s, 1H), 7.08 (br s, 1H), 4.81 (d, J=6.8 Hz, 1H), 4.48 (d, J=6.7 Hz, 1H), 4.24 (br s, 1H), 3.97 (br d, J=7.0 Hz, 1H), 3.65 (d, J=11.8 Hz, 1H), 3.20-3.11 (m, 1H), 2.46-2.32 (m, 1H), 2.29-2.18 (m, 2H), 2.08 (s, 3H), 2.05-1.99 (m, 1H), 1.06 (d, J=6.5 Hz, 3H). LCMS (ESI): m/z 313.2 [M⁺+1]. HPLC: 99.45%. Chiral HPLC: 98.56%.

Preparation of Int-A:
Synthesis of formaldehyde O-benzyl oxime (Int-A):

To a stirring solution of O-benzylhydroxylamine (SM1) (5 g, 40.65 mmol) and aqueous NaOH solution (1.5 mL) in benzene (25 mL) was added 37% formaldehyde solution (3.3 mL, 40.65 mmol) at RT then stirred for 1 h. After consumption of the starting material (by TLC), the reaction mixture was extracted with EtOAc (2×100 mL). Separated organic layer was washed with brine solution, dried over Na₂SO₄ and concentrated under reduced pressure to afford Int-A (5 g, 91%) as pale yellow liquid. $^1$H NMR (400 MHz, CDCl₃): δ 7.38-7.28 (m, 5H), 7.08 (d, J=8.3 Hz, 1H), 6.46 (d, J=8.2 Hz, 1H), 5.12 (s, 2H).

Synthesis of AO-1 & AO-2:

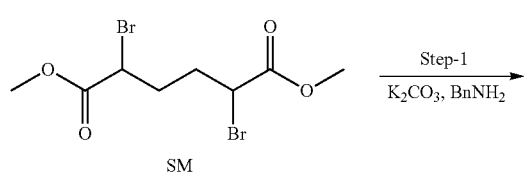

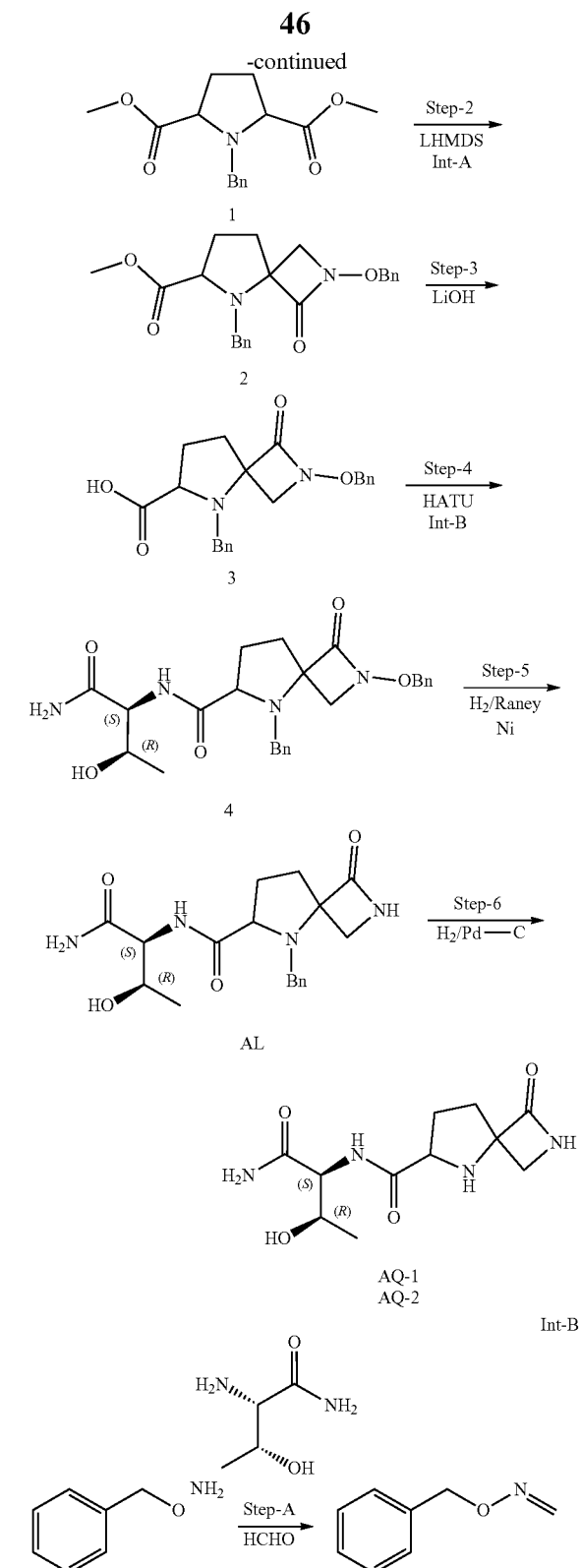

Synthesis of dimethyl 1-benzylpyrrolidine-2,5-dicarboxylate (1)

A mixture of dimethyl 2,5-dibromohexanedioate (SM) (50 g, 150.6 mmol), K₂CO₃ (24.94 g, 180.7 mmol) and benzyl amine (16.11 g, 150.6 mmol) in toluene:water (60 mL, 2:1) were heated to 110° C. and stirred at for 6 h under nitrogen atmosphere. After completion of the reaction, reaction mixture was cooled to RT, organic layer was separated and aqueous layer was extracted with hexane (2×100 mL). Combined organic layer was washed with brine solution, dried over anhydrous $Na_2SO_4$ and concentrated under reduced pressure. Obtained crude material was purified by column chromatography eluting with 20% EtOAc/Hexane to afford compound 1 (25 g, 88%) as yellow oil. $^1$H NMR (400 MHz, $CDCl_3$): δ 7.37-7.22 (m, 5H), 4.01 (s, 2H), 3.59 (s, 6H), 3.58-3.54 (m, 2H), 2.14-2.07 (m, 4H). LCMS (ESI): m/z 278.2 [M$^+$+1].

Synthesis of methyl 5-benzyl-2-(benzyloxy)-1-oxo-2,5-diazaspiro[3.4]octane-6-carboxylate (2)

To a stirring solution of compound 1 (10 g, 36.10 mmol) in THF (50 mL) was added LiHMDS (1 M in THF) (44 mL, 43.32 mmol) drop wise at −70° C. under nitrogen atmosphere. After being stirred for 30 min, a solution of Int-A (4.87 g, 18.05 mmol) in THF (50 mL) was added. The reaction mixture was stirred at −78° C. for 2 h and then slowly raised the temperature to RT over a period of 16 h. After consumption of the starting material (by TLC), the reaction was quenched with aqueous $NH_4Cl$ solution (50 mL) and extracted with EtOAc (2×100 mL). Separated organic layer was dried over $Na_2SO_4$ and concentrated under reduced pressure. Obtained crude material was purified by column chromatography eluting with 20% EtOAc/Hexane to afford compound 2 (7 g, crude) as brown syrup. $^1$H NMR (500 MHz, DMSO-$d_6$): δ 7.45-7.18 (m, 10H), 5.04-4.95 (m, 2H), 4.06 (br d, J=11.0 Hz, 1H), 3.88 (d, J=13.3 Hz, 1H), 3.64 (s, 3H), 3.53 (d, J=11.0 Hz, 1H), 3.41-3.33 (m, 1H), 3.23-3.17 (m, 1H), 2.21-2.12 (m, 1H), 2.04-1.88 (m, 2H), 1.85-1.77 (m, 1H). LCMS (ESI): m/z 381.3 [M$^+$+1].

Synthesis of methyl 5-benzyl-2-(benzyloxy)-1-oxo-2,5-diazaspiro[3.4]octane-6-carboxylate (3)

To a stirring solution of compound 2 (7 g, 18.42 mmol) in MeOH:THF:H2O (90 mL, 1:1:1) was added LiOH.$H_2O$ (1.16 g, 27.63 mmol) at 0° C. and then slowly raised the temperature to RT over a period of 1 h. The reaction mixture was stirred at RT for 1 h. After consumption of the starting material (by TLC), volatiles were removed under reduced pressure to afford compound 3 (7 g, crude) as syrup. $^1$H NMR (500 MHz, DMSO-$d_6$): δ 7.46-7.34 (m, 5H), 7.30-7.18 (m, 5H), 4.97-4.88 (m, 2H), 4.11 (d, J=13.3 Hz, 1H), 3.89 (d, J=11.3 Hz, 1H), 3.37-3.33 (m, 1H), 3.20 (d, J=13.0 Hz, 1H), 3.04 (d, J=6.7 Hz, 1H), 2.17-2.08 (m, 1H), 1.88-1.79 (m, 1H), 1.69-1.57 (m, 2H). LCMS (ESI): m/z 367.3 [M$^+$+1].

Synthesis of N-((2S,3R)-1-amino-3-hydroxy-1-oxobutan-2-yl)-5-benzyl-2-(benzyloxy)-1-oxo-2,5-diazaspiro[3.4]octane-6-carboxamide (4)

To a solution of compound 3 (7 g, 19.12 mmol) in DMF (50 mL) was added HATU (8.72 g, 22.95 mmol) at 0° C. under nitrogen atmosphere and stirred for 10 minutes. Then, Int-B (2.26 mg, 19.12 mmol) followed by DIPEA (5.3 mL, 28.68 mmol) were added. The reaction mixture was brought to RT and stirred for 18 h. After consumption of the starting material (by TLC), the reaction mixture was diluted with water (400 mL) and extracted with EtOAc (3×150 mL). Combined organic layer was washed with 1N HCl solution (50 mL), saturated $NaHCO_3$ solution (50 mL) and brine solution (50 mL). Organic layer was dried over anhydrous $Na_2SO_4$ and concentrated under reduced pressure to afford crude compound which was purified by column chromatography by eluting 3% MeOH/DCM to obtain compound 4 (5 g, 56%) as white solid. $^1$H NMR (400 MHz, DMSO-$d_6$): δ 7.58 (br d, J=8.8 Hz, 1H), 7.52-7.46 (m, 1H), 7.46-7.25 (m, 10H), 7.10 (br d, J=2.3 Hz, 1H), 5.15-4.96 (m, 3H), 4.26-4.22 (m, 0.5H), 4.13-4.00 (m, 2H), 3.95-3.86 (m, 1.5H), 3.58-3.51 (m, 1H), 3.29-3.16 (m, 2H), 2.24-2.07 (m, 1H), 2.05-1.76 (m, 3H), 1.03 (dd, J=6.3, 11.4 Hz, 3H). LCMS (m/z): 467.5 [M$^+$+1].

Synthesis of N-((2S,3R)-1-amino-3-hydroxy-1-oxobutan-2-yl)-5-benzyl-1-oxo-2,5-diazaspiro[3.4]octane-6-carboxamide (AL)

To a stirring solution of compound 4 (5 g, 10.73 mmol) in methanol (60 mL) was added Raney Ni (3 g) at RT and stirred for 16 h under $H_2$ atmosphere (balloon pressure). After consumption of the starting material (by TLC), the reaction mixture was filtered through a pad of celite and the pad was washed with MeOH (300 mL). Obtained filtrate was concentrated under reduced pressure to afford racemic AL-Racemic (3.6 g, 93%) as white solid. $^1$H NMR (500 MHz, DMSO-$d_6$): δ 7.66 (dd, J=3.2, 8.7 Hz, 1H), 7.55 (s, 1H), 7.48-7.24 (m, 6H), 7.11 (s, 1H), 5.20-5.02 (m, 1H), 4.24 (dd, J=2.9, 9.0 Hz, 1H), 4.17-4.04 (m, 2H), 3.58 (d, J=12.4 Hz, 1H), 3.43 (d, J=13.0 Hz, 1H), 3.38-3.24 (m, 1H), 3.05 (br t, J=7.5 Hz, 1H), 2.29-1.94 (m, 3H), 1.89-1.74 (m, 1H), 1.05 (d, J=6.4 Hz, 3H). LCMS (ESI): m/z 361.3 [M$^+$+1].

Synthesis of N-((2S,3R)-1-amino-3-hydroxy-1-oxobutan-2-yl)-5-benzyl-1-oxo-2,5-diazaspiro [3.4]octane-6-carboxamide (AQ)

To a stirring solution of AL-Racemic (3.6 g, 10 mmol) in methanol (50 mL) was added 10% Pd—C (2 g) at RT and stirred for 16 h under $H_2$ atmosphere (balloon pressure). After consumption of the starting material (by TLC), the reaction mixture was filtered through a pad of celite and the pad was washed with hot MeOH (500 mL). Obtained filtrate was concentrated under reduced pressure to afford racemic AQ (2.5 g, 92%) as white solid. 1 g of AQ racemic compound was purified by reverse phase prep. HPLC purification afforded 130 mg of AQ-1 and 120 mg of AQ-2.

AQ-1: $^1$H NMR (400 MHz, $D_2O$): δ 4.37 (d, J=4.1 Hz, 1H), 4.32-4.24 (m, 1H), 3.81 (d, J=6.2 Hz, 1H), 3.61-3.49 (m, 2H), 2.30-2.09 (m, 4H), 1.26 (d, J=6.4 Hz, 3H). LCMS (ESI): m/z 271.3 [M$^+$+1]. HPLC: 99.79%. Chiral HPLC: 100%.

AQ-2: $^1$H NMR (400 MHz, $D_2O$): δ 4.40-4.35 (m, 1H), 4.33-4.24 (m, 1H), 3.82 (d, J=6.0 Hz, 1H), 3.61-3.50 (m, 2H), 2.32-2.09 (m, 4H), 1.24 (d, J=6.3 Hz, 3H). LCMS (ESI): m/z 271.3 [M$^+$+1]. HPLC: 99.46%. Chiral HPLC: 100%.

Preparation of Int-A:
Synthesis of formaldehyde O-benzyl oxime (Int-A):
To a stirring solution of O-benzylhydroxylamine (SM1) (5 g, 40.65 mmol) and aqueous NaOH solution (1.5 mL) in benzene (25 mL) was added 37% formaldehyde solution (3.3 mL, 40.65 mmol) at RT then stirred for 1 h. After consumption of the starting material (by TLC), the reaction mixture was extracted with EtOAc (2×100 mL). Separated organic layer was washed with brine solution, dried over $Na_2SO_4$ and concentrated under reduced pressure to afford Int-A (5 g, 91%) as pale yellow liquid. $^1$H NMR (400 MHz, CDCl$_3$): δ 7.38-7.28 (m, 5H), 7.08 (d, J=8.3 Hz, 1H), 6.46 (d, J=8.2 Hz, 1H), 5.12 (s, 2H).

Synthesis of AR & AS:

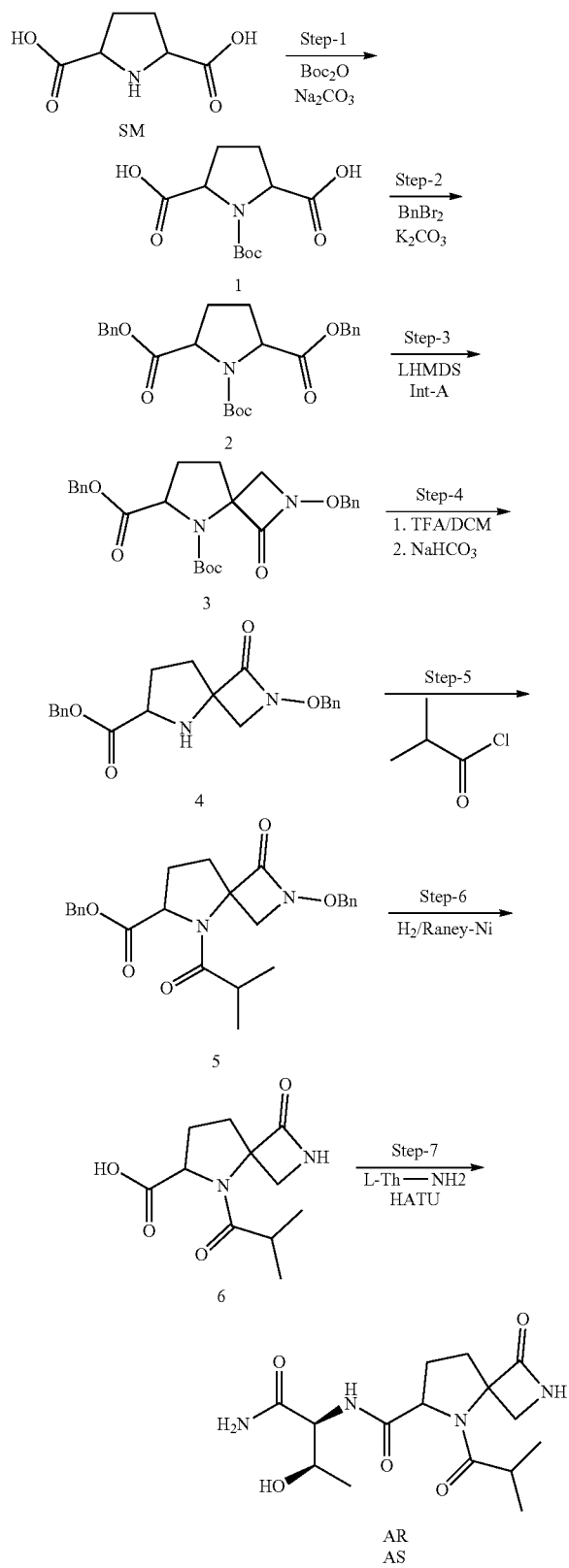

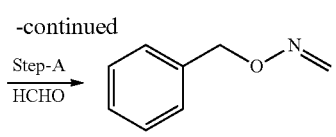

Synthesis of 1-(tert-butoxycarbonyl)pyrrolidine-2,5-dicarboxylic acid (1)

Pyrrolidine-2,5-dicarboxylic acid (SM) (20 g, 125.7 mmol) was diluted with 1,4-dioxane:H$_2$O (400 mL, 1:1), and was added Boc$_2$O (41.1 g, 188.67 mmol) and Na$_2$CO$_3$ (53.3 g, 503.1 mmol)) at 10 C to 15 C. Reaction mixture stirred at RT for 16 hours. After completion of the reaction, reaction mixture was diluted with water (200 mL) and washed with Et$_2$O (200 mL). Aqueous layer acidified using 1N HCl and extracted with EtOAc (200 mL×2). Combined organic layer was washed with brine solution, dried over anhydrous Na$_2$SO$_4$ and concentrated under reduced pressure to afford compound 1 (23 g, 70%) as white solid. $^1$H NMR (500 MHz, DMSO-d$_6$): δ 12.92-12.21 (br s, 2H), 4.24-4.12 (m, 2H), 2.27-2.11 (m, 2H), 1.97-1.84 (m, 2H), 1.36 (s, 9H).

Synthesis of 2,5-dibenzyl 1-(tert-butyl) pyrrolidine-1,2,5-tricarboxylate (2)

To a stirring solution of compound 1 (23 g, 88.80 mmol) in acetonitrile (300 mL) was added K$_2$CO$_3$ (36.23 g, 266.4 mmol) and benzylbromide (23 mL, 195.3 mmol). Reaction mixture stirred at RT for 24 hours. After completion of reaction by TLC, the reaction mixture was filtered through celite and bed washed with EtOAc (200 mL). Clear filtrate was concentrated to get colorless oil which on purification by column chromatography afford compound 2 (37 g, 95%) as colorless oil. $^1$H NMR (500 MHz, CDCl$_3$): δ 7.39-7.25 (m, 10H), 5.24 (d, J=12.7 Hz, 1H), 5.15-5.06 (m, 3H), 4.49 (br dd, J=4.6, 6.9 Hz, 1H), 4.35 (br t, J=6.4 Hz, 1H), 2.28-2.08 (m, 4H), 1.34 (s, 9H). LCMS (m/z): 340.0 [M$^+$-Boc].

Synthesis of 6-benzyl 5-(tert-butyl) 2-(benzyloxy)-1-oxo-2,5-diazaspiro[3.4]octane-5,6-dicarboxylate (3)

To a stirring solution of compound 2 (19 g, 43.28 mmol) in THF (120 mL) was added LiHMDS (1M in THF) (65 mL, 64.92 mmol) drop wise at −70° C. under nitrogen atmosphere. After being stirred for 30 min, a solution of Int-A (7.01 g, 51.93 mmol) in THF (70 mL) was added. The reaction mixture was stirred at −78° C. for 2 h and then slowly raised the temperature to RT over a period of 16 h. After consumption of the starting material (by TLC), the reaction was quenched with aqueous NH$_4$Cl solution (50 mL) and extracted with EtOAc (2×200 mL). Separated organic layer was dried over Na$_2$SO$_4$ and concentrated under reduced pressure. Obtained crude material was purified by column chromatography eluting with 30% EtOAc/Hexane to afford compound 3 (11 g, 54%) as thick syrup. $^1$H NMR (400 MHz, DMSO-d$_6$): δ 7.47-7.30 (m, 10H), 5.23-5.12 (m, 2H), 4.95-4.86 (m, 2H), 4.29 (br d, J=6.3 Hz, 1H), 4.10-3.99 (m, 1H), 3.58 (d, J=10.7 Hz, 1H), 2.35-2.18 (m, 2H), 2.16-2.05 (m, 1H), 1.99-1.91 (s, 1H), 1.34 (s, 9H). LCMS (m/z): 467.6 [M$^+$+1].

Synthesis of benzyl 2-(benzyloxy)-1-oxo-2,5-diazaspiro[3.4]octane-6-carboxylate (4)

To a solution of compound 3 (10 g, 21.45 mmol) in DCM (100 mL) was added TFA (16.5 mL, 214.59 mmol) drop wise at 0° C. under nitrogen atmosphere. The reaction mixture brought to RT over a period of 1 h and then stirred at RT for 16 h. After consumption of the starting material (by TLC), volatiles were evaporated under reduced pressure to obtain 12 g of product crude brown syrup. Another 11 g batch was performed to obtain 13 g of crude brown syrup and both batches were combined. Obtained crude 25 g of TFA salt product was dissolved in EtOAc (500 mL) and washed with saturated $NaHCO_3$ solution. Aqueous layer was separated and again extracted with EtOAc (100 mL). Combined organic layer was washed with brine solution, dried over $Na_2SO_4$ and concentrated under reduced pressure. Obtained crude material was purified by column chromatography eluting with 3% MeOH/DCM to afford compound 4 (15 g, 78%) as brown syrup. $^1$H NMR (500 MHz, DMSO-$d_6$): δ 7.44-7.30 (m, 10H), 5.17 (s, 2H), 4.92-4.85 (m, 2H), 3.64 (d, J=9.5 Hz, 1H), 3.60-3.57 (m, 2H), 3.39 (d, J=9.8 Hz, 1H), 1.98-1.79 (m, 4H). LCMS (m/z): 367.4 [M$^+$+1]. HPLC: 96.27%.

Synthesis of benzyl 2-(benzyloxy)-5-isobutyryl-1-oxo-2,5-diazaspiro[3.4]octane-6-carboxylate (5)

To a stirring solution of compound 4 (4 g, 10.9 mmol) in DCM (80 mL) were added TEA (4 mL, 27.3 mmol), Isobutyryl chloride (1.75 g, 16.3 mmol) at 0-5° C. under nitrogen atmosphere and stirred for 30 min. The reaction mixture brought to RT and then stirred for 16 h. After consumption of the starting material (by TLC), the reaction was diluted with EtOAc (300 mL) and water (100 mL) and stirred for 10 minutes. Separated organic layer was washed with 2N HCl solution and brine solution. Organic layer was dried over anhydrous $Na_2SO_4$, filtered and concentrated under reduced pressure. Obtained crude material was purified by silica gel column chromatography eluting 40% EtOAc/Hexane to afford compound 5 (4 g, 84%) as brown syrup. $^1$H NMR (400 MHz, DMSO-$d_6$): δ 7.46-7.29 (m, 10H), 5.18-5.06 (m, 2H), 4.96-4.84 (m, 2H), 4.74 (d, J=6.5 Hz, 1H), 4.07-4.01 (m, 1H), 3.53 (d, J=10.4 Hz, 1H), 2.84-2.76 (m, 1H), 2.36-2.17 (m, 2H), 2.14-2.00 (m, 2H), 1.00 (d, J=6.7 Hz, 3H), 0.93 (d, J=6.9 Hz, 3H). LCMS (m/z): 437.1 [M$^+$+1]. HPLC: 98.28%.

Synthesis 5-isobutyryl-1-oxo-2,5-diazaspiro[3.4]octane-6-carboxylic acid (6)

To a stirring solution of compound 5 (4 g, 9.17 mmol) in methanol (100 mL) was added Raney Ni (10 g) at RT and stirred for 16 h under $H_2$ atmosphere (balloon pressure). After consumption of the starting material (by TLC), the reaction mixture was filtered through a pad of celite and the pad was washed with warm MeOH (300 mL). Obtained filtrate was concentrated under reduced pressure to afford compound 6 (1.8 g, 82%) as white solid. $^1$H NMR (500 MHz, $D_2O$): δ 4.76-4.72 (m, 1H), 3.93 (d, J=12.4 Hz, 1H), 3.39 (d, J=12.1 Hz, 1H), 2.96-2.84 (m, 1H), 2.55-2.43 (m, 2H), 2.36-2.26 (m, 2H), 1.15 (d, J=6.7 Hz, 3H), 1.06 (d, J=6.9 Hz, 3H). LCMS (ESI): m/z 241.2 [M$^+$+1].

Synthesis of N-((2S,3R)-1-amino-3-hydroxy-1-oxobutan-2-yl)-5-isobutyryl-1-oxo-2,5-diazaspiro[3.4]octane-6-carboxamide (AR, AS)

To a solution of compound 6 (1.8 g, 7.50 mmol) in DMF (10 mL) were added HATU (3.42 g, 9.00 mmol) at RT under nitrogen atmosphere and stirred for 5 minutes. Then, L-Th—$NH_2$ (1.06 g, 9.00 mmol) and DIPEA (2.07 mL, 11.2 mmol) were added and continued stirring at RT for 16 h. After consumption of the starting material (by TLC), the reaction mixture was quenched with ice (5 g) and stirred for 10 minutes. Volatiles were removed under reduced pressure. Obtained crude material was purified by column chromatography by eluting 8% MeOH/DCM to obtain two products, which were further purified by chiral phase preparative HPLC to afford AR (500 mg, 20%) and AS (450 mg, 18%) as white solids.

AR: $^1$H NMR (400 MHz, DMSO-$d_6$): δ 7.65 (s, 1H), 7.20 (d, J=8.4 Hz, 1H), 7.14 (s, 1H), 7.04 (s, 1H), 4.78 (d, J=6.8 Hz, 1H), 4.63 (d, J=6.7 Hz, 1H), 4.28-4.19 (m, 1H), 3.98 (dd, J=2.4, 8.4 Hz, 1H), 3.67 (d, J=11.8 Hz, 1H), 3.15 (dd, J=2.6, 11.8 Hz, 1H), 2.95-2.80 (m, 1H), 2.46-2.35 (m, 1H), 2.29-2.16 (m, 2H), 2.12-1.99 (m, 1H), 1.05 (dd, J=1.6, 6.5 Hz, 6H), 0.94 (d, J=6.8 Hz, 3H). LCMS (ESI): m/z 341.2 [M$^+$+1]. HPLC: 99.48%. Chiral HPLC: 97.33%.

AS: $^1$H NMR (400 MHz, DMSO-$d_6$): δ 7.59 (s, 1H), 7.24 (s, 1H), 7.11-7.01 (m, 2H), 4.76 (d, J=4.9 Hz, 1H), 4.56 (d, J=6.3 Hz, 1H), 4.05 (dd, J=3.3, 8.7 Hz, 1H), 4.02-3.94 (m, 1H), 3.72 (d, J=11.5 Hz, 1H), 3.10 (dd, J=2.6, 11.7 Hz, 1H), 2.81 (dt, J=6.7, 13.4 Hz, 1H), 2.46-2.27 (m, 2H), 2.14-1.96 (m, 2H), 1.04 (d, J=6.7 Hz, 3H), 1.00 (d, J=6.4 Hz, 3H), 0.93 (d, J=6.8 Hz, 3H). LCMS (ESI): m/z 341.2 [M$^+$+1]. HPLC: 99.49%. Chiral HPLC: 100.00%.

Preparation of Int-A:
Synthesis of formaldehyde O-benzyl oxime (Int-A):

To a stirring solution of O-benzylhydroxylamine (SM1) (5 g, 40.65 mmol) and aqueous NaOH solution (1.5 mL) in benzene (25 mL) was added 37% formaldehyde solution (3.3 mL, 40.65 mmol) at RT then stirred for 1 h. After consumption of the starting material (by TLC), the reaction mixture was extracted with EtOAc (2×100 mL). Separated organic layer was washed with brine solution, dried over $Na_2SO_4$ and concentrated under reduced pressure to afford Int-A (5 g, 91%) as pale yellow liquid. $^1$H NMR (400 MHz, $CDCl_3$): δ 7.38-7.28 (m, 5H), 7.08 (d, J=8.3 Hz, 1H), 6.46 (d, J=8.2 Hz, 1H), 5.12 (s, 2H).

Synthesis of AT:

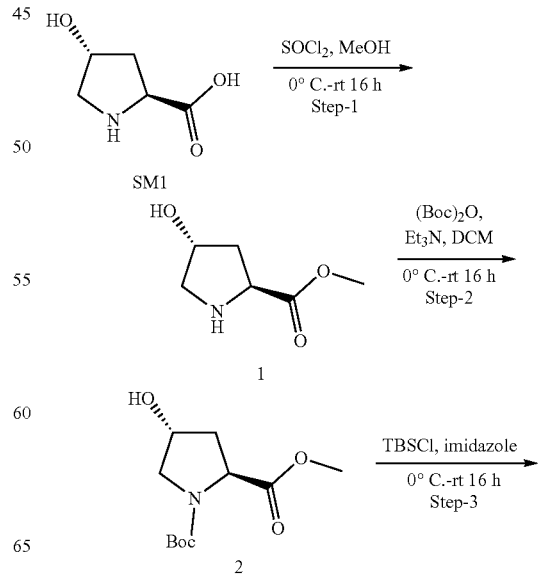

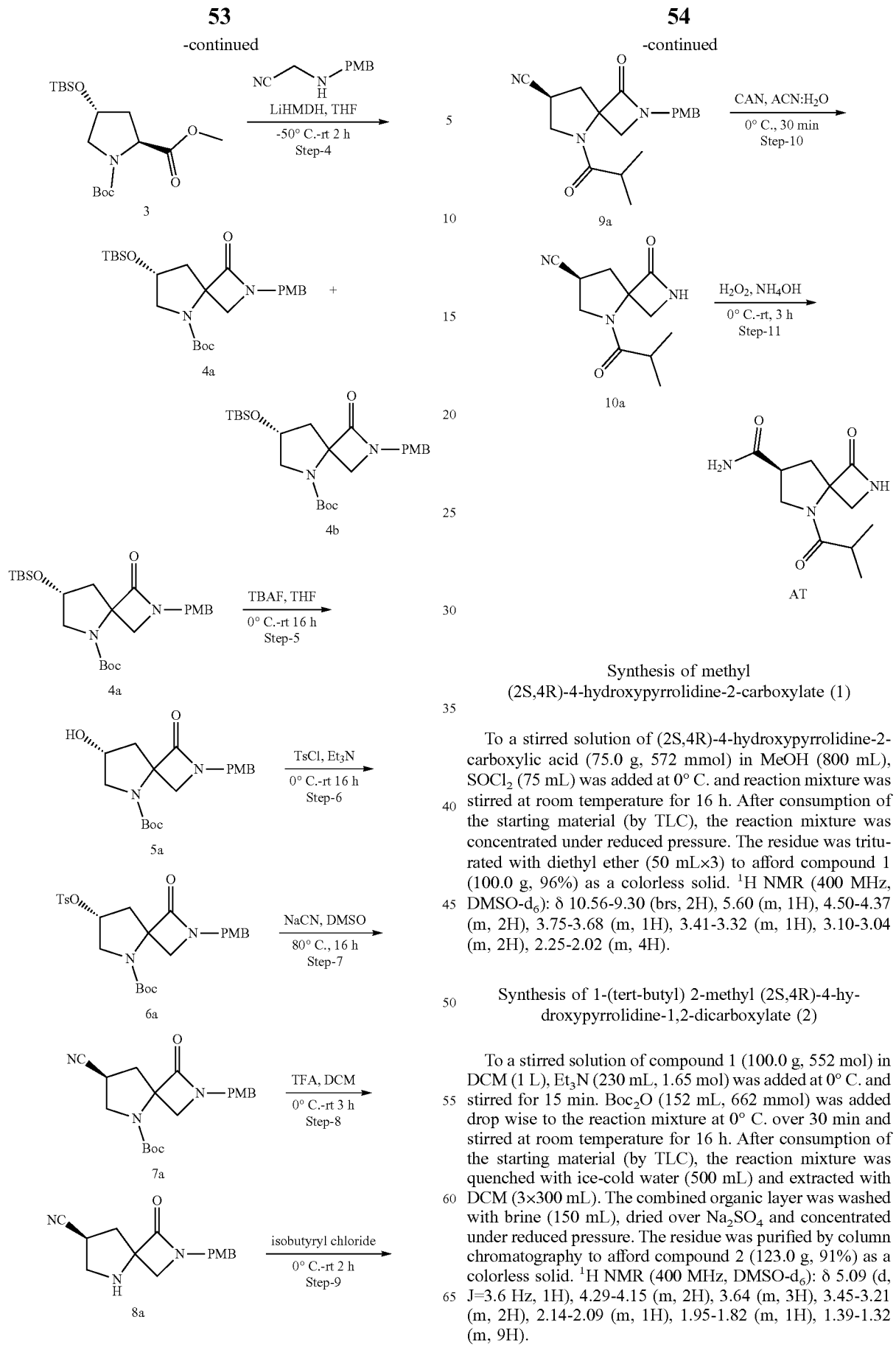

Synthesis of methyl (2S,4R)-4-hydroxypyrrolidine-2-carboxylate (1)

To a stirred solution of (2S,4R)-4-hydroxypyrrolidine-2-carboxylic acid (75.0 g, 572 mmol) in MeOH (800 mL), $SOCl_2$ (75 mL) was added at 0° C. and reaction mixture was stirred at room temperature for 16 h. After consumption of the starting material (by TLC), the reaction mixture was concentrated under reduced pressure. The residue was triturated with diethyl ether (50 mL×3) to afford compound 1 (100.0 g, 96%) as a colorless solid. $^1$H NMR (400 MHz, DMSO-$d_6$): δ 10.56-9.30 (brs, 2H), 5.60 (m, 1H), 4.50-4.37 (m, 2H), 3.75-3.68 (m, 1H), 3.41-3.32 (m, 1H), 3.10-3.04 (m, 2H), 2.25-2.02 (m, 4H).

Synthesis of 1-(tert-butyl) 2-methyl (2S,4R)-4-hydroxypyrrolidine-1,2-dicarboxylate (2)

To a stirred solution of compound 1 (100.0 g, 552 mol) in DCM (1 L), $Et_3N$ (230 mL, 1.65 mol) was added at 0° C. and stirred for 15 min. $Boc_2O$ (152 mL, 662 mmol) was added drop wise to the reaction mixture at 0° C. over 30 min and stirred at room temperature for 16 h. After consumption of the starting material (by TLC), the reaction mixture was quenched with ice-cold water (500 mL) and extracted with DCM (3×300 mL). The combined organic layer was washed with brine (150 mL), dried over $Na_2SO_4$ and concentrated under reduced pressure. The residue was purified by column chromatography to afford compound 2 (123.0 g, 91%) as a colorless solid. $^1$H NMR (400 MHz, DMSO-$d_6$): δ 5.09 (d, J=3.6 Hz, 1H), 4.29-4.15 (m, 2H), 3.64 (m, 3H), 3.45-3.21 (m, 2H), 2.14-2.09 (m, 1H), 1.95-1.82 (m, 1H), 1.39-1.32 (m, 9H).

Synthesis of 1-(tert-butyl) 2-methyl (2S,4R)-4-((tert-butyldimethylsilyl)oxy)pyrrolidine-1,2-dicarboxylate (3)

To a stirred solution of compound 2 (18.0 g, 73.4 mmol) in DCM (200 mL), imidazole (9.9 g, 146 mmol) and TBDMS-Cl (14.3 g, 95.5 mol) was added and stirred at room temperature for 16 h. After consumption of the starting material (by TLC), the reaction mixture was quenched with saturated aqueous NaHCO$_3$ (250 mL) and extracted with DCM (3×250 mL). The combined organic layer was washed with brine (100 mL), dried over Na$_2$SO$_4$ and concentrated under reduced pressure. The residue was purified by column chromatography to afford compound 3 (23.0 g, 87%) as yellow oil. $^1$H NMR (400 MHz, DMSO-d$_6$): δ 4.43-4.40 (m, 1H), 4.21-4.18 (m, 1H), 3.63-3.60 (m, 3H), 3.44 (m, 1H), 3.33-3.21 (m, 1H), 2.16-2.04 (m, 2H), 2.04-1.90 (m, 1H), 1.38-1.32 (m, 9H), 0.85 (m, 9H), 0.06 (m, 6H).

Synthesis of tert-butyl (4R,7R)-7-((tert-butyldimethylsilyl)oxy)-2-(4-methoxybenzyl)-1-oxo-2,5-diazaspiro[3.4]octane-5-carboxylate (4a & 4b)

To a stirred solution of compound 3 (40.0 g, 111 mmol) in THF (300 mL), LiHMDS (1M solution in THF, 334 mL, 334 mmol) was added at −78° C. and stirred at room temperature for 30 min 2-((4-methoxybenzyl) amino) acetonitrile (39.0 g, 222 mmol) was added to the reaction mixture at −50° C. and stirred at room temperature for 2 h. After consumption of the starting material (by TLC), the reaction mixture was quenched with saturated NH$_4$Cl solution (300 mL) and extracted with EtOAc (3×300 mL). The combined organic layer was washed with brine (100 mL), dried over Na$_2$SO$_4$ and concentrated under reduced pressure. The residue was purified by column chromatography to afford diastereomers compound 4a (29.0 g, 54.7%) and compound 4b (10.0 g, 18.8%) as thick oil.

Synthesis of tert-butyl (7R)-7-hydroxy-2-(4-methoxybenzyl)-1-oxo-2,5-diazaspiro[3.4]octane-5-carboxylate (5a)

To a solution of compound 4a (18.5 g, 38.8 mmol) in THF (300 mL), TBAF (1M solution in THF, 58.2 mL, 58.2 mmol) was added drop wise at 0° C. and stirred at room temperature for 16 h. After consumption of the starting material (by TLC), the reaction mixture was quenched with ice-cold water (150 mL) and extracted with EtOAc (2×200 mL). The combined organic layer was washed with NaHCO$_3$ solution (100 mL) and brine (50 mL), dried over Na$_2$SO$_4$ and concentrated under reduced pressure. The residue was purified by column chromatography using 5% MeOH/DCM to afford compound 5a (13.5 g, 96%) as yellow oil. $^1$H NMR (400 MHz, DMSO-d$_6$): δ 7.26-7.13 (m, 2H), 6.91-6.85 (m, 2H), 5.09-5.03 (m, 1H), 4.56 (m, 1H), 4.20 (m, 1H), 3.94 (d, J=15.0 Hz, 1H), 3.74 (m, 3H), 3.56-3.37 (m, 1H), 2.24 (m, 1H), 2.10-1.95 (m, 1H), 1.43-1.32 (m, 9H).

Synthesis of tert-butyl (7R)-2-(4-methoxybenzyl)-1-oxo-7-(tosyloxy)-2,5-diazaspiro[3.4]octane-5-carboxylate (6a)

To a solution of compound 5a (13.5 g, 37.3 mmol) in DCM (200 mL), Et$_3$N (7.5 mL, 74.9 mmol) was added followed by addition of tosyl chloride (10.6 g, 56 mmol) portion wise at 0° C. and stirred at room temperature for 16 h. After consumption of the starting material (by TLC), the reaction mixture was quenched with ice-cold water (250 mL) and extracted with DCM (4×250 mL). The combined organic layer was washed with NaHCO$_3$ solution (300 mL) and brine (100 mL), dried over Na$_2$SO$_4$ and concentrated under reduced pressure. The residue was purified by column chromatography using 1% MeOH/DCM to afford compound 6a (15.6 g, 81%) as yellow oil. $^1$H NMR (400 MHz, DMSO-d$_6$) δ 7.83 (m, 2H), 7.49 (m, 2H), 7.17 (m, 2H), 6.90 (m, 2H), 5.06-4.98 (m, 1H), 4.56 (m, 1H), 4.37 (m, 1H), 4.17 (m, 1H), 3.92 (m, 1H), 3.74 (m, 1H), 3.57-3.38 (m, 3H), 3.12-3.06 (m, 1H), 3.02 (m, 1H), 2.43 (s, 3H), 2.30-2.18 (m, 1H), 1.35 (m, 9H).

Synthesis of tert-butyl (7S)-7-cyano-2-(4-methoxybenzyl)-1-oxo-2,5-diazaspiro[3.4]octane-5-carboxylate (7a)

To a stirred solution of compound 6a (15.5 g, 30.0 mmol) in DMSO (150 mL), NaCN (3.5 g, 72 mmol) was added and stirred at 80° C. for 16 h. After consumption of the starting material (by TLC), the reaction mixture was quenched with water (500 mL) and extracted with diethyl ether (4×250 mL). The combined organic layer was washed with brine (100 mL), dried over Na$_2$SO$_4$ and concentrated under reduced pressure. The residue was purified by column chromatography using 1% MeOH/DCM to afford compound 7a (8.9 g, 80.2%) as yellow oil. $^1$H NMR (400 MHz, DMSO-d$_6$): δ 7.23 (m, 2H), 6.92 (m, 2H), 4.56 (m, 1H), 4.01 (m, 1H), 3.74 (s, 3H), 3.63-3.42 (m, 4H), 3.32-3.22 (m, 3H), 1.42 (m, 9H).

Synthesis of (7S)-2-(4-methoxybenzyl)-1-oxo-2,5-diazaspiro[3.4]octane-7-carbonitrile (8a)

To a stirred solution of compound 7a (8.3 g, 22.4 mmol) in DCM (200 mL), TFA (50 mL) was added 0° C. and stirred for 3 h. After consumption of the starting material (by TLC), the reaction mixture was concentrated under reduced pressure. The residue was triturated with Et$_2$O, filtered and dried to afford compound 8a (7.2 g, crude).

Synthesis of (7S)-5-isobutyryl-2-(4-methoxybenzyl)-1-oxo-2,5-diazaspiro[3.4]octane-7-carbonitrile (9a)

To a stirred solution of compound 8a (7.0 g, 25.8 mmol) in DCM (200 mL), Et$_3$N (7.8 mL, 77.5 mmol) and isobutryl chloride (3.9 mL, 36.1 mmol) was added at 0° C. and stirred at room temperature for 2 h. After consumption of the starting material (by TLC), the reaction mixture was quenched with water (150 mL) and extracted with DCM (2×250 mL). The combined organic layer was washed with brine (50 mL), dried over Na$_2$SO$_4$ and concentrated under reduced pressure. The residue was purified by column chromatography using 1% MeOH/DCM to afford compound 9a (7.3 g, 83%) as thick oil. LCMS: 342 (M+1).

Synthesis of (7S)-5-isobutyryl-1-oxo-2,5-diazaspiro[3.4]octane-7-carbonitrile (10a)

To a stirring solution of compound 9a (2.0 g, 5.83 mmol) in CH$_3$CN (20 mL), ceric ammonium nitrate (12.8 g, 23.4 mmol) in water (20 mL) was added portion wise at 0° C. and stirred at same temperature for 30 min After consumption of the starting material (by TLC), the reaction mixture was quenched with NaHCO$_3$ solution (50 mL) and extracted with EtOAc (2×50 mL). The combined organic layer was washed with brine (50 mL), dried over $Na_2SO_4$ and concentrated under reduced pressure. The residue was purified by column chromatography using 90-100% EtOAc to afford compound 10a (0.22 g, 18%) as thick oil. $^1$H NMR (400 MHz, DMSO-$d_6$): δ 7.97 (s, 1H), 3.89 (dd, J=10.6, 2.8 Hz, 1H), 3.79 (dd, J=10.6, 6.2 Hz, 1H), 3.62-3.47 (m, 2H), 3.23 (d, J=4.7 Hz, 1H), 2.66 (m, 2H), 2.38 (dd, J=13.3, 6.6 Hz, 1H), 0.99 (m, 6H).

Synthesis of (4R,7S)-5-isobutyryl-1-oxo-2,5-diazaspiro[3.4]octane-7-carboxamide (AT)

To a stirred solution of compound 10a (0.5 g, 2.26 mmol) in EtOH (20 mL), aqueous $NH_4OH$ (20 mL) was added followed by addition of aqueous $H_2O_2$ (30%, 0.41 mL) drop wise at 0° C. and allowed to stir at room temperature for 3 h. After consumption of the starting material (by TLC), the reaction mixture was concentrated under reduced pressure. The residue was purified by column chromatography using 15-25% MeOH/DCM to afford AT (160 mg, 30%) as off-white solid. $^1$H NMR (400 MHz, DMSO-$d_6$): δ 7.80 (s, 1H), 7.53 (s, 1H), 6.99 (s, 1H), 3.73-3.64 (m, 2H), 3.55 (d, J=4.8 Hz, 1H), 3.05 (d, J=4.8 Hz, 1H), 2.97-2.94 (m, 1H), 2.67-2.40 (m, 1H), 2.32-2.26 (m, 2H), 1.00 (dd, J=13.9, 6.7 Hz, 6H). LCMS (ESI): m/z 240 [M$^+$+1]. HPLC: 99.5%.

Synthesis of AU, AV, AW & AX and Synthesis of AY-1, AY-2, AY-3 & AY-4:

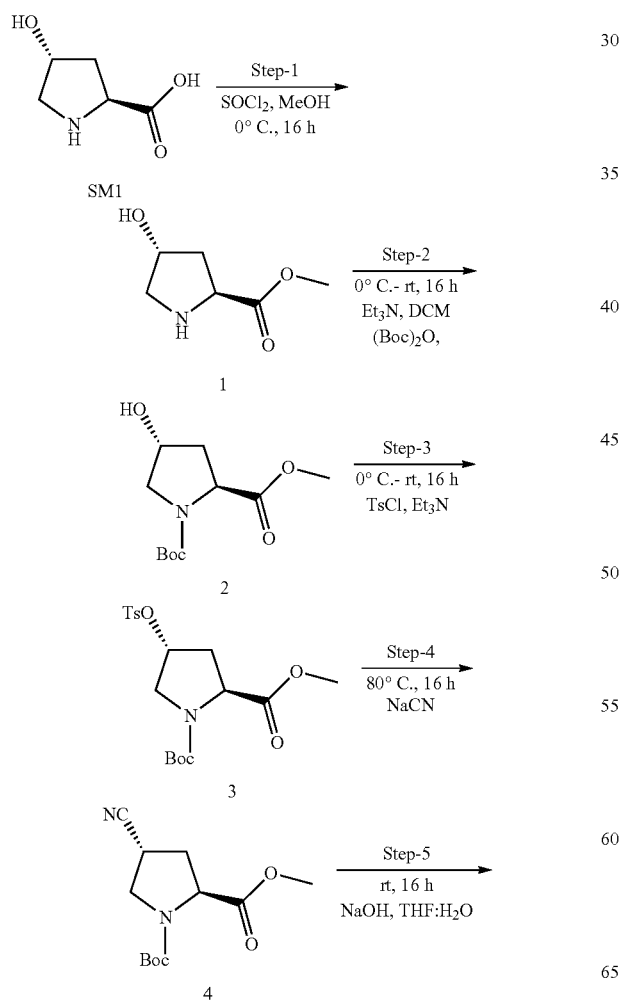

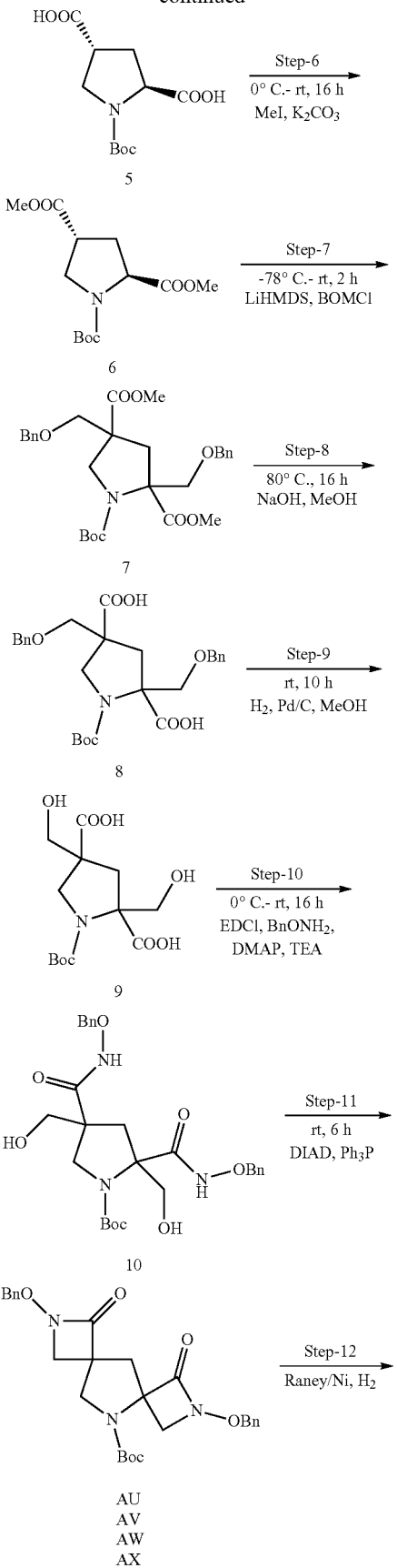

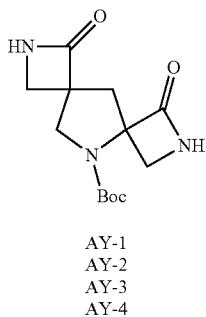

AY-1
AY-2
AY-3
AY-4

Synthesis of methyl (2S,4R)-4-hydroxypyrrolidine-2-carboxylate (1)

To a stirred solution of (2S,4R)-4-hydroxypyrrolidine-2-carboxylic acid (75.0 g, 572 mmol) in MeOH (800 mL), SOCl$_2$ (75 mL) was added at 0° C. and the reaction mixture was stirred at room temperature for 16 h. After consumption of the starting material (by TLC), the reaction mixture was concentrated under reduced pressure. The residue was triturated with Et$_2$O (50 mL×3), filtered, dried to afford 1 (100.0 g, 96%) as a colorless solid. $^1$H NMR (400 MHz, DMSO-d$_6$): δ 10.56-9.30 (brs, 2H), 5.60 (m, 1H), 4.50-4.37 (m, 2H), 3.75-3.68 (m, 1H), 3.41-3.32 (m, 1H), 3.10-3.04 (m, 2H), 2.25-2.02 (m, 4H).

Synthesis of 1-(tert-butyl) 2-methyl (2S,4R)-4-hydroxypyrrolidine-1,2-dicarboxylate (2)

To a stirred solution of compound 1 (100.0 g, 552 mol) in DCM (1 L), Et$_3$N (230 mL, 1.65 mol) was added at 0° C. and stirred for 15 min. Boc$_2$O (152 mL, 662 mmol) was added drop wise at 0° C. over a period of 30 minutes. The reaction mixture was stirred at room temperature for 16 h. After consumption of the starting material (by TLC), the reaction mixture was quenched with ice-cold water (500 mL) and extracted with DCM (3×300 mL). The combined organic layer was washed with brine (150 mL), dried over Na$_2$SO$_4$ and concentrated under reduced pressure. The residue was purified by column chromatography using 40-50% EtOAc/hexane to afford compound 2 (123.0 g, 91%) as a colorless solid. $^1$H NMR (400 MHz, DMSO-d$_6$): δ 5.09 (d, J=3.6 Hz, 1H), 4.29-4.15 (m, 2H), 3.64 (m, 3H), 3.45-3.21 (m, 2H), 2.14-2.09 (m, 1H), 1.95-1.82 (m, 1H), 1.39-1.32 (m, 9H).

Synthesis of 1-(tert-butyl) 2-methyl (2S,4R)-4-(tosyloxy)pyrrolidine-1,2-dicarboxylate (3)

To a stirred solution of compound 2 (123.0 g, 502 mmol) in DCM (1 L), Et$_3$N (140 mL, 1.00 mol) was added followed by addition of tosyl chloride (124.0 g, 652 mmol) portion wise at 0° C. and stirred at room temperature for 16 h. After consumption of the starting material (by TLC), the reaction mixture was quenched with ice-cold water (250 mL) and extracted with DCM (4×250 mL). The combined organic layer was washed with NaHCO$_3$ solution (300 mL) and brine (100 mL), dried over Na$_2$SO$_4$ and concentrated under reduced pressure. The residue was purified by column chromatography by using 10-20% EtOAc/hexane to afford compound 3 (190.0 g, 95%) as yellow oil. $^1$H NMR (400 MHz, DMSO-d$_6$) δ 7.82 (m, 2H), 7.54-7.46 (m, 2H), 5.07 (d, J=3.9 Hz, 1H), 4.23 (m, 1H), 3.63 (m, 3H), 3.50-3.40 (m, 2H), 2.43 (s, 3H), 2.20-2.04 (m, 1H), 1.99 (s, 1H), 1.33 (m, 9H).

Synthesis of 1-(tert-butyl) 2-methyl (2S,4R)-4-cyanopyrrolidine-1,2-dicarboxylate (4)

To a stirred solution of compound 3 (190.0 g, 476 mmol) in DMSO (700 mL), NaCN (51.3 g, 1.04 mol) was added and stirred at 80° C. for 16 h. After consumption of the starting material (by TLC), the reaction mixture was cooled and quenched with water (500 mL) and then extracted with diethyl ether (4×250 mL). The combined organic layer was washed with brine (100 mL), dried over Na$_2$SO$_4$ and concentrated under reduced pressure. The residue was purified by column chromatography using 15-20% EtOAc/hexane to afford compound 4 (36.0 g, 30%) as a yellow oil. $^1$H NMR (400 MHz, DMSO-d$_6$): δ 4.36-4.22 (m, 1H), 3.82-3.62 (m, 3H), 3.48-3.40 (m, 3H), 2.68-2.40 (m, 1H), 2.12-2.04 (m, 1H), 1.40 (m, 9H).

Synthesis of (2S,4R)-1-(tert-butoxycarbonyl)pyrrolidine-2,4-dicarboxylic acid (5)

To a stirring solution of compound 4 (30.0 g, 118 mmol) in THF (150 mL), NaOH (18.9 g, 472 mmol) in water (150 mL) was added and stirred for 16 h. After consumption of the starting material (by TLC), the reaction mixture was neutralized with 1N HCl solution and acidified with citric acid to pH-4-5, and then extracted with EtOAc (3×250 mL). The combined organic layer was washed with brine (100 mL), dried over Na$_2$SO$_4$ and concentrated under reduced pressure to afford compound 5 (21.0 g, crude) as a white solid. The crude was used as such for the next step without further purification. $^1$H NMR (400 MHz, DMSO-d$_6$): δ 12.57 (s, 1H), 4.19-3.96 (m, 2H), 3.62-3.40 (m, 1H), 3.50-3.35 (m, 1H), 3.07-3.0 (m, 1H), 2.37-2.15 (m, 1H), 2.05-2.0 (m, 1H), 1.35 (m, 9H).

Synthesis of 1-(tert-butyl) 2,4-dimethyl (2S,4R)-pyrrolidine-1,2,4-tricarboxylate (6)

To a stirred solution of compound 5 (21.0 g, 81.0 mmol) in DMF (200 mL), K$_2$CO$_3$ (44.7 g, 324 mmol) was added followed by addition of CH$_3$I (17.6 mL, 283 mmol) at 0° C. and the reaction mixture was stirred at room temperature for 16 h. After consumption of the starting material (by TLC), the reaction mixture was quenched with water (250 mL) and extracted with diethyl ether (2×250 mL). The combined organic layer was washed with brine (50 mL), dried over Na$_2$SO$_4$ and concentrated under reduced pressure. The residue was purified by column chromatography using 20% EtOAc/hexane to afford compound 6 (20.2 g, 87%) as an oil. $^1$H NMR (400 MHz, DMSO-d$_6$): δ 4.31-4.17 (m, 1H), 3.66 (m, 6H), 3.48-3.40 (m, 1H), 3.22-3.15 (m, 1H), 2.40-2.35 (m, 1H), 2.11-2.08 (m, 1H), 1.36 (m, 9H).

Synthesis of 1-(tert-butyl) 2,4-dimethyl 2,4-bis((benzyloxy)methyl)pyrrolidine-1,2,4-tricarboxylate (7)

To a stirred solution of compound 6 (24.0 g, 83.6 mmol) in THF (200 mL), LiHMDS (1M solution in THF, 250 mL, 250 mmol) was added at −78° C. and warmed to 0° C. for 30 min. The reaction mixture was cooled to −50° C. and benzyloxymethyl chloride (29.1 mL, 209 mmol) was added drop wise at −50° C. and stirred at room temperature for 2 h. After consumption of the starting material (by TLC), the reaction mixture was quenched with saturated NH$_4$Cl solution (300 mL) and extracted with EtOAc (3×300 mL). The combined organic layer was washed with brine (100 mL), dried over Na$_2$SO$_4$ and concentrated under reduced pressure. The residue was purified by column chromatography using 15% EtOAc/hexane to afford compound 7 (21.0 g, 54%) as thick oil.

Synthesis of 2,4-bis((benzyloxy) methyl)-1-(tert-butoxycarbonyl) pyrrolidine-2,4-di carboxylic acid (8)

To a stirring solution of compound 7 (21.0 g, 39.8 mmol) in MeOH (150 mL), NaOH (6.37 g, 159 mmol) in water (70 mL) was added and stirred at 80° C. for 16 h. After consumption of the starting material (by TLC), the reaction mixture was neutralized with 1N HCl solution and acidified with citric acid to pH-4-5, extracted with EtOAc (3×100 mL). The combined organic layer was washed with brine (100 mL), dried over Na$_2$SO$_4$ and concentrated under reduced pressure. The residue was purified by trituration with n-pentane to afford compound 8 (19.0 g, 96%) as a colorless solid.

Synthesis of 1-(tert-butoxycarbonyl)-2,4-bis(hydroxymethyl)pyrrolidine-2,4-dicarboxylic acid (9)

To a stirring solution of compound 8 (19.0 g, 38.0 mmol) in MeOH (150 mL), 50% wet 10% Pd/C (5.0 g) was added at room temperature and stirred under H$_2$ atmosphere for 10 h. After consumption of the starting material (by TLC), the reaction mixture was filtered through a pad of celite and washed with MeOH (50 mL). The filtrate was concentrated under reduced pressure. The residue was purified by trituration with n-pentane to afford compound 9 (10.6 g, 87%) as a colorless solid.

Synthesis of tert-butyl 2,4-bis((benzyloxy)carbamoyl)-2,4-bis(hydroxymethyl)pyrrolidine-1-carboxylate (10)

To a stirred solution of compound 9 (4.0 g, 12.5 mmol) in DCM (120 mL), O-benzylhydroxylamine hydrochloride (4.98 g, 31.3 mmol), EDC (5.98 g, 31.3 mmol), DMAP (3.03 g, 25.0 mmol) and Et$_3$N (5.2 mL, 37.6 mmol) were added at 0° C. under nitrogen atmosphere and stirred at room temperature for 16 h. After consumption of the starting material (by TLC), the reaction mixture was quenched with saturated KH$_2$PO$_4$ solution (150 mL) and extracted with EtOAc (2×150 mL). The combined organic layer was washed with brine (50 mL), dried over Na$_2$SO$_4$ and concentrated under reduced pressure. The residue was purified by column chromatography by eluting with 5% MeOH/DCM to afford compound 10 (4.2 g, 63%) as thick oil. $^1$H NMR (400 MHz, DMSO-d6): δ 11.2 (brs, 1H), 10.6 (brs, 1H), 7.47-7.27 (m, 10H), 5.10-5.07 (m, 2H), 4.85-4.69 (m, 2H), 4.08-3.84 (m, 2H), 3.83-3.58 (m, 2H), 3.53 (m, 2H), 3.32 (s, 2H), 2.46-2.29 (m, 2H), 1.43-1.27 (m, 9H).

Synthesis of tert-butyl 2,8-bis(benzyloxy)-1,7-dioxo-2,8,10-triazadispiro[3.1.36.24]undecane-10-carboxylate (AU, AV, AW & AX)

To a stirred solution of triphenylphosphine (24.7 g, 94.5 mmol) in THF (100 mL), DIAD (19.0 g, 94.5 mmol) was added drop wise at room temperature under nitrogen atmosphere and stirred for 15 minutes. A solution of compound 10 (10.0 g, 18.9 mmol) in THF (50 mL) was added drop wise and allowed to stir at room temperature for 6 h. After consumption of the starting material (by TLC), the reaction mixture was quenched with water (150 mL) and extracted with EtOAc (2×200 mL). The combined organic layer was washed with brine (50 mL), dried over Na$_2$SO$_4$ and concentrated under reduced pressure. The residue was purified by column chromatography to afford mixture of AU, AV, AW & AX (4.2 g, 63%) as a colorless solid. The mixture was purified by preparative HPLC followed by chiral HPLC to afford AU (70 mg), AV (75 mg), AW (145 mg) and AX (130 mg).

AU: $^1$H NMR (400 MHz, DMSO-d$_6$) δ 7.42-7.36 (m, J=2.8 Hz, 10H), 4.92 (d, J=15.9 Hz, 4H), 3.67-3.49 (m, 6H), 2.37-2.34 (m, 1H), 2.12-2.08 (m, 1H), 1.38 (d, J=19.3 Hz, 9H). LCMS (ESI): m/z 438 [M$^+$-Boc+2Na]. HPLC: 99.93%.

AV: $^1$H NMR (400 MHz, DMSO-d$_6$) δ 7.42-7.36 (m, J=2.8 Hz, 10H), 4.95 (d, J=15.9 Hz, 4H), 3.67-3.49 (m, 6H), 2.37-2.34 (m, 1H), 2.12-2.08 (m, 1H), 1.38 (d, J=19.3 Hz, 9H). LCMS (ESI): m/z 438 [M$^+$-Boc+2Na]. HPLC: 99.79%.

AW: $^1$H NMR (400 MHz, DMSO-d$_6$) δ 7.47-7.36 (m, J=2.8 Hz, 10H), 4.92 (d, J=15.9 Hz, 4H), 3.67-3.49 (m, 6H), 2.27 (d, J=7.6 Hz, 2H), 1.38 (d, J=19.3 Hz, 9H). LCMS (ESI): m/z 438 [M$^+$-Boc+2Na]. HPLC: 98.49%.

AX: $^1$H NMR (400 MHz, DMSO-d$_6$) δ 7.40 (d, J=7.5 Hz, 10H), 4.95-4.85 (m, 4H), 3.59-3.48 (m, 6H), 2.24 (s, 2H), 1.36 (d, J=18.6 Hz, 9H). LCMS (ESI): m/z 438 [M$^+$-Boc+2Na]. HPLC: 99.8%.

AY-2: $^1$H NMR (400 MHz, DMSO-d6) δ 7.91 (t, J=8.1 Hz, 2H), 3.64-3.46 (m, 2H), 3.29-3.13 (m, 4H), 2.43 (d, J=16.4 Hz, 2H), 1.39 (d, J=10.2 Hz, 9H). LCMS (ESI): m/z 226 [M-56]. HPLC: 99.46%.

AY-3: $^1$H NMR (400 MHz, DMSO-d$_6$) δ 7.96 (d, J=19.5 Hz, 2H), 3.68 (dd, J=11.0, 5.1 Hz, 1H), 3.44-3.23 (m, 5H), 2.30 (dd, J=15.4, 12.9 Hz, 2H), 1.38 (d, J=9.8 Hz, 9H). LCMS (ESI): m/z 226 [M-56]. HPLC: 99.67%.

AY-4: $^1$H NMR (400 MHz, DMSO-d$_6$) δ 7.96 (d, J=19.5 Hz, 2H), 3.68 (dd, J=11.2, 5.0 Hz, 1H), 3.44-3.23 (m, 5H), 2.30 (dd, J=15.4, 12.9 Hz, 2H), 1.38 (d, J=9.7 Hz, 9H). LCMS (ESI): m/z 226 [M-56]. HPLC: 99.72%.

Synthesis of BA & BB:

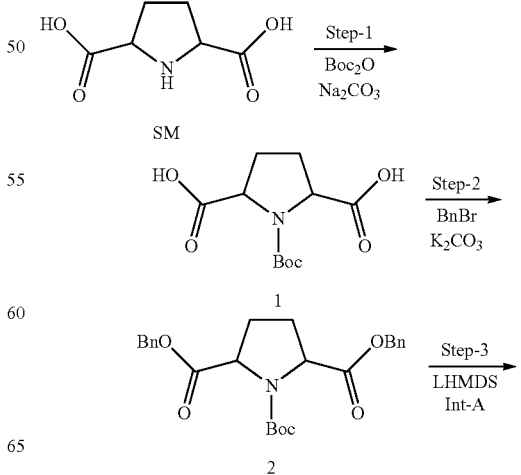

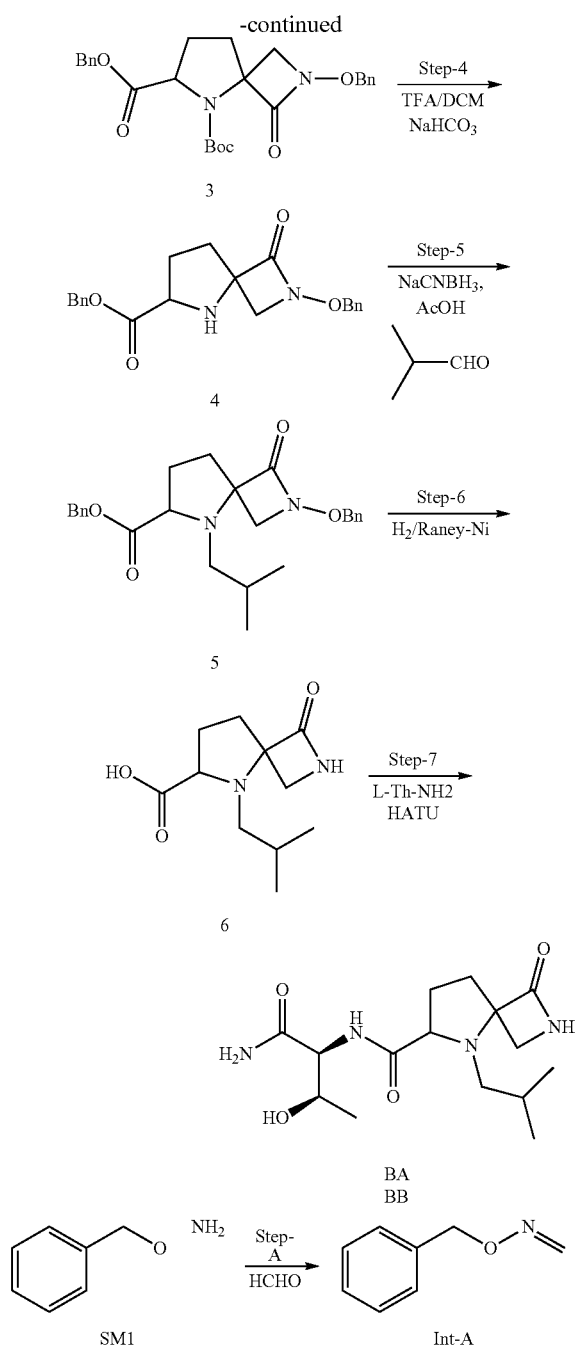

Synthesis of benzyl 2-(benzyloxy)-1-oxo-2,5-diazaspiro[3.4]octane-6-carboxylate (4)

The experimental procedure for the synthesis of compound 4 has been captured under the synthesis of AO & AP (as compound 4).

Synthesis of benzyl 2-(benzyloxy)-5-isobutyl-1-oxo-2,5-diazaspiro[3.4]octane-6-carboxylate (5)

To a stirring solution of compound 4 (2 g, 5.46 mmol) in MeOH (20 mL) were added isobutyraldehyde (2 mL, 21.8 mmol) and AcOH (3 mL) at RT. After being stirred for 1 h, NaCNBH$_3$ (1.37 mg, 21.8 mmol) was added in four lots with 40 minutes interval. The reaction mixture was stirred for 16 h. After consumption of the starting material (by TLC), volatiles were evaporated under reduced pressure. Crude syrup was diluted with ice water (50 mL) and extracted with EtOAc (2×100 mL). Organic layer was basified with aqueous NaHCO$_3$ (20 mL) and washed brine (20 mL). The separated organic layer was dried over Na$_2$SO$_4$ and concentrated under reduced pressure. Obtained crude material was purified by column chromatography eluting with 30% EtOAc/n-hexane to afford compound 5 (1.35 g, 58%) as thick syrup.

Another batch was also performed on 1 g scale and obtained 450 mg of compound 5.

$^1$H NMR (500 MHz, DMSO-d$_6$) δ 7.49-7.31 (m, 10H), 5.22-5.15 (m, 1H), 5.13-5.08 (m, 1H), 4.99-4.89 (m, 2H), 3.89 (d, J=11.0 Hz, 1H), 3.49 (d, J=7.0 Hz, 1H), 3.42 (d, J=11.0 Hz, 1H), 2.26-2.09 (m, 3H), 2.08-1.96 (m, 1H), 1.91-1.75 (m, 2H), 1.65-1.58 (m, 1H), 0.75 (t, J=7.2 Hz, 6H). LCMS (m/z): 423.1 [M$^+$+1].

Synthesis of 5-isobutyl-1-oxo-2,5-diazaspiro[3.4]octane-6-carboxylic acid (6)

To a stirring solution of compound 5 (1.8 g, 4.26 mmol) in MeOH (20 mL) was added Raney Ni (10 g) at RT and stirred under H$_2$ atmosphere (balloon pressure) for 16 h. After consumption of the starting material (by TLC), the reaction mixture was filtered through a pad of celite and the pad was washed with MeOH (30 mL). Obtained filtrate was concentrated under reduced pressure to afford crude solid, which was washed with 40% CH$_2$Cl$_2$/Et$_2$O and dried under vacuum to obtain compound 6 (800 mg, 83%) as off white solid. $^1$H NMR (400 MHz, DMSO-d$_6$) δ 7.27 (br s, 1H), 4.63 (br s, 1H), 3.56 (br d, J=11.9 Hz, 1H), 3.28 (br s, 1H), 3.05 (br d, J=11.3 Hz, 1H), 2.44-2.25 (m, 2H), 2.17 (br d, J=10.4 Hz, 1H), 2.08-1.96 (m, 1H), 1.89 (br s, 1H), 1.80-1.60 (m, 2H), 0.85 (dd, J=6.2, 19.1 Hz, 6H). LCMS (ESI): m/z 227.1 [M$^+$+1].

Synthesis of N-((2S,3R)-1-amino-3-hydroxy-1-oxobutan-2-yl)-5-isobutyl-1-oxo-2,5-diazaspiro[3.4]octane-6-carboxamide (BA, BB)

To a solution of compound 6 (800 mg, 3.53 mmol) in DMF (4 mL) were added HATU (1.61 g, 4.24 mmol) at RT under nitrogen atmosphere and stirred for 10 minutes. Then, L-Th—NH$_2$ (501 mg, 4.24 mmol) and DIPEA (1.0 mL, 5.31 mmol) were added and continued stirring at RT for 8 h. After consumption of the starting material (by TLC), the reaction mixture was quenched with ice water (10 mL) and stirred for 10 minutes. Volatiles were removed under reduced pressure. Obtained crude material was purified by column chromatography by eluting 5-8% MeOH/CH$_2$Cl$_2$ to obtain product (1 g), which were further purified by reverse phase preparative HPLC to obtain BA (270 mg) and BB (240 mg) as white solids.

BA: $^1$H NMR (400 MHz, DMSO-d$_6$) δ 7.37 (s, 1H), 7.33-7.23 (m, 2H), 7.04 (br s, 1H), 4.95 (d, J=5.2 Hz, 1H), 4.15 (dd, J=3.2, 8.9 Hz, 1H), 4.09-3.95 (m, 1H), 3.40 (br d, J=12.5 Hz, 2H), 3.17 (dd, J=2.6, 12.4 Hz, 1H), 2.46 (d, J=10.8 Hz, 1H), 2.31 (dd, J=4.6, 11.9 Hz, 1H), 2.14-1.99 (m, 3H), 1.89-1.72 (m, 2H), 1.03 (d, J=6.3 Hz, 3H), 0.99 (d, J=6.6 Hz, 3H), 0.85 (d, J=6.6 Hz, 3H). LCMS (ESI): m/z 327.2 [M$^+$+1]. HPLC: 98.89%. Chiral HPLC: 95.15%. Column: CHIRALPAK IC (250*4.6 mm, 5 μm); Mobile Phase A: 0.1% DEA in n-hexane; Mobile Phase B: DCM:MeOH (50:50); A:B:: 80:20; Flow rate: 1.0 mL/min; Retention time: 14.041. SOR: −27.36 (c=1 in H$_2$O).

BB: $^1$H NMR (400 MHz, DMSO-d$_6$) δ 7.39 (br s, 1H), 7.34-7.24 (m, 2H), 7.06 (br s, 1H), 5.01 (d, J=3.5 Hz, 1H), 4.17-4.00 (m, 2H), 3.52-3.36 (m, 2H), 3.22-3.13 (m, 1H), 2.42-2.27 (m, 2H), 2.24-2.02 (m, 2H), 2.01-1.91 (m, 1H), 1.88-1.73 (m, 2H), 1.06 (d, J=6.1 Hz, 3H), 0.97 (d, J=6.6 Hz, 3H), 0.86 (d, J=6.6 Hz, 3H). LCMS (ESI): m/z 327.2 [M$^+$+1]. HPLC: 97.14%. Chiral HPLC: 98.24%. Column: CHIRALPAK IC (250*4.6 mm, 5 µm); Mobile Phase A: 0.1% DEA in n-hexane; Mobile Phase B: DCM:MeOH (50:50); A:B:: 80:20; Flow rate: 1.0 mL/min. Retention time: 17.837. SOR: 34.08 (c=1 in H$_2$O).

Synthesis of formaldehyde O-benzyl oxime (Int-A):

The experimental procedure for the synthesis Int-A has been captured under AL-1 & AL-2 (as Int-A).

Synthesis of BC & BD:

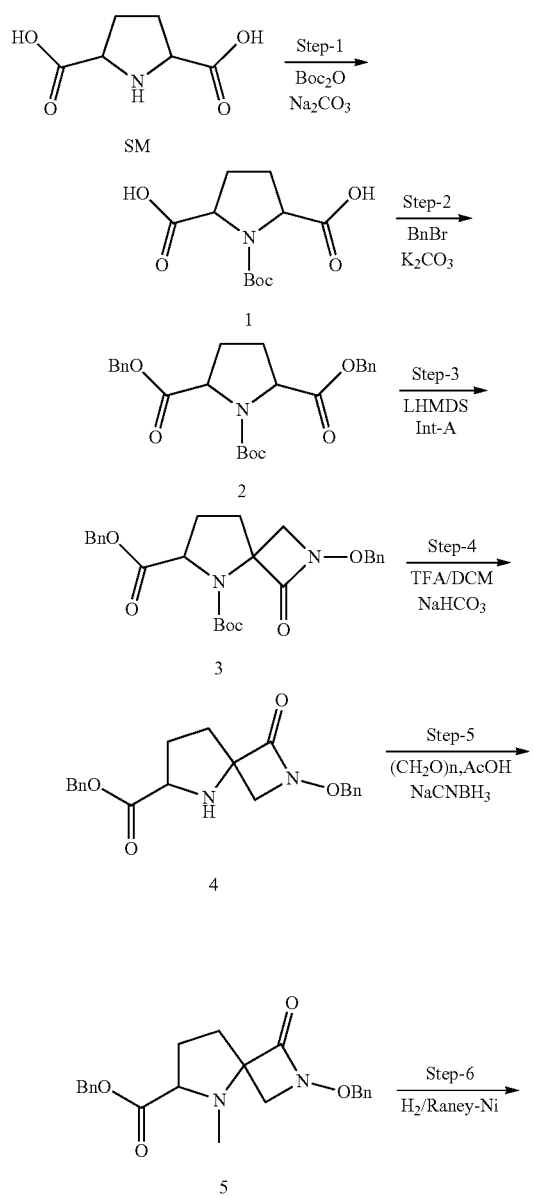

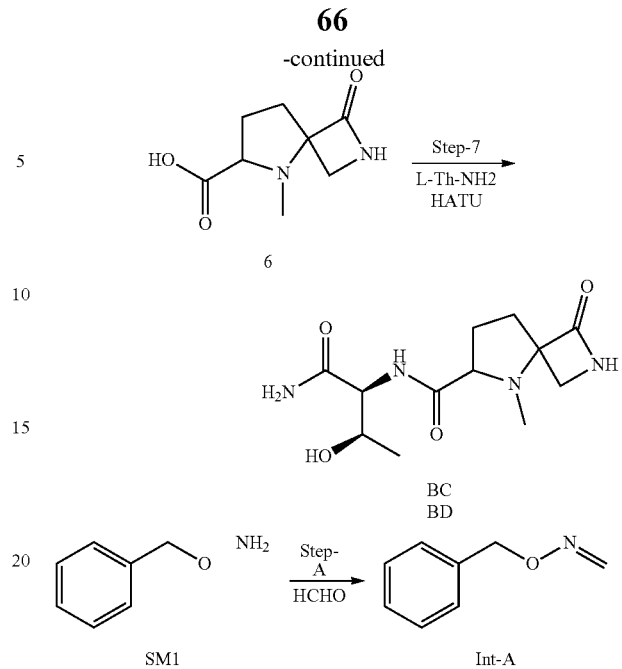

Synthesis of benzyl 2-(benzyloxy)-1-oxo-2,5-diazaspiro[3.4]octane-6-carboxylate (4)

The experimental procedure for the synthesis of compound 4 has been captured under the synthesis of AO & AP (as compound 4).

Synthesis of benzyl 2-(benzyloxy)-5-methyl-1-oxo-2,5-diazaspiro[3.4]octane-6-carboxylate (5)

To a stirring solution of compound 4 (2.5 g, 6.83 mmol) in MeOH (30 mL) were added paraformaldehyde (819 mg, 27.32 mmol) and AcOH (2.5 mL) at RT. After being stirred for 2 h, NaCNBH$_3$ (1.72 g, 27.32 mmol) was added in three lots with 5 minutes interval. The reaction mixture was stirred for 24 h. After consumption of the starting material (by TLC), volatiles were evaporated under reduced pressure. Crude syrup was diluted with ice water (50 mL) and extracted with EtOAc (2×100 mL). Organic layer was washed with NaHCO$_3$ solution (20 mL) and brine solution (20 mL). The separated organic layer was dried over Na$_2$SO$_4$ and distilled to afford compound 5 (2.1 g, 81%) as thick syrup.

Another batch was also performed on 500 mg scale and obtained 400 mg of compound 5.

$^1$H NMR (400 MHz, DMSO-d$_6$) δ 7.48-7.29 (m, 10H), 5.25-5.09 (m, 2H), 5.00-4.88 (m, 2H), 3.95 (d, J=11.0 Hz, 1H), 3.44 (d, J=11.0 Hz, 1H), 3.38 (d, J=6.4 Hz, 1H), 2.28 (s, 3H), 2.17-1.98 (m, 2H), 1.95-1.85 (m, 1H), 1.84-1.75 (m, 1H). LCMS (m/z): 381.1 [M$^+$+1].

Synthesis of 5-methyl-1-oxo-2,5-diazaspiro[3.4] octane-6-carboxylic acid (6)

To a stirring solution of compound 5 (2.5 g, 6.57 mmol) in MeOH (40 mL) was added Raney Ni (10 g) at RT and stirred under H$_2$ atmosphere (balloon pressure) for 24 h. After consumption of the starting material (by TLC), the reaction mixture was filtered through a pad of celite and the pad was washed with hot MeOH (30 mL). Obtained filtrate was concentrated under reduced pressure to afford crude solid, which was washed with 40% CH$_2$Cl$_2$/Et$_2$O and dried under vacuum to obtain compound 6 (1.1 g, 90%) as off white solid.

$^1$H NMR (500 MHz, D$_2$O) δ 4.06-3.70 (m, 2H), 3.65-3.40 (m, 2H), 3.33-3.10 (m, 1H), 2.55 (br s, 2H), 2.41-1.79 (m, 4H). LCMS (ESI): m/z 185.0 [M$^+$+1].

Synthesis of N-((2S,3R)-1-amino-3-hydroxy-1-oxobutan-2-yl)-5-methyl-1-oxo-2,5-diazaspiro[3.4]octane-6-carboxamide (BC, BD)

To a solution of compound 6 (1.1 g, 5.97 mmol) in DMF (6 mL) were added HATU (2.73 g, 7.17 mmol) at RT under nitrogen atmosphere and stirred for 10 minutes. Then, L-Th—NH$_2$ (846 mg, 7.17 mmol) and DIPEA (1.65 mL, 8.96 mmol) were added and continued stirring at RT for 16 h. After consumption of the starting material (by TLC), the reaction mixture was quenched with ice water (10 mL) and stirred for 10 minutes. Volatiles were removed under reduced pressure. Obtained crude material was purified by column chromatography by eluting 5-15% MeOH/CH$_2$Cl$_2$ to obtain product (2 g), which were further purified by reverse phase preparative HPLC followed by normal phase preparative HPLC to obtain BC (180 mg) and BD (160 mg) as off white solids.

BC: $^1$H NMR (400 MHz, DMSO-d$_6$) δ 7.44-7.35 (m, 2H), 7.31 (s, 1H), 7.06 (s, 1H), 5.03 (d, J=5.0 Hz, 1H), 4.11-3.99 (m, 2H), 3.44 (d, J=12.5 Hz, 1H), 3.29 (br s, 1H), 3.23-3.13 (m, 1H), 2.38 (s, 3H), 2.20-2.04 (m, 2H), 2.04-1.95 (m, 1H), 1.83-1.75 (m, 1H), 1.06 (d, J=6.1 Hz, 3H). LCMS (ESI): m/z 285.2 [M$^+$+1]. HPLC: 99.58%. Chiral HPLC: 100.00%. Column: CHIRALPAK IA (250*4.6 mm, 5 μm); Mobile Phase A: 0.1% DEA in n-hexane; Mobile Phase B: DCM:MeOH (50:50); A:B:: 70:30; Flow rate: 1.0 mL/min. Retention time: 9.856.

BD: $^1$H NMR (400 MHz, DMSO-d$_6$) δ 7.48-7.32 (m, 3H), 7.06 (br s, 1H), 4.93 (d, J=5.9 Hz, 1H), 4.17 (dd, J=3.1, 9.0 Hz, 1H), 4.07-4.01 (m, 1H), 3.43 (d, J=12.5 Hz, 1H), 3.29 (br s, 1H), 3.22-3.11 (m, 1H), 2.39 (s, 3H), 2.19-1.98 (m, 3H), 1.84-1.79 (m, 1H), 1.01 (d, J=6.3 Hz, 3H). LCMS (ESI): m/z 285.2 [M$^+$+1]. HPLC: 99.41%. Chiral HPLC: 100.00%. Column: CHIRALPAK IA (250*4.6 mm, 5 μm); Mobile Phase A: 0.1% DEA in n-hexane; Mobile Phase B: DCM:MeOH (50:50); A:B:: 70:30; Flow rate: 1.0 mL/min Retention time: 7.072.

Synthesis of formaldehyde O-benzyl oxime (Int-A):

The experimental procedure for the synthesis Int-A has been captured under AL-1 & AL-2 (as Int-A).

Synthesis of BI, BJ, BK & BL:

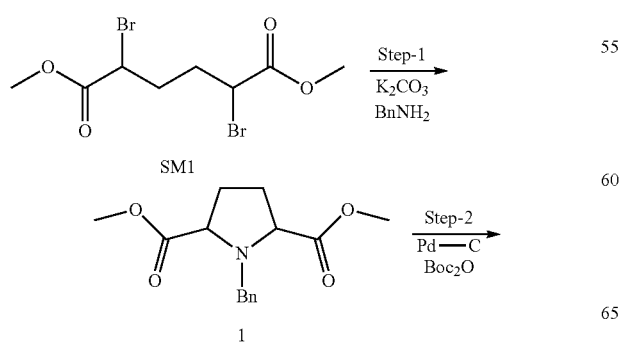

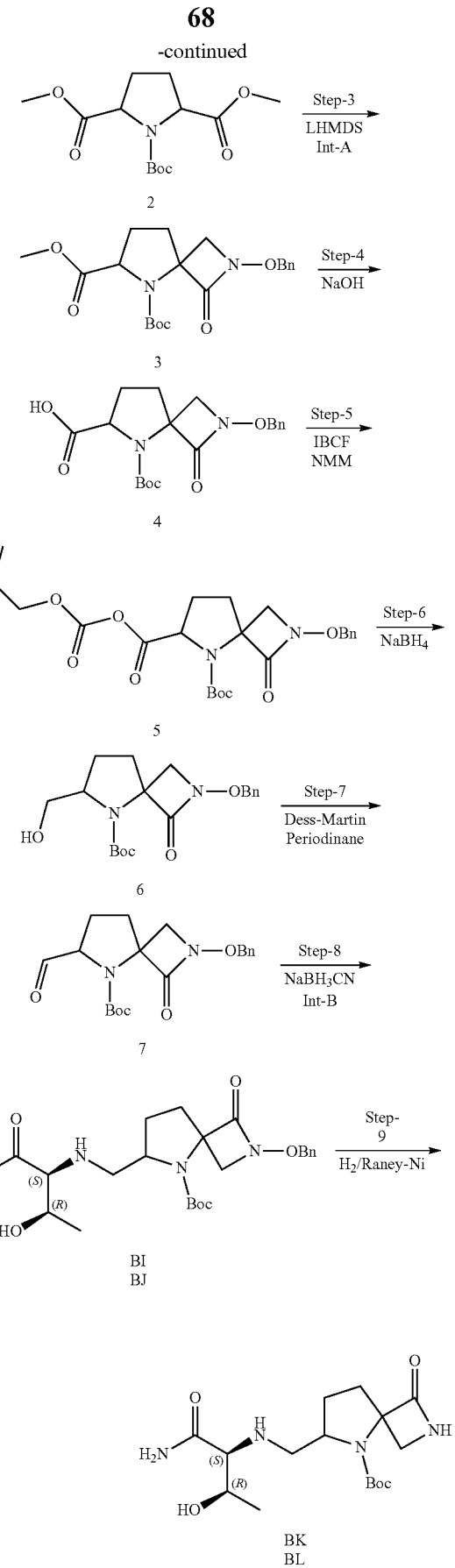

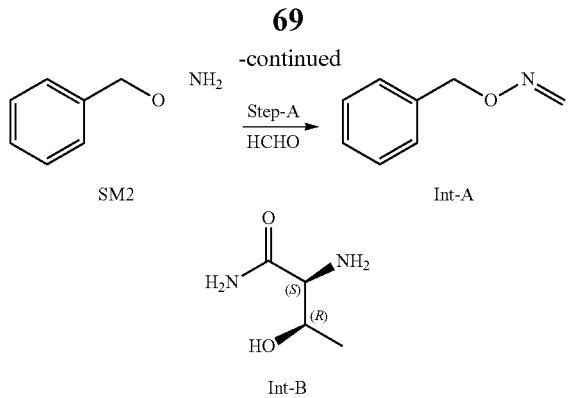

Synthesis of dimethyl 1-benzylpyrrolidine-2,5-dicarboxylate (1)

To a solution of dimethyl 2,5-dibromohexanedioate (SM) (100 g, 0.301 mol) in toluene and water (400 mL, 3:1) were added $K_2CO_3$ (49.88 g, 0.361 mol) and benzylamine (32.23 g, 0.301 mol). The reaction mixture was heated to 80° C. under nitrogen atmosphere and stirred for 16 h. After completion of the reaction, the reaction mixture was cooled to room temperature and added EtOAc (200 mL). After stirring for 10 minutes, the organic layer was separated and washed with brine. The organic layer was dried over anhydrous $Na_2SO_4$ and concentrated under reduced pressure. The residue was purified by column chromatography eluting with 20% EtOAc/n-hexane to afford meso compound 1 (48 g, 57%) as a brown syrup along 13 g of racemic compound. $^1$H NMR: (400 MHz, DMSO-$d_6$) δ 7.28-7.19 (m, 5H), 3.83 (s, 2H), 3.48 (s, 6H), 3.42-3.36 (m, 2H), 2.09-1.98 (m, 2H), 1.94-1.83 (m, 2H). LCMS (ESI): m/z 277.9 [M$^+$+1].

Synthesis of 1-(tert-butyl) 2,5-dimethyl pyrrolidine-1,2,5-tricarboxylate (2)

To a solution of meso compound 1 (48 g, 0.173 mol) in MeOH (480 mL) were added $Boc_2O$ (79.5 mL, 0.346 mol) and 10% Pd/C (50% wet, 19.2 g) and stirred under $H_2$ atmosphere (balloon) for 16 h. After consumption of the starting material (by TLC), the reaction mixture was filtered through a pad of celite and the filtrate was concentrated under reduced pressure. The residue was purified by column chromatography eluting with 30% EtOAc/n-hexane to afford meso compound 2 (40.5 g, 81%) as a white solid. $^1$H NMR: (500 MHz, DMSO-$d_6$) δ 4.27-4.18 (m, 2H), 3.64 (s, 3H), 3.62 (s, 3H), 2.25-2.16 (m, 2H), 1.96-1.85 (m, 2H), 1.36 (s, 9H). LCMS (ESI): m/z 288.2 [M$^+$+1].

Synthesis of 5-(tert-butyl) 6-methyl 2-(benzyloxy)-1-oxo-2,5-diazaspiro[3.4]octane-5,6-dicarboxylate (3)

To a solution of meso compound 2 (35.5 g, 0.123 mol) in THF (300 mL) was added LiHMDS (1M solution in THF, 185.5 mL, 0.185 mol) drop wise at −78° C. under nitrogen atmosphere and stirred for 1 h. A solution of Int-A (20 g, 0.148 mol) in THF (55 mL) was added to the reaction mixture at −78° C. and stirred at room temperature stirred for 3 h. After consumption of the starting material (by TLC), the reaction was quenched with saturated aqueous $NH_4Cl$ (100 mL) and extracted with EtOAc (3×200 mL). The separated organic layer was dried over $Na_2SO_4$ and concentrated under reduced pressure. The residue was purified by column chromatography eluting with 30% EtOAc/n-hexane to afford compound 3 (38 g, 78%) as a colorless thick syrup. $^1$H NMR (400 MHz, DMSO-$d_6$) δ 7.48-7.36 (m, 5H), 4.95-4.85 (m, 2H), 4.29 (br d, J=6.4 Hz, 1H), 4.07-3.99 (m, 1H), 3.71 (s, 3H), 3.55 (d, J=10.7 Hz, 1H), 2.36-2.16 (m, 2H), 2.13-2.02 (m, 1H), 1.98-1.91 (m, 1H), 1.35 (s, 9H). LCMS (ESI): m/z 391.3 [M$^+$+1].

Synthesis of 2-(benzyloxy)-5-(tert-butoxycarbonyl)-1-oxo-2,5-diazaspiro[3.4]octane-6-carboxylic acid (4)

To a solution of compound 3 (32 g, 0.082 mol) in MeOH, THF and water (480 mL, 1:1:1) was added NaOH (9.84 g, 0.246 mol) at 0° C. and then stirred at room temperature for 16 h. After consumption of the starting material (by TLC), reaction mixture was concentrated under reduced pressure. The residue was diluted with water (100 mL) and washed with EtOAc. The aqueous layer was acidified with aqueous 2N HCl (pH~2.0) and extracted with EtOAc (2×200 mL). The organic layer was washed with brine, dried over $Na_2SO_4$ and concentrated under reduced pressure to afford compound 4 (32 g, crude) as a pale yellow semi solid. The crude was forwarded to next step without further purification. $^1$H NMR (500 MHz, DMSO-$d_6$) δ 12.89 (br s, 1H), 7.46-7.28 (m, 5H), 4.92-4.84 (m, 2H), 4.26 (br d, J=7.0 Hz, 1H), 4.05-3.96 (m, 1H), 3.45 (br d, J=11.0 Hz, 1H), 2.31-2.15 (m, 2H), 2.06-1.88 (m, 2H), 1.35 (s, 9H). LCMS (ESI): m/z 375.1 [M$^+$−1].

Synthesis of 2-(benzyloxy)-5-(tert-butoxycarbonyl)-1-oxo-2,5-diazaspiro[3.4]octane-6-carboxylic (isobutyl carbonic) anhydride (5)

To a solution of compound 4 (46 g, 0.122 mol) in THF (460 mL) was added N-methyl morpholine (40.3 mL, 0.367 mol) and isobutylchloroformate (20.5 mL, 0.159 mol) at 0° C. under nitrogen atmosphere. The reaction mixture was stirred at room temperature for 3 h. After consumption of the starting material (by TLC), the reaction mixture was quenched with water (230 mL) and extracted with EtOAc (3×100 mL). The organic layer was dried over anhydrous $Na_2SO_4$ and concentrated under reduced pressure to afford compound 5 (35 g, crude) as a colorless thick syrup. The crude was forwarded to next step without further purification. $^1$H NMR (400 MHz, DMSO-$d_6$) δ 7.47-7.33 (m, 5H), 4.94-4.84 (m, 2H), 4.27 (br d, J=6.7 Hz, 1H), 4.12-3.96 (m, 1H), 3.86 (d, J=6.7 Hz, 1H), 3.63-3.51 (m, 1H), 3.46 (d, J=10.7 Hz, 1H), 2.39-2.36 (m, 1H), 2.28-2.16 (m, 2H), 2.07-1.82 (m, 2H), 1.36 (s, 9H), 0.88 (d, J=6.8 Hz, 3H), 0.82 (d, J=6.7 Hz, 3H)

Synthesis of tert-butyl 2-(benzyloxy)-6-(hydroxymethyl)-1-oxo-2,5-diazaspiro[3.4]octane-5-carboxylate (6)

To a solution of compound 5 (35 g, 0.073 mol) in MeOH (350 mL) was added sodium borohydride (2.79 g, 0.073 mol) at 0° C. under nitrogen atmosphere. The reaction mixture was stirred at 0° C. for 2 h. After consumption of the starting material (by TLC), the reaction mixture was quenched with ice and volatiles were evaporated under reduced pressure. The crude was diluted with EtOAc (200 mL) and washed with water followed by brine. The organic layer was dried over anhydrous $Na_2SO_4$ and concentrated under reduced pressure. The residue was purified by column chromatography eluting with 30% EtOAc/n-hexane to afford compound 6 (6.7 g, 25%) as a colorless thick syrup. $^1$H NMR (400 MHz, DMSO-$d_6$) δ 7.47-7.35 (m, 5H), 4.96-4.82 (m, 3H), 4.25 (d, J=7.3 Hz, 1H), 3.90 (dd, J=5.6, 11.2 Hz, 1H), 3.77-3.66 (m, 2H), 3.34 (d, J=10.4 Hz, 1H), 2.17-2.07 (m, 1H), 2.02-1.91 (m, 1H), 1.83-1.73 (m, 2H), 1.38 (s, 9H). LCMS (ESI): m/z 363.1 [M$^+$+1].

Synthesis of tert-butyl 2-(benzyloxy)-6-formyl-1-oxo-2,5-diazaspiro[3.4]octane-5-carboxylate (7)

To a solution of crude compound 6 (6.7 g, 0.018 mol) in CH$_2$Cl$_2$ (67 mL) was added Dess-Martin periodinane (9.42 g, 0.022 mol) at 0° C. under nitrogen atmosphere and the reaction mixture was stirred at room temperature for 2 h. After consumption of the starting material (by TLC), the reaction mixture was quenched with saturated aqueous NaHCO$_3$. The organic layer was separated, washed with brine and concentrated under reduced pressure. The residue was purified by column chromatography eluting with 40% EtOAc/n-hexane to afford compound 7 (5.8 g, 87%) as a colorless thick syrup. $^1$H NMR (500 MHz, DMSO-$d_6$) δ 9.50 (s, 1H), 7.48-7.35 (m, 5H), 4.96-4.84 (m, 2H), 4.30 (br s, 1H), 3.85 (br d, J=10.4 Hz, 1H), 3.59-3.47 (m, 1H), 2.26 (br s, 2H), 2.05-1.98 (m, 1H), 1.82 (br s, 1H), 1.36 (s, 9H).

Synthesis of tert-butyl 6-(4(2S,3R)-1-amino-3-hydroxy-1-oxobutan-2-yl)amino)methyl)-2-(benzyloxy)-1-oxo-2,5-diazaspiro[3.4]octane-5-carboxylate (BI & BJ)

To a solution of crude compound 7 (5.8 g, 0.016 mol) in MeOH (87 mL) was added Int-B (2.28 g, 0.019 mol) under nitrogen atmosphere and stirred at room temperature for 30 minutes. NaBH$_3$CN (2.02 g, 0.032 mol) was added to the reaction mixture and stirred at room temperature for 16 h. After consumption of the starting material (by TLC), volatiles were evaporated under reduced pressure. The reaction mixture was diluted with water (20 mL) and extracted with EtOAc (2×100 mL). The organic layer was washed with brine, dried over Na$_2$SO$_4$ and concentrated under reduced pressure. The residue was purified by column chromatography eluting with 2% MeOH/DCM to afford diasteromeric mixture (3.4 g, 46%) as a white solid.

620 mg of diasteromeric mixture was purified by normal phase preparative HPLC purification to obtain BI (170 mg) and BJ (180 mg) as a white solid.

BI: $^1$H NMR (400 MHz, DMSO-$d_6$) δ 7.45-7.36 (m, 5H), 7.23 (s, 1H), 7.06 (d, J=1.4 Hz, 1H), 4.91-4.83 (m, 2H), 4.54 (d, J=4.3 Hz, 1H), 4.24 (d, J=7.0 Hz, 1H), 3.74-3.64 (m, 2H), 3.41 (d, J=10.3 Hz, 1H), 3.11 (br dd, J=4.5, 11.9 Hz, 1H), 2.85 (br t, J=10.5 Hz, 1H), 2.79-2.73 (m, 1H), 2.30-2.20 (m, 1H), 2.10 (br d, J=6.1 Hz, 1H), 2.01-1.91 (m, 1H), 1.85-1.73 (m, 2H), 1.38 (s, 9H), 1.06 (d, J=6.3 Hz, 3H). LCMS (ESI): m/z 463.2 [M$^+$+1]. HPLC: 99.71%. Chiral HPLC: 100.00%. Column: CHIRALPAK IC (250*4.6 mm, 5 μm); Mobile Phase A: 0.1% DEA in n-hexane; Mobile Phase B: DCM:MeOH (80:20); A:B:: 60:40; Flow rate: 1.0 mL/min. Retention time: 8.383.

BJ: $^1$H NMR (400 MHz, DMSO-$d_6$): δ 7.45-7.34 (m, 5H), 7.18 (br d, J=2.4 Hz, 1H), 7.05 (br d, J=1.9 Hz, 1H), 4.91-4.81 (m, 3H), 4.23 (d, J=7.2 Hz, 1H), 3.68-3.58 (m, 2H), 3.40 (d, J=10.4 Hz, 1H), 3.00 (br d, J=9.8 Hz, 1H), 2.76-2.64 (m, 2H), 2.44-2.25 (m, 2H), 2.02-1.87 (m, 1H), 1.83-1.70 (m, 2H), 1.39 (s, 9H), 1.06 (d, J=6.1 Hz, 3H). LCMS (ESI): m/z 463.2 [M$^+$+1]. HPLC: 99.89%. Chiral HPLC: 100.00%; Column: CHIRALPAK IC (250*4.6 mm, 5 μm); Mobile Phase A: 0.1% DEA in n-hexane; Mobile Phase B: DCM:MeOH (80:20); A:B:: 60:40; Flow rate: 1.0 mL/min. Retention time: 9.962.

Synthesis of tert-butyl 6-(4(2S,3R)-1-amino-3-hydroxy-1-oxobutan-2-yl)amino)methyl)-1-oxo-2,5-diazaspiro[3.4]octane-5-carboxylate (BK & BL)

To a suspension of Raney Nickel (1 g) in MeOH (10 mL) was added diasteromeric mixture BI & BJ (1 g, 0.002 mol) MeOH (10 mL) and stirred under H$_2$ atmosphere (balloon) at room temperature for 16 h. After consumption of the starting material (by TLC), the reaction mixture was filtered through a pad of celite and washed with MeOH (20 mL). The filtrate was concentrated under reduced pressure and dried to afford diasteromeric mixture (700 mg, 91%) as a white solid.

810 mg of diasteromeric mixture was purified by chiral preparative HPLC purification to afford BK (180 mg) and BL (185 mg) as a white solid.

BK: $^1$H NMR (400 MHz, DMSO-$d_6$) δ 7.43 (s, 1H), 7.25 (s, 1H), 7.06 (br d, J=1.8 Hz, 1H), 4.58 (s, 1H), 4.07 (d, J=6.7 Hz, 1H), 3.70 (quin, J=6.0 Hz, 1H), 3.31-3.28 (m, 1H), 3.11 (dd, J=5.9, 11.9 Hz, 1H), 3.05 (dd, J=2.8, 11.4 Hz, 1H), 2.86-2.72 (m, 2H), 2.36-2.23 (m, 1H), 2.18-2.09 (m, 1H), 2.00-1.83 (m, 2H), 1.79-1.69 (m, 1H), 1.38 (s, 9H), 1.07 (d, J=6.3 Hz, 3H). LCMS (ESI): m/z 357.1 [M$^+$+1]. HPLC: 97.87%. Chiral HPLC: 100.00%. Column: CHIRALPAK IC (250*4.6 mm, 5 μm); Mobile Phase A: 0.1% DEA in n-hexane; Mobile Phase B: DCM:MeOH (80:20); A:B:: 60:40; Flow rate: 1.0 mL/min; Retention time: 12.865.

BL: $^1$H NMR (400 MHz, DMSO-$d_6$) δ 7.43 (s, 1H), 7.18 (br d, J=2.5 Hz, 1H), 7.05 (br d, J=2.1 Hz, 1H), 4.91 (br s, 1H), 4.07 (d, J=6.9 Hz, 1H), 3.62 (quin, J=6.5 Hz, 1H), 3.28 (br d, J=11.5 Hz, 1H), 3.04-2.93 (m, 2H), 2.68 (br dd, J=3.1, 7.2 Hz, 2H), 2.47-2.37 (m, 1H), 2.31-2.23 (m, 1H), 1.93-1.89 (m, 1H), 1.85-1.69 (m, 2H), 1.39 (s, 9H), 1.07 (d, J=6.1 Hz, 3H). LCMS (ESI): m/z 357.1 [M$^+$+1]. HPLC: 98.39%. Chiral HPLC: 100.00%. Column: CHIRALPAK IC (250*4.6 mm, 5 μm); Mobile Phase A: 0.1% DEA in n-hexane; Mobile Phase B: DCM:MeOH (80:20); A:B:: 60:40; Flow rate: 1.0 mL/min; Retention time: 16.945.

Synthesis of formaldehyde O-benzyl oxime (Int-A):

The experimental procedure for the synthesis Int-A has been captured under AL-1 & AL-2 (as Int-A).

Synthesis of BE, BF, BG & BH:

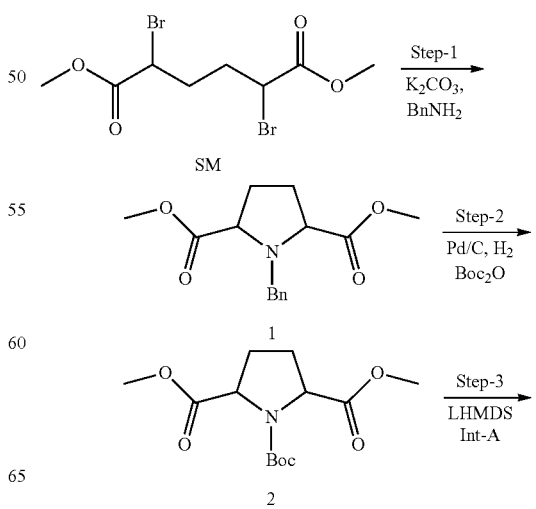

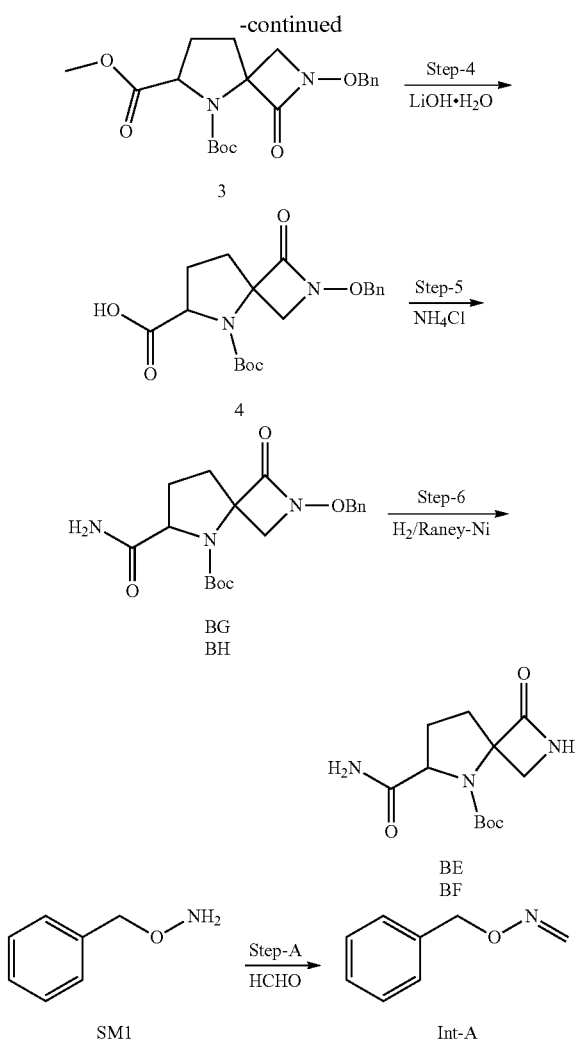

Synthesis of 5-(tert-butyl) 6-methyl 2-(benzyloxy)-1-oxo-2,5-diazaspiro[3.4]octane-5,6-dicarboxylate (3)

The experimental procedure for the synthesis of compound 3 has been captured under the synthesis of BI, BJ, BK & BL (as compound 3).

Synthesis of 2-(benzyloxy)-5-(tert-butoxycarbonyl)-1-oxo-2,5-diazaspiro[3.4]octane-6-carboxylic acid (4)

To a stirring solution of compound 3 (4 g, 10.25 mmol) in THF:H$_2$O (80 mL, 3:1) was added LiOH.H$_2$O (4.4 g, 30.75 mmol) at 0° C. and then stirred at room temperature for 16 h. After consumption of the starting material (by TLC), reaction mixture was concentrated, co-distilled with toluene (2×60 mL) and dried to afford compound 4 (4.5 g, crude) as an off white solid. LCMS (ESI): m/z 375.2 [M$^+$−1].

Synthesis of tert-butyl 2-(benzyloxy)-6-carbamoyl-1-oxo-2,5-diazaspiro[3.4]octane-5-carboxylate (BG and BH)

To a solution of crude compound 4 (4.5 g, 11.77 mmol) in DMF (40 mL) was added HATU (6.7 g, 17.66 mmol), NH$_4$Cl (1.27 g, 23.54 mmol) and DIPEA (6.2 mL, 35.31 mmol) at 0° C. under nitrogen atmosphere. The reaction mixture was brought to RT and stirred for 16 h. After consumption of the starting material (by TLC), the reaction mixture was diluted with water (50 mL) and extracted with EtOAc (3×100 mL). Organic layer was dried over anhydrous Na$_2$SO$_4$ and concentrated under reduced pressure to afford crude compound which was purified by CombiFlash chromatography by eluting 50% EtOAc/Hexane to obtain the product (1.4 g), which upon chiral preparative purification afforded BG (570 mg) and BH (560 mg) as white solids.

BG: $^1$H NMR (500 MHz, DMSO-d$_6$): δ 7.47-7.34 (m, 6H), 7.14 (br s, 1H), 4.94-4.81 (m, 2H), 4.25 (br d, J=6.1 Hz, 1H), 3.99 (d, J=10.7 Hz, 1H), 3.41 (d, J=10.7 Hz, 1H), 2.26-2.16 (m, 2H), 2.07-1.88 (m, 2H), 1.36 (s, 9H). LCMS (m/z): 376.2 [M$^+$+1]. HPLC: 99.35%. Chiral HPLC: 100.00%. Column: CHIRALPAK IA (250*4.6 mm, 5 μm); Mobile Phase A: 0.1% DEA in n-hexane; Mobile Phase B: DCM:MeOH (50:50); A:B:: 80:20; Flow rate: 1.0 mL/min. Retention time: 8.011.

BH: $^1$H NMR (400 MHz, DMSO-d$_6$): δ 7.47-7.35 (m, 6H), 7.14 (br s, 1H), 4.94-4.82 (m, 2H), 4.25 (br d, J=6.5 Hz, 1H), 3.99 (d, J=10.8 Hz, 1H), 3.41 (d, J=10.8 Hz, 1H), 2.27-2.15 (m, 2H), 2.06-1.88 (m, 2H), 1.36 (s, 9H). LCMS (m/z): 376.2 [M$^+$+1]. HPLC: 99.38%. Chiral HPLC: 100.00%; Column: CHIRALPAK IA (250*4.6 mm, 5 μm); Mobile Phase A: 0.1% DEA in n-hexane; Mobile Phase B: DCM:MeOH (50:50); A:B:: 80:20; Flow rate: 1.0 mL/min. Retention time: 11.776.

Synthesis of tert-butyl 2-(benzyloxy)-6-carbamoyl-1-oxo-2,5-diazaspiro[3.4]octane-5-carboxylate (BE)

To a stirring solution of BG (380 mg, 1.01 mmol) in methanol (10 mL) was added Raney Nickel (200 mg) under nitrogen atmosphere. Reaction mixture was de-gassed and then stirred for 16 h under H$_2$ atmosphere (balloon pressure). After consumption of the starting material (by TLC), the reaction mixture was filtered through a pad of celite and the pad was washed with MeOH (50 mL). Obtained filtrate was concentrated under reduced pressure and dried to afford BE (230 mg, 84%) as white solid.

BE: $^1$H NMR (400 MHz, DMSO-d$_6$): δ 7.46 (s, 1H), 7.30 (br s, 1H), 7.05 (br s, 1H), 4.08 (d, J=5.8 Hz, 1H), 3.65 (d, J=11.9 Hz, 1H), 3.08 (dd, J=2.6, 12.0 Hz, 1H), 2.30-2.06 (m, 3H), 1.92-1.83 (m, 1H), 1.36 (s, 9H). LCMS (ESI): m/z 270.2 [M$^+$+1]. HPLC: 94.58%. Chiral HPLC: 100.00%. Column: CHIRALPAK IA (250*4.6 mm, 5 μm); Mobile Phase A: 0.1% TFA in n-hexane; Mobile Phase B: DCM:MeOH (50:50); A:B 75:25; Flow rate: 1.0 mL/min. Retention time: 9.759.

Synthesis of tert-butyl 2-(benzyloxy)-6-carbamoyl-1-oxo-2,5-diazaspiro[3.4]octane-5-carboxylate (BF)

To a stirring solution of BH (380 mg, 1.01 mmol) in methanol (10 mL) was added Raney Nickel (200 mg) under nitrogen atmosphere. Reaction mixture was de-gassed and then stirred for 16 h under H$_2$ atmosphere (balloon pressure). After consumption of the starting material (by TLC), the reaction mixture was filtered through a pad of celite and the pad was washed with MeOH (50 mL). Obtained filtrate was concentrated under reduced pressure and dried to afford BF (210 mg, 77%) as white solid.

BF: $^1$H NMR (400 MHz, DMSO-d$_6$): δ 7.46 (s, 1H), 7.29 (br s, 1H), 7.05 (br s, 1H), 4.11-4.05 (m, 1H), 3.63 (s, 1H), 3.08 (dd, J=2.6, 12.0 Hz, 1H), 2.30-2.07 (m, 3H), 1.92-1.83

(m, 1H), 1.36 (s, 9H). LCMS (ESI): m/z 270.5 [M++1]. HPLC: 99.50%. Chiral HPLC: 98.63%. Column: CHIRAL-PAK IA (250*4.6 mm, 5 μm); Mobile Phase A: 0.1% TFA in n-hexane; Mobile Phase B: DCM:MeOH (50:50); A:B 75:25; Flow rate: 1.0 mL/min; Retention time: 17.406.

Synthesis of formaldehyde O-benzyl oxime (Int-A):

The experimental procedure for the synthesis Int-A has been captured under AL-1 & AL-2 (as Int-A).

Synthesis of BM, BN, BO & BP:

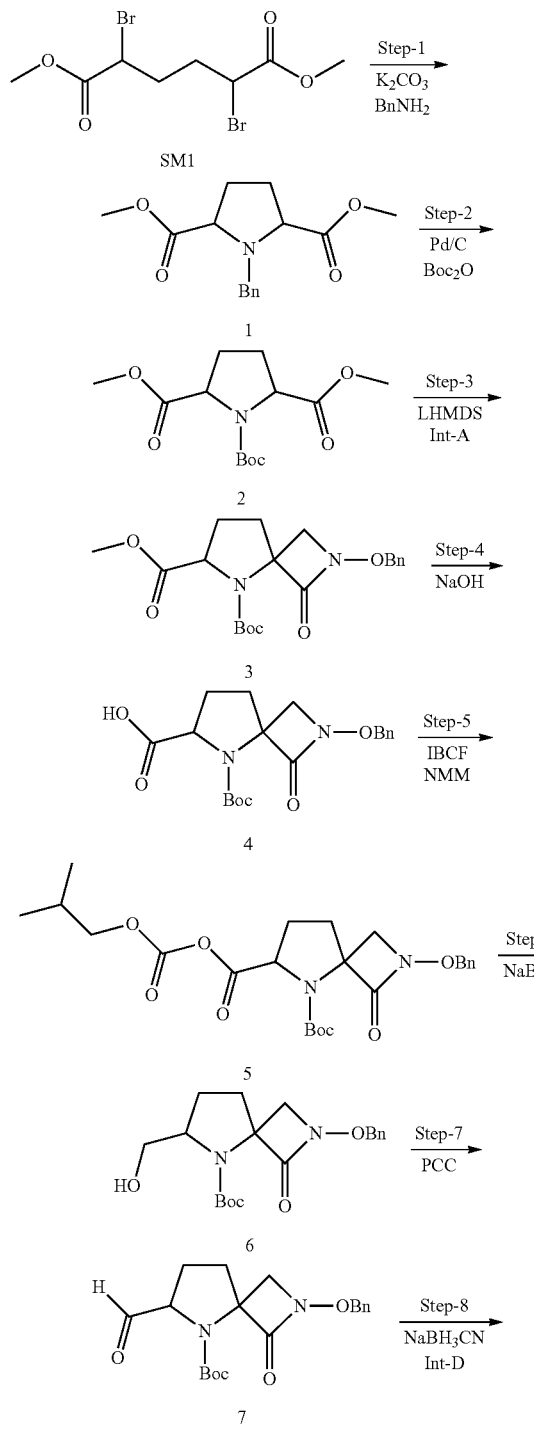

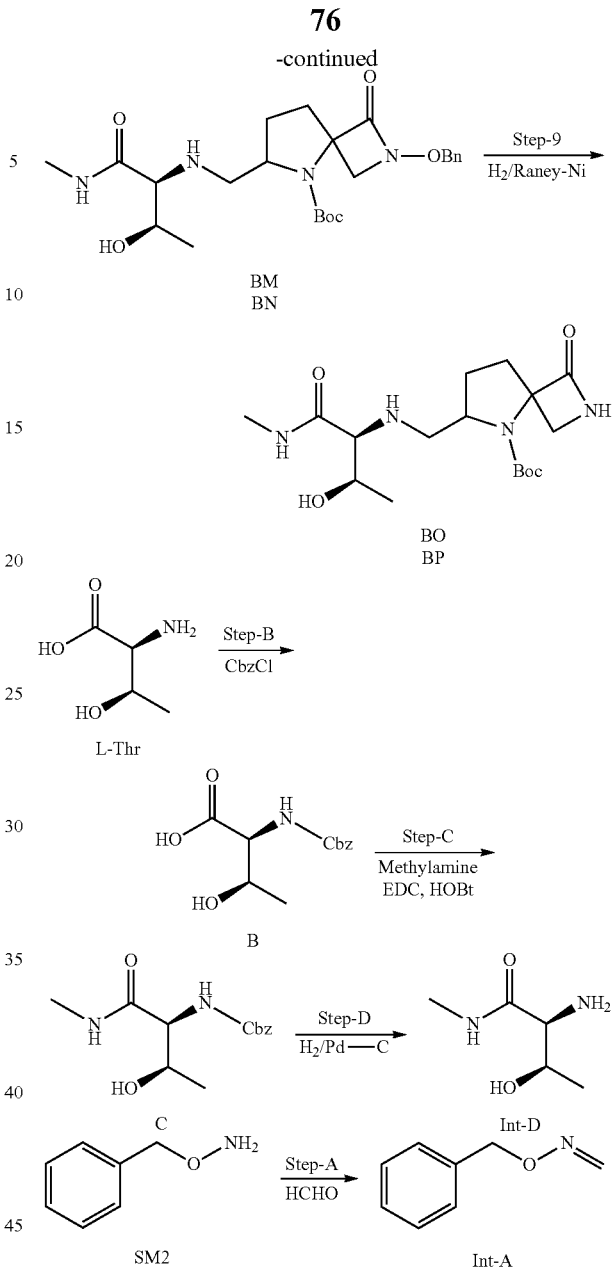

Synthesis of tert-butyl 2-(benzyloxy)-6-formyl-1-oxo-2,5-diazaspiro[3.4]octane-5-carboxylate (7)

The experimental procedure for the synthesis compound 7 has been captured under the synthesis of BI, BJ, BK & BL (as compound 7).

Synthesis of tert-butyl 2-(benzyloxy)-6-(4(2S,3R)-3-hydroxy-1-(methylamino)-1-oxobutan-2-yl)amino) methyl)-1-oxo-2,5-diazaspiro[3.4]octane-5-carboxylate (BM & BN)

To a solution of compound 7 (1.7 g, 4.72 mmol) in MeOH (20 mL) were added Int-D (623 mg, 4.72 mmol) and AcOH (0.2 mL) under nitrogen atmosphere and stirred at room temperature for 40 minutes. NaBH$_3$CN (890 mg, 14.16 mmol) was added to the reaction mixture and stirred at room temperature for 16 h. After consumption of the starting material (by TLC), the reaction mixture was quenched saturated aqueous NaHCO₃ and volatiles were evaporated under reduced pressure. The crude was diluted with saturated aqueous NaHCO₃ (50 mL) and extracted with EtOAc (3×100 mL). The organic layer was washed with brine, dried over Na₂SO₄ and concentrated under reduced pressure. The residue was purified by Combi-Flash chromatography eluting with 5% MeOH/EtOAc to afford diasteromeric mixture (1 g, 44%) as a white solid. 750 mg of diasteromeric mixture was again purified by normal phase preparative HPLC purification to afford BM (300 mg) and BN (300 mg) as a white solid.

BM: $^1$H NMR (500 MHz, DMSO-$d_6$) δ 7.76 (d, J=4.6 Hz, 1H), 7.45-7.33 (m, 5H), 4.91-4.82 (m, 2H), 4.55 (s, 1H), 4.23 (d, J=7.5 Hz, 1H), 3.68 (d, J=9.9 Hz, 2H), 3.40 (d, J=10.4 Hz, 1H), 3.05 (dd, J=6.4, 12.2 Hz, 1H), 2.85 (t, J=10.4 Hz, 1H), 2.75 (dd, J=5.5, 8.4 Hz, 1H), 2.61 (d, J=4.6 Hz, 3H), 2.29-2.18 (m, 1H), 2.15-2.07 (m, 1H), 2.02-1.91 (m, 1H), 1.85-1.73 (m, 2H), 1.38 (s, 9H), 1.03 (d, J=5.8 Hz, 3H). LCMS (ESI): m/z 477.5 [M⁺+1]. HPLC: 98.34%. Chiral HPLC: 100.00%. Column: CHIRALPAK IC (250*4.6 mm, 5 µm); Mobile Phase A: 0.1% DEA in n-hexane; Mobile Phase B: DCM:MeOH (50:50); A:B 85:15; Flow rate: 1.0 mL/min. Retention time: 17.870.

BN: $^1$H NMR (500 MHz, DMSO-$d_6$) δ 7.71 (d, J=4.6 Hz, 1H), 7.46-7.34 (m, 5H), 4.91-4.81 (m, 2H), 4.23 (d, J=7.0 Hz, 1H), 3.67-3.56 (m, 2H), 3.43 (d, J=10.4 Hz, 1H), 3.00 (dd, J=3.8, 11.3 Hz, 1H), 2.72 (dd, J=2.9, 7.0 Hz, 1H), 2.66-2.56 (m, 4H), 2.45-2.35 (m, 2H), 2.31-2.22 (m, 1H), 2.04-1.90 (m, 1H), 1.83-1.72 (m, 2H), 1.39 (s, 9H), 1.03 (d, J=6.4 Hz, 3H). LCMS (ESI): m/z 477.5 [M⁺+1]. HPLC: 99.74%. Chiral HPLC: 100.00%. Column: CHIRALPAK IC (250*4.6 mm, 5 µm); Mobile Phase A: 0.1% DEA in n-hexane; Mobile Phase B: DCM:MeOH (50:50); A:B 85:15; Flow rate: 1.0 mL/min; Retention time: 23.561.

Synthesis of tert-butyl 6-(4(2S,3R)-3-hydroxy-1-(methylamino)-1-oxobutan-2-yl)amino)methyl)-1-oxo-2,5-diazaspiro[3.4]octane-5-carboxylate (BO & BP)

To a solution of Raney Nickel (3 g) in MeOH (40 mL) was added diasteromeric mixture (BM & BN) (1 g, 2.11 mmol) in MeOH (20 mL) and stirred under H₂ atmosphere (balloon) for 6 h. After consumption of the starting material (by TLC), the reaction mixture was filtered through a pad of celite and washed with MeOH (50 mL). The filtrate was concentrated under reduced pressure and the residue (750 g) was purified by chiral preparative HPLC purification to afford BO (250 mg) and BP (270 mg) as a white solid.

BO: $^1$H NMR (400 MHz, DMSO-$d_6$) δ 7.76 (q, J=4.4 Hz, 1H), 7.44 (s, 1H), 4.56 (d, J=4.3 Hz, 1H), 4.07 (d, J=6.7 Hz, 1H), 3.69 (dd, J=5.4, 10.5 Hz, 1H), 3.30 (s, 1H), 3.12-3.00 (m, 2H), 2.87-2.72 (m, 2H), 2.61 (d, J=4.6 Hz, 3H), 2.35-2.22 (m, 1H), 2.10 (br d, J=6.1 Hz, 1H), 2.01-1.83 (m, 2H), 1.80-1.69 (m, 1H), 1.38 (s, 9H), 1.04 (d, J=6.3 Hz, 3H). LCMS (ESI): m/z 371.3 [M⁺+1]. HPLC: 98.65%. Chiral HPLC: 99.62%. Column: CHIRALPAK IC (250*4.6 mm, 5 µm); Mobile Phase A: 0.1% DEA in n-hexane; Mobile Phase B: DCM:MeOH (50:50); A:B:: 80:20; Flow rate: 1.0 mL/min. Retention time: 12.852.

BP: $^1$H NMR (400 MHz, DMSO-$d_6$) δ 7.68 (q, J=4.4 Hz, 1H), 7.43 (s, 1H), 4.91 (br s, 1H), 4.07 (d, J=6.9 Hz, 1H), 3.62 (d, J=3.1 Hz, 1H), 3.26 (d, J=11.4 Hz, 1H), 2.99 (dd, J=2.6, 11.4 Hz, 2H), 2.72 (dd, J=3.1, 7.3 Hz, 1H), 2.66-2.63 (m, 1H), 2.60 (d, J=4.6 Hz, 3H), 2.43 (br s, 1H), 2.31-2.25 (m, 1H), 2.01-1.88 (m, 1H), 1.87-1.70 (m, 2H), 1.39 (s, 9H), 1.04 (d, J=6.3 Hz, 3H). LCMS (ESI): m/z 371.3 [M⁺+1]. HPLC: 99.00%. Chiral HPLC: 99.14%. Column: CHIRALPAK IC (250*4.6 mm, 5 µm); Mobile Phase A: 0.1% DEA in n-hexane; Mobile Phase B: DCM:MeOH (50:50); A:B:: 80:20; Flow rate: 1.0 mL/min. Retention time: 13.831.

Synthesis of formaldehyde O-benzyl oxime (Int-A):

The experimental procedure for the synthesis Int-A has been captured under AL-1 & AL-2 (as Int-A).

Preparation of Int-D:

Synthesis of ((benzyloxy)carbonyl)-L-threonine (B):

To a solution of L-threonine (20 g, 0.17 mol) in 1,4-dioxane and water (1:1, 200 mL) was added NaOH (27.35 g, 0.683 mol) followed by drop wise addition of CbzCl (50% solution in toluene, 87 mL, 0.256 mol) at 0° C. and stirred at room temperature for 16 h. The reaction mixture was diluted with cold water (100 mL) and washed with EtOAc (100 mL). The aqueous layer was acidified with aqueous 1N HCl and extracted with EtOAc (3×100 mL). The combined organic layer was washed with brine (100 mL) and dried over anhydrous Na₂SO₄, concentrated under reduced pressure to afford compound B (32 g, 75%) as a white solid. $^1$H NMR (400 MHz, DMSO-$d_6$) δ 12.64 (br s, 1H), 7.40-7.28 (m, 5H), 6.95 (d, J=8.9 Hz, 1H), 5.03 (s, 2H), 4.62-4.53 (m, 1H), 4.12-4.00 (m, 1H), 3.98-3.93 (m, 1H), 1.09 (d, J=6.4 Hz, 3H). LCMS (ESI): m/z 254.1 [M⁺+1].

Synthesis of benzyl ((2S,3R)-3-hydroxy-1-(methylamino)-1-oxobutan-2-yl)carbamate (C)

To a solution of compound B (6 g, 23.71 mmol) in CH₂Cl₂ (100 mL) were added HOBt (4.8 g, 35.57 mmol), EDC.HCl (6.83 g, 35.57 mmol), methylamine (2M in THF) (23.7 mL, 47.43 mmol) and DIPEA (13 mL, 71.14 mmol) at 0° C. under nitrogen atmosphere and stirred at room temperature for 16 h. After consumption of the starting material (by TLC), the reaction mixture was quenched with water (200 mL) and extracted with DCM (2×200 mL). The combined organic layer was washed with aqueous 10% citric acid (100 mL), saturated aqueous NaHCO₃ (100 mL), brine (100 mL), dried over Na₂SO₄ and concentrated under reduced pressure. The residue was purified by Combi-Flash chromatography eluting with 80% EtOAc/n-hexane to afford compound C (2.5 g, 39%) as a white solid. $^1$H NMR (400 MHz, DMSO-$d_6$) δ 7.77 (br d, J=4.4 Hz, 1H), 7.40-7.27 (m, 5H), 6.84 (br d, J=8.8 Hz, 1H), 5.10-4.98 (m, 2H), 4.74 (d, J=6.0 Hz, 1H), 3.99-3.88 (m, 1H), 3.85 (dd, J=4.2, 8.7 Hz, 1H), 2.59 (d, J=4.6 Hz, 3H), 1.03 (d, J=6.4 Hz, 3H). LCMS (ESI): m/z 267.1 [M⁺+1].

Synthesis of (2S,3R)-2-amino-3-hydroxy-N-methylbutanamide (Int-D)

To a solution of compound C (2.5 g, 9.39 mmol) in MeOH (30 mL), 10% Pd/C (50% wet, 1 g) was added and stirred under H₂ atmosphere (balloon) for 16 h. After consumption of the starting material (by TLC), the reaction mixture was filtered through a pad of celite and washed with MeOH and H₂O (250 mL, 1:1). The filtrate was concentrated under reduced pressure to afford Int-D (1.1 g, 88%) as a white solid. $^1$H NMR (400 MHz, DMSO-$d_6$) δ 7.82 (br d, J=2.5 Hz, 1H), 4.56 (br s, 1H), 3.83-3.75 (m, 1H), 2.88 (d, J=4.5 Hz, 1H), 2.59 (d, J=4.8 Hz, 3H), 2.34-1.83 (m, 2H), 1.03 (d, J=6.4 Hz, 3H). LCMS (ESI): m/z 133.2 [M⁺+1].

Synthesis of BO, BR, BS & BT:

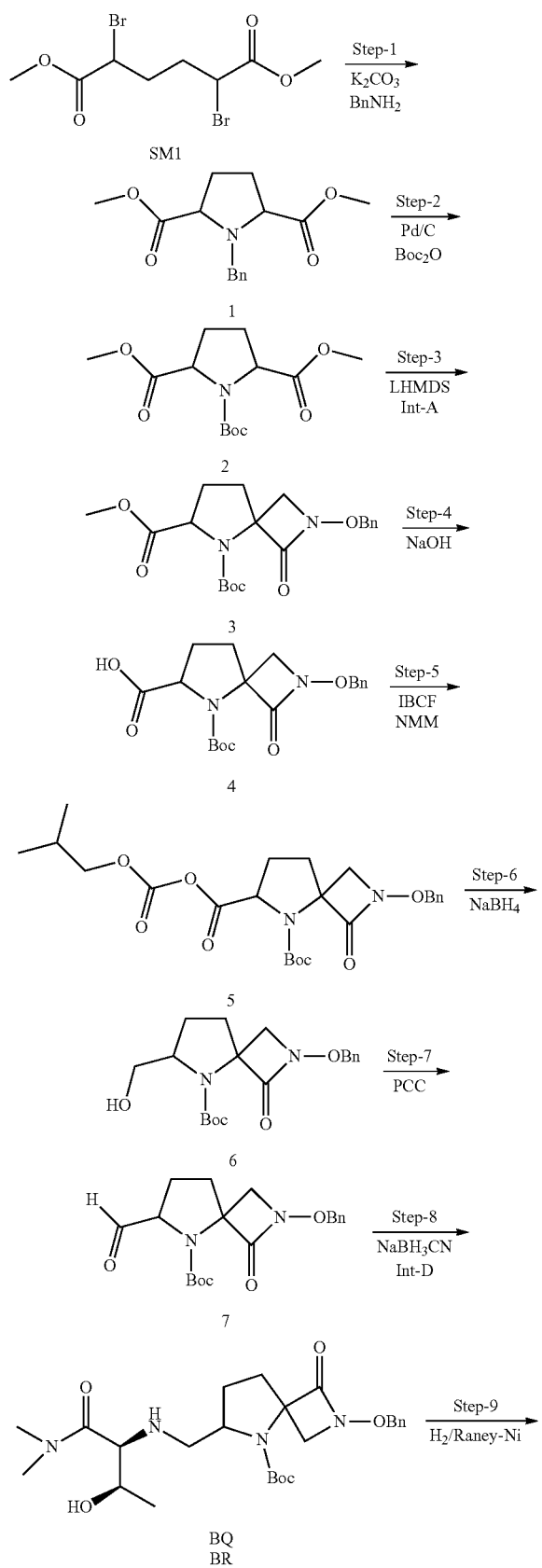

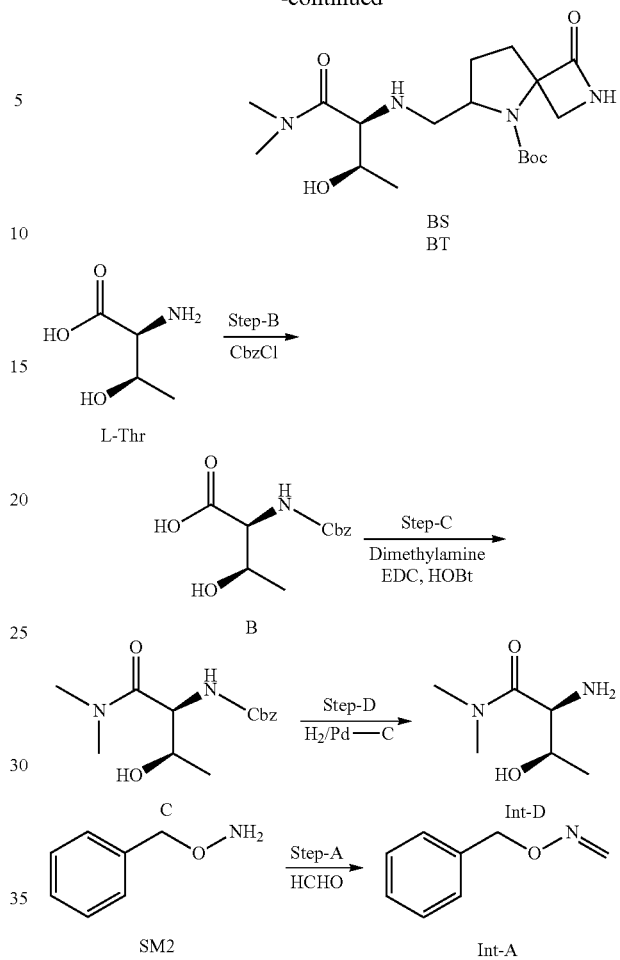

Synthesis of tert-butyl 2-(benzyloxy)-6-formyl-1-oxo-2,5-diazaspiro[3.4]octane-5-carboxylate (7)

The experimental procedure for the synthesis of compound 7 has been captured under the synthesis of BI, BJ, BK & BL (as compound 7).

Synthesis of tert-butyl 2-(benzyloxy)-6-(4(2S,3R)-1-(dimethylamino)-3-hydroxy-1-oxobutan-2-yl) amino)methyl)-1-oxo-2,5-diazaspiro[3.4]octane-5-carboxylate (BQ & BR)

To a solution of compound 7 (1 g, 2.77 mmol) in MeOH (20 mL) were added Int-D (487 mg, 3.33 mmol) and AcOH (0.1 mL) at room temperature under nitrogen atmosphere and stirred for 40 minutes. NaBH$_3$CN (525 mg, 8.33 mmol) was added to the reaction mixture and stirred at room temperature for 16 h. After consumption of the starting material (by TLC), the reaction mixture was quenched saturated aqueous NaHCO$_3$ and volatiles were evaporated under reduced pressure. The crude was diluted with aqueous NaHCO$_3$ (50 mL) and extracted with EtOAc (2×200 mL). The organic layer was washed with brine, dried over Na$_2$SO$_4$ and concentrated under reduced pressure. The residue was purified by Combi-Flash chromatography eluting with 5% MeOH/EtOAc to afford diasteromeric mixture (610 mg, 44%). 610 mg of diasteromeric mixture was separated by normal phase preparative HPLC purification to afford BQ (270 mg) and BR (180 mg) as a white solid.

BQ: $^1$H NMR (500 MHz, DMSO-d$_6$) δ 7.44-7.36 (m, 5H), 4.86 (q, J=9.9 Hz, 2H), 4.40 (d, J=4.1 Hz, 1H), 4.23 (d, J=7.0 Hz, 1H), 3.73-3.59 (m, 2H), 3.47-3.34 (m, 2H), 3.10-3.08 (m, 1H), 3.00 (s, 3H), 2.85 (s, 3H), 2.74 (br s, 1H), 2.27-2.23 (t, J=10.4 Hz, 1H), 2.09-1.90 (m, 2H), 1.83-1.71 (m, 2H), 1.38 (s, 9H), 1.03 (d, J=6.4 Hz, 3H). LCMS (ESI): m/z 491.5 [M$^+$+1]. HPLC: 97.68%. Chiral HPLC: 100.00%. Column: CHIRALPAK IC (250*4.6 mm, 5 μm); Mobile Phase A: 0.1% DEA in n-hexane; Mobile Phase B: DCM:MeOH (50:50); A:B:: 80:20; Flow rate: 1.0 mL/min. Retention time: 16.822.

BR: $^1$H NMR (500 MHz, DMSO-d$_6$) δ 7.44-7.32 (m, 5H), 4.84 (q, J=10.0 Hz, 2H), 4.57 (d, J=2.9 Hz, 1H), 4.21 (d, J=7.0 Hz, 1H), 3.73-3.62 (m, 2H), 3.43 (d, J=6.4 Hz, 1H), 3.34 (d, J=10.4 Hz, 1H), 3.04 (s, 3H), 2.90-2.84 (m, 2H), 2.82 (s, 3H), 2.33-2.11 (m, 2H), 1.93-1.89 (m, 1H), 1.83-1.68 (m, 2H), 1.36 (s, 9H), 0.99 (d, J=6.4 Hz, 3H). LCMS (ESI): m/z 491.5 [M$^+$+1]. HPLC: 99.65%. Chiral HPLC: 100.00%. Column: CHIRALPAK IC (250*4.6 mm, 5 μm); Mobile Phase A: 0.1% DEA in n-hexane; Mobile Phase B: DCM:MeOH (50:50); A:B:: 80:20; Flow rate: 1.0 mL/min. Retention time: 24.172.

Synthesis of tert-butyl 6-(4(2S,3R)-1-(dimethylamino)-3-hydroxy-1-oxobutan-2-yl)amino)methyl)-1-oxo-2,5-diazaspiro[3.4]octane-5-carboxylate (BS & BT)

To a solution of Raney Nickel (2 g) in MeOH (10 mL) was added diasteromeric mixture BQ & BR (1.05 mg, 2.14 mmol) in MeOH (20 mL) at room temperature under nitrogen atmosphere and stirred under H$_2$ atmosphere (balloon pressure) for 16 h. After consumption of the starting material (by TLC), the reaction mixture was filtered through a pad of celite and washed with MeOH (10 mL). The filtrate was concentrated under reduced pressure to afford diasteromeric mixture (680 mg, 82%). The diasteromeric mixture was separated by chiral preparative HPLC purification to obtain BS (225 mg) and BT (210 mg) as a white solid.

BS: $^1$H NMR (400 MHz, DMSO-d$_6$) δ 7.40 (s, 1H), 4.40 (d, J=4.1 Hz, 1H), 4.06 (d, J=6.7 Hz, 1H), 3.74-3.63 (m, 1H), 3.43 (br s, 1H), 3.28 (br d, J=11.5 Hz, 1H), 3.12-3.00 (m, 5H), 2.85 (s, 3H), 2.77-2.65 (m, 1H), 2.36-2.24 (m, 1H), 2.06 (br s, 1H), 1.99-1.80 (m, 2H), 1.79-1.69 (m, 1H), 1.38 (s, 9H), 1.04 (d, J=6.3 Hz, 3H). LCMS (ESI): m/z 385.4 [M$^+$+1]. HPLC: 99.87%. Chiral HPLC: 100.00%. Column: CHIRALPAK IA (250*4 mm, 5 μm); Mobile Phase A: 0.1% DEA in n-hexane; Mobile Phase B: DCM:MeOH (50:50); A:B:: 85:15; Flow rate: 1.0 mL/min. Retention time: 8.926.

BT: $^1$H NMR (400 MHz, DMSO-d$_6$) δ 7.41 (s, 1H), 4.62 (br s, 1H), 4.06 (d, J=6.7 Hz, 1H), 3.76-3.66 (m, 1H), 3.45 (br s, 1H), 3.28 (s, 1H), 3.08 (s, 3H), 3.01-2.88 (m, 3H), 2.84 (s, 3H), 2.35-2.26 (m, 1H), 2.17 (br s, 1H), 1.98-1.79 (m, 2H), 1.78-1.68 (m, 1H), 1.38 (s, 9H), 1.02 (d, J=6.1 Hz, 3H). LCMS (ESI): m/z 385.4 [M$^+$+1]. HPLC: 98.65%. Chiral HPLC: 98.92%. Column: CHIRALPAK IA (250*4 mm, 5 μm); Mobile Phase A: 0.1% DEA in n-hexane; Mobile Phase B: DCM:MeOH (50:50); A:B 85:15; Flow rate: 1.0 mL/min. Retention time: 11.018.

Synthesis of formaldehyde O-benzyl oxime (Int-A):
The experimental procedure for the synthesis Int-A has been captured under AL-1 & AL-2 (as Int-A).

Preparation of Int-D:
Synthesis of ((benzyloxy)carbonyl)-L-threonine (B):
To a solution of L-threonine (20 g, 0.17 mol) in 1,4-dioxane and water (1:1, 200 mL) was added NaOH (27.35 g, 0.683 mol) followed by drop wise addition of CbzCl (50% solution in toluene, 87 mL, 0.256 mol) at 0° C. and stirred at room temperature for 16 h. The reaction was diluted with cold water (100 mL) and washed with EtOAc (100 mL). The aqueous layer acidified with 1N HCl solution and extracted with EtOAc (3×100 mL). The organic layer was washed with brine solution (100 mL) and dried over anhydrous Na$_2$SO$_4$, concentrated under reduced pressure to afford compound B (32 g, 75%) as a white solid. $^1$H NMR (400 MHz, DMSO-d$_6$) δ 12.64 (br s, 1H), 7.40-7.28 (m, 5H), 6.95 (d, J=8.9 Hz, 1H), 5.03 (s, 2H), 4.62-4.53 (m, 1H), 4.12-4.00 (m, 1H), 3.98-3.93 (m, 1H), 1.09 (d, J=6.4 Hz, 3H). LCMS (ESI): m/z 254.1 [M$^+$+1].

Synthesis of benzyl ((2S,3R)-1-(dimethylamino)-3-hydroxy-1-oxobutan-2-yl)carbamate (C)

To a solution of compound B (10 g, 39.52 mmol) in CH$_2$Cl$_2$ (100 mL) was added HOBt (8 g, 59.23 mmol), EDC.HCl (11.35 g, 59.23 mmol), dimethylamine hydrochloride (6.44 g, 79.05 mmol) and DIPEA (22 mL, 118.5 mmol) at 0° C. under nitrogen atmosphere and stirred at room temperature for 16 h. After consumption of the starting material (by TLC), the reaction mixture was quenched with water (100 mL) and extracted with DCM (2×200 mL). The combined organic layer was washed with brine (50 mL), dried over Na$_2$SO$_4$ and concentrated under reduced pressure. The residue was purified by Combi-Flash chromatography eluting with 60% EtOAc/n-hexane to afford compound C (9 g, 81%) as a white solid. $^1$H NMR (400 MHz, DMSO-d$_6$) δ 7.40-7.27 (m, 5H), 7.04 (br d, J=8.4 Hz, 1H), 5.08-4.97 (m, 2H), 4.72 (d, J=5.9 Hz, 1H), 4.41 (dd, J=5.4, 8.4 Hz, 1H), 3.86-3.78 (m, 1H), 3.07 (s, 3H), 2.83 (s, 3H), 1.03 (d, J=6.3 Hz, 3H). LCMS (ESI): m/z 281.1 [M$^+$+1].

Synthesis of (2S,3R)-2-amino-3-hydroxy-N,N-dimethylbutanamide (Int-D)

To a solution of compound C (11 g, 39.28 mmol) in MeOH (100 mL), 10% Pd/C (50% wet, 4 g) was added at room temperature and stirred under H$_2$ atmosphere (balloon) for 16 h. After consumption of the starting material (by TLC), the reaction mixture was filtered through a pad of celite and washed with MeOH (50 mL). The filtrate was concentrated under reduced pressure to afford Int-D (5 g, 87%) as a white solid. $^1$H NMR (400 MHz, DMSO-d$_6$) δ 3.57 (quin, J=6.2 Hz, 1H), 3.46 (d, J=6.0 Hz, 1H), 3.03 (s, 3H), 2.83 (s, 3H), 0.99 (d, J=6.3 Hz, 3H). LCMS (ESI): m/z 147.0 [M$^+$+1].

Synthesis of BU & BV:

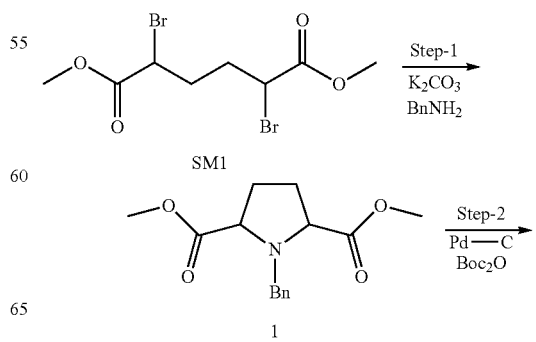

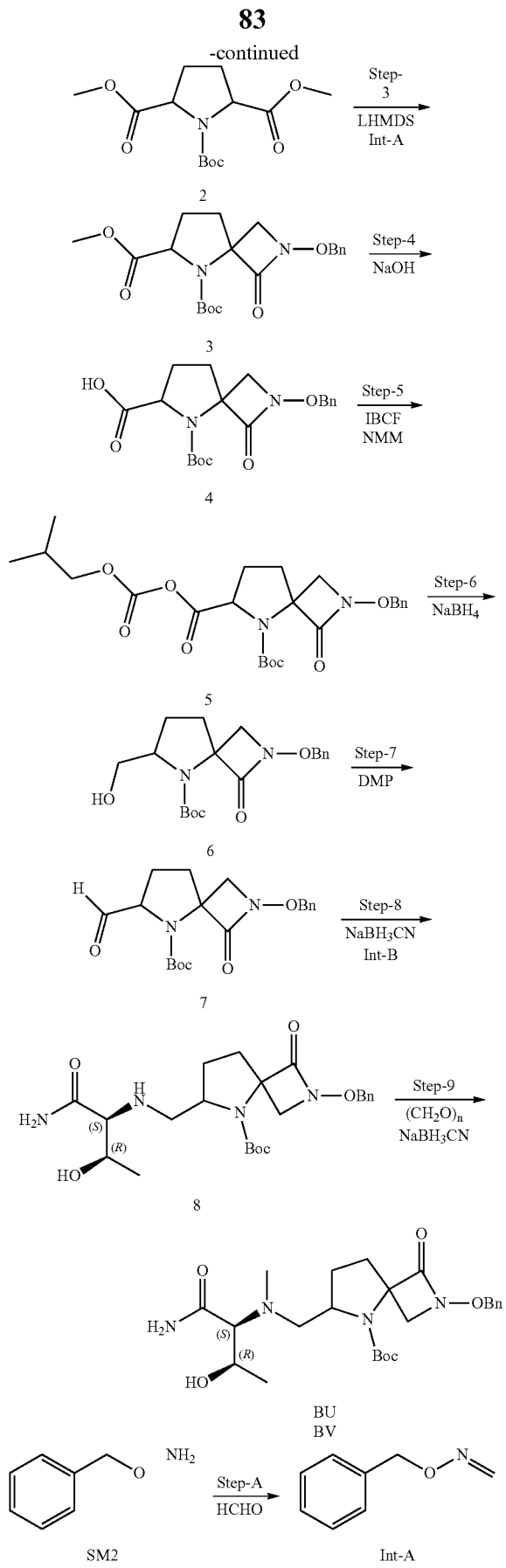

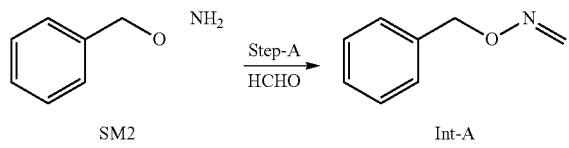

Int-B

Synthesis of tert-butyl 2-(benzyloxy)-6-formyl-1-oxo-2,5-diazaspiro[3.4]octane-5-carboxylate (7)

The experimental procedure for the synthesis of compound 7 has been captured under the synthesis of BI, BJ, BK & BL (as compound 7).

Synthesis of tert-butyl 6-(4(2S,3R)-1-amino-3-hydroxy-1-oxobutan-2-yl)amino)methyl)-2-(benzyloxy)-1-oxo-2,5-diazaspiro[3.4]octane-5-carboxylate (8)

To a solution of compound 7 (5.8 g, 0.016 mol) in MeOH (87 mL) was added Int-B (2.28 g, 0.019 mol) under nitrogen atmosphere and stirred at room temperature for 30 minutes. NaBH$_3$CN (2.02 g, 0.032 mol) was added and stirred at room temperature for 16 h. After consumption of the starting material (by TLC), volatiles were evaporated under reduced pressure. The reaction mixture was diluted with water (20 mL) and extracted with EtOAc (2×100 mL). The organic layer was washed with brine, dried over Na$_2$SO$_4$ and concentrated under reduced pressure. The residue was purified by column chromatography eluting with 2% MeOH/CH$_2$Cl$_2$ to afford diasteromeric mixture (3.4 g, 46%) as a white solid. $^1$H NMR (400 MHz, DMSO-d$_6$) δ 7.45-7.36 (m, 5H), 7.26-7.19 (m, 1H), 7.07-7.03 (m, 1H), 4.93-4.78 (m, 3H), 4.23-4.17 (m, 1H), 3.71-3.62 (m, 2H), 3.43-3.37 (m, 1H), 3.12-2.94 (m, 1H), 2.86-2.84 (m, 1H), 2.73-2.67 (m, 2H), 2.38-2.24 (m, 1H), 1.96-1.91 (m, 1H), 1.81-1.76 (m, 2H), 1.39 (s, 9H), 1.07-1.04 (m, 3H). LCMS (ESI): m/z 463.2 [M$^+$+1].

Synthesis of tert-butyl 6-(((((2S,3R)-1-amino-3-hydroxy-1-oxobutan-2-yl)(methyl)amino)methyl)-2-(benzyloxy)-1-oxo-2,5-diazaspiro[3.4]octane-5-carboxylate (BU & BV)

To a solution of compound 8 (1.8 g, 3.89 mmol) in MeOH (36 mL) were added paraformaldehyde (701 mg, 23.3 mmol) and AcOH (0.11 mL, 1.94 mmol). The reaction mixture was stirred at room temperature for 30 minutes. NaCNBH$_3$ (734 mg, 11.6 mmol) was added to reaction mixture and stirred at 60° C. for 16 h. After consumption of the starting material (by TLC), cooled to room temperature and volatiles were evaporated. The reaction mixture was diluted with water (30 mL) and extracted with EtOAc (3×100 mL). The organic layer was dried over Na$_2$SO$_4$ and concentrated under reduced pressure. The residue was purified by column chromatography by eluting 4% MeOH/EtOAc to afford diastereomeric mixture BU & BV (1.3 g, 70%) as a white solid.

1.05 g of diasteromeric mixture was purified by chiral preparative HPLC purification to afford BU (300 mg) and BV (235 mg) as a white solid.

BU: $^1$H NMR (400 MHz, DMSO-d$_6$) δ 7.48-7.36 (m, 5H), 7.32 (s, 1H), 7.00 (s, 1H), 4.92-4.80 (m, 2H), 4.22 (d, J=6.8

Hz, 1H), 4.02 (s, 1H), 3.79 (d, J=10.2 Hz, 2H), 3.48 (d, J=10.3 Hz, 1H), 3.30-3.13 (m, 2H), 2.79 (d, J=9.3 Hz, 1H), 2.41 (br s, 1H), 2.35 (s, 3H), 2.04-1.72 (m, 3H), 1.38 (s, 9H), 1.00 (d, J=6.1 Hz, 3H). LCMS (ESI): m/z 477.2 [M$^+$+1]. HPLC: 99.52%.

BV: $^1$H NMR (400 MHz, DMSO-d$_6$) δ 7.45-7.36 (m, 5H), 7.29 (s, 1H), 6.97 (s, 1H), 4.88-4.82 (m, 2H), 4.23 (d, J=7.2 Hz, 1H), 4.13 (s, 1H), 3.84 (dd, J=6.6, 8.3 Hz, 1H), 3.78 (d, J=10.2 Hz, 1H), 3.34-3.27 (m, 2H), 3.13 (d, J=14.4 Hz, 1H), 2.74 (d, J=9.2 Hz, 1H), 2.46-2.42 (m, 1H), 2.37 (s, 3H), 2.02-1.91 (m, 1H), 1.82-1.72 (m, 2H), 1.38 (s, 9H), 1.02 (d, J=6.1 Hz, 3H). LCMS (ESI): m/z 477.2 [M$^+$+1]. HPLC: 99.39%.

Synthesis of formaldehyde O-benzyl oxime (Int-A):

The experimental procedure for the synthesis Int-A has been captured under AL-1 & AL-2 (as Int-A).

Synthesis of BW & BX:

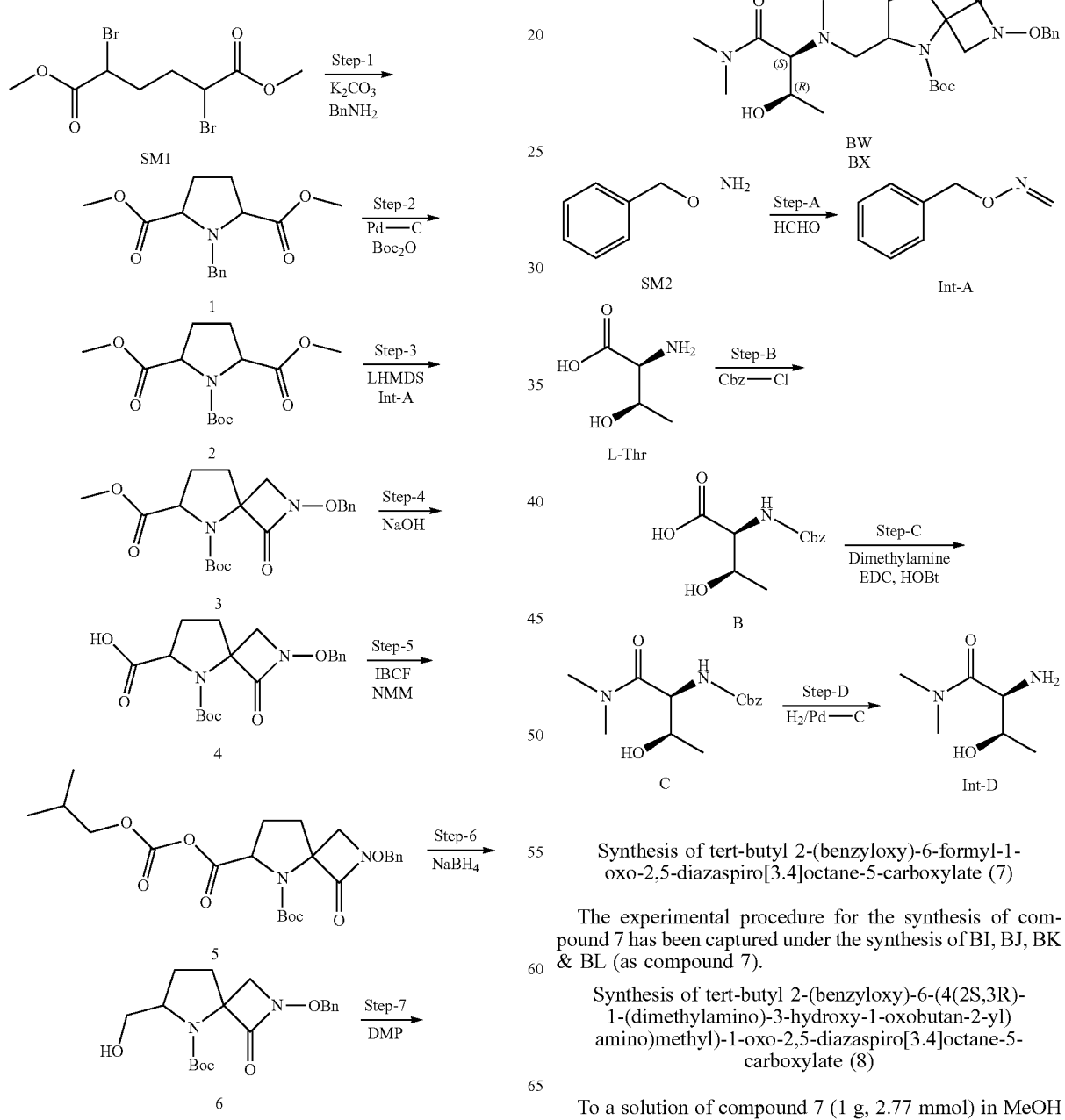

Synthesis of tert-butyl 2-(benzyloxy)-6-formyl-1-oxo-2,5-diazaspiro[3.4]octane-5-carboxylate (7)

The experimental procedure for the synthesis of compound 7 has been captured under the synthesis of BI, BJ, BK & BL (as compound 7).

Synthesis of tert-butyl 2-(benzyloxy)-6-(4(2S,3R)-1-(dimethylamino)-3-hydroxy-1-oxobutan-2-yl) amino)methyl)-1-oxo-2,5-diazaspiro[3.4]octane-5-carboxylate (8)

To a solution of compound 7 (1 g, 2.77 mmol) in MeOH (20 mL) were added Int-D (487 mg, 3.33 mmol) and AcOH (0.1 mL) under nitrogen atmosphere and stirred at room temperature for 40 minutes. NaBH$_3$CN (525 mg, 8.33 mmol) was added to the reaction mixture and stirred at room temperature for 16 h. After consumption of the starting material (by TLC), the reaction mixture was quenched saturated aqueous NaHCO$_3$ and volatiles were evaporated under reduced pressure. The reaction mixture was diluted with saturated aqueous NaHCO$_3$ (50 mL) and extracted with EtOAc (2×200 mL). The organic layer was washed with brine, dried over Na$_2$SO$_4$ and concentrated under reduced pressure. The residue was purified by Combi-Flash chromatography eluting with 5% MeOH/EtOAc to afford diastereomeric mixture compound 8 (610 mg, 44%) as a white semi solid. $^1$H NMR (500 MHz, DMSO-d$_6$) δ 7.44-7.36 (m, 5H), 4.89-4.78 (m, 2H), 4.38-4.36 (m, 1H), 4.23-4.18 (m, 1H), 3.73-3.59 (m, 2H), 3.43-3.31 (m, 2H), 3.14-3.08 (m, 1H), 2.98 (s, 3H), 2.84 (s, 3H), 2.74-2.68 (m, 1H), 2.27-2.23 m, 1H), 1.96-1.90 (m, 2H), 1.79-1.73 (m, 2H), 1.38 (s, 9H), 1.05-1.01 (m, 3H). LCMS (ESI): m/z 491.5 [M$^+$+1].

Synthesis of tert-butyl 2-(benzyloxy)-6-(4(2S,3R)-1-(dimethylamino)-3-hydroxy-1-oxobutan-2-yl)(methyl)amino)methyl)-1-oxo-2,5-diazaspiro[3.4]octane-5-carboxylate (BW & BX)

To a solution of compound 8 (900 mg, 1.83 mmol) in MeOH (18 mL) were added paraformaldehyde (330 mg, 11.01 mmol) and AcOH (0.05 mL, 0.91 mmol) and stirred at room temperature for 30 minutes. NaCNBH$_3$ (461 mg, 7.34 mmol) was added to the reaction mixture stirred at 60° C. for 16 h. After consumption of the starting material (by TLC), cooled to room temperature and volatiles were evaporated. The residue was diluted with water (30 mL) and extracted with EtOAc (3×100 mL). The organic layer was dried over Na$_2$SO$_4$ and concentrated under reduced pressure. The residue was purified by column chromatography by eluting 4% MeOH/EtOAc to afford diastereomeric mixture of BW & BX (850 mg, 91%) as a white solid.

Another batch from 100 mg of SM afforded diastereomeric mixture of BW & BX (50 mg) as a white solid.

900 mg of diasteromeric mixture was purified by chiral preparative HPLC purification to afford BX (303 mg) and BW (358 mg) as a white solid.

BW: $^1$H NMR (400 MHz, DMSO-d$_6$) δ 7.46-7.36 (m, 5H), 4.86 (q, J=10.1 Hz, 2H), 4.27 (d, J=4.6 Hz, 1H), 4.21 (d, J=7.0 Hz, 1H), 3.96 (ddd, J=4.8, 6.0, 9.1 Hz, 1H), 3.75 (d, J=10.3 Hz, 1H), 3.35 (s, 1H), 3.31-3.20 (m, 3H), 3.03 (s, 3H), 2.81 (s, 3H), 2.41 (s, 3H), 2.39-2.30 (m, 1H), 2.02-1.87 (m, 1H), 1.82-1.67 (m, 2H), 1.38 (s, 9H), 0.94 (d, J=6.0 Hz, 3H). LCMS (ESI): m/z 505.2 [M$^+$+1]. HPLC: 99.53%. Chiral HPLC: 100.00%. Column: CHIRALPAK IA (250*4.6 mm, 5 μm); Mobile Phase A: 0.1% DEA in n-hexane; Mobile Phase B: DCM:MeOH (50:50); A:B:: 90:10; Flow rate: 1.0 mL/min. Retention time: 7.764.

BX: $^1$H NMR (400 MHz, DMSO-d$_6$) δ 7.45-7.36 (m, 5H), 4.92-4.78 (m, 2H), 4.38 (d, J=4.9 Hz, 1H), 4.21 (d, J=7.0 Hz, 1H), 4.12-4.00 (m, 1H), 3.62 (d, J=10.3 Hz, 1H), 3.35 (s, 1H), 3.28-3.14 (m, 3H), 3.01 (s, 3H), 2.78 (s, 3H), 2.54 (s, 3H), 2.36-2.25 (m, 1H), 2.02-1.89 (m, 1H), 1.84-1.73 (m, 1H), 1.72-1.62 (m, 1H), 1.39 (s, 9H), 0.95 (d, J=6.0 Hz, 3H). LCMS (ESI): m/z 505.2 [M$^+$+1]. HPLC: 96.52%. Chiral HPLC: 96.89%. Column: CHIRALPAK IA (250*4.6 mm, 5 μm); Mobile Phase A: 0.1% DEA in n-hexane; Mobile Phase B: DCM:MeOH (50:50); A:B:: 90:10; Flow rate: 1.0 mL/min. Retention time: 9.390.

Synthesis of formaldehyde O-benzyl oxime (Int-A):

The experimental procedure for the synthesis Int-A has been captured under AL-1 & AL-2 (as Int-A).

Synthesis of (2S,3R)-2-amino-3-hydroxy-N,N-dimethylbutanamide (Int-D)

The experimental procedure for the synthesis Int-D has been captured under BQ, BR, BS & BT (as Int-D).

Synthesis of BY:

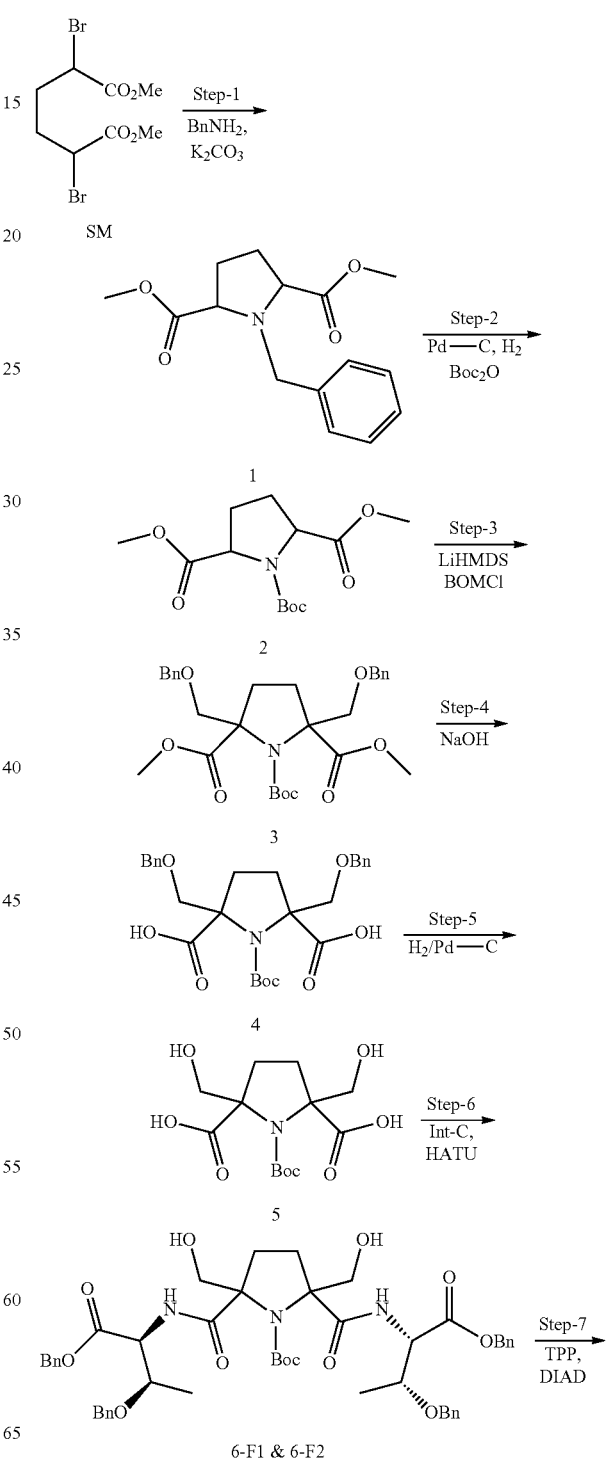

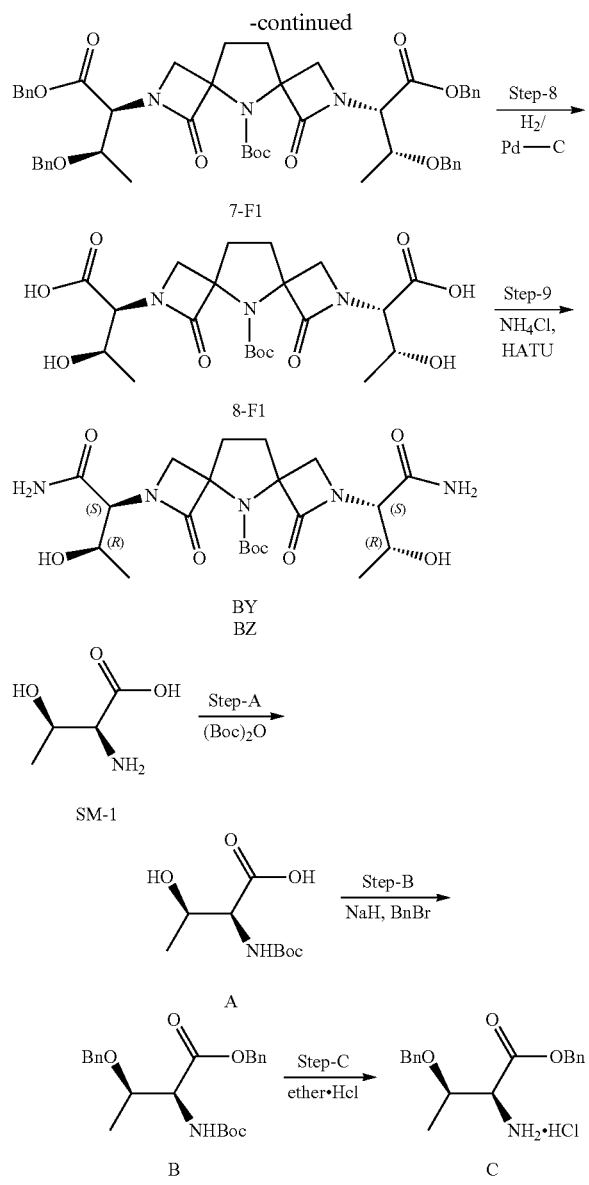

Synthesis of 1-(tert-butyl) 2,5-dimethyl pyrrolidine-1,2,5-tricarboxylate (2)

The experimental procedure for the synthesis of compound 2 has been captured under the synthesis of BI, BJ, BK & BL (as compound 2).

Synthesis of 1-(tert-butyl) 2,5-dimethyl 2,5-bis((benzyloxy)methyl)pyrrolidine-1,2,5-tricarboxylate (3)

To a stirring solution of compound 2-isomeric mixture (10 g, 0.034 mol) in THF (100 mL) was added LiHMDS (1.0M in THF) (139 mL, 0.139 mol) at −10° C. under nitrogen atmosphere. After stirring for 1 h, BOM-Cl (16.2 g, 0.104 mol) was added at −10° C. The reaction mixture was brought to RT and stirred for 4 h. After consumption of the starting material (by TLC), the reaction was quenched with NH$_4$Cl solution (50 mL) and extracted with EtOAc (3×500 mL). Separated organic layer was dried over Na$_2$SO$_4$ and concentrated to obtain crude compound which was purified by column chromatography by eluting 10% EtOAc/Hexane to afford compound 3-isomeric mixture (10.4 g, 56%) as white solid. $^1$H NMR (400 MHz, CDCl$_3$): δ 7.40-7.21 (m, 10H), 4.69-4.55 (m, 4H), 4.16 (d, J=9.9 Hz, 1H), 4.08 (d, J=9.9 Hz, 1H), 4.01 (d, J=10.0 Hz, 1H), 3.85 (d, J=9.9 Hz, 1H), 3.63 (d, J=15.3 Hz, 6H), 2.47-2.15 (m, 4H), 1.35 (s, 9H). LCMS (ESI): m/z 428.1 [M$^+$+1-Boc]; HPLC: 95.74%.

Synthesis of 2,5-bis((benzyloxy)methyl)-1-(tert-butoxycarbonyl)pyrrolidine-2,5-dicarboxylic acid (4)

To a solution of compound 3-isomeric mixture (10.4 g, 0.0197 mol) in MeOH:THF:H$_2$O (90 mL, 1:1:1) was added NaOH (4.7 g, 0.118 mol) at RT and stirred 10 minutes. The reaction mixture was heated to 80° C. and stirred for 16 h. After consumption of the starting material (by TLC), reaction mixture was brought to RT, volatiles were evaporated under reduced pressure. Crude material was diluted with water (100 mL). Aqueous layer was acidified using 2N HCl solution (pH-2) and extracted with EtOAc (3×200 mL). Combined organic layers were dried over Na$_2$SO$_4$ and concentrated to afford compound 4-isomeric mixture (6.4 g, 65%) as white solid. LCMS (ESI): m/z 500.2 [M$^+$+1].

Synthesis of 1-(tert-butoxycarbonyl)-2,5-bis(hydroxymethyl)pyrrolidine-2,5-dicarboxylic acid (5)

To a stirring solution of compound 4-isomeric mixture (6.4 g, 0.128 mol) in methanol (100 mL) was added 50% wet 10% Pd—C (32 g) at RT and stirred for 16 h under H$_2$ atmosphere. After consumption of the starting material (by TLC), the reaction mixture was filtered through a pad of celite and the pad was washed with Et$_2$O. Obtained filtrate was concentrated under reduced pressure to afford compound 5-isomeric mixture (3.4 g, 83%) as white solid. LCMS (ESI): m/z 219.9 [M$^+$+1-Boc].

Synthesis of dibenzyl 2,2'-((1-(tert-butoxycarbonyl)-2,5-bis(hydroxymethyl)pyrrolidine-2,5-dicarbonyl)bis(azanediyl))(2S,2'S,3R,3'R)-bis(3-(benzyloxy)butanoate) (6)

To a stirring solution of compound 5-isomeric mixture (4.4 g, 0.013 mol) in DCM (50 mL) were added DIPEA (14.6 mL, 0.082 mol), HATU (15.7 g, 0.041 mol) and Int C (8.2 g, 0.027 mol) at 0° C. under nitrogen atmosphere. The reaction mixture was brought to RT and stirred for 16 h. After consumption of the starting material (by TLC), the reaction mixture was diluted with water (100 mL) and extracted with DCM (2×200 mL). Organic layer was washed with NH$_4$Cl solution and brine solution, dried over anhydrous Na$_2$SO$_4$ and concentrated under reduced pressure to afford crude compound which was purified by column chromatography by eluting 30-40% EtOAc/n-hexane followed by MPLC column chromatography to obtain compound 6-F1 (4.4 g, 36%) and compound 6-F2 (2 g, 16%) as thick syrup.

Compound 6-F1: $^1$H NMR (400 MHz, DMSO-d$_6$): δ 9.51 (dd, J=8.2, 15.5 Hz, 2H), 7.36-7.20 (m, 20H), 5.76-5.68 (m, 2H), 5.07 (s, 4H), 4.55-4.31 (m, 8H), 4.27-3.94 (m, 2H), 3.88-3.61 (m, 2H), 2.23 (br d, J=5.0 Hz, 2H), 1.99-1.85 (m, 2H), 1.29 (s, 9H), 1.21-1.06 (m, 6H). LCMS (m/z): 782.3 [M$^+$+1-Boc].

Synthesis of dibenzyl 2,2'-(5-(tert-butoxycarbonyl)-1,7-dioxo-2,5,8-triazadispiro[3.1.36.24]undecane-2,8-diyl)(2S,2'S,3R,3'R)-bis(3-(benzyloxy)butanoate) (7-F1)

To a mixture of TPP (11.8 g, 0.045 mol) and DIAD (10.5 g, 0.045 mol) in THF (25 mL) was added compound 6-F1 (4 g, 0.045 mol) at 0° C. under nitrogen atmosphere. The reaction mixture was stirred at 0° C. for 3 h. After consumption of the starting material (by TLC), quenched with ice and volatiles were evaporated under reduced pressure. Obtained crude material was purified by column chromatography by eluting 10% EtOAc/Hexane to afford compound 7-F1 (1.3 g, 34%) as thick syrup. $^1$H NMR (500 MHz, DMSO-$d_6$): δ 7.43-7.18 (m, 20H), 5.22-5.07 (m, 4H), 4.59-4.48 (m, 4H), 4.30 (d, J=11.9 Hz, 2H), 4.10-4.00 (m, 2H), 3.96-3.80 (m, 2H), 3.61-3.41 (m, 2H), 2.13 (br s, 2H), 2.02-1.93 (m, 2H), 1.25 (s, 9H), 1.13 (br s, 6H). LCMS (ESI): m/z 790.6 [M$^+$+1-56].

Synthesis of (2S,2'S,3R,3'R)-2,2'-(5-(tert-butoxycarbonyl)-1,7-dioxo-2,5,8-triazadispiro[3.1.36.24]undecane-2,8-diyl)bis(3-hydroxybutanoic acid) (8-F1)

To a solution of compound 7-F1 (1.3 g, 1.53 mmol) in methanol (25 mL) was added 50% wet 10% Pd—C (1.3 g) at RT and stirred for 16 h under H$_2$ atmosphere. After consumption of the starting material (by TLC), the reaction mixture was filtered through a pad of celite and the pad was washed with Et$_2$O. Obtained filtrate was concentrated under reduced pressure and triturated with Et$_2$O to afford compound 8-F1 (750 mg, crude) as off white solid. $^1$H NMR (400 MHz, DMSO-$d_6$): δ 12.99-12.78 (m, 2H), 5.14-4.91 (m, 2H), 4.11-4.04 (m, 3H), 3.86-3.81 (m, 2H), 3.71-3.47 (m, 3H), 2.15 (br s, 4H), 1.32 (s, 9H), 1.14-1.03 (m, 6H). LCMS (ESI): m/z 430 [M$^+$+1-56].

Synthesis of tert-butyl 2,8-bis((2S,3R)-1-amino-3-hydroxy-1-oxobutan-2-yl)-1,7-dioxo-2,5,8-triazadispiro[3.1.36.24]undecane-5-carboxylate (BY)

To a stirring solution of crude compound 8-F1 (750 mg, 1.54 mmol) in DCM (25 mL) were added DIPEA (1.61 mL, 9.27 mmol), HATU (1.7 g, 4.62 mmol) and NH$_4$Cl (412 mg, 7.73 mmol) at 0° C. under nitrogen atmosphere. The reaction mixture was brought to RT and stirred for 16 h. After consumption of the starting material (by TLC), volatiles were evaporated under reduced pressure. Obtained crude material was purified by column chromatography by eluting 2% MeOH/DCM followed by trituration with ether to obtain BY (90 mg, 8%) as white solid. $^1$H NMR (400 MHz, DMSO-$d_6$): δ 7.63 (br s, 1H), 7.47-7.30 (m, 2H), 7.08 (br s, 1H), 4.91 (dd, J=5.6, 17.4 Hz, 2H), 4.26 (dd, J=5.1, 10.0 Hz, 1H), 4.01 (d, J=7.9 Hz, 1H), 3.95 (d, J=3.6 Hz, 1H), 3.87-3.76 (m, 1H), 3.64 (s, 3H), 3.53 (s, 1H), 2.21-2.10 (m, 4H), 1.34 (s, 9H), 1.10-1.04 (m, 6H). LCMS (ESI): m/z 483.5 [M$^+$+1]. Chiral HPLC: 100.00%. Column: CHIRALPAK IC (250*4.6 mm, 5 μm); Mobile Phase A: 0.1% TFA in n-hexane; Mobile Phase B: DCM:MeOH (50:50); A:B:: 70:30; Flow rate: 1.0 mL/min; Retention time: 10.840.

Preparation of Int-C:

Synthesis of (2S)-2-((tert-butoxycarbonyl) amino)-3-hydroxybutanoic acid (A)

To a solution of SM-1 (100 g, 456 mmol) in 1, 4 dioxane (450 mL_ and H$_2$(400 mL) were added NaOH (36.5 g, 913 mmol), Boc$_2$O (119 g, 547 mmol) at 0° C. The reaction mixture was stirred at room temperature for 16 h. After consumption of the starting material (by TLC), the reaction mixture was acidified with aqueous 2N HCl (pH-4) and extracted with EtOAc (5×500 mL). The combined organic extracts were dried over anhydrous Na$_2$SO$_4$ and concentrated under reduced pressure to afford compound A (55 g, 55%) as a yellow syrup. $^1$H NMR (400 MHz, DMSO-$d_6$) δ 6.29 (d, J=8.8 Hz, 1H), 4.04-3.98 (m, 1H), 3.87-3.84 (m, 1H), 1.30 (s, 9H), 1.05 (d, J=6.4 Hz, 3H).

Synthesis of benzyl (2S)-3-(benzyloxy)-2-((tert-butoxycarbonyl) amino)butanoate (B)

To a solution of compound A (50 g, 156 mmol) in DMF (200 mL) was added NaH (60%) (7.52 g, 313 mmol) at −15° C. and stirred for 2 h. Benzyl bromide (32.0 g, 188 mmol) was added slowly to the resulting reaction mixture. The reaction mixture temperature was warmed to room temperature and stirred for 12 h. After consumption of the starting material (by TLC), the reaction mixture was poured into chilled water (200 mL) and extracted with diethyl ether (4×250 mL). The aqueous layer was acidified with citric acid (pH-4) and extracted with EtOAc (4×500 mL). The combined organic layers were washed with water (3×250 mL). The organic extracts were dried over anhydrous Na$_2$SO$_4$, filtered and concentrated under reduced pressure to afford compound B (20 g, 31.2%) as a brown syrup. LCMS (ESI): m/z 300.15 [M$^+$-Boc].

Synthesis of benzyl (2S)-2-amino-3-(benzyloxy) butanoate hydrochloride I (Int-C)

To a solution of compound B (20.0 g, 48.8 mmol) in HCl in ether (20 mL) was added at 0° C. and stirred at room temperature for 12 h. The obtained precipitate was filtered and triturated with diethyl ether (2×100 mL) and hexane (2×200 mL). The filtered compound was dried under vacuum to afford Int-C (14.0 g, 96.4%) as a white solid. $^1$H NMR (400 MHz, DMSO-$d_6$) δ 8.68 (s, 3H), 7.50-7.25 (m, 10H), 5.24-5.13 (m, 2H), 4.53 (d, J=11.6 Hz, 1H), 4.35 (d, J=11.6 Hz, 1H), 4.23 (d, J=3.2 Hz, 1H), 4.11-4.07 (m, 1H), 1.27 (d, J=6.4 Hz, 3H).

Synthesis of CA, CB, CC & CD:

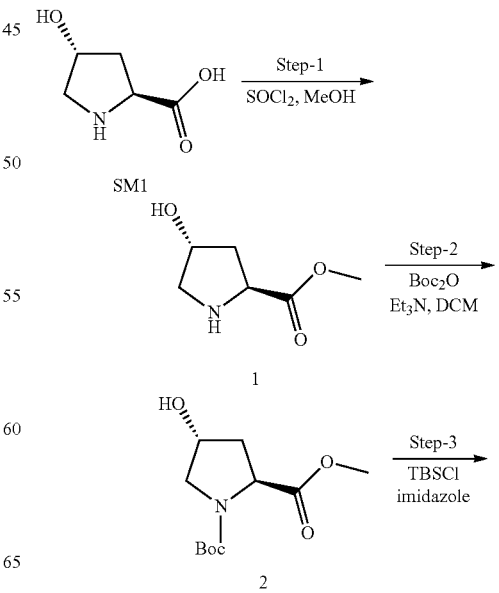

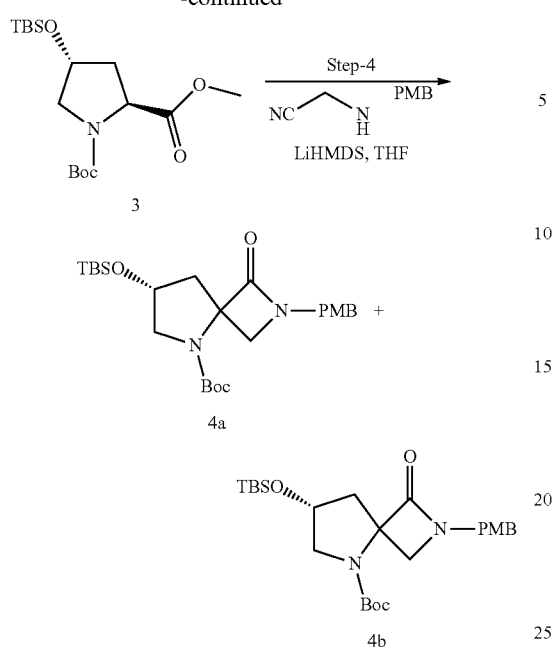
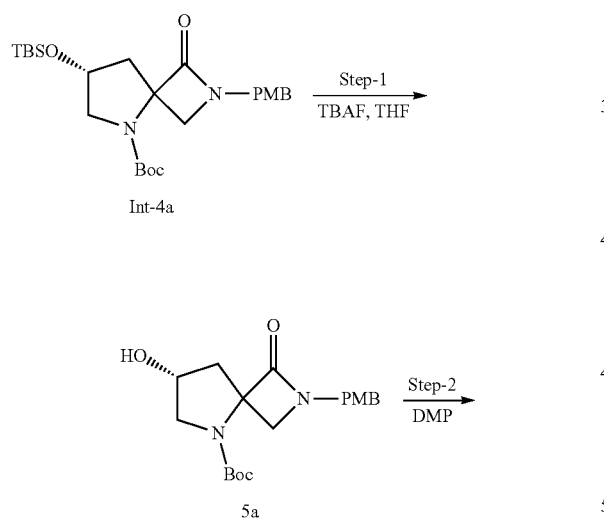
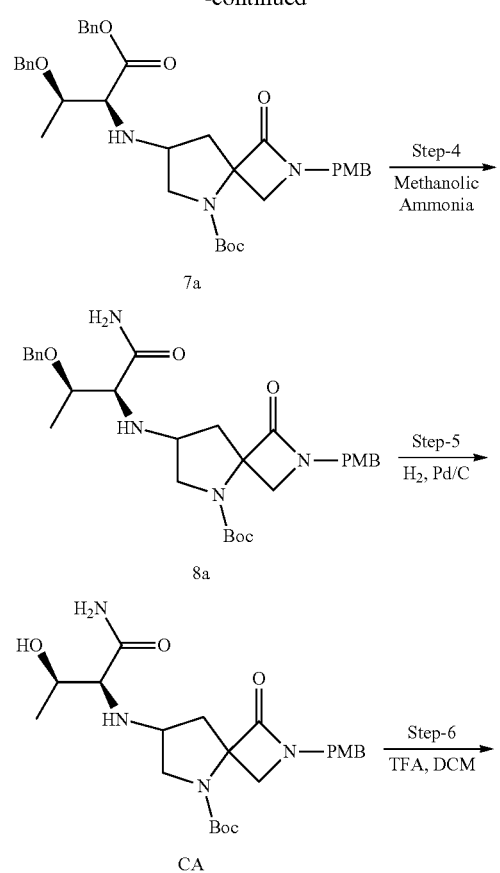
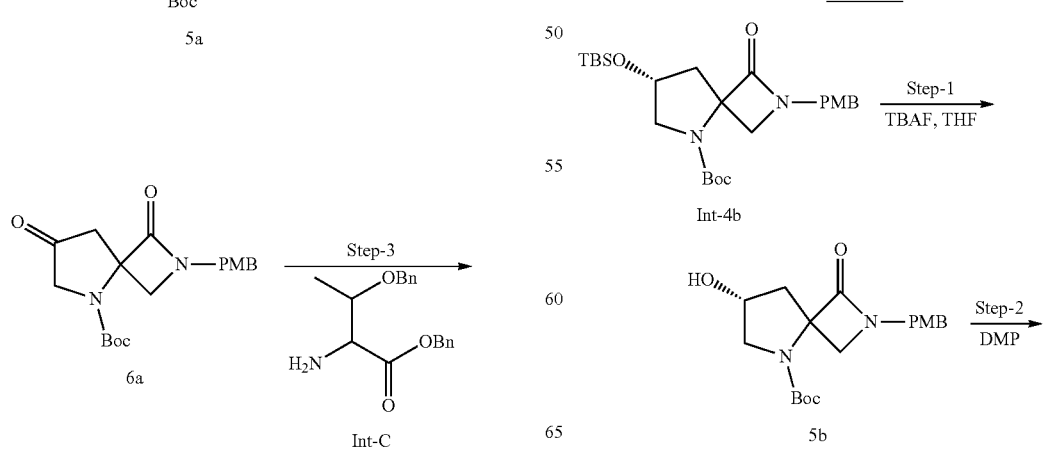

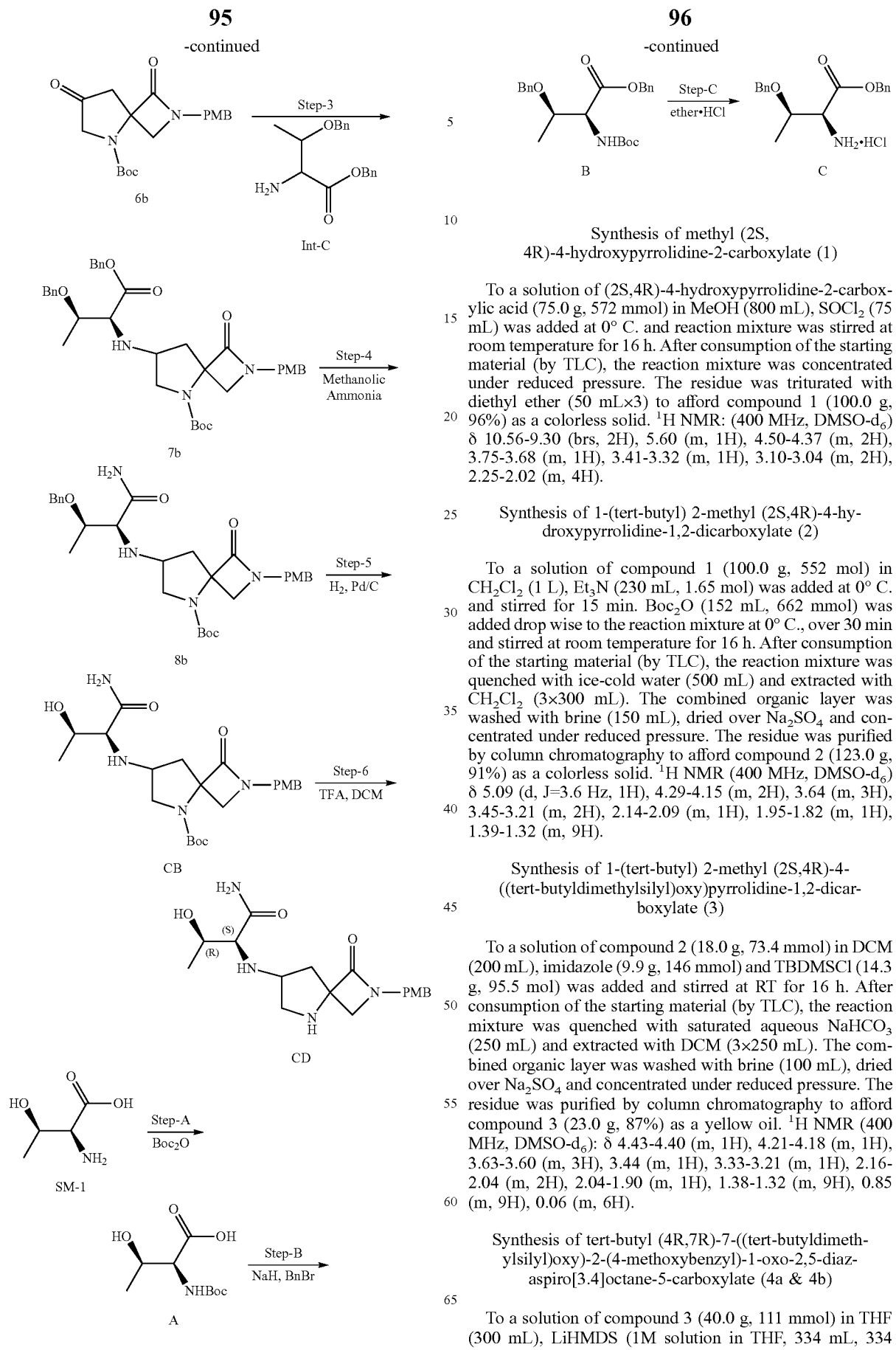

Synthesis of methyl (2S, 4R)-4-hydroxypyrrolidine-2-carboxylate (1)

To a solution of (2S,4R)-4-hydroxypyrrolidine-2-carboxylic acid (75.0 g, 572 mmol) in MeOH (800 mL), SOCl₂ (75 mL) was added at 0° C. and reaction mixture was stirred at room temperature for 16 h. After consumption of the starting material (by TLC), the reaction mixture was concentrated under reduced pressure. The residue was triturated with diethyl ether (50 mL×3) to afford compound 1 (100.0 g, 96%) as a colorless solid. ¹H NMR: (400 MHz, DMSO-d₆) δ 10.56-9.30 (brs, 2H), 5.60 (m, 1H), 4.50-4.37 (m, 2H), 3.75-3.68 (m, 1H), 3.41-3.32 (m, 1H), 3.10-3.04 (m, 2H), 2.25-2.02 (m, 4H).

Synthesis of 1-(tert-butyl) 2-methyl (2S,4R)-4-hydroxypyrrolidine-1,2-dicarboxylate (2)

To a solution of compound 1 (100.0 g, 552 mol) in CH₂Cl₂ (1 L), Et₃N (230 mL, 1.65 mol) was added at 0° C. and stirred for 15 min. Boc₂O (152 mL, 662 mmol) was added drop wise to the reaction mixture at 0° C., over 30 min and stirred at room temperature for 16 h. After consumption of the starting material (by TLC), the reaction mixture was quenched with ice-cold water (500 mL) and extracted with CH₂Cl₂ (3×300 mL). The combined organic layer was washed with brine (150 mL), dried over Na₂SO₄ and concentrated under reduced pressure. The residue was purified by column chromatography to afford compound 2 (123.0 g, 91%) as a colorless solid. ¹H NMR (400 MHz, DMSO-d₆) δ 5.09 (d, J=3.6 Hz, 1H), 4.29-4.15 (m, 2H), 3.64 (m, 3H), 3.45-3.21 (m, 2H), 2.14-2.09 (m, 1H), 1.95-1.82 (m, 1H), 1.39-1.32 (m, 9H).

Synthesis of 1-(tert-butyl) 2-methyl (2S,4R)-4-((tert-butyldimethylsilyl)oxy)pyrrolidine-1,2-dicarboxylate (3)

To a solution of compound 2 (18.0 g, 73.4 mmol) in DCM (200 mL), imidazole (9.9 g, 146 mmol) and TBDMSCl (14.3 g, 95.5 mol) was added and stirred at RT for 16 h. After consumption of the starting material (by TLC), the reaction mixture was quenched with saturated aqueous NaHCO₃ (250 mL) and extracted with DCM (3×250 mL). The combined organic layer was washed with brine (100 mL), dried over Na₂SO₄ and concentrated under reduced pressure. The residue was purified by column chromatography to afford compound 3 (23.0 g, 87%) as a yellow oil. ¹H NMR (400 MHz, DMSO-d₆): δ 4.43-4.40 (m, 1H), 4.21-4.18 (m, 1H), 3.63-3.60 (m, 3H), 3.44 (m, 1H), 3.33-3.21 (m, 1H), 2.16-2.04 (m, 2H), 2.04-1.90 (m, 1H), 1.38-1.32 (m, 9H), 0.85 (m, 9H), 0.06 (m, 6H).

Synthesis of tert-butyl (4R,7R)-7-((tert-butyldimethylsilyl)oxy)-2-(4-methoxybenzyl)-1-oxo-2,5-diazaspiro[3.4]octane-5-carboxylate (4a & 4b)

To a solution of compound 3 (40.0 g, 111 mmol) in THF (300 mL), LiHMDS (1M solution in THF, 334 mL, 334 mmol) was added at −78° C. and stirred at room temperature for 30 min 2-((4-methoxybenzyl) amino) acetonitrile (39.0 g, 222 mmol) was added to the reaction mixture at −50° C. and stirred at room temperature for 2 h. After consumption of the starting material (by TLC), the reaction mixture was quenched with saturated NH$_4$Cl solution (300 mL) and extracted with EtOAc (3×300 mL). The combined organic layer was washed with brine (100 mL), dried over Na$_2$SO$_4$ and concentrated under reduced pressure. The residue was purified by column chromatography to afford diastereomers compound 4a (29.0 g, 54.7%) and compound 4b (10.0 g, 18.8%) as a thick oil.
Scheme A Synthesis of tert-butyl (7R)-7-hydroxy-2-(4-methoxybenzyl)-1-oxo-2,5-diazaspiro[3.4]octane-5-carboxylate (5a)

To a solution of compound 4a (28.0 g, 58.8 mmol) in THF (200 mL), TBAF (1M solution in THF, 88.2 mL, 88.2 mmol) was added drop wise at 0° C. and stirred at 50° C. for 3 h. After consumption of the starting material (by TLC), the reaction mixture was quenched with ice-cold water (150 mL) and extracted with EtOAc (3×200 mL). The combined organic layer was washed with saturate aqueous NaHCO$_3$ (150 mL) and brine (150 mL), dried over Na$_2$SO$_4$ and concentrated under reduced pressure. The residue was purified by column chromatography using 50% EtOAc/hexane to afford compound 5a (20.0 g, 94.3%) as a yellow oil. LCMS (ESI): m/z 307 [M$^+$-55].

Synthesis of tert-butyl 2-(4-methoxybenzyl)-1,7-dioxo-2,5-diazaspiro[3.4]octane-5-carboxylate (6a)

To a solution of compound 5a (20.0 g, 55.2 mmol) in CH$_2$Cl$_2$ (300 mL), Dess-martin periodinene (46.8 g, 110 mmol) was added at 0° C. and stirred at room temperature for 16 h. After consumption of the starting material (by TLC), the reaction mixture was filtered through a bed of celite. The filtrate was diluted with water (250 mL) and extracted with EtOAc (4×250 mL). The combined organic layer was washed with saturated aqueous NaHCO$_3$ (300 mL) and brine (100 mL), dried over Na$_2$SO$_4$ and concentrated under reduced pressure. The residue was purified by column chromatography using 25% EtOAc/hexane to afford compound 6a (12.0 g, 60%) as a white solid. LCMS (ESI): m/z 359 [M$^+$−1].

Synthesis of tert-butyl 7-0(2S,3R)-1,3-bis(benzyloxy)-1-oxobutan-2-yl)amino)-2-(4-methoxybenzyl)-1-oxo-2,5-diazaspiro[3.4]octane-5-carboxylate (7a)

To a solution of compound 6a (7.0 g, 19.4 mmol), Int-C (6.3 g, 21.3 mmol) in MeOH (200 mL) and AcOH (2.5 mL) was added and the reaction mixture was stirred at room temperature for 16 h. Sodium triacetoxy borohydride (3.7 g, 58.3 mmol) was added at 0° C. portion wise over period of 10 minutes and the reaction mixture was stirred at room temperature for 4 h. After consumption of the starting material (by TLC), the reaction mixture was concentrated under reduced pressure. The residue was dissolved in water (200 mL) and extracted with EtOAc (3×100 mL). The combined organic layer was washed with brine (150 mL), dried over Na$_2$SO$_4$ and concentrated under reduced pressure. The residue was purified by column chromatography to afford compound 7a (7.0 g, 56%) as a thick oil. LCMS (ESI): m/z 644 [M$^+$+1].

Synthesis of tert-butyl 7-0(2S,3R)-1-amino-3-(benzyloxy)-1-oxobutan-2-yl)amino)-2-(4-methoxybenzyl)-1-oxo-2,5-diazaspiro[3.4]octane-5-carboxylate (8a)

To a solution of compound 7a (7.0 g, 10.8 mmol) in MeOH (10 mL), methanolic ammonia (50 mL) was added at 0° C. and stirred at same temperature for 4.5 h. After consumption of starting material (by TLC), RM was evaporated to afford residue. The residue was purified by SFC chromatography to afford compound 8a (1.4 g, 23%). LCMS (ESI): m/z 553 [M$^+$+1].

Synthesis of tert-butyl 7-(((2S,3R)-1-amino-3-hydroxy-1-oxobutan-2-yl)amino)-2-(4-methoxybenzyl)-1-oxo-2,5-diazaspiro[3.4]octane-5-carboxylate (CA)

To a solution of compound 8a (1.3 g, 2.35 mmol) in MeOH (30 mL), 10% Pd/C (400 mg) was added at room temperature and stirred under H$_2$ atmosphere (balloon) for 12 h. After consumption of the starting material (by TLC), the reaction mixture was filtered through a pad of celite and washed with MeOH (50 mL). The filtrate was concentrated under reduced pressure to afford CA (0.9 g, 90%). $^1$H NMR (400 MHz, DMSO-d6) δ 7.52 (d, J=11.6 Hz, 1H), 7.20 (d, J=8.4 Hz, 1H), 7.18 (dd, J=8.4 Hz, 1H), 7.02 (d, J=3.1 Hz, 1H), 6.91 (dd, J=8.4, 6.1 Hz, 2H), 4.57 (dd, J=9.2, 5.0 Hz, 2H), 4.45-4.33 (m, 1H), 3.94 (d, J=15.0 Hz, 1H), 3.74 (s, 3H), 3.71-3.62 (m, 1H), 3.42-3.40 (m, 2H), 3.24-3.03 (m, 3H), 2.76 (d, J=5.7 Hz, 1H), 2.27 (m, 2H), 1.38 (s, 9H), 1.11-1.02 (m, 3H). LCMS (ESI): m/z 463 [M$^+$+1]. HPLC: 99.6%.

Synthesis of (2S,3R)-3-hydroxy-2-(44S)-2-(4-methoxybenzyl)-1-oxo-2,5-diazaspiro [3.4]octan-7-yl) amino) butanamide (CC)

To a stirred solution of CA (0.58 g, 1.25 mmol) in DCM (15 mL), TFA (10 mL) was added 0° C. and stirred at RT for 16 h. After consumption of the starting material (by TLC), the reaction mixture was concentrated under reduced pressure. The residue was purified by Flash column chromatography to afford CC (0.16 g, 36%) as a sticky solid. $^1$H NMR (400 MHz, DMSO-d6) δ 7.44 (d, J=4.0 Hz, 1H), 7.15 (d, J=8.4 Hz, 2H), 7.04 (s, 1H), 6.91 (d, J=8.4 Hz, 2H), 4.61 (d, J=4.4 Hz, 1H), 4.24 (s, 2H), 3.74 (s, 3H), 3.67-3.54 (m, 1H), 3.32-3.0 (m, 2H), 3.06 (d, J=5.2 Hz, 1H) 2.95-2.91 (m, 1H), 2.71 (d, J=6.4 Hz, 1H), 2.65-2.63 (m, 1H), 2.14-2.07 (m, 2H), 1.76-1.76 (m, 1H), 1.05 (d, J=6.2 Hz, 3H). LCMS (ESI): m/z 363 [M+1]$^+$. HPLC: 95.6%. Chiral HPLC: >99%.
Scheme B Synthesis of tert-butyl (7R)-7-hydroxy-2-(4-methoxybenzyl)-1-oxo-2,5-diazaspiro[3.4]octane-5-carboxylate (5b)

To a solution of compound 4b (16.0 g, 33.6 mmol) in THF (100 mL), TBAF (1M solution in THF, 50.4 mL, 50.4 mmol) was added drop wise at 0° C. and stirred at 50° C. for 3 h. After consumption of the starting material (by TLC), the reaction mixture was quenched with ice-cold water (150 mL) and extracted with EtOAc (2×250 mL). The combined organic layer was washed with saturated aqueous NaHCO$_3$ (150 mL) and brine (150 mL), dried over Na$_2$SO$_4$ and concentrated under reduced pressure. The residue was purified by column chromatography using 50% EtOAc/hexane to afford compound 5b (10.0 g, 82%) as a yellow oil. LCMS (ESI): m/z 361 [M$^+$−1]$^+$.

Synthesis of tert-butyl-2-(4-methoxybenzyl)-1,7-dioxo-2,5-diazaspiro[3.4]octane-5-carboxylate (6b)

To a solution of compound 5b (10.0 g, 27.6 mmol) in CH$_2$Cl$_2$ (150 mL), Dess-martin periodinane (23.0 g, 55.2 mmol) was added at 0° C. and stirred at room temperature for 16 h. After consumption of the starting material (by TLC), the reaction mixture was filtered through a bed of celite. The filtrate was diluted with water (250 mL) and extracted with EtOAc (3×250 mL). The combined organic layer was washed with saturated aqueous NaHCO$_3$ (300 mL) and brine (100 mL), dried over Na$_2$SO$_4$ and concentrated under reduced pressure. The residue was purified by column chromatography using 25% EtOAc/hexane to afford 6b (6.0 g, 60%) as a white solid. LCMS (ESI): m/z 305.05 [M$^+$-55].

Synthesis of tert-butyl-7-((1,3-bis(benzyloxy)-1-oxobutan-2-yl)amino)-2-(4-methoxybenzyl)-1-oxo-2,5-diazaspiro [3.4]octane-5-carboxylate (7b)

To a solution of compound 6b (6.0 g, 16.6 mmol), Int C (5.4 g, 18.3 mmol) in AcOH (4 mL), MeOH (200 mL) was added and stirred at room temperature for 16 h. To the resulting reaction mixture, Sodium cyano borohydride (3.2 g, 49.9 mmol) was added at 0° C. portion wise over period of 10 minutes and the reaction mixture was stirred at room temperature for 4 h. After consumption of the starting material (by TLC), the reaction mixture was concentrated under reduced pressure. The residue was dissolved in water (200 mL) and extracted with EtOAc (3×100 mL). The combined organic layer was washed with brine (150 mL), dried over Na$_2$SO$_4$ and concentrated under reduced pressure. The residue was purified by column chromatography to afford compound 7b (4.5 g, 42%) as a thick oil. LCMS (ESI): m/z 644 [M$^+$+1].

Synthesis of tert-butyl-7-((1-amino-3-(benzyloxy)-1-oxobutan-2-yl)amino)-2-(4-methoxybenzyl)-1-oxo-2,5-diazaspiro[3.4]octane-5-carboxylate (8b)

To a solution of compound 7b (4.5 g, 6.90 mmol) in MeOH (50 mL), methanolic ammonia (50 mL) was added at 0° C. and stirred at same temperature for 4 days. After consumption of the starting material (by TLC), and the reaction mixture was concentrated under reduced pressure. The residue was purified by column chromatography to afford compound 8b (1.2 g, 31%). LCMS (ESI): m/z 551 [M$^+$−1].

Synthesis of tert-butyl 7-((1-amino-3-hydroxy-1-oxobutan-2-(4)amino)-2-(4-methoxybenzyl)-1-oxo-2,5-diazaspiro[3.4]octane-5-carboxylate (CB)

To a solution of compound 8b (1.2 g, 2.17 mmol) in MeOH (60 mL), 10% Pd/C (500 mg) was added at room temperature and stirred under H$_2$ atmosphere (balloon) for 12 h. After consumption of the starting material (by TLC), the reaction mixture was filtered through a pad of celite and washed with MeOH (50 mL). The filtrate was concentrated under reduced pressure to afford CB (0.9 g, 90%). $^1$H NMR (400 MHz, DMSO-d$_6$) δ 7.37 (s, 1H), 7.22 (d, J=8.4 Hz, 1H), 7.16 (d, J=8 Hz, 1H), 7.06 (s, 1H), 6.91 (m, 2H), 4.56-4.54 (m, 2H), 4.37-4.19 (m, 1H), 3.94 (d, J=15.0 Hz, 1H), 3.74 (s, 3H), 3.69-3.36 (m, 3H), 3.24-3.08 (m, 2H), 3.08-2.96 (m, 1H), 2.74 (d, J=5.9 Hz, 1H), 2.21 (dd, J=12.3, 5.5 Hz, 1H), 1.99 (m, 1H), 1.38 (d, J=24.7 Hz, 9H), 1.04 (d, J=6.3 Hz, 3H. LCMS (ESI): m/z 463 [M+1]$^+$. HPLC: 97.0%.

Synthesis of (2S,3R)-3-hydroxy-24(2-(4-methoxybenzyl)-1-oxo-2,5-diazaspiro[3.4]octan-7-yl)amino) butanamide (CD)

To a solution of CB (0.6 g, 1.29 mmol) in CH$_2$Cl$_2$ (20 mL), TFA (10 mL) was added 0° C. and stirred at room temperature for 16 h. After consumption of the starting material (by TLC), the reaction mixture was concentrated under reduced pressure. The residue was basified with saturated aqueous NaHCO$_3$ and stirred at room temperature for 30 min. The reaction mixture was evaporated under reduced pressure and the residue was purified by column chromatography to afford CD (0.25 g, 53%) as a yellow sticky solid.

CD: $^1$H NMR (400 MHz, DMSO-d$_6$) δ 7.35 (bs, 1H), 7.19-7.11 (m, 2H), 7.05 (s, 1H), 6.92-6.90 (m, 2H), 4.58 (d, J=4.5 Hz, 1H), 4.30-4.17 (m, 2H), 3.74 (s, 3H), 3.59-3.57 (m, 1H), 3.11 (m, 3H), 3.05-2.91 (m, 3H), 2.71 (d, J=6.3 Hz, 1H), 2.64-2.62 (m, 1H), 2.14-2.04 (m, 1H), 1.77 (dd, J=12.9, 6.7 Hz, 1H), 1.04 (d, J=6.3 Hz, 3H). LCMS (ESI): m/z 363 [M+1]$^+$. HPLC: 96.5%.

Synthesis of benzyl O-benzyl-L-threoninate hydrochloride (Int-C):

The experimental procedure for the synthesis Int-C has been captured under BY (as Int-C).

Synthesis of CE & CF:

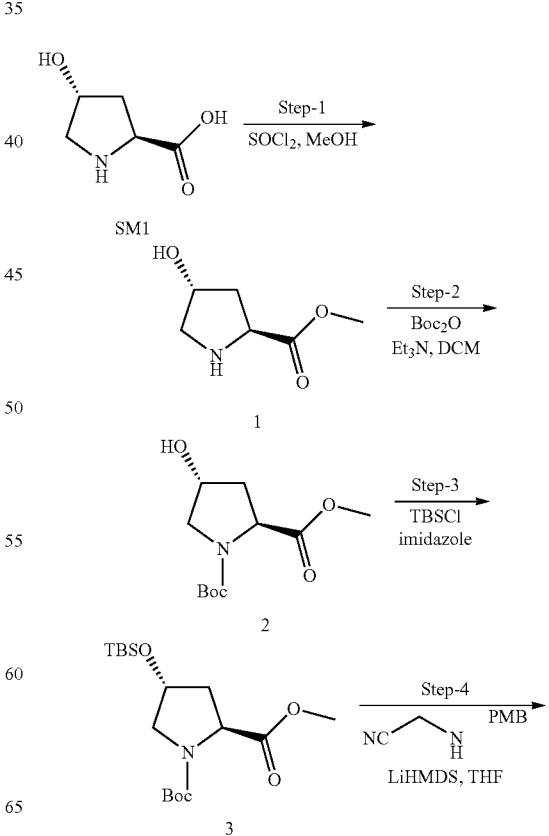

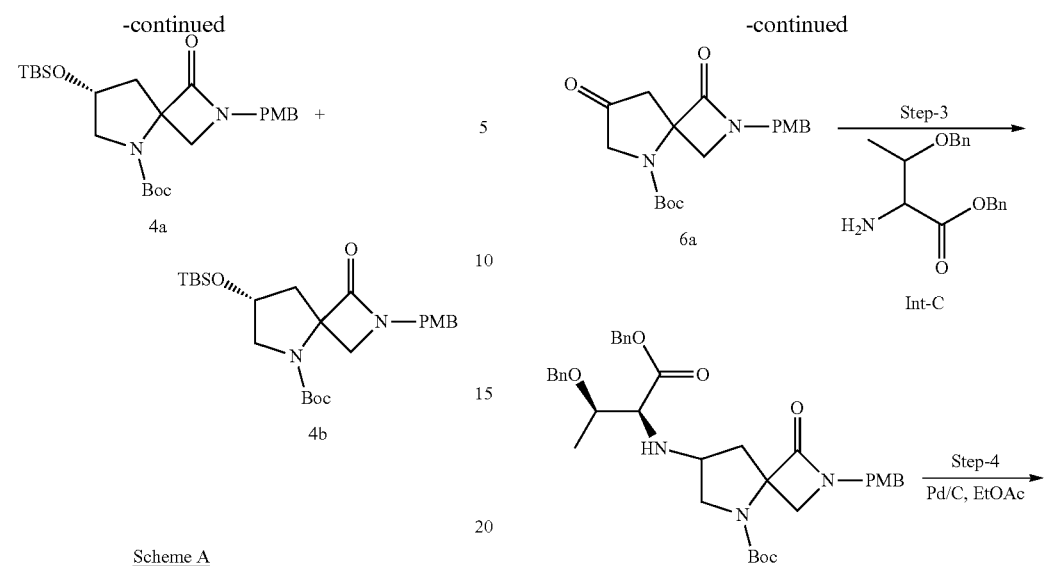
Scheme A
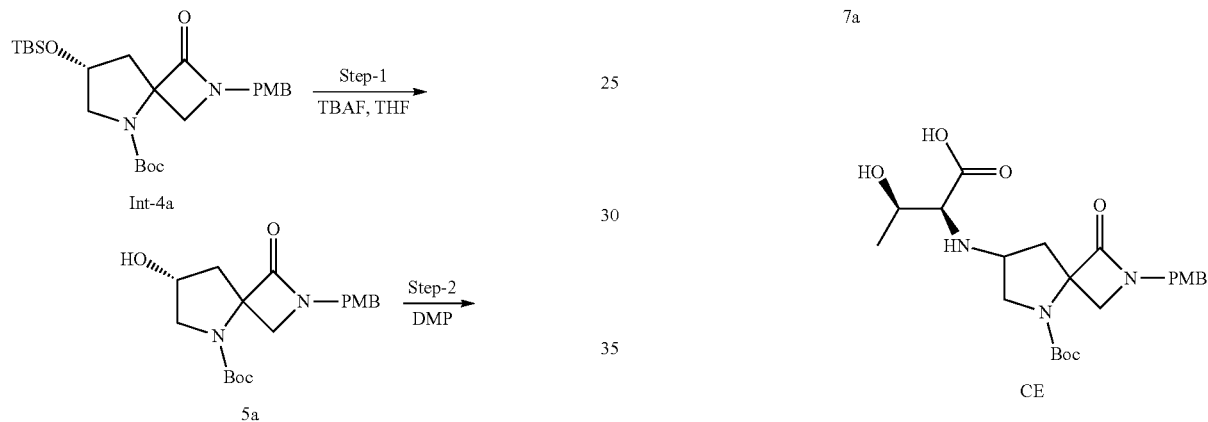
Scheme B
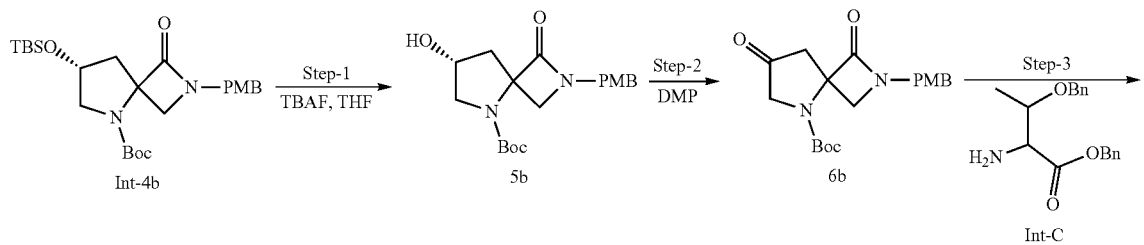
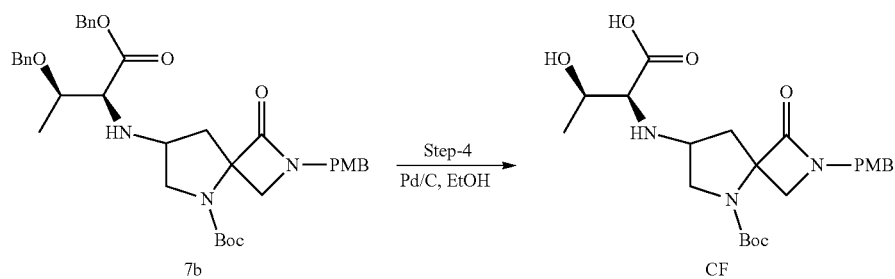

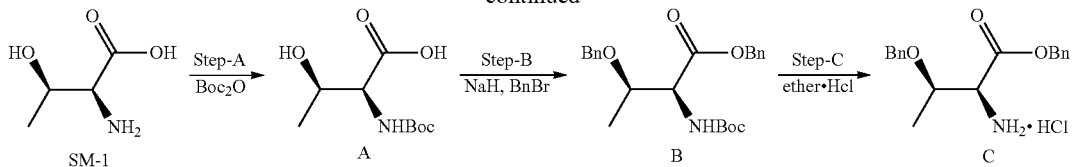

Synthesis of tert-butyl (7R)-7-((tert-butyldimethylsilyl)oxy)-2-(4-methoxybenzyl)-1-oxo-2,5-diazaspiro[3.4]octane-5-carboxylate (4a & 4b)

The experimental procedure for the synthesis of compounds 4a & 4b has been captured under the synthesis of CB & CD (as compounds 4a & 4b).

Synthesis of tert-butyl 7-0(2S,3R)-1,3-bis(benzyloxy)-1-oxobutan-2-(4)amino)-2-(4-methoxybenzyl)-1-oxo-2,5-diazaspiro[3.4]octane-5-carboxylate (Int-7a & Int-7b)

The experimental procedure for the synthesis Int-7a & Int-7b has been captured under CB & CD (as Int-7a & Int-7b).

Scheme A:

Synthesis of (5-(tert-butoxycarbonyl)-2-(4-methoxybenzyl)-1-oxo-2,5-diazaspiro[3.4]octan-7-yl)-L-threonine (CE)

To a solution of compound 7a (0.6 g, 0.93 mmol) in EtOAc (50 mL), 10% Pd/C (50% wet, 250 mg) was added at room temperature and stirred under $H_2$ atmosphere (balloon) for 12 h. After consumption of the starting material (by TLC), the reaction mixture was filtered through a pad of celite and washed with MeOH (50 mL). The filtrate was concentrated under reduced pressure to afford CE (0.25 g, 58%).

CE: $^1$H NMR (400 MHz, DMSO-$d_6$) δ 7.23-7.15 (m, 2H), 6.92-6.90 (m, 2H), 4.56 (d, J=15.1 Hz, 1H), 4.20 (d, J=15.2 Hz, 1H), 3.95 (d, J=15.1 Hz, 1H), 3.81 (bs, 1H), 3.62-3.42 (m, 5H), 3.38-3.11 (m, 3H), 3.05 (s, 1H), 2.24 (s, 1H), 2.04 (s, 1H), 1.34 (s, 9H), 1.26-1.15 (m, 3H). LCMS (ESI): m/z 464.10 [1\4+1]$^+$. HPLC: 99.03%.

Scheme B:

Synthesis of (5-(tert-butoxycarbonyl)-2-(4-methoxybenzyl)-1-oxo-2,5-diazaspiro[3.4]octan-7-yl)-L-threonine (CF)

To a solution of compound 7b (1.0 g, 1.55 mmol) in EtOH (60 mL), 10% Pd/C (500 mg) was added at room temperature and stirred under $H_2$ atmosphere (balloon) for 12 h. After consumption of the starting material (by TLC), the reaction mixture was filtered through a pad of celite and washed with MeOH (50 mL). The filtrate was concentrated under reduced pressure to afford CF (0.4 g, 57%).

CF: $^1$H NMR (400 MHz, DMSO-$d_6$) δ 7.22 (d, J=8.4 Hz, 1H), 7.15 (dd, J=8.4 Hz, 1H), 6.92-6.88 (m, 2H), 4.56 (d, J=15.0 Hz, 1H), 4.35 (d, J=15.3 Hz, 1H), 4.21 (d, J=15.2 Hz, 1H), 3.95 (d, J=15.0 Hz, 1H), 3.73 (s, 3H), 3.67 (s, 1H), 3.44-3.37 (m, 2H), 3.24 (s, 1H), 3.12-3-05 (m, 2H), 2.98 (s, 1H), 2.32-2.24 (m, 1H), 2.02 (s, 1H), 1.87 (s, 1H), 1.37 (d, 9H), 1.05 (d, J=6.2 Hz, 3H).
LCMS (ESI): m/z 464.20 [M+1]$^+$. HPLC: 99.22%.

Synthesis of benzyl O-benzyl-L-threoninate hydrochloride (Int-C):

The experimental procedure for the synthesis Int-C has been captured under BY (as Int-C).

Synthesis of CG & CH:

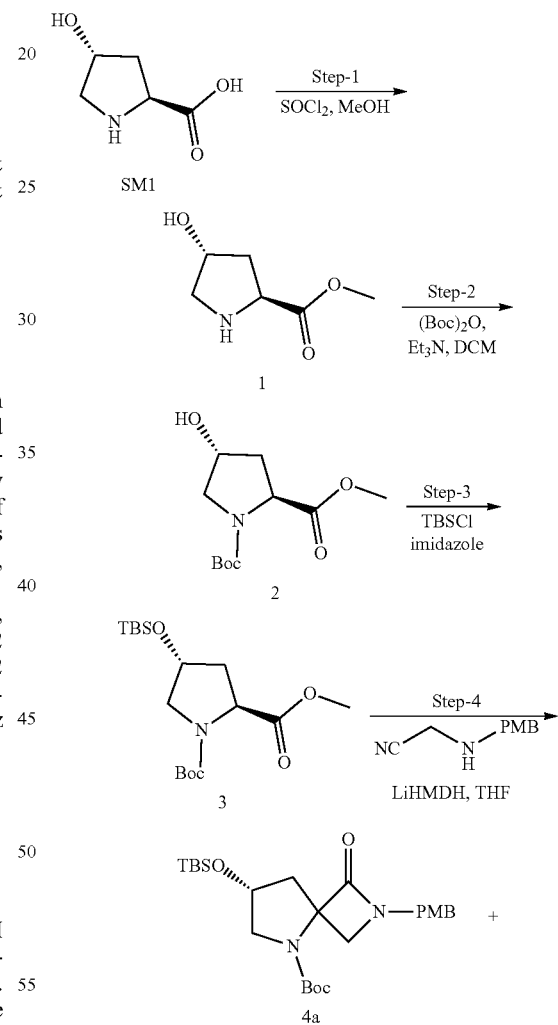

Scheme A
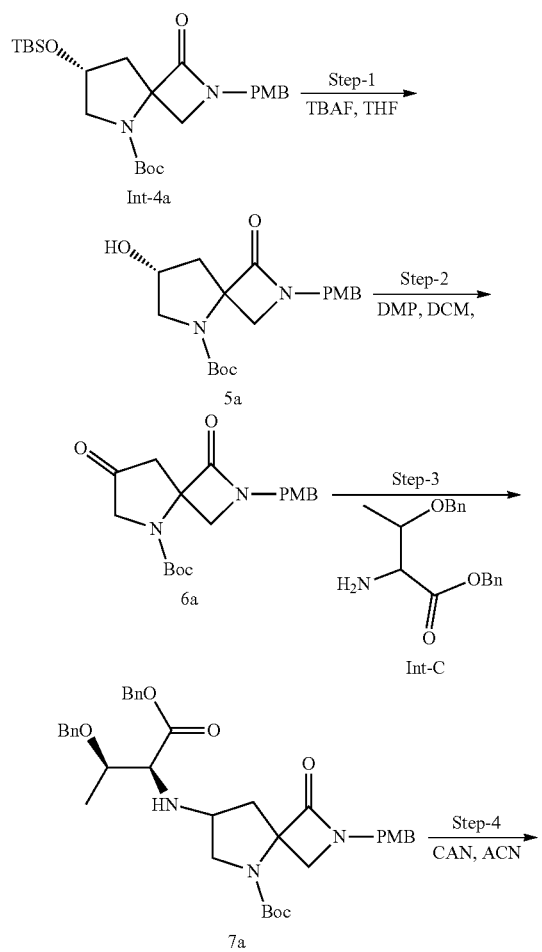
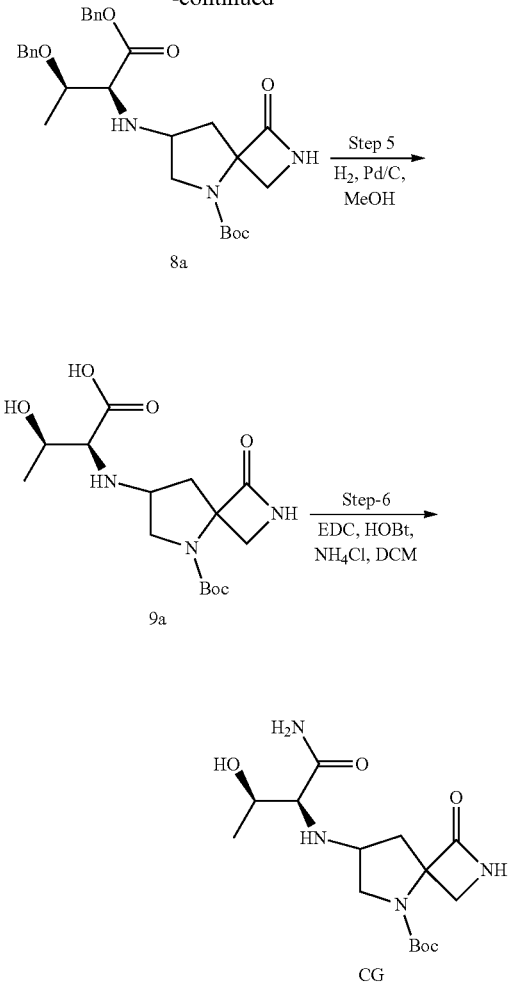
Scheme B
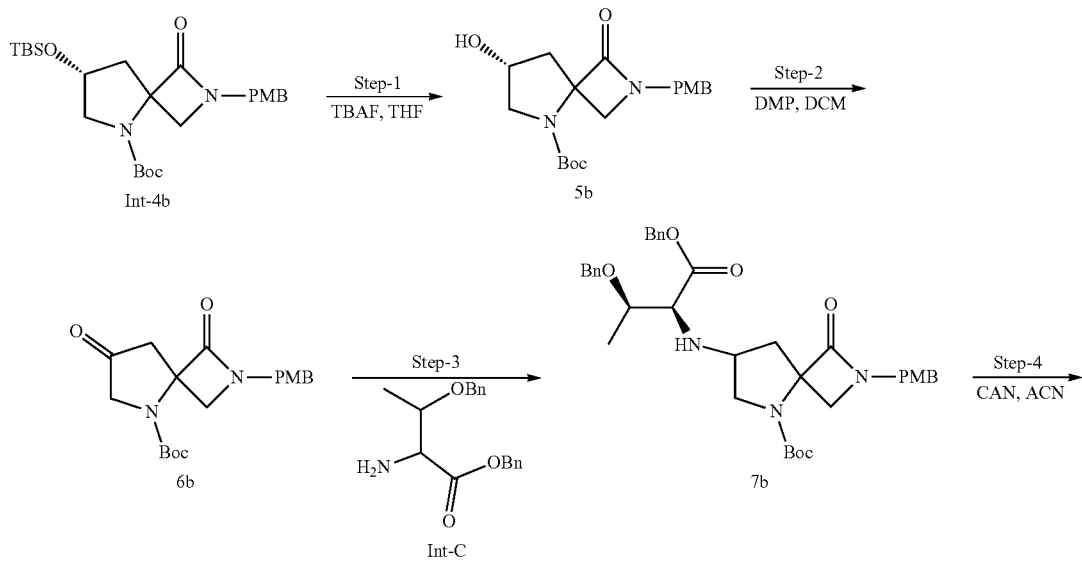

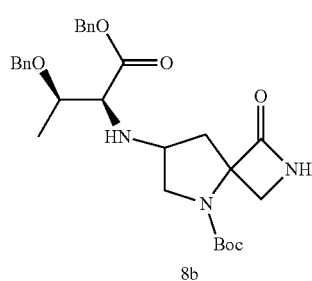
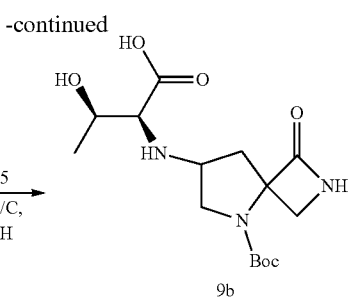
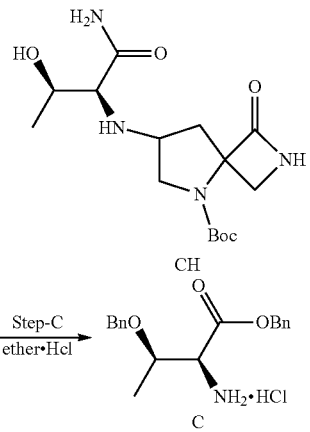
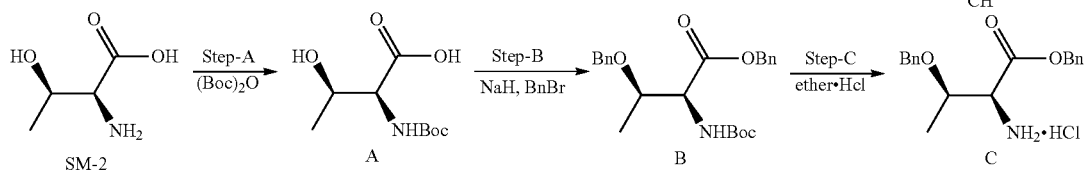

Synthesis of tert-butyl (7R)-7-((tert-butyldimethylsilyl)oxy)-2-(4-methoxybenzyl)-1-oxo-2,5-diazaspiro[3.4]octane-5-carboxylate (4a & 4b)

The experimental procedure for the synthesis of compounds 4a & 4b has been captured under the synthesis of CB & CD (as compounds 4a & 4b).

Synthesis of tert-butyl 7-0(2S,3R)-1,3-bis(benzyloxy)-1-oxobutan-2-(4)amino)-2-(4-methoxybenzyl)-1-oxo-2,5-diazaspiro[3.4]octane-5-carboxylate (7a & 7b)

The experimental procedure for the synthesis compounds 7a & 7b has been captured under the synthesis of CB & CD (as compounds 7a & 7b).
Scheme A:

Synthesis of tert-butyl 7-0(2S,3R)-1,3-bis(benzyloxy)-1-oxobutan-2-(4)amino)-1-oxo-2,5-diazaspiro[3.4]octane-5-carboxylate (8a)

To a stirred solution of compound 7a (5.5 g, 8.54 mmol) in acetonitrile (50 mL), ceric ammonium nitrate (9.36 g, 17.0 mmol) in $H_2O$ (50 mL) was added dropwise at −10° C., reaction mixture was stirred at same temperature for 2 h. The reaction mixture was stirred at RT for 16 h. After consumption of the starting material (by TLC), mixture was quenched with saturated $NaHCO_3$ solution (100 mL) and extracted with EtOAc (3×75 mL). The combined organic layer was washed with brine (100 mL), dried over $Na_2SO_4$ and concentrated under reduced pressure. The residue was purified by column chromatography using 20-40% EtOAc/hexane to afford compound 8a (1.5 g, 34%) as a white solid. LCMS (ESI): m/z 524.0 [M$^+$+1]

Synthesis of (5-(tert-butoxycarbonyl)-1-oxo-2,5-diazaspiro[3.4]octan-7-yl)-L-threonine (9a)

To a stirred solution of compound 8a (3.0 g, 5.72 mmol) in MeOH (60 mL), 10% Pd/C (50% wet, 1.0 g) was added at RT and stirred under $H_2$ atmosphere (balloon) for 12 h. After consumption of the starting material (by TLC), reaction mixture was filtered through a pad of celite and washed with MeOH (100 mL). The filtrate was concentrated under reduced pressure to afford compound 9a (1.6 g, 81%) as an off white solid.

Synthesis of tert-butyl 7-0(2S,3R)-1-amino-3-hydroxy-1-oxobutan-2-yl)amino)-1-oxo-2,5-diazaspiro[3.4]octane-5-carboxylate (CG)

To a stirred solution of compound 9a (0.45 g, 1.31 mmol) in DCM (30 mL), EDCI.HCl (0.37 g, 1.96 mmol), HOBt (0.30 g, 1.96 mmol), DIPEA (0.68 mL, 3.93 mmol), and $NH_4Cl$ (0.20 g, 3.93 mmol), were added at 0° C. and reaction mixture stirred at room temperature for 16 h. After consumption of the starting material (by TLC), the reaction mixture was quenched with water (30 mL) and extracted with DCM (3×30 mL). Combined organic layer was washed with brine (30 mL), dried over $Na_2SO_4$ and concentrated under reduced pressure. The residue was purified by reverse phase column chromatography to afford CG (0.13 g, 29%) as an off white solid. $^1$H NMR (400 MHz, DMSO-$d_6$) δ 7.89-7.85 (brs, 1H), 7.51-7.50 (brs, 1H), 7.03 (s, 1H), 4.59-4.58 (d, J=4.8 Hz, 1H), 3.67-3.64 (m, 1H), 3.46-3.40 (m, 2H), 3.18-3.17, (brs, 1H), 3.12-3.03 (m, 2H), 2.77-2.74 (t, J=6.2 Hz, 1H), 2.50-2.26 (m, 2H), 2.0-1.93 (m, 1H), 1.39-1.36 (d, J=6.4 Hz, 9H), 1.06-1.05 (d, J=6.4 Hz, 3H). ELSD (ESI): m/z 343.0 [M$^+$+1]. HPLC: 98.33%.

Scheme B:

Synthesis of tert-butyl 7-0(2S,3R)-1,3-bis(benzyloxy)-1-oxobutan-2-yl)amino)-1-oxo-2,5-diazaspiro[3.4]octane-5-carboxylate (8b)

To a stirred solution of compound 7b (4.2 g, 6.52 mmol) in acetonitrile (50 mL) ceric ammonium nitrate (7.15 g, 13.0 mmol) in H$_2$O (50 mL) was added dropwise at −10° C., reaction mixture was stirred at same temperature for 2 h and then at RT for 16 h. After consumption of the starting material (by TLC), reaction mixture was quenched with saturated NaHCO$_3$ solution (100 mL) and extracted with EtOAc (3×75 mL). The combined organic layer was washed with brine (100 mL), dried over Na$_2$SO$_4$ and concentrated under reduced pressure. The residue was purified by column chromatography using 20-50% EtOAc/hexane to afford compound 8b (1.5 g, 45%) as a white solid.

Synthesis of (5-(tert-butoxycarbonyl)-1-oxo-2,5-diazaspiro[3.4]octan-7-yl)-L-threonine (9b)

To a stirring solution of compound 8b (2.3 g, 2.86 mmol) in MeOH (50 mL), 10% Pd/C (50% wet, 1.0 g) was added at RT and stirred under H$_2$ atmosphere (balloon) for 12 h. After consumption of starting material (by TLC), the reaction mixture was filtered through a pad of celite and washed with MeOH (100 mL). The filtrate was concentrated under reduced pressure to afford compound 9b (1.2 g, 80%) as an off white solid. ELSD (ESI): m/z 344.0 [M$^+$+1].

Synthesis of tert-butyl 7-(((2S,3R)-1-amino-3-hydroxy-1-oxobutan-2-yl)amino)-1-oxo-2,5-diazaspiro[3.4]octane-5-carboxylate (CH)

To a stirred solution of compound 9b (0.6 g, 1.74 mmol) in DCM (30 mL), EDCI.HCl (0.5 g, 2.62 mmol), HOBt (0.4 g, 2.62 mmol), DIPEA (0.6 mL, 3.48 mmol), NH$_4$Cl (0.18 g, 3.48 mmol), were added at 0° C. and reaction mixture stirred at room temperature for 16 h. After consumption of the starting material (by TLC), reaction mixture was quenched with water (30 mL) and extracted with DCM (3×30 mL). The combined organic layer was washed with brine (30 mL), dried over Na$_2$SO$_4$ and concentrated under reduced pressure. The residue was purified by reverse phase column chromatography to afford CH (0.13 g, 22%) as an off white solid. $^1$H NMR (400 MHz, DMSO-d$_6$) δ 7.89-7.84 (brs, 1H), 7.38 (brs, 1H), 7.06 (brs, 1H), 4.59-4.55 (s, 1H), 3.61 (m, 1H), 3.53-3.48 (m, 1H), 3.41-3.39 (d, J=4.8 Hz, 1H), 3.17 (m, 1H), 3.12-3.10 (d, J=5.2 Hz, 1H), 3.08-3.06 (d, J=4.8 Hz, 1H), 3.0-2.96 (t, J=8.8 Hz, 1H), 2.75-2.73 (t, J=6.4 Hz, 1H), 2.26-2.23 (m, 1H), 1.99-1.93 (m, 1H),1.39-1.36 (d, J=6.4 Hz, 9H), 1.05-1.03 (d, J=6 Hz, 3H). ELSD (ESI): m/z 343.0 [M$^+$+1]. HPLC: 98.46%.

Synthesis of benzyl O-benzyl-L-threoninate hydrochloride (Int-C):

The experimental procedure for the synthesis Int-C has been captured under BY (as Int-C).

Synthesis of CI & CJ:

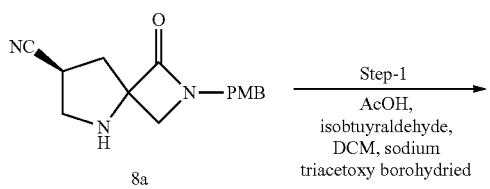

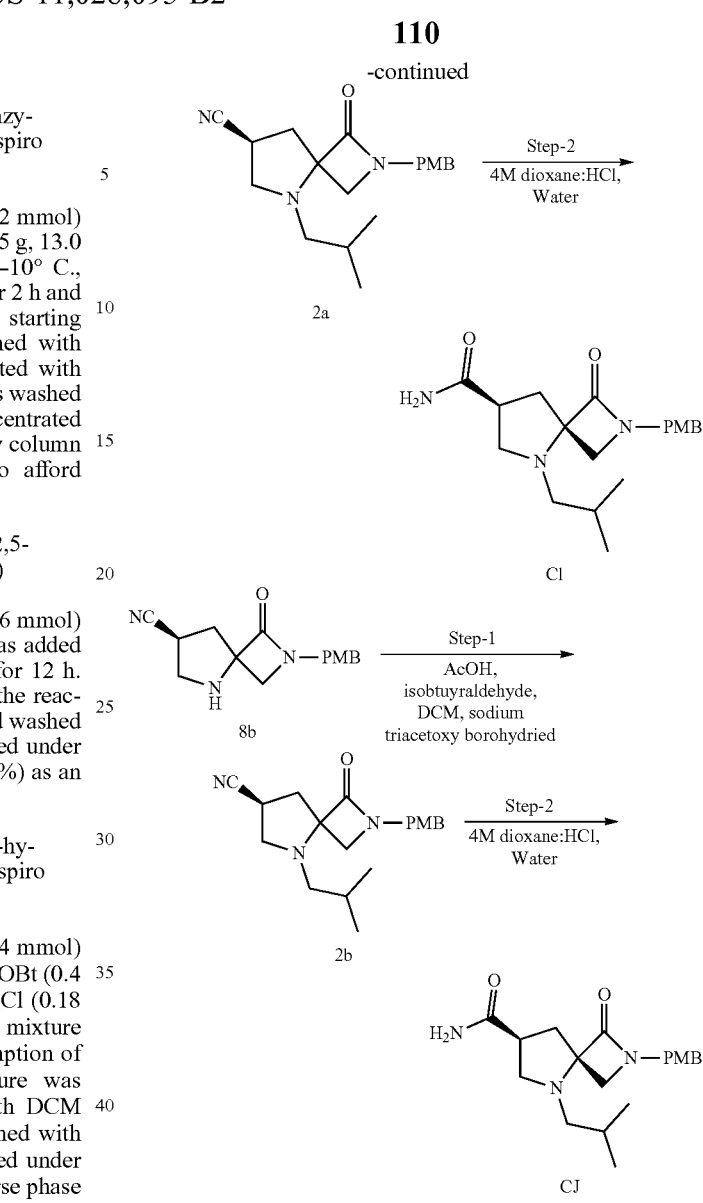

Synthesis of (7S)-2-(4-methoxybenzyl)-1-oxo-2,5-diazaspiro[3.4]octane-7-carbonitrile (8a)

The experimental procedure for the synthesis of compound 8a has been captured under the synthesis of AT (as compound 8a).

Synthesis of (7S)-5-isobutyl-2-(4-methoxybenzyl)-1-oxo-2,5-diazaspiro[3.4]octane-7-carbonitrile (2a)

To a stirred solution of (7S)-2-(4-methoxybenzyl)-1-oxo-2,5-diazaspiro[3.4]octane-7-carbonitrile (compound 8a) (2.2 g, 9.40 mmol) in DCM (25 mL), AcOH (2.5 mL), isobutyraldehyde (0.6 mL, 9.0 mmol) and sodium triacetoxy borohydride (3.89 g, 18.4 mmol) was added at 0° C. portion wise over period of 10 min. The reaction mixture was stirred at room temperature for 20 h. After consumption of the starting material (by TLC), the reaction mixture was quenched with water (100 mL) and extracted with DCM (3×100 mL). The combined organic layer was washed with brine (150 mL), dried over Na$_2$SO$_4$ and concentrated under reduced pressure. The residue was purified by column chromatography to afford compound 2a (2.1 g, 69%) as a colorless semisolid. Analytical data for 2a: LCMS: 328(M$^+$+1).

Compound 2b was prepared using compound 8b following similar procedure reported for synthesis of compound 2a in 63% yield as white solid. Analytical data for 2b: $^1$H NMR (400 MHz, DMSO-d6): δ 7.26-7.19 (m, 2H), 6.92 (d, J=8.4 Hz, 2H), 4.56 (d, J=15 Hz, 1H), 4.39-4.23 (m, 1H), 4.01 (d, J=15 Hz, 1H), 3.74 (s, 3H), 3.58-3.56 (m, 2H), 3.54-3.52 (m, 1H), 3.48-3.46 (m, 1H), 3.27-3.24 (m, 4H), 1.36 (s, 6H).

Synthesis of (4S,7S)-5-isobutyl-2-(4-methoxybenzyl)-1-oxo-2,5-diazaspiro[3.4]octane-7-carboxamide (CI)

To a stirring solution of compound 2a (1.6 g, 4.60 mmol) in dioxane (15 mL), 4M dioxane in HCl (10 mL) was added followed by addition of water (0.5 mL) and stirred at room temperature for 4 h. After consumption of the starting material (by TLC), the reaction mixture was concentrated under reduced pressure. The residue was purified by column chromatography to afford CI (0.25 g, 15.6%) as off white solid.

CI: $^1$H NMR (400 MHz, DMSO-d$_6$) δ 7.22 (brs, 1H), 7.20-7.12 (m, 2H), 6.96-6.84 (m, 2H), 6.83 (brs, 1H), 4.31 (d, J=14.9 Hz, 1H), 4.18 (d, J=14.9 Hz, 1H), 3.74 (s, 3H), 3.05 (q, J=5.7 Hz, 2H), 3.00-2.85 (m, 2H), 2.6 (t, J=7.9 Hz, 1H), 2.35-2.21 (m, 2H), 2.12, 2.06 (m, 2H), 1.58-1.50 (m, 1H), 0.78 (dd, J=13.6, 6.5 Hz, 6H). LCMS (ESI): m/z 346 [M$^+$+1]. HPLC: 99.14%.

CJ: This was prepared using 2b (1.2 g, 2.9 mmol) and following similar procedure reported for synthesis of CI in 31% yield as white solid. Analytical data for CJ: $^1$H NMR (400 MHz, DMSO-d$_6$) δ 7.32 (s, 1H), 7.20-7.11 (m, 2H), 6.96-6.88 (m, 2H), 6.81 (brs, 1H), 4.32-4.15 (m, 2H), 3.74 (s, 3H), 3.13-3.04 (m, 2H), 3.04 (d, J=5.9 Hz, 2H), 2.81-2.77 (m, 1H), 2.40-2.05 (m, 4H), 1.61-1.58 (m, 1H), 0.79 (dd, J=8.7, 6.5 Hz, 6H). LCMS (ESI): m/z 346 [M$^+$+1]. HPLC: 95.72%.

Synthesis of CK, CL, CM & CN:

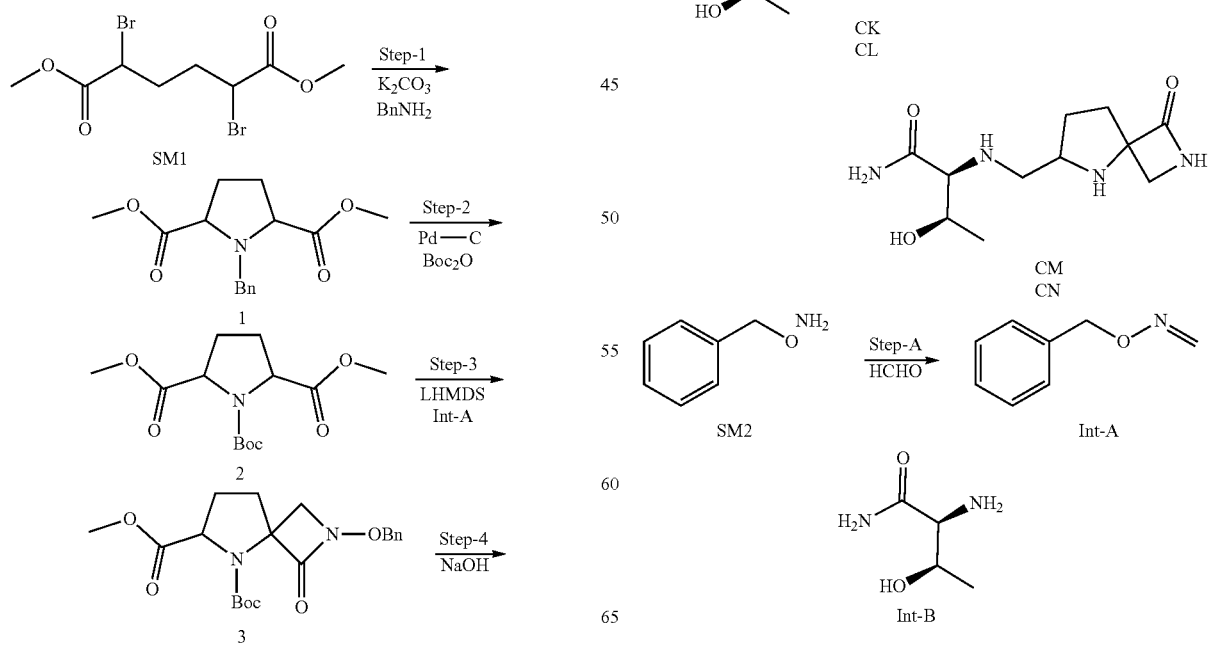

Synthesis of dimethyl 1-benzylpyrrolidine-2,5-dicarboxylate (1)

To a solution of dimethyl 2,5-dibromohexanedioate (SM) (100 g, 0.301 mol) in toluene and water (400 mL, 3:1) were added $K_2CO_3$ (49.88 g, 0.361 mol) and benzylamine (32.23 g, 0.301 mol). The reaction mixture was heated to 80° C. under nitrogen atmosphere and stirred for 16 h. After completion of the reaction, the reaction mixture was cooled to room temperature and added EtOAc (200 mL). After stirring for 10 minutes, the organic layer was separated and washed with brine. The organic layer was dried over anhydrous $Na_2SO_4$ and concentrated under reduced pressure. The residue was purified by column chromatography eluting with 20% EtOAc/n-hexane to afford meso compound 1 (48 g, 57%) as a brown syrup along 13 g of racemic compound. $^1H$ NMR (400 MHz, DMSO-$d_6$) δ 7.28-7.19 (m, 5H), 3.83 (s, 2H), 3.48 (s, 6H), 3.42-3.36 (m, 2H), 2.09-1.98 (m, 2H), 1.94-1.83 (m, 2H). LCMS (ESI): m/z 277.9 [$M^+$+1].

Synthesis of 1-(tert-butyl) 2,5-dimethyl pyrrolidine-1,2,5-tricarboxylate (2)

To a solution of meso compound 1 (48 g, 0.173 mol) in MeOH (480 mL) were added $Boc_2O$ (79.5 mL, 0.346 mol) and 10% Pd/C (50% wet, 19.2 g) and stirred under $H_2$ atmosphere (balloon) for 16 h. After consumption of the starting material (by TLC), the reaction mixture was filtered through a pad of celite and the filtrate was concentrated under reduced pressure. The residue was purified by column chromatography eluting with 30% EtOAc/n-hexane to afford meso compound 2 (40.5 g, 81%) as a white solid. $^1H$ NMR (500 MHz, DMSO-$d_6$) δ 4.27-4.18 (m, 2H), 3.64 (s, 3H), 3.62 (s, 3H), 2.25-2.16 (m, 2H), 1.96-1.85 (m, 2H), 1.36 (s, 9H). LCMS (ESI): m/z 288.2 [$M^+$+1].

Synthesis of 5-(tert-butyl) 6-methyl 2-(benzyloxy)-1-oxo-2,5-diazaspiro[3.4]octane-5,6-dicarboxylate (3)

To a solution of meso compound 2 (35.5 g, 0.123 mol) in THF (300 mL) was added LiHMDS (1M solution in THF, 185.5 mL, 0.185 mol) drop wise at −78° C. under nitrogen atmosphere and stirred for 1 h. A solution of Int-A (20 g, 0.148 mol) in THF (55 mL) was added to the reaction mixture at −78° C. and stirred at room temperature stirred for 3 h. After consumption of the starting material (by TLC), the reaction was quenched with saturated aqueous $NH_4Cl$ (100 mL) and extracted with EtOAc (3×200 mL). The separated organic layer was dried over $Na_2SO_4$ and concentrated under reduced pressure. The residue was purified by column chromatography eluting with 30% EtOAc/n-hexane to afford compound 3 (38 g, 78%) as a colorless thick syrup. $^1H$ NMR (400 MHz, DMSO-$d_6$) δ 7.48-7.36 (m, 5H), 4.95-4.85 (m, 2H), 4.29 (br d, J=6.4 Hz, 1H), 4.07-3.99 (m, 1H), 3.71 (s, 3H), 3.55 (d, J=10.7 Hz, 1H), 2.36-2.16 (m, 2H), 2.13-2.02 (m, 1H), 1.98-1.91 (m, 1H), 1.35 (s, 9H). LCMS (ESI): m/z 391.3 [$M^+$+1].

Synthesis of 2-(benzyloxy)-5-(tert-butoxycarbonyl)-1-oxo-2,5-diazaspiro[3.4]octane-6-carboxylic acid (4)

To a solution of compound 3 (32 g, 0.082 mol) in MeOH, THF and water (480 mL, 1:1:1) was added NaOH (9.84 g, 0.246 mol) at 0° C. and then stirred at room temperature for 16 h. After consumption of the starting material (by TLC), the reaction mixture was concentrated under reduced pressure. The residue was diluted with water (100 mL) and washed with EtOAc. The aqueous layer was acidified with aqueous 2N HCl (pH ~2.0) and extracted with EtOAc (2×200 mL). The organic layer was washed with brine, dried over $Na_2SO_4$ and concentrated under reduced pressure to afford compound 4 (32 g, crude) as a pale yellow semi solid. The crude was forwarded to next step without further purification. $^1H$ NMR (500 MHz, DMSO-$d_6$) δ 12.89 (br s, 1H), 7.46-7.28 (m, 5H), 4.92-4.84 (m, 2H), 4.26 (br d, J=7.0 Hz, 1H), 4.05-3.96 (m, 1H), 3.45 (br d, J=11.0 Hz, 1H), 2.31-2.15 (m, 2H), 2.06-1.88 (m, 2H), 1.35 (s, 9H). LCMS (ESI): m/z 375.1 [$M^+$−1].

Synthesis of 2-(benzyloxy)-5-(tert-butoxycarbonyl)-1-oxo-2,5-diazaspiro[3.4]octane-6-carboxylic (Isobutyl Carbonic) Anhydride (5)

To a solution of compound 4 (46 g, 0.122 mol) in THF (460 mL) was added N-methyl morpholine (40.3 mL, 0.367 mol) and isobutylchloroformate (20.5 mL, 0.159 mol) at 0° C. under nitrogen atmosphere. The reaction mixture was stirred at room temperature for 3 h. After consumption of the starting material (by TLC), the reaction mixture was quenched with water (230 mL) and extracted with EtOAc (3×100 mL). The organic layer was dried over anhydrous $Na_2SO_4$ and concentrated under reduced pressure to afford compound 5 (35 g, crude) as a colorless thick syrup. The crude was forwarded to next step without further purification. $^1H$ NMR (400 MHz, DMSO-$d_6$) δ 7.47-7.33 (m, 5H), 4.94-4.84 (m, 2H), 4.27 (br d, J=6.7 Hz, 1H), 4.12-3.96 (m, 1H), 3.86 (d, J=6.7 Hz, 1H), 3.63-3.51 (m, 1H), 3.46 (d, J=10.7 Hz, 1H), 2.39-2.36 (m, 1H), 2.28-2.16 (m, 2H), 2.07-1.82 (m, 2H), 1.36 (s, 9H), 0.88 (d, J=6.8 Hz, 3H), 0.82 (d, J=6.7 Hz, 3H).

Synthesis of tert-butyl 2-(benzyloxy)-6-(hydroxymethyl)-1-oxo-2,5-diazaspiro[3.4]octane-5-carboxylate (6)

To a solution of compound 5 (35 g, 0.073 mol) in MeOH (350 mL) was added sodium borohydride (2.79 g, 0.073 mol) at 0° C. under nitrogen atmosphere. The reaction mixture was stirred at 0° C. for 2 h. After consumption of the starting material (by TLC), the reaction mixture was quenched with ice and volatiles were evaporated under reduced pressure. The crude was diluted with EtOAc (200 mL) and washed with water followed by brine. The organic layer was dried over anhydrous $Na_2SO_4$ and concentrated under reduced pressure. The residue was purified by column chromatography eluting with 30% EtOAc/n-hexane to afford compound 6 (6.7 g, 25%) as a colorless thick syrup. $^1H$ NMR (400 MHz, DMSO-$d_6$) δ 7.47-7.35 (m, 5H), 4.96-4.82 (m, 3H), 4.25 (d, J=7.3 Hz, 1H), 3.90 (dd, J=5.6, 11.2 Hz, 1H), 3.77-3.66 (m, 2H), 3.34 (d, J=10.4 Hz, 1H), 2.17-2.07 (m, 1H), 2.02-1.91 (m, 1H), 1.83-1.73 (m, 2H), 1.38 (s, 9H). LCMS (ESI): m/z 363.1 [$M^+$+1].

Synthesis of tert-butyl 2-(benzyloxy)-6-formyl-1-oxo-2,5-diazaspiro[3.4]octane-5-carboxylate (7)

To a solution of crude compound 6 (6.7 g, 0.018 mol) in $CH_2Cl_2$ (67 mL) was added Dess-Martin periodinane (9.42 g, 0.022 mol) at 0° C. under nitrogen atmosphere and the reaction mixture was stirred at room temperature for 2 h. After consumption of the starting material (by TLC), the reaction mixture was quenched with saturated aqueous NaHCO$_3$. The organic layer was separated, washed with brine and concentrated under reduced pressure. The residue was purified by column chromatography eluting with 40% EtOAc/n-hexane to afford compound 7 (5.8 g, 87%) as a colorless thick syrup. $^1$H NMR (500 MHz, DMSO-d$_6$) δ 9.50 (s, 1H), 7.48-7.35 (m, 5H), 4.96-4.84 (m, 2H), 4.30 (br s, 1H), 3.85 (br d, J=10.4 Hz, 1H), 3.59-3.47 (m, 1H), 2.26 (br s, 2H), 2.05-1.98 (m, 1H), 1.82 (br s, 1H), 1.36 (s, 9H).

Synthesis of tert-butyl 6-(4(2S,3R)-1-amino-3-hydroxy-1-oxobutan-2-yl)amino)methyl)-2-(benzyloxy)-1-oxo-2,5-diazaspiro[3.4]octane-5-carboxylate (BI & BJ)

To a solution of crude compound 7 (5.8 g, 0.016 mol) in MeOH (87 mL) was added Int-B (2.28 g, 0.019 mol) under nitrogen atmosphere and stirred at room temperature for 30 minutes. NaBH$_3$CN (2.02 g, 0.032 mol) was added to the reaction mixture and stirred at room temperature for 16 h. After consumption of the starting material (by TLC), volatiles were evaporated under reduced pressure. The reaction mixture was diluted with water (20 mL) and extracted with EtOAc (2×100 mL). The organic layer was washed with brine, dried over Na$_2$SO$_4$ and concentrated under reduced pressure. The residue was purified by column chromatography eluting with 2% MeOH/DCM to afford diasteromeric mixture (3.4 g, 46%) as a white solid.

BI: $^1$H NMR (400 MHz, DMSO-d$_6$) δ 7.45-7.36 (m, 5H), 7.23 (s, 1H), 7.06 (d, J=1.4 Hz, 1H), 4.91-4.83 (m, 2H), 4.54 (d, J=4.3 Hz, 1H), 4.24 (d, J=7.0 Hz, 1H), 3.74-3.64 (m, 2H), 3.41 (d, J=10.3 Hz, 1H), 3.11 (br dd, J=4.5, 11.9 Hz, 1H), 2.85 (br t, J=10.5 Hz, 1H), 2.79-2.73 (m, 1H), 2.30-2.20 (m, 1H), 2.10 (br d, J=6.1 Hz, 1H), 2.01-1.91 (m, 1H), 1.85-1.73 (m, 2H), 1.38 (s, 9H), 1.06 (d, J=6.3 Hz, 3H). LCMS (ESI): m/z 463.2 [M$^+$+1]. HPLC: 99.71%. Chiral HPLC: 100.00%.

BJ: $^1$H NMR (400 MHz, DMSO-d$_6$): δ 7.45-7.34 (m, 5H), 7.18 (br d, J=2.4 Hz, 1H), 7.05 (br d, J=1.9 Hz, 1H), 4.91-4.81 (m, 3H), 4.23 (d, J=7.2 Hz, 1H), 3.68-3.58 (m, 2H), 3.40 (d, J=10.4 Hz, 1H), 3.00 (br d, J=9.8 Hz, 1H), 2.76-2.64 (m, 2H), 2.44-2.25 (m, 2H), 2.02-1.87 (m, 1H), 1.83-1.70 (m, 2H), 1.39 (s, 9H), 1.06 (d, J=6.1 Hz, 3H). LCMS (ESI): m/z 463.2 [M$^+$+1]. HPLC: 99.89%. Chiral HPLC: 100.00%.

Synthesis of (2S,3R)-2-(42-(benzyloxy)-1-oxo-2,5-diazaspiro[3.4]octan-6-yl)methyl) amino)-3-hydroxybutanamide (CK)

To a stirring solution of BI (1 g, 2.16 mmol) in CH$_2$Cl$_2$ (20 mL) were added molecular sieves (1 g) and BF$_3$.Oet$_2$ (49%) (614 mg, 4.32 mmol) drop wise at RT under nitrogen atmosphere. The reaction mixture was stirred for 4 h. After consumption of the starting material (by TLC), volatiles were evaporated under reduced pressure. The crude material was purified by reverse phase preparative HPLC to remove boron trifluoride diethyl etherate salts and to obtain CK (270 mg, 34%) as a white sticky solid. $^1$H NMR (400 MHz, DMSO-d$_6$) δ 7.54-7.36 (m, 5H), 7.28 (d, J=2.0 Hz, 1H), 7.04 (d, J=1.9 Hz, 1H), 4.93-4.76 (m, 2H), 4.58 (d, J=4.4 Hz, 1H), 3.71-3.61 (m, 1H), 3.55-3.44 (m, 2H), 3.18 (d, J=9.7 Hz, 1H), 3.07 (br s, 1H), 2.72 (d, J=5.8 Hz, 1H), 2.68-2.60 (m, 1H), 2.55-2.50 (m, 1H), 2.09 (s, 1H), 1.92-1.75 (m, 2H), 1.70-1.48 (m, 2H), 1.06 (d, J=6.3 Hz, 3H). LCMS (ESI): m/z 363.1 [M$^+$+1]. HPLC: 99.41%. Chiral HPLC: 100.00%. Column: CHIRALPAK IA (250*4.6 mm, 5 μm); Mobile Phase A: 0.1% DEA in n-Hexane; Mobile Phase B: DCM:MeOH (50:50); A:B:: 70:30; Flow rate: 1.0 mL/min. Retention time: 13.769.

Synthesis of (2S,3R)-2-(42-(benzyloxy)-1-oxo-2,5-diazaspiro[3.4]octan-6-yl)methyl) amino)-3-hydroxybutanamide (CL)

To a stirring solution of BJ (1 g, 2.16 mmol) in CH$_2$Cl$_2$ (20 mL) were added molecular sieves (1 g) and BF$_3$.Oet$_2$ (49%) (614 mg, 4.32 mmol) drop wise at RT under nitrogen atmosphere. The reaction mixture was stirred for 4 h. After consumption of the starting material (by TLC), volatiles were evaporated under reduced pressure. The crude material was purified by reverse phase preparative HPLC to remove boron trifluoride diethyl etherate salts and to obtain CL (300 mg, 38%) as white sticky solid.

$^1$H NMR (400 MHz, DMSO-d$_6$) δ 7.46-7.31 (m, 5H), 7.23 (d, J=2.0 Hz, 1H), 7.03 (d, J=2.0 Hz, 1H), 4.96-4.83 (m, 2H), 4.62 (d, J=4.6 Hz, 1H), 3.70-3.59 (m, 1H), 3.53-3.40 (m, 2H), 3.19 (d, J=9.0 Hz, 1H), 3.08 (br s, 1H), 2.71-2.58 (m, 3H), 2.14 (br s, 1H), 1.92-1.73 (m, 2H), 1.71-1.64 (m, 1H), 1.55-1.45 (m, 1H), 1.05 (d, J=6.3 Hz, 3H). LCMS (ESI): m/z 363.1 [M$^+$+1]. HPLC: 99.89%. Chiral HPLC: 100.00%. Column: CHIRALPAK IA (250*4.6 mm, 5 μm); Mobile Phase A: 0.1% DEA in n-Hexane; Mobile Phase B: DCM:MeOH (50:50); A:B:: 70:30; Flow rate: 1.0 mL/min. Retention time: 9.497.

Synthesis of (2S,3R)-3-hydroxy-2-(01-oxo-2,5-diazaspiro[3.4]octan-6-yl)methyl) amino) butanamide (CM & CN)

To a stirring mixture of CK & CL (900 mg, 2.40 mmol) in MeOH (100 mL) was added Raney Ni (1 g) at RT and stirred for 16 h under H$_2$ atmosphere. After consumption of the starting material (by TLC), the reaction mixture was filtered through a pad of celite and the pad was washed with MeOH (100 mL). Obtained filtrate was concentrated under reduced pressure to afford mixture of CM & CN (390 mg) as sticky solid, which was purified by chiral preparative HPLC purification to obtain CM (90 mg) as a hygroscopic white solid and CN (85 mg) as a hygroscopic white solid.

CM: $^1$H NMR (400 MHz, DMSO-d$_6$) δ 7.24 (s, 1H), 7.14 (s, 1H), 7.04 (s, 1H), 4.65 (d, J=3.76 Hz, 1H), 3.69-3.57 (m, 1H), 3.33-3.31 (m, 1H), 3.15 (d, J=10.9 Hz, 1H), 2.90 (dd, J=10.9, 2.6 Hz, 1H), 2.80 (s, 1H), 2.65-2.59 (m, 2H), 2.53-2.46 (m, 1H), 2.19-2.17 (m, 1H), 1.92-1.68 (m, 3H), 1.66-1.57 (m, 1H), 1.06 (d, J=6.3 Hz, 3H). LCMS (ESI): m/z 257.1 [M$^+$+1]. HPLC: 99.78%. Chiral HPLC: 99.96%. Column: CHIRALCEL OX-H (250*4.6 mm, 5 μm); Mobile Phase: Hexanes/EtOH/MeOH/DEA (50/20/30/0.1); Diluent: Mobile Phase; Flow rate: 0.7 mL/min Retention time: 10.25.

CN: $^1$H NMR (400 MHz, DMSO-d$_6$) δ 7.27 (s, 1H), 7.13 (s, 1H), 7.04 (s, 1H), 4.60 (d, J=4.4 Hz, 1H), 3.71-3.61 (m, 1H), 3.33-3.31 (m, 1H), 3.17 (d, J=10.8 Hz, 1H), 2.89 (dd, J=10.9, 2.6 Hz, 1H), 2.76 (s, 1H), 2.72 (d, J=6.0 Hz, 1H), 2.65-2.59 (m, 1H), 2.53 (d, J=8.4 Hz, 1H), 2.34-2.32 (m, 1H), 1.91-1.76 (m, 2H), 1.73-1.58 (m, 2H), 1.06 (d, J=6.3 Hz, 3H). LCMS (ESI): m/z 257.0 [M$^+$+1]. HPLC: 97.24%. Chiral HPLC: 98.13%. Column: CHIRALCEL OX-H (250*4.6 mm, 5 μm); Mobile Phase: Hexanes/EtOH/MeOH/DEA (50/20/30/0.1); Diluent:Mobile Phase; Flow rate: 0.7 mL/min. Retention time: 10.18.

Preparation of Int-A:
Synthesis of Formaldehyde O-Benzyl Oxime (Int-A):

To a stirring solution of O-benzylhydroxylamine (SM1) (200 g, 1.62 mol) and NaOH (13 g in 50 mL H₂O, 0.325 mol) in toluene (1 L) was added 37% formaldehyde solution (158 mL, 1.951 mol) at RT then stirred for 2 h. After consumption of the starting material (by TLC), the reaction mixture was extracted with EtOAc (2×500 mL). Separated organic layer was washed with brine solution, dried over Na₂SO₄ and concentrated under reduced pressure to afford Int-A (180 g, 82%) as colorless liquid. ¹H NMR (400 MHz, CDCl₃): δ 7.38-7.28 (m, 5H), 7.08 (d, J=8.3 Hz, 1H), 6.46 (d, J=8.2 Hz, 1H), 5.12 (s, 2H).

Synthesis of CO & CP, CO & CR:

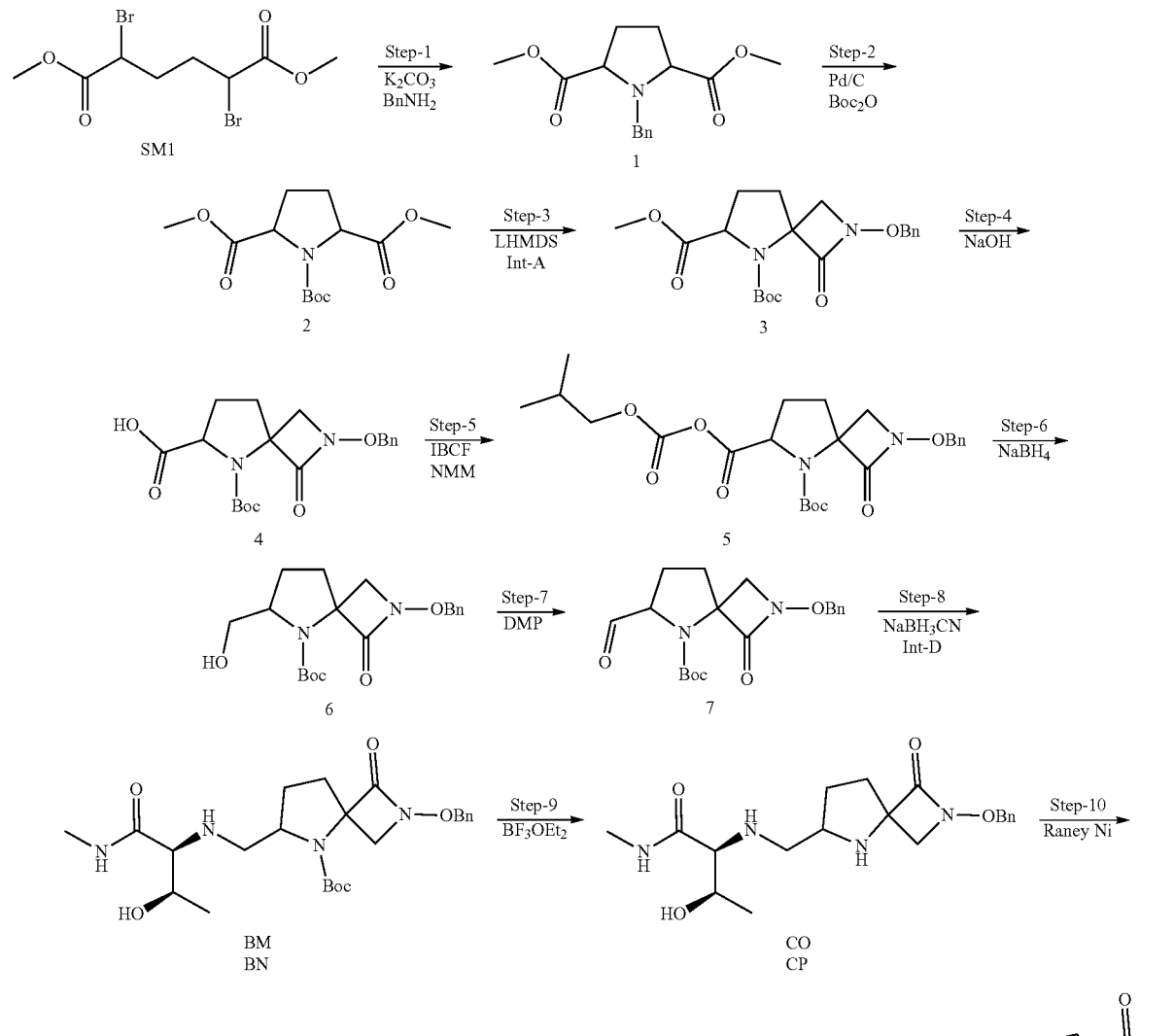

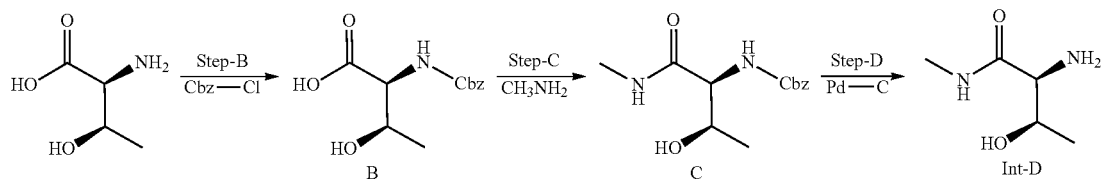

-continued

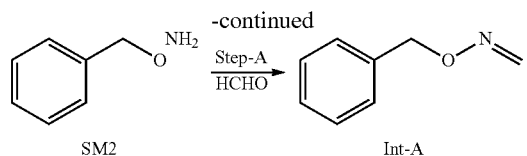

The experimental procedure for the synthesis of compound 1 to compound 7 and Int-A are captured under the synthesis of CK & CL.

Synthesis of tert-butyl 2-(benzyloxy)-6-(4(2S,3R)-3-hydroxy-1-(methylamino)-1-oxobutan-2-yl)amino)methyl)-1-oxo-2,5-diazaspiro[3.4]octane-5-carboxylate (BM & BN)

To a solution of crude compound 7 (6 g, 16.6 mmol) in MeOH (70 mL) were added Int-D (2.6 g, 19.9 mmol) and AcOH (0.47 mL) at RT under nitrogen atmosphere. After being stirred for 30 minutes, NaBH$_3$CN (3.1 g, 49.9 mmol) was added portion wise and allowed to stir at RT for 16 h. After consumption of the starting material (by TLC), the reaction mixture was quenched aqueous NaHCO$_3$ solution and volatiles were evaporated under reduced pressure. Crude material was diluted with NaHCO$_3$ solution (500 mL). The reaction mixture was diluted with water (500 mL) and extracted with EtOAc (3×500 mL). The organic layer was washed with brine solution, dried over Na$_2$SO$_4$ and concentrated under reduced pressure. Obtained crude material was purified by column chromatography eluting with 3% MeOH/CH$_2$Cl$_2$ to afford diasteromeric mixture (5 g, 63%) as white solid. 2 g of diasteromeric mixture was separated by normal phase preparative HPLC purification to obtain BM (750 mg) and BN (740 mg) as white solids.

BM: $^1$H NMR (500 MHz, DMSO-d$_6$): δ 7.76 (d, J=4.6 Hz, 1H), 7.45-7.33 (m, 5H), 4.91-4.82 (m, 2H), 4.55 (s, 1H), 4.23 (d, J=7.5 Hz, 1H), 3.68 (d, J=9.9 Hz, 2H), 3.40 (d, J=10.4 Hz, 1H), 3.05 (dd, J=6.4, 12.2 Hz, 1H), 2.85 (t, J=10.4 Hz, 1H), 2.75 (dd, J=5.5, 8.4 Hz, 1H), 2.61 (d, J=4.6 Hz, 3H), 2.29-2.18 (m, 1H), 2.15-2.07 (m, 1H), 2.02-1.91 (m, 1H), 1.85-1.73 (m, 2H), 1.38 (s, 9H), 1.03 (d, J=5.8 Hz, 3H). LCMS (ESI): m/z 477.5 [M$^+$+1]. HPLC: 94.17%. Chiral HPLC: 93.40%.

BN: $^1$H NMR (500 MHz, DMSO-d$_6$) δ 7.71 (d, J=4.6 Hz, 1H), 7.46-7.34 (m, 5H), 4.91-4.81 (m, 2H), 4.23 (d, J=7.0 Hz, 1H), 3.67-3.56 (m, 2H), 3.43 (d, J=10.4 Hz, 1H), 3.00 (dd, J=3.8, 11.3 Hz, 1H), 2.72 (dd, J=2.9, 7.0 Hz, 1H), 2.66-2.56 (m, 4H), 2.45-2.35 (m, 2H), 2.31-2.22 (m, 1H), 2.04-1.90 (m, 1H), 1.83-1.72 (m, 2H), 1.39 (s, 9H), 1.03 (d, J=6.4 Hz, 3H). LCMS (ESI): m/z 477.5 [M$^+$+1]. HPLC: 96.40%. Chiral HPLC: 98.00%.

Synthesis of (2S,3R)-2-(42-(benzyloxy)-1-oxo-2,5-diazaspiro[3.4]octan-6-yl)methyl) amino)-3-hydroxy-N-methylbutanamide (CO)

To a stirring solution of BN (740 mg, 1.55 mmol) in CH$_2$Cl$_2$ (20 mL) were added molecular sieves (740 mg) and BF$_3$.OEt$_2$ (49%) (441 mg, 3.11 mmol) drop wise at RT under nitrogen atmosphere. The reaction mixture was stirred for 4 h. After consumption of the starting material (by TLC), volatiles were evaporated under reduced pressure. The crude material was washed with Et$_2$O and n-pentane and purified by reverse phase HPLC to obtain CO (266 mg) as hygroscopic white solid.

CO: $^1$H NMR (500 MHz, DMSO-d$_6$) δ 7.76 (d, J=4.5 Hz, 1H), 7.41-7.32 (m, 5H), 4.92-4.81 (m, 2H), 4.59 (s, 1H), 3.66-6.63 (m, 1H), 3.52-3.44 (m, 2H), 3.19 (d, J=9.6 Hz, 1H), 3.13 (s, 1H), 2.71 (d, J=6.1 Hz, 1H), 2.63-2.41 (m, 6H), 1.93-1.79 (m, 2H), 1.62-1.44 (m, 2H), 1.01 (d, J=6.1 Hz, 3H). LCMS (ESI): m/z 377.3 [M$^+$+1]. HPLC: 98.83%. Chiral HPLC: 100.00%; Column: CHIRALPAK IC (250*4.6 mm, 5 μm); Mobile Phase A: 0.1% DEA in n-Hexane; Mobile Phase B: DCM:MeOH (50:50); A:B:: 60:40; Flow rate: 1.0 mL/min; Retention time: 11.245.

Synthesis of (2S,3R)-2-(42-(benzyloxy)-1-oxo-2,5-diazaspiro[3.4]octan-6-yl)methyl) amino)-3-hydroxy-N-methylbutanamide (CP)

To a stirring solution of BM (720 mg, 1.55 mmol) in CH$_2$Cl$_2$ (20 mL) were added molecular sieves (740 mg) and BF$_3$.OEt$_2$ (49%) (429 mg, 3.01 mmol) drop wise at RT under nitrogen atmosphere. The reaction mixture was stirred for 4 h. After consumption of the starting material (by TLC), volatiles were evaporated under reduced pressure. The crude material was washed with Et$_2$O and n-pentane and dried under vacuum to afford to obtain CP (236 mg) as hygroscopic white solid. $^1$H NMR (500 MHz, DMSO-d$_6$): δ 7.73 (d, J=4.5 Hz, 1H), 7.45-7.32 (m, 5H), 4.98-4.76 (m, 2H), 4.63 (s, 1H), 3.65 (s, 1H), 3.48 (d, J=7.4 Hz, 2H), 3.19 (d, J=9.6 Hz, 1H), 3.10 (s, 1H), 2.71 (d, J=6.1 Hz, 1H), 2.60 (d, J=4.6 Hz, 3H), 2.58-2.51 (m, 3H), 1.92-1.77 (m, 2H), 1.73-1.62 (m, 1H), 1.53-1.46 (m, 1H), 1.03 (d, J=6.2 Hz, 3H). LCMS (ESI): m/z 377.3 [M$^+$+1]. HPLC: 99.84%. Chiral HPLC: 98.26%. Column: CHIRALPAK IC (250*4.6 mm, 5 μm); Mobile Phase A: 0.1% DEA in n-Hexane; Mobile Phase B: DCM:MeOH (50:50); A:B:: 60:40; Flow rate: 1.0 mL/min. Retention time: 8.090.

Synthesis of (2S,3R)-3-hydroxy-N-methyl-2-0(1-oxo-2,5-diazaspiro[3.4]octan-6-yl) methyl)amino)butanamide (CQ & CR)

To a stirring mixture of CO & CP (2.8 g, 7.44 mmol) in MeOH (30 mL) was added Raney Ni (9 g) at RT and stirred for 16 h under H$_2$ atmosphere. After consumption of the starting material (by TLC), the reaction mixture was filtered through a pad of celite and the pad was washed with MeOH (100 mL). Obtained filtrate was concentrated under reduced pressure to afford mixture of CQ & CR (2 g) as semi solid. Mixture of CQ & CR (1 g) was purified by normal phase chiral HPLC purification to obtain CQ (264 mg) as hygroscopic white solid and CR (265 mg) as hygroscopic white solid.

CQ: $^1$H NMR (400 MHz, DMSO-d$_6$) δ 7.76-7.72 (m, 1H), 7.13 (s, 1H), 4.66 (d, J=4.0 Hz, 1H), 3.71-3.63 (m, 1H), 3.33-3.31 (m, 1H), 3.13 (d, J=10.8 Hz, 1H), 2.89 (dd, J=10.9, 2.6 Hz, 1H), 2.80 (s, 1H), 2.72 (d, J=5.6 Hz, 1H), 2.60 (d, J=4.8 Hz, 3H), 2.57-2.55 (m, 2H), 2.15 (s, 1H), 1.92-1.70 (m, 3H), 1.65-1.55 (m, 1H), 1.04 (d, J=6.3 Hz, 3H); LCMS (ESI): m/z 271.1 [M$^+$+1]. HPLC: 99.69%. Chiral HPLC: 99.92%. Column: CHIRALPAK IG (250*4.6 mm, 5 μm). Mobile Phase: Hexanes/EtOH/MeOH (50/20/30); Diluent:Mobile Phase; Flow rate: 0.7 mL/min; Retention time: 8.94.

CR: $^1$H NMR (400 MHz, DMSO-$d_6$) δ 7.79-7.76 (m, 1H), 7.13 (s, 1H), 4.61 (d, J=4.4 Hz, 1H), 3.75-3.56 (m, 1H), 3.33-3.31 (m, 1H), 3.18 (d, J=10.9 Hz, 1H), 2.88 (dd, J=10.9, 2.6 Hz, 1H), 2.75 (d, J=10.2 Hz, 2H), 2.60 (d, J=4.8 Hz, 3H), 2.56 (s, 2H), 2.08 (s, 1H), 1.90-1.76 (m, 2H), 1.70-1.59 (m, 2H), 1.04 (d, J=6.4 Hz, 3H). LCMS (ESI): m/z 271.1 [M$^+$+1]. HPLC: 98.63%. Chiral HPLC: 99.66%. Column: CHIRALPAK IG (250*4.6 mm, 5 μm); Mobile Phase: Hexanes/EtOH/MeOH (50/20/30); Diluent:Mobile Phase; Flow rate: 0.7 mL/min; Retention time: 9.03.

Preparation of Int-D:

Synthesis of ((benzyloxy)carbonyl)-L-threonine (B):

To a stirring solution of L-threonine (20 g, 0.17 mol) in 1,4-dioxane:water (1:1, 200 mL) was added NaOH (27.35 g, 0.683 mol) followed by drop wise addition of Cbz-Cl (50% solution in toluene, 87 mL, 0.256 mol) at 0° C. The reaction mixture was brought to RT and stirred for 16 h. The reaction was diluted with cold water (100 mL) and washed with EtOAc (100 mL). Aqueous layer acidified with 1N HCl solution and extracted with EtOAc (3×100 mL). The organic layer washed with brine solution (100 mL) and dried over anhydrous Na$_2$SO$_4$, concentrated under reduced pressure to afford compound B (32 g, 75%) as white solid. $^1$H NMR (400 MHz, DMSO-$d_6$): δ 12.64 (br s, 1H), 7.40-7.28 (m, 5H), 6.95 (d, J=8.9 Hz, 1H), 5.03 (s, 2H), 4.62-4.53 (m, 1H), 4.12-4.00 (m, 1H), 3.98-3.93 (m, 1H), 1.09 (d, J=6.4 Hz, 3H). LCMS (ESI): m/z 254.1 [M$^+$+1].

Synthesis of benzyl ((2S,3R)-3-hydroxy-1-(methylamino)-1-oxobutan-2-yl)carbamate (C)

To a stirred solution of compound B (6 g, 23.71 mmol) in DCM (100 mL), HOBt (4.8 g, 35.57 mmol), EDC.HCl (6.83 g, 35.57 mmol), methylamine (2M in THF) (23.7 mL, 47.43 mmol) and DIPEA (13 mL, 71.14 mmol) were added at 0° C. under nitrogen atmosphere and stirred at RT for 16 h. After consumption of the starting material (by TLC), the reaction mixture was quenched with water (200 mL) and extracted with DCM (2×200 mL). The combined organic layer was washed with 10% citric acid solution (100 mL), saturated NaHCO$_3$ solution (100 mL), brine (100 mL), dried over Na$_2$SO$_4$ and concentrated under reduced pressure. The residue was purified by Combi-Flash chromatography eluting with 80% EtOAc/Hexane to afford compound C (2.5 g, 39%) as a white solid. $^1$H NMR (400 MHz, DMSO-$d_6$): δ 7.77 (br d, J=4.4 Hz, 1H), 7.40-7.27 (m, 5H), 6.84 (br d, J=8.8 Hz, 1H), 5.10-4.98 (m, 2H), 4.74 (d, J=6.0 Hz, 1H), 3.99-3.88 (m, 1H), 3.85 (dd, J=4.2, 8.7 Hz, 1H), 2.59 (d, J=4.6 Hz, 3H), 1.03 (d, J=6.4 Hz, 3H). LCMS (ESI): m/z 267.1 [M$^+$+1].

Synthesis of (2S,3R)-2-amino-3-hydroxy-N-methylbutanamide (Int-D)

To a stirred solution of C (2.5 g, 9.39 mmol) in MeOH (30 mL), 10% Pd/C (50% wet, 1 g) was added at RT and stirred under H$_2$ atmosphere (balloon) for 16 h. After consumption of the starting material (by TLC), the reaction mixture was filtered through a pad of celite and washed with MeOH:H$_2$O (250 mL, 1:1). The filtrate was concentrated under reduced pressure to afford Int-D (1.1 g, 88%) as a white solid. $^1$H NMR (400 MHz, DMSO-$d_6$): δ 7.82 (br d, J=2.5 Hz, 1H), 4.56 (br s, 1H), 3.83-3.75 (m, 1H), 2.88 (d, J=4.5 Hz, 1H), 2.59 (d, J=4.8 Hz, 3H), 2.34-1.83 (m, 2H), 1.03 (d, J=6.4 Hz, 3H). LCMS (ESI): m/z 133.2 [M$^+$+1].

Synthesis of CS, CT, CU & CV:

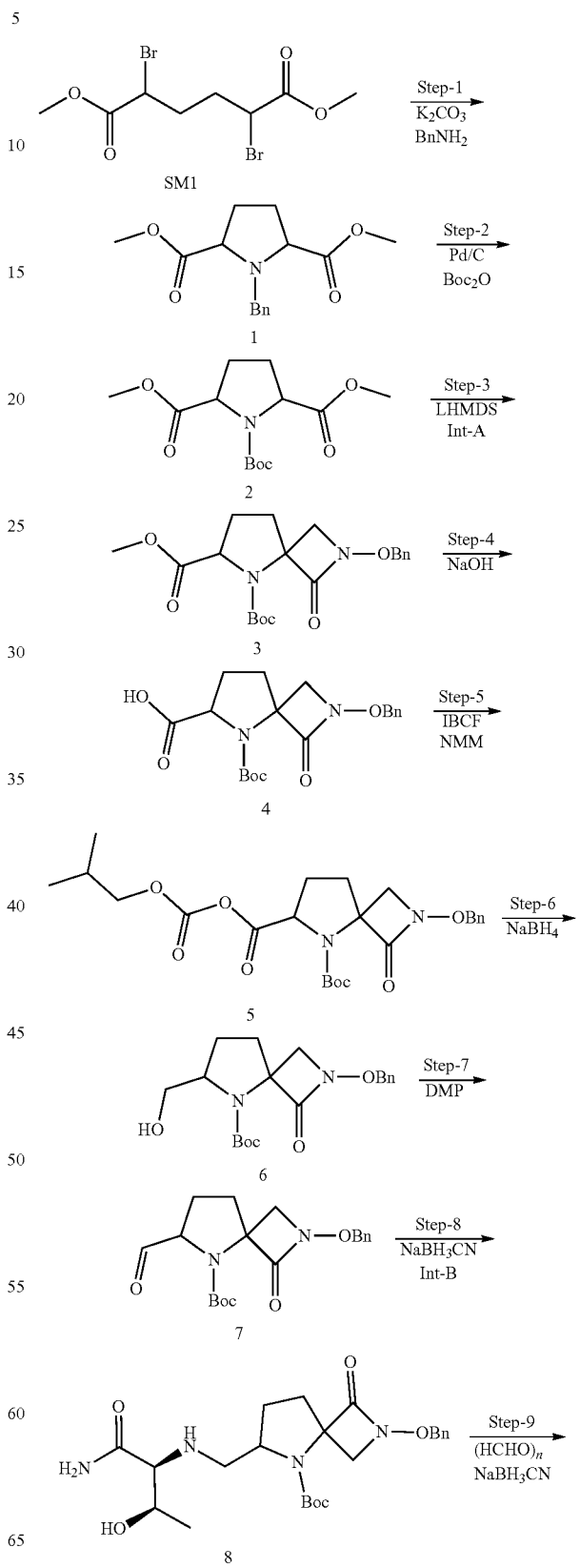

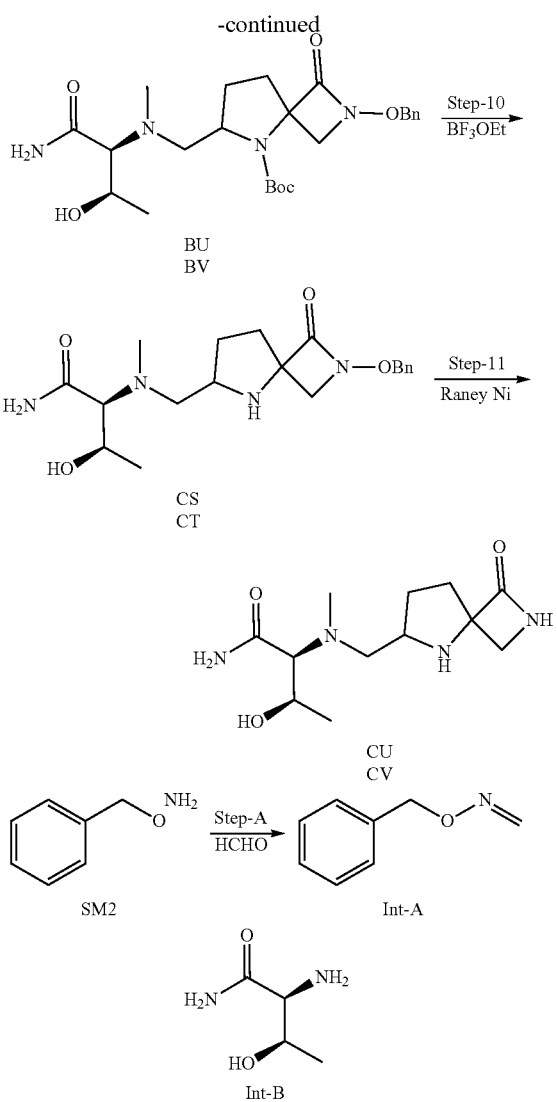

3.12-2.94 (m, 1H), 2.86-2.84 (m, 1H), 2.73-2.67 (m, 2H), 2.38-2.24 (m, 1H), 1.96-1.91 (m, 1H), 1.81-1.76 (m, 2H), 1.39 (s, 9H), 1.07-1.04 (m, 3H). LCMS (ESI): m/z 463.2 [M$^+$+1].

Synthesis of tert-butyl 6-(4(2S,3R)-1-amino-3-hydroxy-1-oxobutan-2-yl)(methyl) amino)methyl)-2-(benzyloxy)-1-oxo-2,5-diazaspiro[3.4]octane-5-carboxylate (BU & BV)

To a solution of compound 8 (1.8 g, 3.89 mmol) in MeOH (36 mL) were added paraformaldehyde (701 mg, 23.3 mmol) and AcOH (0.11 mL, 1.94 mmol). The reaction mixture was stirred at room temperature for 30 minutes. NaCNBH$_3$ (734 mg, 11.6 mmol) was added to reaction mixture and stirred at 60° C. for 16 h. After consumption of the starting material (by TLC), cooled to room temperature and volatiles were evaporated. The reaction mixture was diluted with water (30 mL) and extracted with EtOAc (3×100 mL). The organic layer was dried over Na$_2$SO$_4$ and concentrated under reduced pressure. The residue was purified by column chromatography by eluting 4% MeOH/EtOAc to afford diastereomeric mixture BU & BV (1.3 g, 70%) as a white solid.

1.05 g of diasteromeric mixture was purified by chiral preparative HPLC purification to afford BU (300 mg) and BV (235 mg) as a white solid.

BU: $^1$H NMR (400 MHz, DMSO-d$_6$) δ 7.48-7.36 (m, 5H), 7.32 (s, 1H), 7.00 (s, 1H), 4.92-4.80 (m, 2H), 4.22 (d, J=6.8 Hz, 1H), 4.02 (s, 1H), 3.79 (d, J=10.2 Hz, 2H), 3.48 (d, J=10.3 Hz, 1H), 3.30-3.13 (m, 2H), 2.79 (d, J=9.3 Hz, 1H), 2.41 (br s, 1H), 2.35 (s, 3H), 2.04-1.72 (m, 3H), 1.38 (s, 9H), 1.00 (d, J=6.1 Hz, 3H). LCMS (ESI): m/z 477.2 [M$^+$+1]. HPLC: 99.52%. Chiral HPLC: 100.00%.

BV: $^1$H NMR (400 MHz, DMSO-d$_6$) δ 7.45-7.36 (m, 5H), 7.29 (s, 1H), 6.97 (s, 1H), 4.88-4.82 (m, 2H), 4.23 (d, J=7.2 Hz, 1H), 4.13 (s, 1H), 3.84 (dd, J=6.6, 8.3 Hz, 1H), 3.78 (d, J=10.2 Hz, 1H), 3.34-3.27 (m, 2H), 3.13 (d, J=14.4 Hz, 1H), 2.74 (d, J=9.2 Hz, 1H), 2.46-2.42 (m, 1H), 2.37 (s, 3H), 2.02-1.91 (m, 1H), 1.82-1.72 (m, 2H), 1.38 (s, 9H), 1.02 (d, J=6.1 Hz, 3H). LCMS (ESI): m/z 477.2 [M$^+$+1]. HPLC: 99.39%. Chiral HPLC: 100.00%.

Synthesis of (2S,3R)-2-(42-(benzyloxy)-1-oxo-2,5-diazaspiro[3.4]octan-6-yl)methyl) (methyl) amino)-3-hydroxybutanamide (CS)

To a stirring solution of BU (800 mg, 1.68 mmol) in CH$_2$Cl$_2$ (16 mL) were added molecular sieves (800 mg) and BF$_3$.Oet$_2$ (49%) (477 mg, 3.36 mmol) drop wise at RT under nitrogen atmosphere. The reaction mixture was stirred for 4 h. After consumption of the starting material (by TLC), volatiles were evaporated under reduced pressure. The crude material was purified by reverse phase preparative HPLC to remove boron trifluoride diethyl etherate salts and to obtain CS (170 mg, 27%) as a white solid. $^1$H NMR (400 MHz, DMSO-d$_6$) δ 7.50-7.33 (m, 6H), 6.94 (s, 1H), 4.94-4.76 (m, 2H), 4.23 (s, 1H), 3.82-3.70 (m, 1H), 3.66 (d, J=9.8 Hz, 1H), 3.45 (d, J=6.7 Hz, 1H), 3.24 (s, 1H), 3.07 (d, J=9.7 Hz, 1H), 2.75-2.63 (m, 3H), 2.34 (s, 3H), 1.95-1.74 (m, 2H), 1.52-1.48 (m, 2H), 0.99 (d, J=6.0 Hz, 3H). LCMS (ESI): m/z 377.1 [M$^+$+1]. HPLC: 99.79%. Chiral HPLC: 100.00%. Column: DIOL (150*4.6 mm, 3 μm); Mobile Phase A: n-Hexane; Mobile Phase B: DCM:MeOH (50:50); A:B:: 80:20; Flow rate: 1.0 mL/min. Retention time: 11.412.

The experimental procedure for the synthesis of compound 1 to compound 7 captured under the synthesis of CK & CL.

Synthesis of tert-butyl 6-(4(2S,3R)-1-amino-3-hydroxy-1-oxobutan-2-yl)amino)methyl)-2-(benzyloxy)-1-oxo-2,5-diazaspiro[3.4]octane-5-carboxylate (8)

To a solution of compound 7 (5.8 g, 0.016 mol) in MeOH (87 mL) was added Int-B (2.28 g, 0.019 mol) under nitrogen atmosphere and stirred at room temperature for 30 minutes. NaBH$_3$CN (2.02 g, 0.032 mol) was added and stirred at room temperature for 16 h. After consumption of the starting material (by TLC), volatiles were evaporated under reduced pressure. The reaction mixture was diluted with water (20 mL) and extracted with EtOAc (2×100 mL). The organic layer was washed with brine, dried over Na$_2$SO$_4$ and concentrated under reduced pressure. The residue was purified by column chromatography eluting with 2% MeOH/CH$_2$Cl$_2$ to afford diasteromeric mixture 8 (3.4 g, 46%) as a white solid. $^1$H NMR (400 MHz, DMSO-d$_6$) δ 7.45-7.36 (m, 5H), 7.26-7.19 (m, 1H), 7.07-7.03 (m, 1H), 4.93-4.78 (m, 3H), 4.23-4.17 (m, 1H), 3.71-3.62 (m, 2H), 3.43-3.37 (m, 1H), Synthesis of (2S,3R)-2-(42-(benzyloxy)-1-oxo-2,5-diazaspiro[3.4]octan-6-yl)methyl) (methyl) amino)-3-hydroxybutanamide (CT)

To a stirring solution of BV (700 mg, 1.47 mmol) in CH$_2$Cl$_2$ (14 mL) were added molecular sieves (700 mg) and BF$_3$.Oet$_2$ (49%) (417 mg, 2.94 mmol) drop wise at RT under nitrogen atmosphere. The reaction mixture was stirred for 4 h. After consumption of the starting material (by TLC), volatiles were evaporated under reduced pressure. The crude material was purified by reverse phase preparative HPLC to remove boron trifluoride diethyl etherate salts and to obtain CT (235 mg, 42%) as a white solid. $^1$H NMR (400 MHz, DMSO-d$_6$) δ 7.50-7.27 (m, 6H), 6.94 (s, 1H), 4.94-4.77 (m, 2H), 4.79-4.70 (m, 1H), 3.80-3.71 (m, 1H), 3.50-3.42 (m, 2H), 3.20-3.03 (m, 2H), 2.72 (d, J=9.4 Hz, 1H), 2.41 (d, J=14.7 Hz, 1H), 2.35 (s, 3H), 1.94-1.65 (m, 3H), 1.49-1.43 (m, 1H), 1.00 (d, J=6.0 Hz, 3H). LCMS (ESI): m/z 377.1 [M$^+$+1]. HPLC: 96.47%. Chiral HPLC: 100.00%. Column: DIOL (150*4.6 mm, 3 μm); Mobile Phase A: n-Hexane; Mobile Phase B: DCM:MeOH (50:50); A:B:: 80:20; Flow rate: 1.0 mL/min; Retention time: 10.995.

Synthesis of (2S,3R)-3-hydroxy-2-(methyl((l-oxo-2,5-diazaspiro[3.4]octan-6-yl)methyl) amino)butanamide (CU & CV)

To a stirring mixture of CS & CT (1.2 g, 3.19 mmol) in MeOH (24 mL) was added Raney Ni (1.2 g) at RT and stirred for 16 h under H$_2$ atmosphere. After consumption of the starting material (by TLC), the reaction mixture was filtered through a pad of celite and the pad was washed with MeOH (100 mL). Obtained filtrate was concentrated under reduced pressure to afford mixture of CU & CV (800 mg, 92%) as white solid, which was purified by chiral preparative HPLC purification to obtain CU (210 mg) as a hygroscopic white solid and CV (190 mg) as a hygroscopic white solid.

CU: $^1$H NMR (400 MHz, DMSO-d$_6$) δ 7.40 (br s, 1H), 7.15 (s, 1H), 6.93 (s, 1H), 5.02 (s, 1H), 3.80-3.68 (m, 1H), 3.28 (d, J=6.0 Hz, 1H), 3.14-3.06 (m, 3H), 2.82 (dd, J=11.1, 2.6 Hz, 1H), 2.72 (d, J=9.4 Hz, 1H), 2.39 (s, 3H), 2.37-2.33 (m, 1H), 1.92-1.74 (m, 3H), 1.63-1.51 (m, 1H), 0.99 (d, J=6.0 Hz, 3H). LCMS (ESI): m/z 271.1 [M$^+$+1]. HPLC: 99.25%. Chiral HPLC: 100.00%. Column: CHIRALPAK IC (250*20 mm, 5 μm); Mobile Phase A: 0.1% DEA in n-Hexane; Mobile Phase B: DCM:MeOH (90:10); A:B 25:75; Flow rate: 1.0 mL/min. Retention time: 19.841.

CV: $^1$H NMR (400 MHz, DMSO-d$_6$) δ 7.36 (s, 1H), 7.13 (s, 1H), 6.94 (s, 1H), 4.28 (s, 1H), 3.84-3.67 (m, 1H), 3.38-3.27 (m, 2H), 2.95 (s, 1H), 2.83-2.65 (m, 4H), 2.37 (s, 3H), 1.94-1.74 (m, 2H), 1.69-1.52 (m, 2H), 0.99 (d, J=6.1 Hz, 3H). LCMS (ESI): m/z 271.1 [M$^+$+1]. HPLC: 99.69%. Chiral HPLC: 100.00%. Column: CHIRALPAK IC (250*20 mm, 5 μm); Mobile Phase A: 0.1% DEA in n-Hexane; Mobile Phase B: DCM:MeOH (90:10); A:B 25:75; Flow rate: 1.0 mL/min; Retention time: 23.713.

Synthesis of CW & CX:

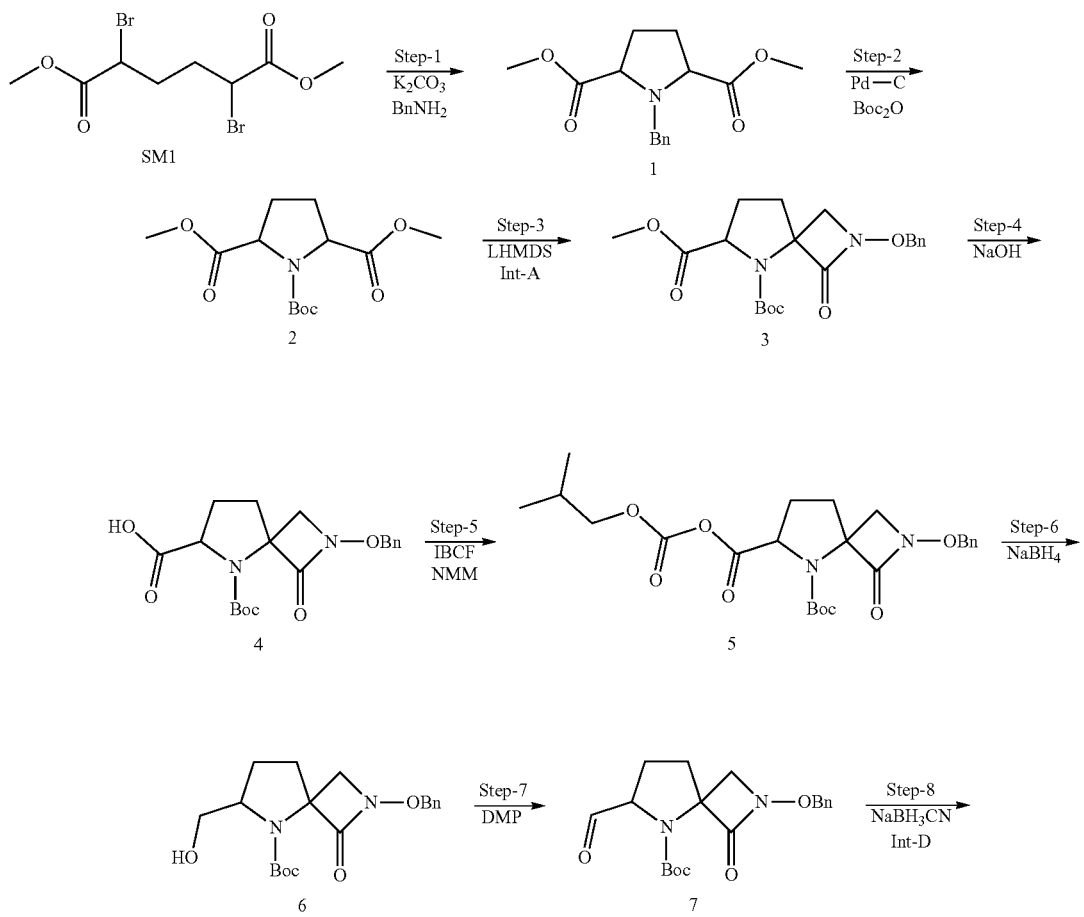

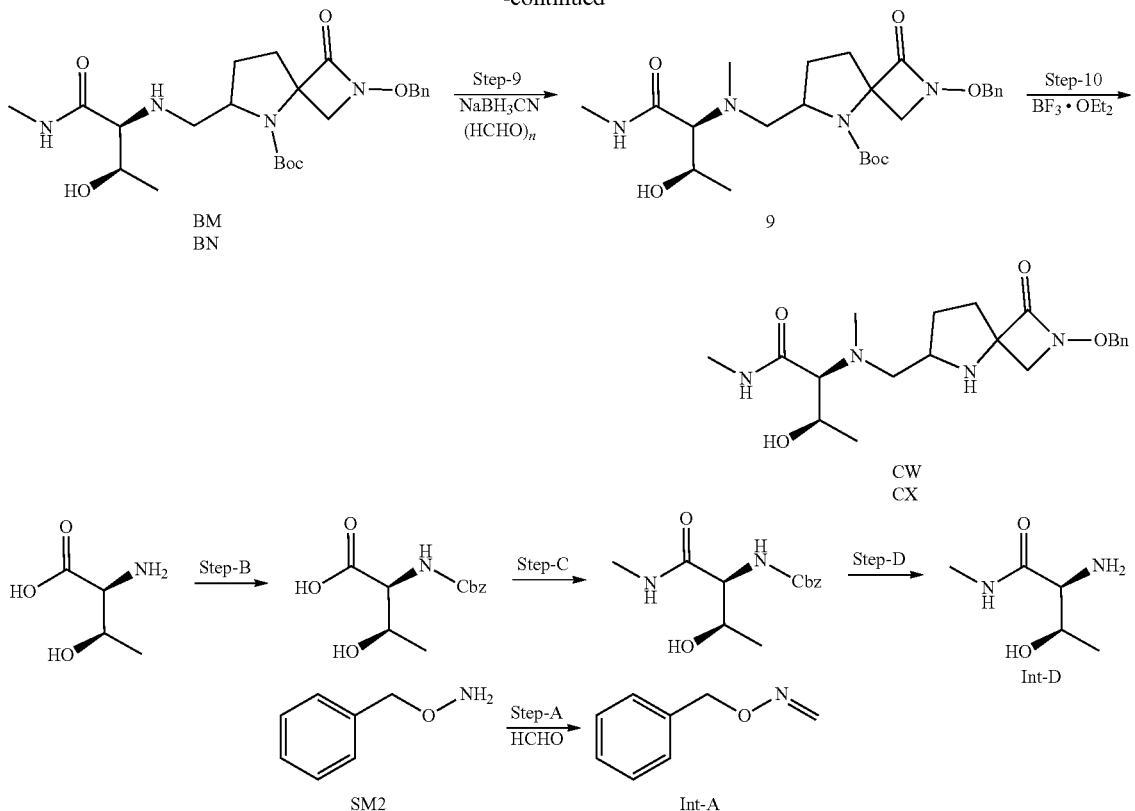

The experimental procedure for the synthesis of compound 1 to BM & BN, and Int-D is captured under the synthesis of CO & CP, whereas the experimental procedure for the synthesis of Int-A is captured under CK & CL.

Synthesis of tert-butyl 2-(benzyloxy)-6-(4(2S,3R)-3-hydroxy-1-(methylamino)-1-oxobutan-2-yl)(methyl)amino)methyl)-1-oxo-2,5-diazaspiro[3.4]octane-5-carboxylate (9)

To a stirred solution mixture of BM & BN (2.5 g, 5.25 mmol) in MeOH (50 mL) was added paraformaldehyde (945 mg, 31.5 mmol) and acetic acid (0.2 mL, 2.62 mmol) at room temperature. After stirred for 1 h, sodium cyanoborohydride (989 mg, 15.7 mmol) was added portion wise. The reaction mixture was stirred at 70° C. for 16 h. After consumption of the starting material (by TLC), the reaction mixture was quenched aqueous NaHCO$_3$ and extracted with EtOAc (2×100 mL). Separated organic layer was washed with brine, dried over Na$_2$SO$_4$ and concentrated under reduced pressure. Obtained crude material was purified by column chromatography eluting with 3% MeOH/CH$_2$Cl$_2$ to afford diasteromeric mixture (2.3 g, 92%) as an off white solid, which was separated by normal phase preparative HPLC purification to obtain 9-F1 (800 mg) and 9-F2 (750 mg) as white solids.

9-F1: $^1$H NMR (500 MHz, DMSO-d$_6$) δ 7.83 (d, J=4.5 Hz, 1H), 7.45-7.33 (m, 5H), 4.90-4.84 (m, 2H), 4.22 (d, J=7.0 Hz, 1H), 4.05 (d, J=2.9 Hz, 1H), 3.83-3.82 (m, 1H), 3.78 (d, J=10.3 Hz, 1H), 3.48 (d, J=10.1 Hz, 1H), 3.29 (s, 1H), 3.14 (d, J=14.3 Hz, 1H), 2.76 (d, J=9.1 Hz, 1H), 2.59 (d, J=4.3 Hz, 3H), 2.43-2.36 (m, 1H), 2.35 (s, 3H), 2.00-1.74 (m, 3H), 1.38 (s, 9H), 0.96 (d, J=6.1 Hz, 3H). LCMS (ESI): m/z 491.1 [M$^+$+1].

9-F2: $^1$H NMR (500 MHz, DMSO-d$_6$) δ 7.80-7.77 (m, 1H), 7.44-7.34 (m, 5H), 4.95-4.77 (m, 2H), 4.22 (d, J=7.1 Hz, 1H), 4.12 (d, J=3.5 Hz, 1H), 3.88-3.85 (m, 1H), 3.77 (d, J=10.1 Hz, 1H), 3.32 (d, J=10.4 Hz, 1H), 3.27-3.21 (m, 1H), 3.12 (d, J=14.3 Hz, 1H), 2.70 (d, J=9.1 Hz, 1H), 2.57 (d, J=4.5 Hz, 3H), 2.50-2.48 (m, 1H), 2.37 (s, 3H), 2.02-1.91 (m, 1H), 1.82-1.72 (m, 2H), 1.37 (s, 9H), 0.97 (d, J=6.1 Hz, 3H). LCMS (ESI): m/z 491.1 [M$^+$+1].

Synthesis of (2S,3R)-2-(42-(benzyloxy)-1-oxo-2,5-diazaspiro[3.4]octan-6-yl)methyl) (methyl)amino)-3-hydroxy-N-methylbutanamide (CW)

To a stirring solution of 9-F1 (800 mg, 1.63 mmol) in CH$_2$Cl$_2$ (20 mL) were added molecular sieves (800 mg) and BF$_3$·Oet$_2$ (49%) (463 mg, 3.26 mmol) drop wise at RT under nitrogen atmosphere. The reaction mixture was stirred for 4 h. After consumption of the starting material (by TLC), volatiles were evaporated under reduced pressure. The crude material was washed with Et$_2$O and n-pentane and purified by reverse phase HPLC to obtain CW (410 mg) as hygroscopic white solid. $^1$H NMR (500 MHz, DMSO-d$_6$) δ 7.84 (d, J=4.5 Hz, 1H), 7.44-7.35 (m, 5H), 4.94-4.81 (m, 2H), 4.26 (s, 1H), 3.83-3.74 (m, 1H), 3.65 (d, J=9.7 Hz, 1H), 3.45 (d, J=6.7 Hz, 1H), 3.23 (br s, 1H), 3.06 (d, J=9.7 Hz, 1H), 2.74-2.61 (m, 4H), 2.57 (d, J=4.5 Hz, 3H), 2.34 (s, 2H), 1.90-1.73 (m, 2H), 1.51-1.47 (m, 2H), 0.94 (d, J=5.9 Hz, 3H). LCMS (ESI): m/z 391.3 [M$^+$+1]. HPLC: 99.86%. Chiral HPLC: 100.00%. Column: CHIRALPAK IA (250*4.6 mm, 5 μm); Mobile Phase A: 0.1% DEA in n-Hexane; Mobile Phase B: EtOH:MeOH (10:90); A:B 85:15; Flow rate: 1.0 mL/min Retention time: 8.665.

Synthesis of (2S,3R)-2-(42-(benzyloxy)-1-oxo-2,5-diazaspiro[3.4]octan-6-yl)methyl) (methyl)amino)-3-hydroxy-N-methylbutanamide (CX)

To a stirring solution of 9-F2 (740 mg, 1.51 mmol) in CH$_2$Cl$_2$ (20 mL) were added molecular sieves (740 mg) and BF$_3$.Oet$_2$ (49%) (428 mg, 3.02 mmol) drop wise at RT under nitrogen atmosphere. The reaction mixture was stirred for 4 h. After consumption of the starting material (by TLC), volatiles were evaporated under reduced pressure. The crude material was washed with Et$_2$O and n-pentane and dried under vacuum to afford to obtain CX (210 mg) as a hygroscopic white solid. $^1$H NMR (500 MHz, DMSO-d$_6$) δ 7.89 (d, J=4.2 Hz, 1H), 7.47-7.33 (m, 5H), 4.90-4.84 (m, 2H), 4.80 (s, 1H), 3.78-3.75 (m, 1H), 3.48-3.41 (m, 2H), 3.12 (d, J=9.7 Hz, 1H), 3.06 (d, J=14.6 Hz, 1H), 2.69 (d, J=9.3 Hz, 1H), 2.57 (d, J=4.2 Hz, 3H), 2.37 (d, J=14.5 Hz, 1H), 2.33 (s, 3H), 1.92-1.68 (m, 3H), 1.50-1.41 (m, 1H), 0.95 (d, J=5.9 Hz, 3H). LCMS (ESI): m/z 391.3 [M$^+$+1]. HPLC: 99.59%. Chiral HPLC: 100.00%. Column: CHIRALPAK IA (250*4.6 mm, 5 μm); Mobile Phase A: 0.1% DEA in n-Hexane; Mobile Phase B: EtOH:MeOH (10:90); A:B 85:15; Flow rate: 1.0 mL/min Retention time: 12.566.

Synthesis of CY, CZ, DA, DB, DC & DD:

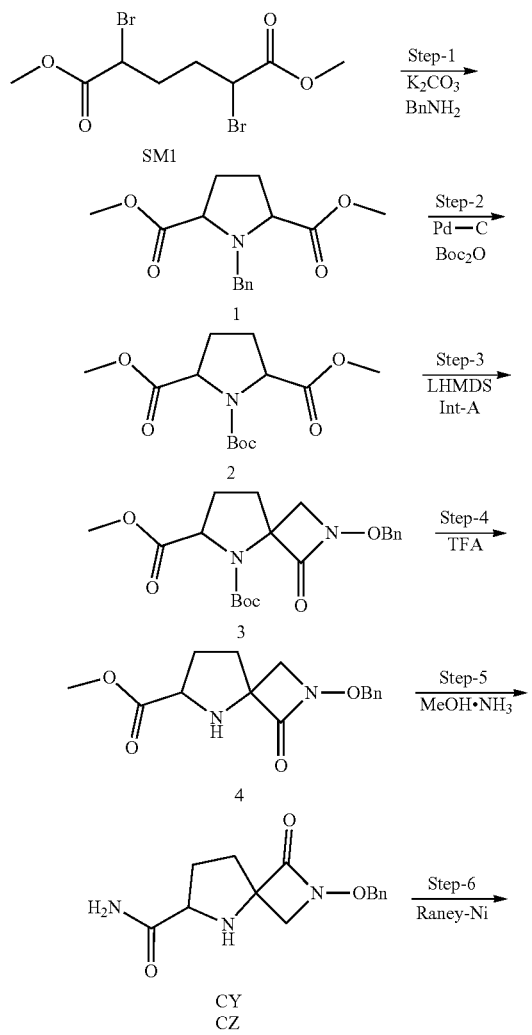

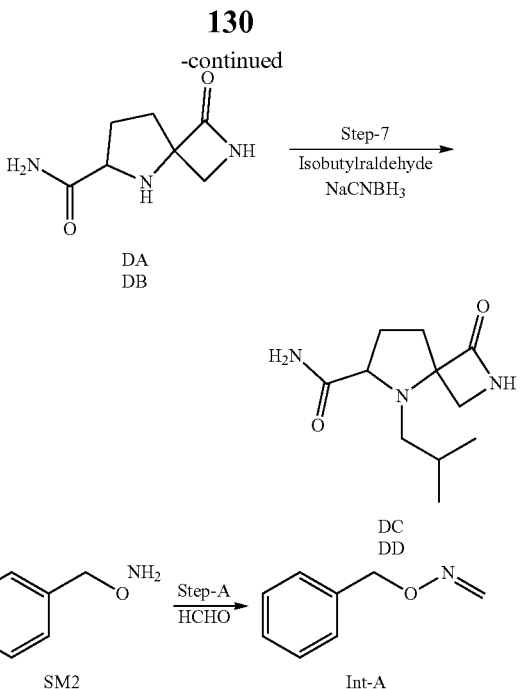

Synthesis of dimethyl 1-benzylpyrrolidine-2,5-dicarboxylate (1)

To a solution of dimethyl 2,5-dibromohexanedioate (SM) (200 g, 0.602 mol) in toluene and water (800 mL, 3:1) were added K$_2$CO$_3$ (100 g, 0.72 mol) and benzyl amine (64.45 g, 0.602 mol). The reaction mixture was heated to 80° C. and stirred for 20 h under nitrogen atmosphere. After completion of the reaction, reaction mixture was cooled to RT, diluted with EtOAc (1 L). After stirring for 10 minutes, organic layer was separated and washed with brine solution. Combined organic layer was dried over anhydrous Na$_2$SO$_4$ and concentrated under reduced pressure. Obtained crude material was purified by column chromatography eluting with 20% EtOAc/Hexane to afford meso compound 1 (111 g, 66%) as brown syrup. $^1$H NMR (400 MHz, DMSO-d$_6$): δ 7.28-7.19 (m, 5H), 3.83 (s, 2H), 3.48 (s, 6H), 3.42-3.36 (m, 2H), 2.09-1.98 (m, 2H), 1.94-1.83 (m, 2H). LCMS (ESI): m/z 277.9 [M++1].

Synthesis of 1-(tert-butyl) 2,5-dimethyl pyrrolidine-1,2,5-tricarboxylate (2)

To a stirring solution of meso compound 1 (111 g, 0.40 mol) in methanol (1 L) were added Boc$_2$O (175 g, 0.80 mol) and 10% Pd/C (50% wet, 40 g) at RT under nitrogen atmosphere and stirred for 48 h under H$_2$ atmosphere (balloon pressure). After consumption of the starting material (by TLC), the reaction mixture was filtered through a pad of celite and the filtrate was concentrated under reduced pressure. The crude was purified by silica gel column chromatography eluting with 30% EtOAc/Hexane to afford compound 2 (90 g, 78%) as a white solid. $^1$H NMR (500 MHz, DMSO-d$_6$): δ 4.27-4.18 (m, 2H), 3.64 (s, 3H), 3.62 (s, 3H), 2.25-2.16 (m, 2H), 1.96-1.85 (m, 2H), 1.36 (s, 9H). LCMS (ESI): m/z 288.2 [M$^+$+1].

Synthesis of 5-(tert-butyl) 6-methyl 2-(benzyloxy)-1-oxo-2,5-diazaspiro[3.4]octane-5,6-dicarboxylate (3)

To a solution of compound 2 (90 g, 0.313 mol) in THF (800 mL) was added to a LiHMDS solution (1M solution in THF) (470 mL, 0.47 mol) drop wise at −78° C. under nitrogen atmosphere. After being stirred at −78° C. for 1 h, a solution of Int-A (50.8 g, 0.376 mol) in THF (100 mL) was added. The reaction mixture was brought to RT stirred for 16 h. After consumption of the starting material (by TLC), the reaction was quenched with aqueous $NH_4Cl$ solution (500 mL) and extracted with EtOAc (2×500 mL). Separated organic layer was washed with brine, dried over $Na_2SO_4$ and concentrated under reduced pressure. Obtained crude material was purified by column chromatography eluting with 30% EtOAc/Hexane to afford compound 3 (84 g, 68%) as brown thick syrup. $^1$H NMR (400 MHz, DMSO-$d_6$): δ 7.48-7.36 (m, 5H), 4.95-4.85 (m, 2H), 4.29 (br d, J=6.4 Hz, 1H), 4.07-3.99 (m, 1H), 3.71 (s, 3H), 3.55 (d, J=10.7 Hz, 1H), 2.36-2.16 (m, 2H), 2.13-2.02 (m, 1H), 1.98-1.91 (m, 1H), 1.35 (s, 9H). LCMS (ESI): m/z 391.3 [M$^+$+1].

Synthesis of methyl 2-(benzyloxy)-1-oxo-2,5-diazaspiro[3.4]octane-6-carboxylate (4)

To a stirring solution of compound 3 (37 g, 0.094 mol) in $CH_2Cl_2$ (370 mL) was added TFA (77.3 mL, 0.948 mol) at 0° C. and stirred at RT for 4 h. After consumption of the starting material (by TLC), reaction mixture was concentrated under reduced pressure. Crude material was diluted with $CH_2Cl_2$ (500 mL) and adjusted pH to 10-11 with saturated aqueous $NaHCO_3$. Organic layer was extracted with $CH_2Cl_2$ (2×500 mL), dried over $Na_2SO_4$ and concentrated under reduced pressure to afford compound 4 (27 g, 98%) as a thick syrup. 1H NMR (500 MHz, DMSO-$d_6$) δ 7.46-7.25 (m, 5H), 4.96-4.75 (m, 2H), 3.67 (s, 3H), 3.65-3.50 (m, 3H), 3.36 (d, J=9.6 Hz, 1H), 1.97-1.74 (m, 4H). LCMS (ESI): m/z 290.9 [M$^+$+1].

Synthesis of 2-(benzyloxy)-1-oxo-2,5-diazaspiro [3.4]octane-6-carboxamide (CY & CZ)

To a solution of compound 4 (27 g, 0.093 mol) in MeOH (270 mL) was added methanolic ammonia (7.0 N) (270 mL) at −20° C. in a sealed tube under nitrogen atmosphere. The reaction mixture was stirred at RT for 16 h. After consumption of the starting material (by TLC), volatiles were evaporated under reduced pressure. Crude was triturated with $Et_2O$ and dried under vacuum to afford mixture of CY & CZ (20 g, 79%) as white solid. 800 mg of mixture CY & CZ was separated by chiral preparative HPLC purification to obtain CY (180 mg) as white solid and CZ (220 mg) as a white solid.

CY: $^1$H NMR (500 MHz, DMSO-$d_6$) δ 7.46-7.35 (m, 5H), 7.23-7.11 (m, 2H), 4.96-4.76 (m, 2H), 3.73 (s, 1H), 3.56 (d, J=7.0 Hz, 1H), 3.53-3.43 (m, 2H), 1.99-1.89 (m, 1H), 1.85-1.67 (m, 3H). LCMS (ESI): m/z 275.9 [M$^+$+1]. HPLC: 99.57%. Chiral HPLC: 100.00%. Column: CHIRALPAK IC (250*20 mm, 5 μm); Mobile Phase A: 0.1% DEA in n-Hexane; Mobile Phase B: DCM:MeOH (50:50); A:B 50:50; Flow rate: 1.0 mL/min Retention time: 6.412.

CZ: $^1$H NMR (500 MHz, DMSO-$d_6$): δ 7.46-7.34 (m, 5H), 7.21-7.14 (m, 2H), 4.97-4.81 (m, 2H), 3.72 (s, 1H), 3.56 (d, J=7.0 Hz, 1H), 3.53-3.42 (m, 2H), 1.99-1.90 (m, 1H), 1.86-1.68 (m, 3H). LCMS (ESI): m/z 275.9 [M$^+$+1]. HPLC: 98.82%. Chiral HPLC: 99.23%. Column: CHIRALPAK IC (250*20 mm, 5 μm); Mobile Phase A: 0.1% DEA in n-Hexane; Mobile Phase B: DCM:MeOH (50:50); A:B 50:50; Flow rate: 1.0 mL/min Retention time: 6.868.

Synthesis of 1-oxo-2,5-diazaspiro[3.4]octane-6-carboxamide (DA & DB)

To a stirring solution of Raney Nickel (16 g) in MeOH (150 mL) was added mixture of CY & CZ (16 g, 0.058 mol) MeOH (50 mL) at RT under nitrogen atmosphere. Reaction mixture was stirred for 16 h under $H_2$ atmosphere (balloon pressure). After consumption of the starting material (by TLC), the reaction mixture was filtered through a pad of celite and the pad was washed with MeOH (10 mL). Obtained filtrate was concentrated under reduced pressure. Crude material was triturated with $Et_2O$ and n-Pentane and dried under vacuum to afford mixture of DA & DB (9.4 g, 95%) as white solid. 800 mg of mixture DA & DB was separated by chiral preparative HPLC purification to DA (230 mg) as white solid and DB (200 mg) as white solids.

DA: $^1$H NMR (400 MHz, DMSO-$d_6$) δ 7.25 (br s, 1H), 7.14 (d, J=3.3 Hz, 2H), 3.44-3.39 (m, 2H), 3.22 (d, J=1.8 Hz, 2H), 1.97-1.81 (m, 4H). LCMS (ESI): m/z 169.9 [M$^+$+1]. HPLC: 98.47%. Chiral HPLC: 100.00%. Column: CHIRALPAK IC (250*4.6 mm, 5 μm); Mobile Phase A: DCM; Mobile Phase B: IPA; A:B 85:15; Flow rate: 1.0 mL/min. Retention time: 12.505.

DB: $^1$H NMR (400 MHz, DMSO-$d_6$) δ 7.24 (br s, 1H), 7.14 (d, J=3.1 Hz, 2H), 3.43-3.39 (m, 2H), 3.21 (d, J=1.8 Hz, 2H), 1.98-1.79 (m, 4H). LCMS (ESI): m/z 169.9 [M$^+$+1]. HPLC: 98.89%. Chiral HPLC: 99.10%. Column: CHIRALPAK IC (250*4.6 mm, 5 μm); Mobile Phase A: DCM; Mobile Phase B: IPA; A:B 85:15; Flow rate: 1.0 mL/min. Retention time: 16.052.

Synthesis of 5-isobutyl-1-oxo-2,5-diazaspiro[3.4] octane-6-carboxamide (DC & DD)

To a mixture of DA & DB (3 g, 17.7 mmol) in MeOH (30 mL) were added isobutyraldehyde (1.917 g, 26.6 mmol) and AcOH (0.31 mL) at RT under nitrogen atmosphere. After being stirred for 45 minutes, $NaBH_3CN$ (3.35 g, 53.1 mmol) was added and allowed to stir at RT for 16 h. After consumption of the starting material (by TLC), the reaction mixture was quenched aqueous $NaHCO_3$ solution and volatiles were evaporated under reduced pressure. Crude material was purified by silica gel column chromatography eluting with 5% MeOH/$CH_2Cl_2$ to afford mixture of DC & DD (200 mg) as white solid, which was separated by chiral preparative HPLC purification to obtain DC (50 mg) as a white solid and DD (52 mg) as a white solid.

DC: $^1$H NMR (400 MHz, DMSO-$d_6$) δ 7.40-7.23 (m, 2H), 6.84 (s, 1H), 3.44 (d, J=12.5 Hz, 1H), 3.37-3.35 (m, 1H), 3.09 (dd, J=12.5, 2.6 Hz, 1H), 2.38-2.32 (m, 1H), 2.20-2.15 (m, 2H), 2.13-2.03 (m, 1H), 2.03-1.88 (m, 1H), 1.85-1.78 (m, 1H), 1.77-1.71 (m, 1H), 0.93 (d, J=6.5 Hz, 3H), 0.86 (d, J=6.5 Hz, 3H). LCMS (ESI): m/z 226.0 [M$^+$+1]. HPLC: 96.76%. Chiral HPLC: 100.00%. Column: CHIRALPAK IC (250*4.6 mm, 5 μm); Mobile Phase A: 0.1% DEA in n-Hexane; Mobile Phase B: EtOH:MeOH (50:50); A:B 85:15; Flow rate: 1.0 mL/min. Retention time: 20.917.

DD: $^1$H NMR (400 MHz, DMSO-$d_6$) δ 7.42-7.22 (m, 2H), 6.83 (br s, 1H), 3.43 (d, J=12.5 Hz, 1H), 3.38-3.33 (m, 1H), 3.09 (dd, J=12.5, 2.6 Hz, 1H), 2.37-2.30 (m, 1H), 2.19-2.14 (m, 1H), 2.12-2.02 (m, 2H), 2.01-1.90 (m, 1H), 1.84-1.78 (m, 1H), 1.77-1.69 (m, 1H), 0.92 (d, J=6.5 Hz, 3H), 0.84 (d, J=6.7 Hz, 3H). LCMS (ESI): m/z 226.0 [M$^+$+1]. HPLC: 95.23%. Chiral HPLC: 100%. Column: CHIRALPAK IC (250*4.6 mm, 5 μm); Mobile Phase A: 0.1% DEA in n-Hexane; Mobile Phase B: EtOH:MeOH (50:50). A:B 85:15; Flow rate: 1.0 mL/min. Retention time: 24.402.

Synthesis of DE & DF:

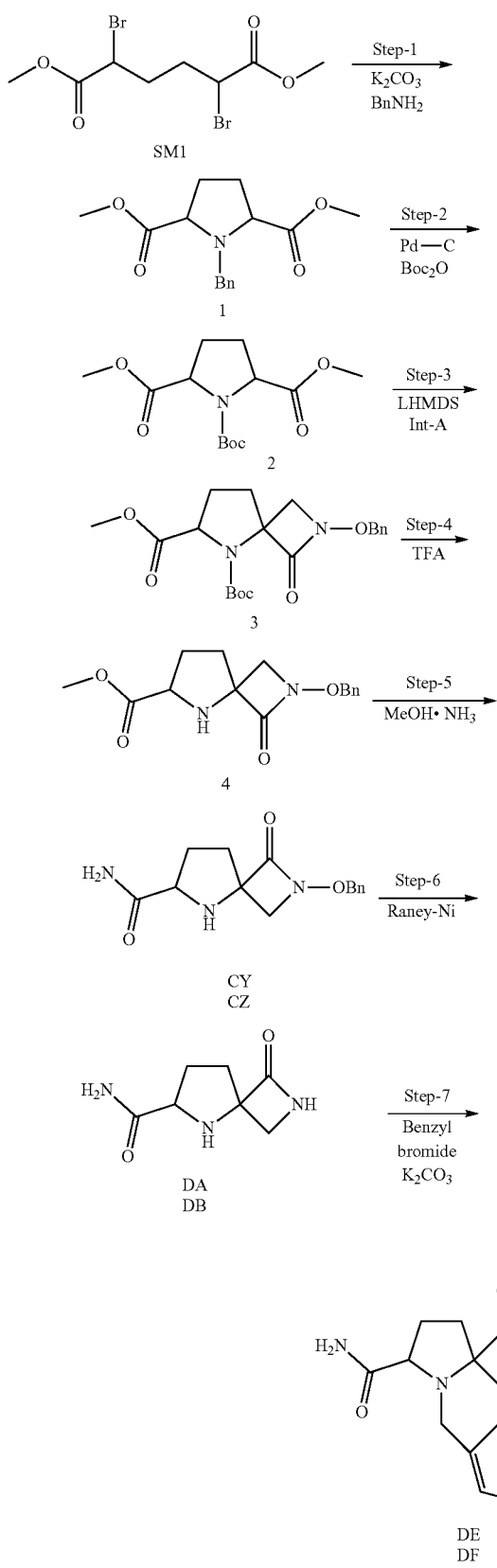

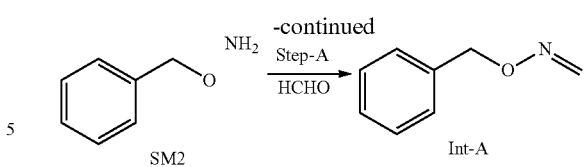

The experimental procedure for the synthesis of compound 1 to DA & DB is captured under the synthesis of DA & DB.

Synthesis of 5-benzyl-1-oxo-2,5-diazaspiro[3.4]octane-6-carboxamide (DE & DF)

To a mixture of DA & DB (2 g, 11.8 mmol) in DMF (20 mL) were added $K_2CO_3$ (4.89 g, 35.4 mmol) and benzyl bromide (2.1 mL, 17.7 mmol) at RT and stirred for 16 h. After consumption of the starting material (by TLC), volatiles were evaporated under reduced pressure. Crude material was purified by silica gel column chromatography eluting with 5% MeOH/$CH_2Cl_2$ to afford mixture DE & DF (2.1 g, 68%) as white solid. 800 mg of mixture DE & DF was separated by chiral preparative HPLC purification to obtain DE (230 mg) white solid and DF (240 mg) as white solid.

DE: $^1$H NMR (400 MHz, DMSO-$d_6$): δ 7.49 (s, 1H), 7.41-7.22 (m, 7H), 3.87 (d, J=13.6 Hz, 1H), 3.58 (d, J=12.5 Hz, 1H), 3.43 (d, J=13.6 Hz, 1H), 3.21 (dd, J=12.5, 2.6 Hz, 1H), 3.02 (d, J=5.4 Hz, 1H), 2.20-2.11 (m, 1H), 2.09-1.96 (m, 2H), 1.84-1.71 (m, 1H). LCMS (ESI): m/z 260.0 [M$^+$+1]. HPLC: 98.97%. Chiral HPLC: 100.00%. Column: CHIRALPAK IC (250*20 mm, 5 μm). Mobile Phase A: 0.1% DEA in n-Hexane:THF (80:20); Mobile Phase B: DCM:MeOH (80:20); A:B:: 80:20; Flow rate: 1.0 mL/min Retention time: 15.237.

DF: $^1$H NMR (400 MHz, DMSO-$d_6$) δ 7.48 (s, 1H), 7.40-7.25 (m, 7H), 3.87 (d, J=13.6 Hz, 1H), 3.58 (d, J=12.7 Hz, 1H), 3.43 (d, J=13.6 Hz, 1H), 3.21 (dd, J=12.7, 2.6 Hz, 1H), 3.02 (d, J=5.3 Hz, 1H), 2.21-2.09 (m, 1H), 2.08-1.98 (m, 2H), 1.87-1.75 (m, 1H). LCMS (ESI): m/z 259.9 [M$^+$+1]. HPLC: 99.67%. Chiral HPLC: 100.00%. Column: CHIRALPAK IC (250*20 mm, 5 μm); Mobile Phase A: 0.1% DEA in n-Hexane:THF (80:20); Mobile Phase B: DCM:MeOH (80:20); A:B:: 80:20; Flow rate: 1.0 mL/min Retention time: 17.347.

Synthesis of DG & DH:

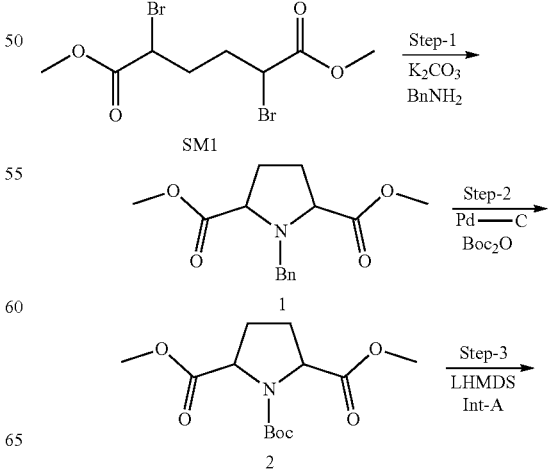

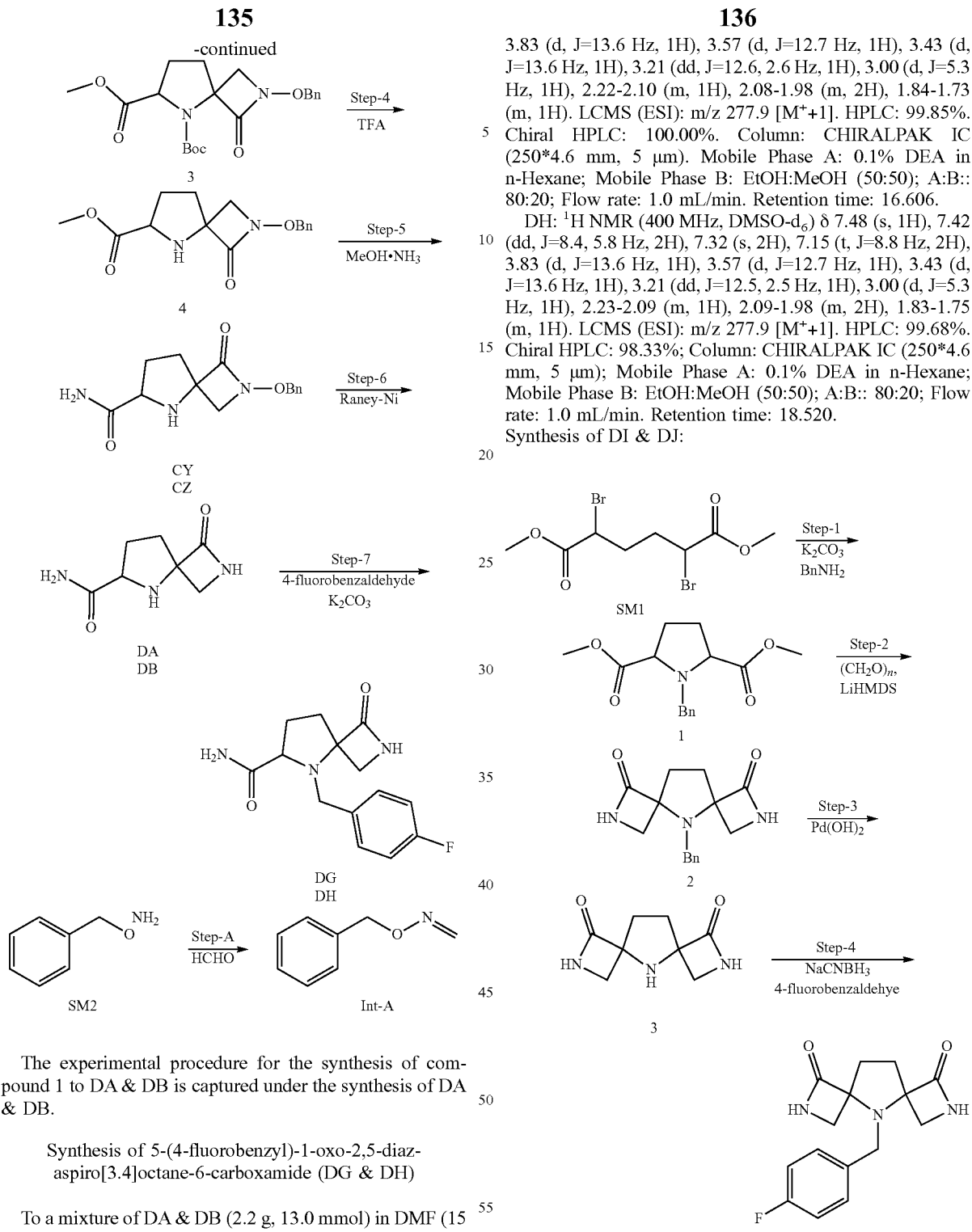

3.83 (d, J=13.6 Hz, 1H), 3.57 (d, J=12.7 Hz, 1H), 3.43 (d, J=13.6 Hz, 1H), 3.21 (dd, J=12.6, 2.6 Hz, 1H), 3.00 (d, J=5.3 Hz, 1H), 2.22-2.10 (m, 1H), 2.08-1.98 (m, 2H), 1.84-1.73 (m, 1H). LCMS (ESI): m/z 277.9 [M$^+$+1]. HPLC: 99.85%. Chiral HPLC: 100.00%. Column: CHIRALPAK IC (250*4.6 mm, 5 μm). Mobile Phase A: 0.1% DEA in n-Hexane; Mobile Phase B: EtOH:MeOH (50:50); A:B:: 80:20; Flow rate: 1.0 mL/min. Retention time: 16.606.

DH: $^1$H NMR (400 MHz, DMSO-d$_6$) δ 7.48 (s, 1H), 7.42 (dd, J=8.4, 5.8 Hz, 2H), 7.32 (s, 2H), 7.15 (t, J=8.8 Hz, 2H), 3.83 (d, J=13.6 Hz, 1H), 3.57 (d, J=12.7 Hz, 1H), 3.43 (d, J=13.6 Hz, 1H), 3.21 (dd, J=12.5, 2.5 Hz, 1H), 3.00 (d, J=5.3 Hz, 1H), 2.23-2.09 (m, 1H), 2.09-1.98 (m, 2H), 1.83-1.75 (m, 1H). LCMS (ESI): m/z 277.9 [M$^+$+1]. HPLC: 99.68%. Chiral HPLC: 98.33%; Column: CHIRALPAK IC (250*4.6 mm, 5 μm); Mobile Phase A: 0.1% DEA in n-Hexane; Mobile Phase B: EtOH:MeOH (50:50); A:B:: 80:20; Flow rate: 1.0 mL/min. Retention time: 18.520.

Synthesis of DI & DJ:

The experimental procedure for the synthesis of compound 1 to DA & DB is captured under the synthesis of DA & DB.

Synthesis of 5-(4-fluorobenzyl)-1-oxo-2,5-diazaspiro[3.4]octane-6-carboxamide (DG & DH)

To a mixture of DA & DB (2.2 g, 13.0 mmol) in DMF (15 mL) were added K$_2$CO$_3$ (5.38 g, 39.0 mmol) and 4-fluorobenzaldehyde (2.1 mL, 19.5 mmol) at RT and stirred for 16 h. After consumption of the starting material (by TLC), volatiles were evaporated under reduced pressure. Crude material was purified by silica gel column chromatography eluting with 6% MeOH/CH$_2$Cl$_2$ to afford mixture DG & DH (2.2 g, 75%) as white solid. 600 mg of mixture was separated by chiral preparative HPLC purification to obtain DG (117 mg) white solid and DH (153 mg) as white solids.

DG: $^1$H NMR (400 MHz, DMSO-d$_6$): δ 7.48 (s, 1H), 7.42 (dd, J=8.5, 5.7 Hz, 2H), 7.32 (s, 2H), 7.15 (t, J=8.9 Hz, 2H),

Synthesis of dimethyl 1-benzylpyrrolidine-2,5-dicarboxylate (1)

To a stirring solution of dimethyl 2,5-dibromohexanedioate (SM) (50 g, 0.15 mol) in toluene:water (150 mL, 2:1) were added benzyl amine (16 mL, 0.15 mol) and K$_2$CO$_3$ (24 g, 0.18 mol) at room temperature. The reaction mixture was heated to reflux at 110° C. and stirred for 4 h. After consumption of the starting material (by TLC), reaction mixture was cooled to room temperature and extracted with diethyl ether (2×50 mL). Separated organic layer was dried over anhydrous $Na_2SO_4$ and concentrated under reduced pressure to obtain compound 1-mixture (39 g, 93%) as liquid. This material was purified by silica gel column chromatography eluting with 20% EtOAc/n-hexane to afford compound 1-F1 (10 g), compound 1-F2 (13 g) and compound 1-F1 & F2 (16 g) as liquid. $^1H$ NMR (500 MHz, $CDCl_3$): δ 7.32-7.17 (m, 5H), 3.89 (s, 2H), 3.55 (s, 6H), 3.45-3.38 (m, 2H), 2.08-1.99 (m, 4H). LCMS (m/z): 278.2 $[M^++1]$.

Synthesis of 5-benzyl-2,5,8-triazadispiro[3.1.36.24] undecane-1,7-dione (2)

To a stirring solution of compound 1 (20 g, 0.069 mol) in THF (100 mL) were added paraformaldehyde (4.1 g, 0.139 mol) and LiHMDS (1.0 M in THF) (348 mL, 0.348 mol) at −78° C. under nitrogen atmosphere. The reaction mixture was brought to RT and stirred for 16 h. After consumption of the starting material (by TLC), the reaction was quenched with ice water (500 mL) and extracted with EtOAc (2×500 mL) and 10% $MeOH/CH_2Cl_2$ (2×500 mL). The combined organic layer was dried over $Na_2SO_4$ and concentrated to obtain crude compound which was purified by column chromatography by eluting 5% $MeOH/CH_2Cl_2$ to afford compound 2 (2 g, 10%) as off white solid. $^1H$ NMR (400 MHz, DMSO-$d_6$): δ 7.69 (s, 2H), 7.37-7.17 (m, 5H), 3.91 (s, 2H), 3.11-3.01 (m, 4H), 2.24-2.13 (m, 2H), 2.13-2.02 (m, 2H). LCMS (ESI): m/z 271.9 $[M^++1]$.

Synthesis of 2,5,8-triazadispiro[3.1.36.24]undecane-1,7-dione (3)

To a stirring solution of compound 2 (2 g, 7.38 mmol) in methanol (30 mL) was added $Pd(OH)_2$ (2 g) at RT and stirred for 16 h under $H_2$ atmosphere (balloon pressure). After consumption of the starting material (by TLC), the reaction mixture was filtered through a pad of celite and the pad was washed with MeOH (100 mL). Obtained filtrate was concentrated under reduced pressure. Crude material was triturated with $Et_2O$ and dried under vacuum to afford compound 3 (1.1 g, 84%) as an off white solid. $^1H$ NMR (400 MHz, DMSO-$d_6$): δ 7.73 (br s, 2H), 3.94 (s, 1H), 3.20 (d, J=5.3 Hz, 2H), 3.10 (d, J=5.3 Hz, 2H), 2.01-1.98 (m, 4H). LCMS (ESI): m/z 182.19 $[M^++1]$.

Synthesis of 5-(4-fluorobenzyl)-2,5,8-triazadispiro [3.1.36.24]undecane-1,7-dione (DI & DJ)

To a solution of compound 3 (1 g, 5.52 mmol) in MeOH (10 mL) were added 4-fluorobenzaldehyde (1.37 g, 11.04 mmol) and AcOH (0.1 mL) at RT under nitrogen atmosphere. After being stirred for 30 minutes, $NaBH_3CN$ (996 mg, 16.5 mmol) was added portion wise and allowed to stir at RT for 16 h. After consumption of the starting material (by TLC), volatiles were evaporated under reduced pressure. Crude material was purified by silica gel column chromatography eluting with 5% MeOH/EtOAc to afford mixture of DI & DJ (500 mg, 31%) as white solid, which was separated by chiral preparative HPLC purification to obtain DI (114 mg) as white solid and DJ (120 mg) as white solid.

DI: $^1H$ NMR (400 MHz, DMSO-$d_6$) δ 7.83 (s, 2H), 7.43-7.32 (m, 2H), 7.10 (t, J=8.8 Hz, 2H), 3.87-3.76 (m, 2H), 3.08-2.95 (m, 4H), 2.09 (s, 4H). LCMS (ESI): m/z 289.9 $[M^++1]$. HPLC: 99.80%. Chiral HPLC: 100.00%. Column: CHIRALPAK IC (250*4.6 mm, 5 μm); Mobile Phase A: 0.1% DEA in n-Hexane; Mobile Phase B: EtOH; A:B 85:15; Flow rate: 1.0 mL/min. Retention time: 13.635.

DJ: $^1H$ NMR (400 MHz, DMSO-$d_6$) δ 7.83 (s, 2H), 7.42-7.32 (m, 2H), 7.10 (t, J=8.9 Hz, 2H), 3.87-3.76 (m, 2H), 3.05-2.98 (m, 4H), 2.09 (s, 4H). LCMS (ESI): m/z 289.8 $[M^++1]$. HPLC: 97.71%. Chiral HPLC: 99.08%. Column: CHIRALPAK IC (250*4.6 mm, 5 μm); Mobile Phase A: 0.1% DEA in n-Hexane; Mobile Phase B: EtOH; A:B 85:15; Flow rate: 1.0 mL/min. Retention time: 15.419.

Synthesis of DK, DL, DM & DN:

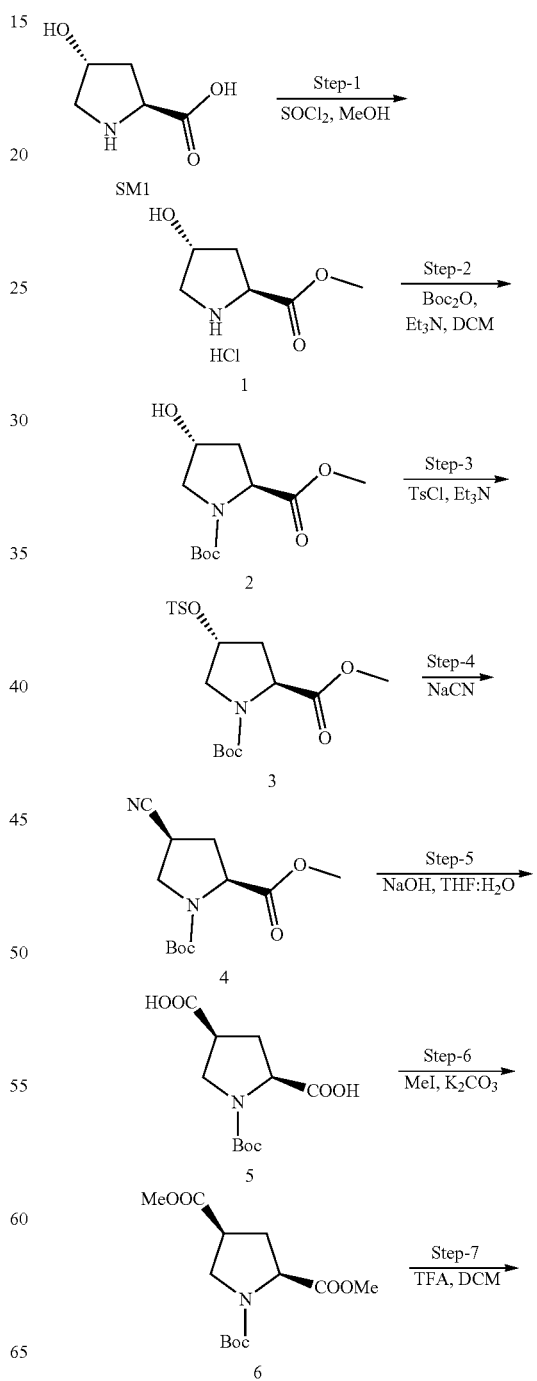

-continued

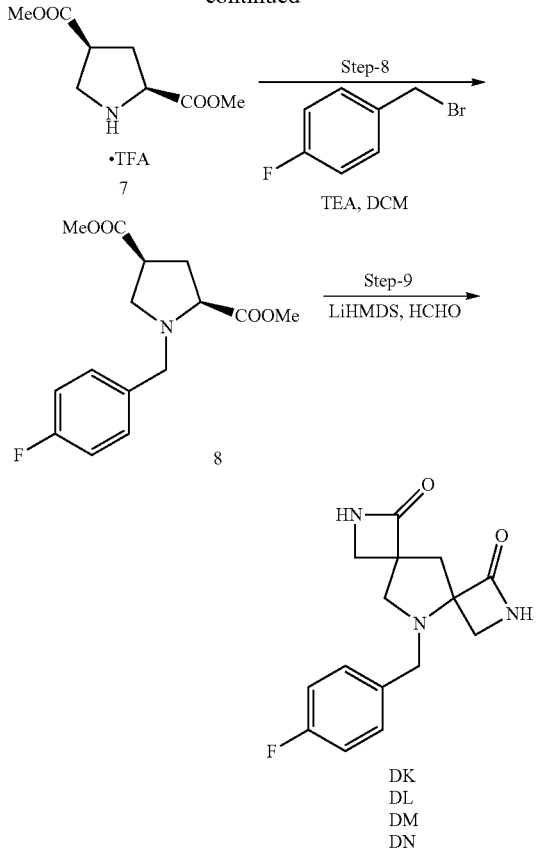

Synthesis of methyl (2S,4R)-4-hydroxypyrrolidine-2-carboxylate (1)

To a stirred solution of (2S,4R)-4-hydroxypyrrolidine-2-carboxylic acid (75.0 g, 572 mmol) in MeOH (800 mL), $SOCl_2$ (75 mL) was added at 0° C. and the reaction mixture was stirred at room temperature for 16 h. After consumption of the starting material (by TLC), the reaction mixture was concentrated under reduced pressure. The residue was triturated with $Et_2O$ (500 mL×2), filtered, dried to afford compound 1 (100.0 g, 96%) as a white solid as a HCl salt of compound 1. LCMS (ESI): m/z 146.0 [M++1].

Synthesis of 1-(tert-butyl) 2-methyl (2S,4R)-4-hydroxypyrrolidine-1,2-dicarboxylate (2)

To a stirred solution of compound 1 (100.0 g, 552 mmol) in DCM (1 L), $Et_3N$ (230 mL, 1657 mmol) was added at 0° C. and stirred for 15 min. $Boc_2O$ (152 mL, 662 mmol) was added drop wise at 0° C. Over a 30 minutes. The reaction mixture was stirred at room temperature for 16 h. After consumption of the starting material (by TLC), the reaction mixture was quenched with ice-cold water (500 mL) and extracted with DCM (3×300 mL). The combined organic layer was washed with brine (500 mL), dried over $Na_2SO_4$ and concentrated under reduced pressure. The residue was triturated with hexane (500 mL×2), filtered, dried to afford compound 2 (123.0 g, 91%) as off white solid. $^1$H NMR (400 MHz, DMSO-$d_6$) δ 5.09 (d, J=3.6 Hz, 1H), 4.29-4.15 (m, 2H), 3.64 (m, 3H), 3.45-3.21 (m, 2H), 2.14-2.09 (m, 1H), 1.95-1.82 (m, 1H), 1.39-1.32 (m, 9H).

Synthesis of 1-(tert-butyl) 2-methyl (2S,4R)-4-(tosyloxy)pyrrolidine-1,2-dicarboxylate (3)

To a stirred solution of compound 2 (123.0 g, 502 mmol) in DCM (1 L), $Et_3N$ (140 mL, 1004 mmol), DMAP (catalytic) was added. To reaction mixture (RM) tosyl chloride was added in portion (124.0 g, 652 mmol) at 0° C. and RM was stirred at room temperature for 16 h. After consumption of the starting material (by TLC), the reaction mixture was quenched with ice-cold water (500 mL) and extracted with DCM (2×500 mL). The combined organic layer was washed with $NaHCO_3$ solution (500 mL) and brine (500 mL), dried over $Na_2SO_4$ and concentrated under reduced pressure. The residue was triturated with hexane (1000 mL), filtered, dried to afford compound 3 (190.0 g, 95%) as light brown solid. $^1$H NMR (400 MHz, DMSO-$d_6$) δ 7.82 (m, 2H), 7.54-7.46 (m, 2H), 5.07 (d, J=3.9 Hz, 1H), 4.23 (m, 1H), 3.63 (m, 3H), 3.50-3.40 (m, 2H), 2.43 (s, 3H), 2.20-2.04 (m, 1H), 1.99 (s, 1H), 1.33 (m, 9H).

Synthesis of 1-(tert-butyl) 2-methyl (2S,4S)-4-cyanopyrrolidine-1,2-dicarboxylate (4)

To a stirred solution of compound 3 (190.0 g, 476 mmol) in DMSO (700 mL), NaCN (46.6 g, 952 mmol) was added and stirred at 80° C. for 6 h. After consumption of the starting material (by TLC), the reaction mixture was cooled and quenched with water (500 mL) and then extracted with diethyl ether (3×500 mL). The combined organic layer was washed with brine (500 mL), dried over $Na_2SO_4$ and concentrated under reduced pressure. The residue was purified by column chromatography using 15-20% EtOAc/hexane to afford compound 4 (50.0 g, 41.33%) as a yellow oil. $^1$H NMR (400 MHz, DMSO-$d_6$): δ 4.36-4.22 (m, 1H), 3.82-3.62 (m, 3H), 3.48-3.40 (m, 3H), 2.68-2.40 (m, 1H), 2.12-2.04 (m, 1H), 1.40 (m, 9H).

Synthesis of (2S,4S)-1-(tert-butoxycarbonyl)pyrrolidine-2,4-dicarboxylic acid (5)

To a stirring solution of compound 4 (30.0 g, 118 mmol) in THF (150 mL), NaOH (18.9 g, 472 mmol) in water (150 mL) was added and stirred for 16 h. After consumption of the starting material (by TLC), the reaction mixture was neutralized with 1N HCl solution and acidified with citric acid to pH-4-5, and then extracted with EtOAc (3×300 mL). The combined organic layer was washed with brine (300 mL), dried over $Na_2SO_4$ and concentrated under reduced pressure to afford compound 5 (21.0 g, crude) as off white solid. The crude was used as such for the next step without further purification. $^1$H NMR (400 MHz, DMSO-$d_6$) δ 12.57 (bs, 2H), 4.19-3.96 (m, 1H), 3.62-3.40 (m, 1H), 3.50-3.35 (m, 1H), 3.07-3.0 (m, 1H), 2.37-2.15 (m, 1H), 2.05-2.0 (m, 1H), 1.35 (m, 9H).

Synthesis of 1-(tert-butyl) 2,4-dimethyl (2S,4S)-pyrrolidine-1,2,4-tricarboxylate (6)

To a stirred solution of compound 5 (21.0 g, 81.0 mmol) in DMF (200 mL), $K_2CO_3$ (44.7 g, 324 mmol) was added followed by addition of $CH_3I$ (17.6 mL, 283 mmol) at 0° C. and the reaction mixture was stirred at room temperature for 16 h. After consumption of the starting material (by TLC), the reaction mixture was quenched with water (250 mL) and extracted with diethyl ether (2×250 mL). The combined organic layer was washed with brine (250 mL), dried over $Na_2SO_4$ and concentrated under reduced pressure. The residue was purified by column chromatography using 20% EtOAc/hexane to afford compound 6 (20.2 g, 87%) as an oil. $^1$H NMR (400 MHz, DMSO-$d_6$) δ 4.31-4.17 (m, 1H), 3.66 (m, 7H), 3.48-3.40 (m, 1H), 3.22-3.15 (m, 1H), 2.40-2.35 (m, 1H), 2.11-2.08 (m, 1H), 1.36 (m, 9H).

Synthesis of dimethyl (2S,4S)-pyrrolidine-2,4-dicarboxylate (7)

To a stirred solution of compound 6 (150 g, 522.08 mmol) in DCM (750 mL) added TFA (399.4 mL, 5220.8 mmol) at 0° C. and stirred at room temperature for 2 h. After consumption of the starting material (by TLC), the reaction mixture was concentrated under reduced pressure to afford compound 7 (150 g, 95%) oil as a TFA salt of compound 7. LCMS (ESI): m/z 188.0 [M$^+$+1].

Synthesis of dimethyl (2S,4S)-1-(4-fluorobenzyl) pyrrolidine-2,4-dicarboxylate (8)

To a stirring solution of compound 7 (40.0 g, 132.8 mmol) in DCM (200 mL), Et$_3$N (93.1 mL, 664.4 mmol) was added at 0° C. dropwise and stirred for 30 mins 1-(bromomethyl)-4-fluorobenzene (24.8 mL, 199.3 mmol) was added at 0° C. and stirred at room temperature for 16 h. After consumption of the starting material (by TLC), the reaction mixture was quenched with water and extracted with DCM (3×300 mL). The combined organic layer was washed with brine (300 mL), dried over Na$_2$SO$_4$ and concentrated under reduced pressure. The residue was purified by column chromatography using 15% EtOAc/hexane to afford compound 8 (35.0 g, 89.2%) as colorless oil. LCMS (ESI): m/z 296.35 [M++1].

Synthesis of 10-(4-fluorobenzyl)-2,8,10-triazadispiro[3.1.3$^6$.2$^4$]undecane-1,7-dione (DK, DL, DM, and DN)

To a stirred solution of compound 8 (25.0 g, 84.7 mmol) in THF (200 mL), LiHMDS (1M solution in THF, 423.7 mL, 423.7 mmol) was added at −78° C. and stirred for 30 min, paraformaldehyde (6.35 g, 211.8 mmol) was added to the reaction mixture at −78° C. and stirred at room temperature for 6 h. After consumption of the starting material (by TLC), the reaction mixture was quenched with saturated NH$_4$Cl solution (300 mL) and extracted with EtOAc (3×300 mL). The combined organic layer was washed with brine (200 mL), dried over Na$_2$SO$_4$ and concentrated under reduced pressure. The residue was purified by column chromatography to afford mixture of diastereomers (3.3 g). The mixture was purified by chiral HPLC SFC to afford DK (120 mg), DL (220 mg), DM (120 mg), and DN (120 mg) as an off white solid.

DK: $^1$H NMR (400 MHz, DMSO-$d_6$) δ 7.95 (s, 1H), 7.73 (s, 1H), 7.36-7.33 (m, 2H), 7.15-7.11 (m, 2H), 3.77 (d, J=13.2 Hz, 1H), 3.56 (d, J=13.6 Hz, 1H), 3.39 (d, J=6.4 Hz, 1H), 3.23 (d, J=6 Hz, 1H), 3.17-3.16 (m, 2H), 2.93-2.85 (m, 2H), 2.39 (s, 2H). LCMS (ESI): m/z 290.1 [M$^+$+1]. HPLC: 97.78%. Chiral HPLC: 100%. Column: CHIRALPAK IC (250×4.6 mm, 5u). HPLC condition Mobile Phase: A) CO$_2$ B) 0.1% NH$_3$+Methanol Isocratic: 25% B, Diluent: Mobile Phase; Flow rate: 3 mL/min; Wavelength: 210-400 nm; Retention time: 5.01.

DL: $^1$H NMR (400 MHz, DMSO-$d_6$) δ 7.95 (s, 1H), 7.73 (s, 1H), 7.36-7.33 (m, 2H), 7.15-7.10 (m, 2H), 3.77 (d, J=13.2 Hz, 1H), 3.56 (d, J=13.6 Hz, 1H), 3.39 (d, J=6.4 Hz, 1H), 3.23 (d, J=6 Hz, 1H), 3.17-3.16 (m, 2H), 2.93-2.85 (m, 2H), 2.39 (s, 2H). LCMS (ESI): m/z 290.15 [M$^+$+1]. HPLC: 99.14%. Chiral HPLC: 100%. Column: CHIRALPAK IC (250×4.6 mm, 5u). HPLC condition Mobile Phase: A) CO$_2$ B) 0.1% NH$_3$+Methanol Isocratic: 25% B; Diluent:Mobile Phase; Flow rate: 3 mL/min; Wavelength: 210-400 nm; Retention time: 6.15.

DM: $^1$H NMR (400 MHz, DMSO-$d_6$) δ 7.93 (s, 1H), 7.78 (s, 1H), 7.35-7.32 (m, 2H), 7.15-7.10 (m, 2H), 3.77 (d, J=13.2 Hz, 1H), 3.62 (d, J=13.2 Hz, 1H), 3.26 (d, J=4.8 Hz, 2H), 3.21 (d, J=6 Hz, 1H), 3.08 (d, J=5.2 Hz, 1H), 2.89 (d, J=9.2 Hz, 1H), 2.76 (d, J=9.2 Hz, 1H), 2.43 (s, 2H). LCMS (ESI): m/z 290.1 [M$^+$+1]. HPLC: 98.87%. Chiral HPLC: 100%. Column: CHIRALPAK IC (250×4.6 mm, 5u). HPLC condition Mobile Phase: A) CO$_2$ B) 0.1% NH$_3$+Methanol Isocratic: 25% B, Diluent:Mobile Phase; Flow rate: 3 mL/min; Wavelength: 210-400 nm; Retention time: 7.60.

DN: $^1$H NMR (400 MHz, DMSO-$d_6$) δ 7.94 (s, 1H), 7.78 (s, 1H), 7.35-7.32 (m, 2H), 7.15-7.10 (m, 2H), 3.77 (d, J=13.6 Hz, 1H), 3.62 (d, J=14, Hz, 1H), 3.26 (d, J=4.8 Hz, 2H), 3.21 (d, J=6 Hz, 1H), 3.08 (d, J=5.2 Hz, 1H), 2.89 (d, J=9.2 Hz, 1H), 2.76 (d, J=9.2 Hz, 1H), 2.43 (s, 2H). LCMS (ESI): m/z 290.1 [M$^+$+1]. HPLC: 99.52%. Chiral HPLC: 100%. Column: CHIRALPAK IC (250×4.6 mm, 5u); HPLC condition Mobile Phase: A) CO$_2$ B) 0.1% NH$_3$+Methanol Isocratic: 25% B, Diluent:Mobile Phase; Flow rate: 3 mL/min; Wavelength: 210-400 nm; Retention time: 9.05.

Synthesis of DO, DP, DO & DR:

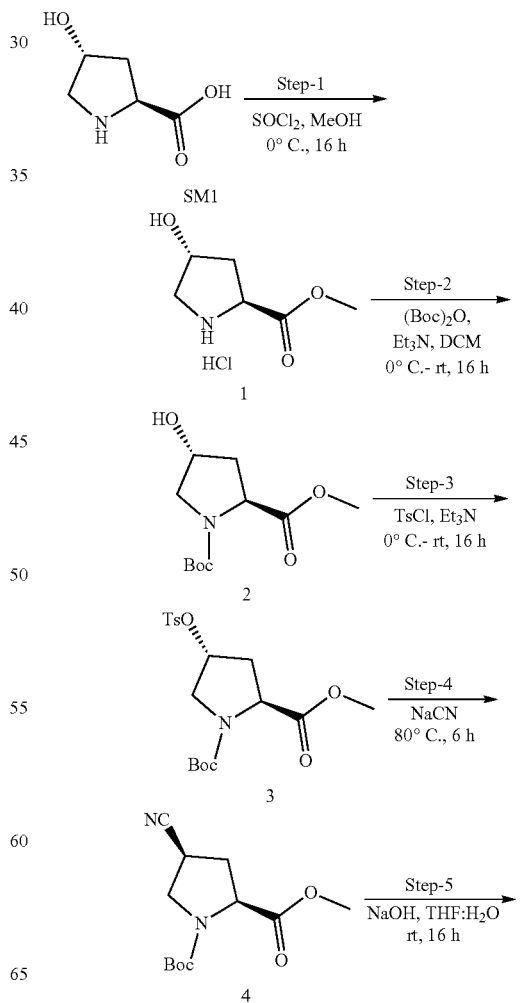

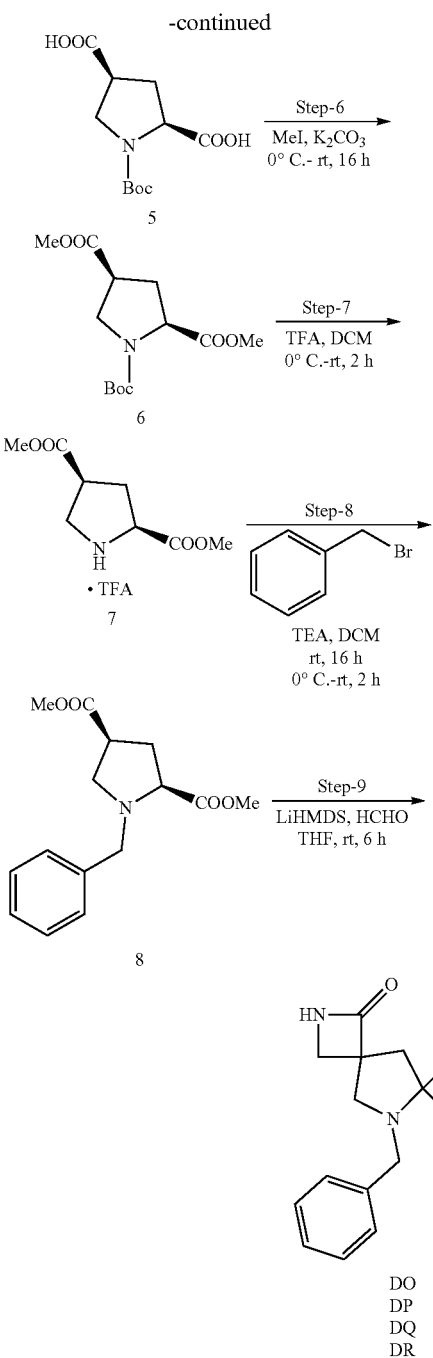

The experimental procedure for the synthesis of compound 1 to compound 7 is captured under the synthesis of DK, DL, DM & DN.

Synthesis of dimethyl (2S,4S)-1-benzylpyrrolidine-2,4-dicarboxylate (8)

To a stirring solution of compound 7 (40.0 g, 132.8 mmol) in DCM (200 mL), Et$_3$N (93.1 mL, 664.4 mmol) was added at 0° C. dropwise and stirred for 30 mins Benzyl bromide (22.8 mL, 199.3 mmol) was added at 0° C. and stirred at RT for 16 h. After consumption of the starting material (by TLC), the reaction mixture was diluted with water and extracted with DCM (3×300 mL). The combined organic layer was washed with brine (300 mL), dried over Na$_2$SO$_4$ and concentrated under reduced pressure. The residue was purified by column chromatography using 15% EtOAc/hexane to afford compound 8 (22.0 g, 60%) as off white solid.

LCMS (ESI): m/z 278.30 [M$^+$+1]

Synthesis of 10-benzyl-2,8,10-triazadispiro [3.1.3$^6$.2$^4$]undecane-1,7-dione (DO, DP, DQ and DR)

To a stirred solution of compound 8 (22.0 g, 79.4 mmol) in THF (250 mL), LiHMDS (1M solution in THF, 397.1 mL, 397.1 mmol) was added at −78° C. and stirred for 30 min paraformaldehyde (5.96 g, 198.8 mmol) was added to the reaction mixture at −78° C. and stirred at room temperature for 6 h. After consumption of the starting material (by TLC), the reaction mixture was quenched with saturated NH$_4$Cl solution (300 mL) and extracted with EtOAc (3×300 mL). The combined organic layer was washed with brine (200 mL), dried over Na$_2$SO$_4$ and concentrated under reduced pressure. The residue was purified by column chromatography to afford mixture of diastereomers (2.4 g). The mixture of diastereomers was purified by SFC followed by chiral HPLC to afford DO (90 mg), DP (120 mg), DQ (42 mg), and DR (44 mg) as an off white solids.

DO: $^1$H NMR (400 MHz, DMSO-d$_6$) δ 7.95 (s, 1H), 7.72 (s, 1H), 7.32-7.22 (m, 5H), 3.79 (d, J=13.2 Hz, 1H), 3.58 (d, J=13.2 Hz, 1H), 3.39 (d, J=6 Hz, 1H), 3.23 (d, J=5.2 Hz, 1H), 3.18-3.16 (m, 2H), 2.93-2.87 (m, 2H), 2.40 (s, 2H). LCMS (ESI): m/z 272.1 [M$^+$+1]. HPLC: 98.13%. Chiral HPLC: 98.95%. Column: CHIRALPAK IC (250×4.6 mm, 5u); HPLC condition Mobile Phase: A) CO$_2$ B) Methanol, Isocratic: 30% B; Diluent:Mobile Phase; Flow rate: 3 mL/min; Wavelength: 210-400 nm; Retention time: 4.72.

DP: $^1$H NMR (400 MHz, DMSO-d$_6$) δ 7.95 (s, 1H), 7.72 (s, 1H), 7.33-7.22 (m, 5H), 3.79 (d, J=13.2 Hz, 1H), 3.58 (d, J=13.2 Hz, 1H), 3.39 (d, J=6.4 Hz, 1H), 3.23 (d, J=6 Hz, 1H), 3.18-3.16 (m, 2H), 2.93-2.87 (m, 2H), 2.40 (s, 2H). LCMS (ESI): m/z 272.15 [M$^+$+1]. HPLC: 99.12%. Chiral HPLC: 97.82%. Column: CHIRALPAK IC (250×4.6 mm, 5u). HPLC condition Mobile Phase: A) CO$_2$ B) Methanol, Isocratic: 30% B; Diluent:Mobile Phase; Flow rate: 3 mL/min; Wavelength: 210-400 nm; Retention time: 6.49.

DQ: $^1$H NMR (400 MHz, DMSO-d$_6$) δ 7.94 (s, 1H), 7.78 (s, 1H), 7.34-7.24 (m, 5H), 3.78 (d, J=13.2 Hz, 1H), 3.63 (d, J=13.2 Hz, 1H), 3.29-3.22 (m, 3H), 3.07 (d, J=5.6 Hz, 1H), 2.90 (d, J=9.2 Hz, 1H), 2.76 (d, J=9.6 Hz, 1H), 2.44 (s, 2H). LCMS (ESI): m/z 272.0 [M$^+$+1]. HPLC: 99.06%. Chiral HPLC: 100%. Column: CHIRALPAK IC (250×4.6 mm, 5u); HPLC condition Mobile Phase: A) CO$_2$ B) Ethanol, Isocratic: 30% B; Diluent:Mobile Phase; Flow rate: 3 mL/min; Wavelength: 210-400 nm; Retention time: 9.0.

DR: $^1$H NMR (400 MHz, DMSO-d$_6$) δ 7.94 (s, 1H), 7.78 (s, 1H), 7.30-7.24 (m, 5H), 3.78 (d, J=13.6 Hz, 1H), 3.63 (d, J=13.2 Hz, 1H), 3.26-3.22 (m, 3H), 3.07 (d, J=5.2 Hz, 1H), 2.90 (d, J=9.2 Hz, 1H), 2.76 (d, J=8.8 Hz, 1H), 2.44 (s, 2H). LCMS (ESI): m/z 272.0 [M$^+$+1]. HPLC: 99.84%. Chiral HPLC: 100%. Column: CHIRALPAK IC (250×4.6 mm, 5u); HPLC condition Mobile Phase Mobile Phase: A) CO$_2$ B) Ethanol, Isocratic: 30% B, Diluent: Mobile Phase; Flow rate: 3 mL/min; Wavelength: 210-400 nm; Retention time: 9.87.

Following the above procedures, the following compounds and stereoisomers thereof were or are prepared:

| Compound | Structure |
|---|---|
| UA | 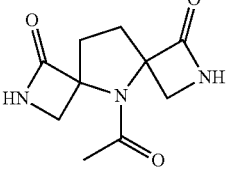 |
| UB | 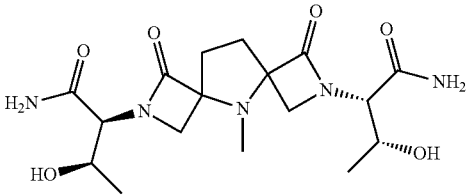 [SMILES: C[C@@H](O)[C@@H](C(N)=O)N1CC2(CCC3(CN([C@H](C(N)=O)[C@@H](C)O)C3=O)N2C)C1=O] |
| UC | 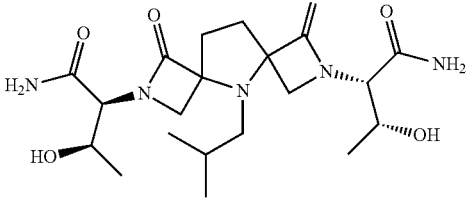 |
| UD | 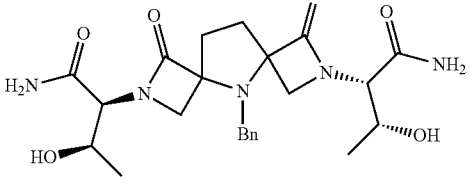 |
| UE | 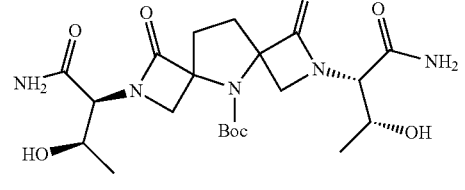 |
| UF | 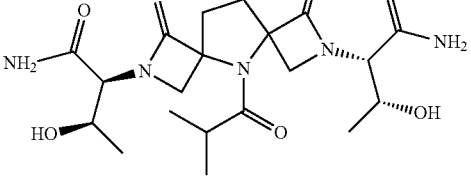 |
| UG | 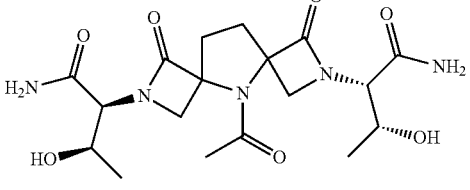 |

-continued

| Compound | Structure |
|---|---|
| UH | (spiro bis-azetidinone pyrrolidine, N-methyl) |
| UI | (spiro bis-azetidinone pyrrolidine, N-isobutyl) |
| UJ | (spiro bis-azetidinone pyrrolidine, N-Bn) |
| UK | (spiro bis-azetidinone pyrrolidine, N-Boc) |
| UL | (spiro bis-azetidinone pyrrolidine, N-isobutyryl) |
| UM | (spiro bis-azetidinone pyrrolidine, N-acetyl) |

-continued
| Compound | Structure |
|---|---|
| UN | 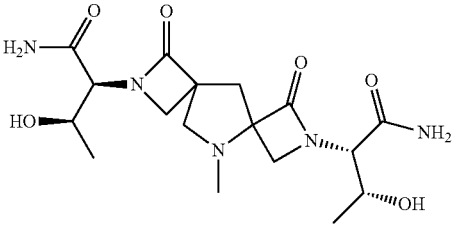 [SMILES: C[C@@H](O)[C@@H](C(N)=O)N1CC2(CN(C)C3(CN([C@H](C(N)=O)[C@@H](C)O)C3=O)C2)C1=O] |
| UO | 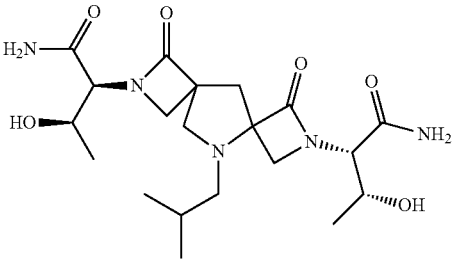 [SMILES: CC(C)CN1CC2(CN([C@H](C(N)=O)[C@@H](C)O)C2=O)CC12CN([C@H](C(N)=O)[C@@H](C)O)C2=O] |
| UP | 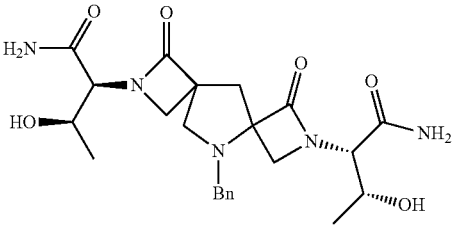 [SMILES: C[C@@H](O)[C@@H](C(N)=O)N1CC2(CN(Cc3ccccc3)C3(CN([C@H](C(N)=O)[C@@H](C)O)C3=O)C2)C1=O] |
| UQ | 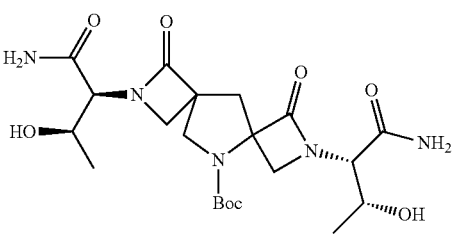 |
| UR | 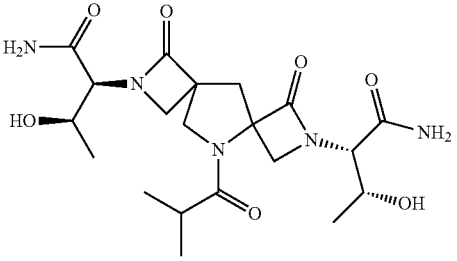 [SMILES: CC(C)C(=O)N1CC2(CN([C@H](C(N)=O)[C@@H](C)O)C2=O)CC12CN([C@H](C(N)=O)[C@@H](C)O)C2=O] |
| US | 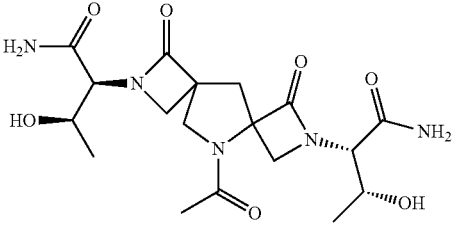 [SMILES: CC(=O)N1CC2(CN([C@H](C(N)=O)[C@@H](C)O)C2=O)CC12CN([C@H](C(N)=O)[C@@H](C)O)C2=O] |

-continued

| Compound | Structure |
|---|---|
| UT | *(structure)* |
| UV | *(structure)* |
| UW | *(structure)* |
| AD | *(structure)* |
| AE | *(structure)* |
| AF | *(structure)* |
| AT | *(structure)* |

-continued

| Compound | Structure |
|---|---|
| AU | 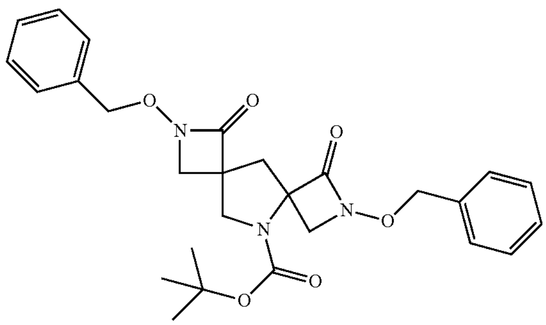 [SMILES: CC(C)(C)OC(=O)N1CC2(CN(OCc3ccccc3)C2=O)CC12CN(OCc1ccccc1)C2=O] |
| AV | 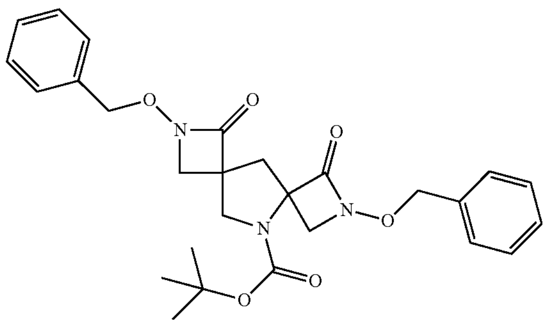 [SMILES: CC(C)(C)OC(=O)N1CC2(CN(OCc3ccccc3)C2=O)CC12CN(OCc1ccccc1)C2=O] |
| AW | 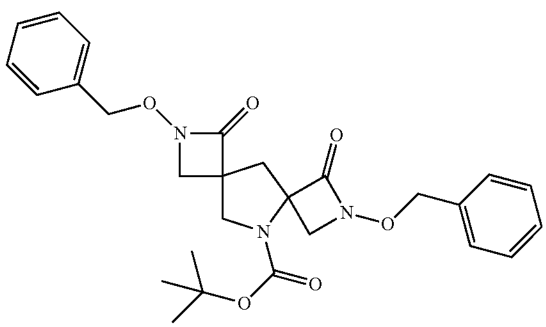 [SMILES: CC(C)(C)OC(=O)N1CC2(CN(OCc3ccccc3)C2=O)CC12CN(OCc1ccccc1)C2=O] |
| AX | 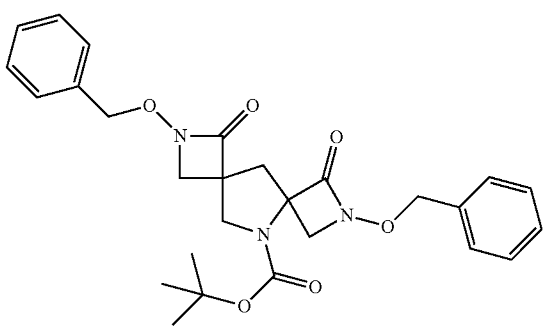 [SMILES: CC(C)(C)OC(=O)N1CC2(CN(OCc3ccccc3)C2=O)CC12CN(OCc1ccccc1)C2=O] |
| AM | 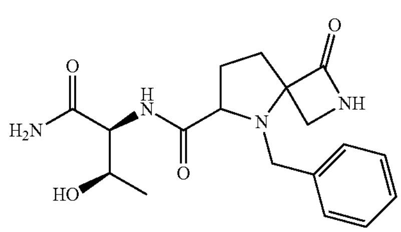 [SMILES: C[C@@H](O)[C@H](NC(=O)C1CCC2(CNC2=O)N1Cc1ccccc1)C(N)=O] |

-continued

| Compound | Structure |
|---|---|
| AN | 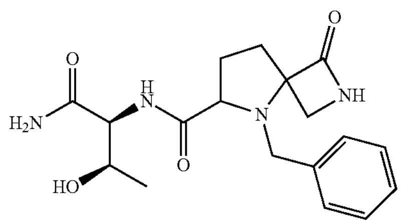 [SMILES: C[C@@H](O)[C@H](NC(=O)C1CCC2(CNC2=O)N1Cc1ccccc1)C(N)=O] |
| AG | 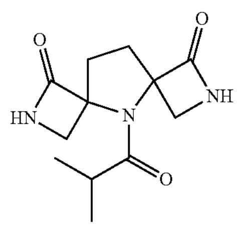 [SMILES: CC(C)C(=O)N1C2(CCC13CNC3=O)CNC2=O] |
| AH | 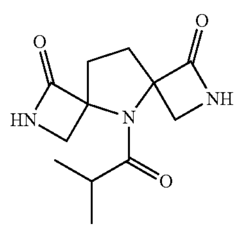 [SMILES: CC(C)C(=O)N1C2(CCC13CNC3=O)CNC2=O] |
| AI | 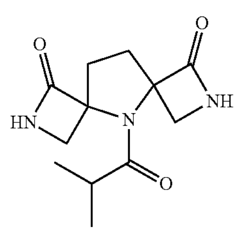 [SMILES: CC(C)C(=O)N1C2(CCC13CNC3=O)CNC2=O] |
| AJ | 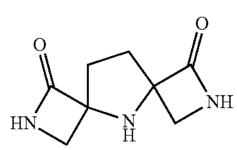 [SMILES: O=C1NCC12CCC1(CNC1=O)N2] |
| AK | 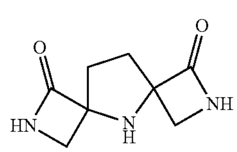 [SMILES: O=C1NCC12CCC1(CNC1=O)N2] |
| BE | 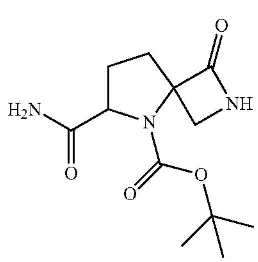 [SMILES: CC(C)(C)OC(=O)N1C(C(N)=O)CCC12CNC2=O] |

-continued

| Compound | Structure |
|---|---|
| BF | 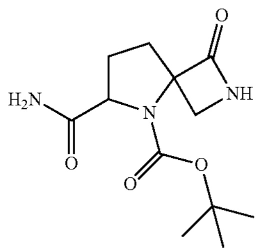 [SMILES: CC(C)(C)OC(=O)N1C(C(N)=O)CCC12CNC2=O] |
| BG | 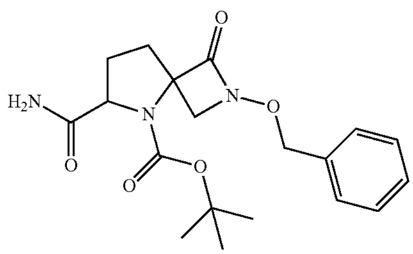 [SMILES: CC(C)(C)OC(=O)N1C(C(N)=O)CCC12CN(OCc1ccccc1)C2=O] |
| BH | 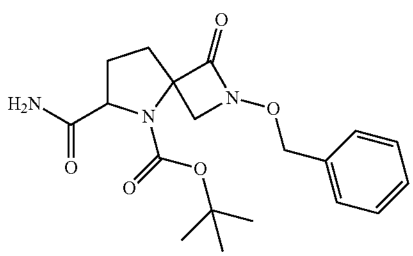 [SMILES: CC(C)(C)OC(=O)N1C(C(N)=O)CCC12CN(OCc1ccccc1)C2=O] |
| AR | 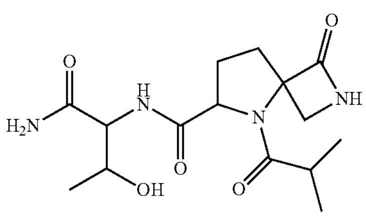 [SMILES: CC(C)C(=O)N1C(C(=O)NC(C(N)=O)C(C)O)CCC12CNC2=O] |
| AS | 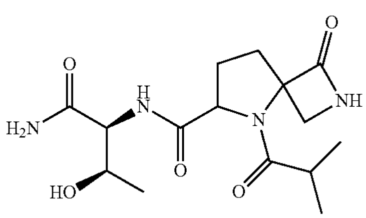 [SMILES: CC(C)C(=O)N1C(C(=O)N[C@H](C(N)=O)[C@@H](C)O)CCC12CNC2=O] |
| AO | 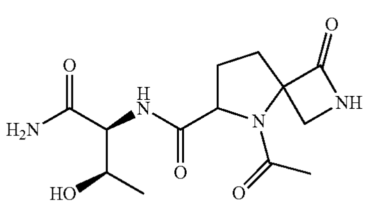 [SMILES: CC(=O)N1C(C(=O)N[C@H](C(N)=O)[C@@H](C)O)CCC12CNC2=O] |
| AP | 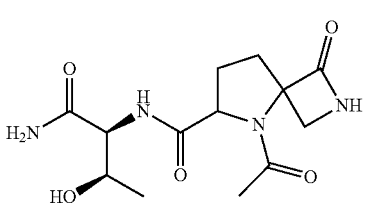 [SMILES: CC(=O)N1C(C(=O)N[C@H](C(N)=O)[C@@H](C)O)CCC12CNC2=O] |

-continued
| Compound | Structure |
|---|---|
| CI | 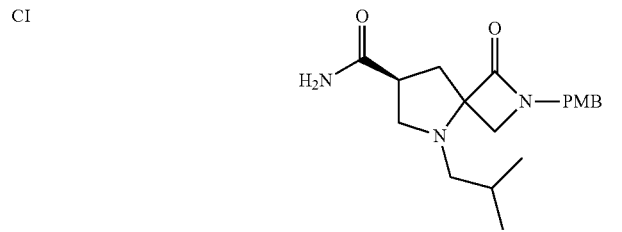 |
| CJ | 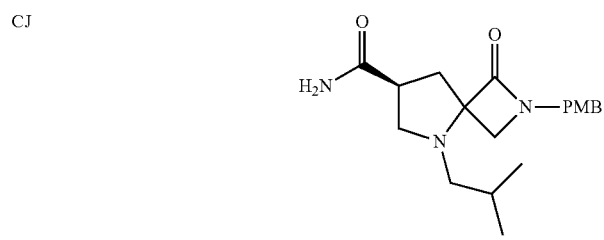 |
| CA | 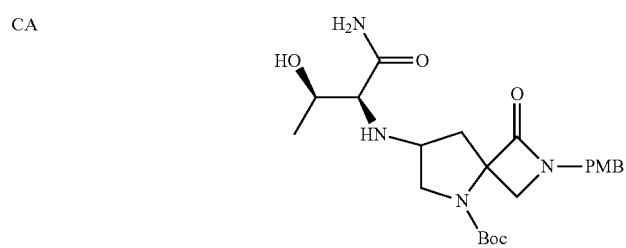 |
| CB | 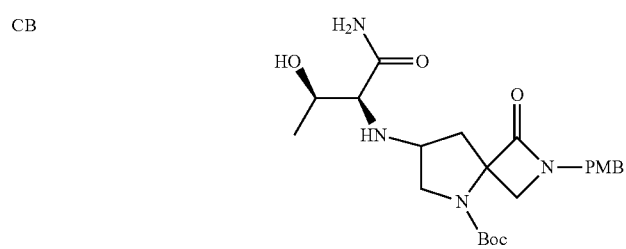 |
| CC | 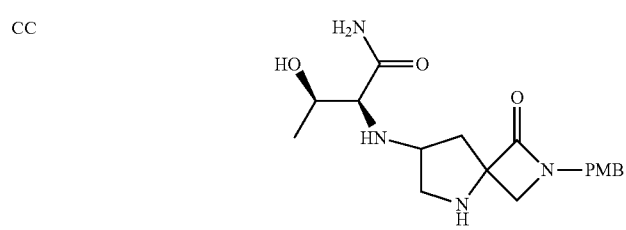 |
| CD | 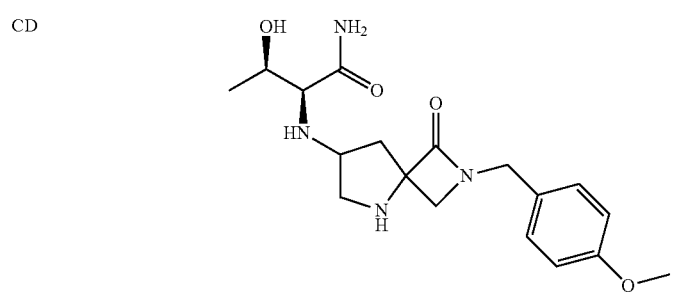 |

-continued

| Compound | Structure |
|---|---|
| CE | (structure) |
| CF | (structure) |
| BI | (structure) |
| BJ | (structure) |
| BK | (structure) |
| BL | (structure) |
| BQ | (structure) |

-continued
| Compound | Structure |
|---|---|
| BR | 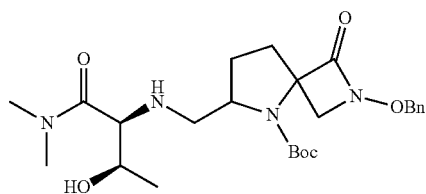 [SMILES: C[C@@H](O)[C@H](NCC1CCC2(CN(OCc3ccccc3)C2=O)N1C(=O)OC(C)(C)C)C(=O)N(C)C] |
| BS | 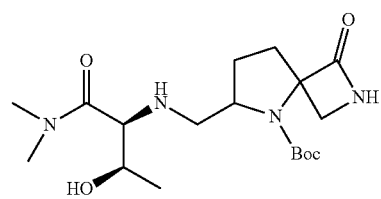 [SMILES: C[C@@H](O)[C@H](NCC1CCC2(CNC2=O)N1C(=O)OC(C)(C)C)C(=O)N(C)C] |
| BT | 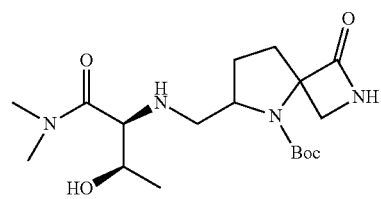 [SMILES: C[C@@H](O)[C@H](NCC1CCC2(CNC2=O)N1C(=O)OC(C)(C)C)C(=O)N(C)C] |
| BM | 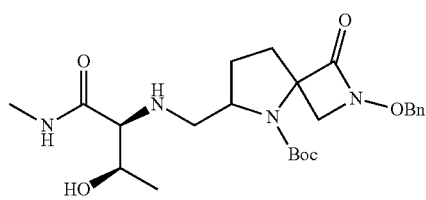 [SMILES: CNC(=O)[C@@H](NCC1CCC2(CN(OCc3ccccc3)C2=O)N1C(=O)OC(C)(C)C)[C@@H](C)O] |
| BN | 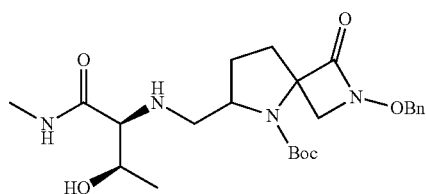 [SMILES: CNC(=O)[C@@H](NCC1CCC2(CN(OCc3ccccc3)C2=O)N1C(=O)OC(C)(C)C)[C@@H](C)O] |
| BO | 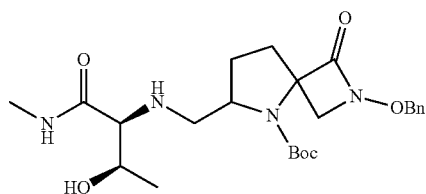 [SMILES: CNC(=O)[C@@H](NCC1CCC2(CN(OCc3ccccc3)C2=O)N1C(=O)OC(C)(C)C)[C@@H](C)O] |
| BP | 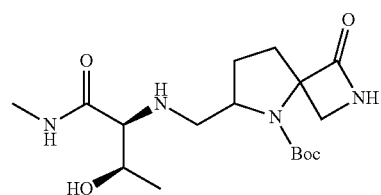 [SMILES: CNC(=O)[C@@H](NCC1CCC2(CNC2=O)N1C(=O)OC(C)(C)C)[C@@H](C)O] |

-continued
| Compound | Structure |
|---|---|
| BU | 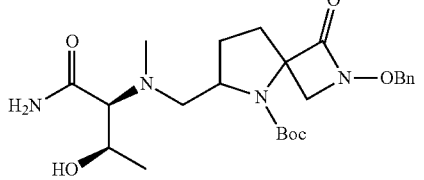 |
| BV | 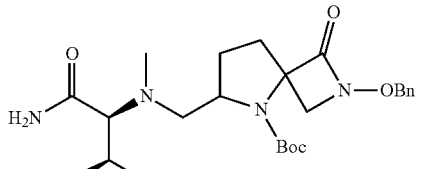 |
| BW | 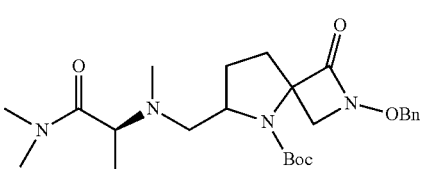 |
| BX | 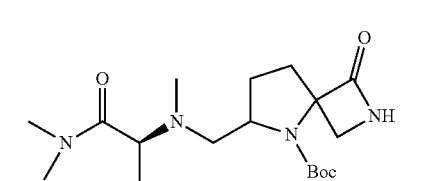 |
| BX-2 | 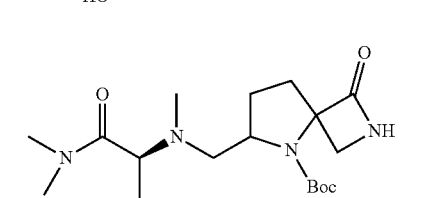 |
| AA-1 | 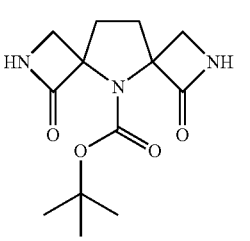 [SMILES: CC(C)(C)OC(=O)N1C2(CCC13CNC3=O)CNC2=O] |
| AA-2 | 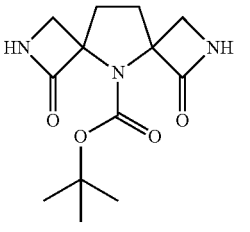 [SMILES: CC(C)(C)OC(=O)N1C2(CCC13CNC3=O)CNC2=O] |

-continued
| Compound | Structure |
|---|---|
| AA-3 | 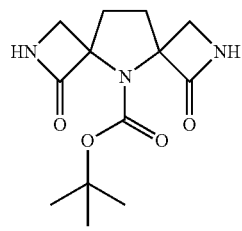 [SMILES: CC(C)(C)OC(=O)N1C2(CCC13CNC3=O)CNC2=O] |
| AB-1 | 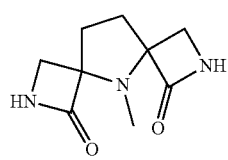 |
| AB-2 | 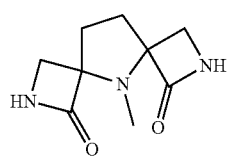 |
| AB-3 | 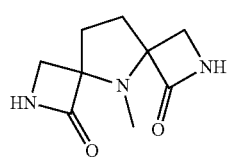 |
| AC-1 | 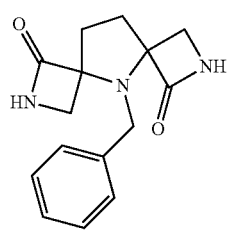 [SMILES: O=C1NCC12CCC1(CNC1=O)N2Cc1ccccc1] |
| AC-2 | 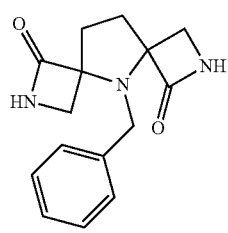 [SMILES: O=C1NCC12CCC1(CNC1=O)N2Cc1ccccc1] |
| AC-3 | 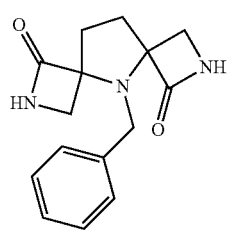 [SMILES: O=C1NCC12CCC1(CNC1=O)N2Cc1ccccc1] |

-continued
| Compound | Structure |
|---|---|
| AL-1 | 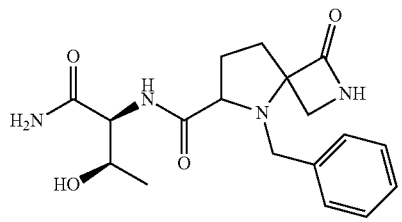 [SMILES: C[C@@H](O)[C@H](NC(=O)C1CCC2(CNC2=O)N1Cc1ccccc1)C(N)=O] |
| AL-2 | 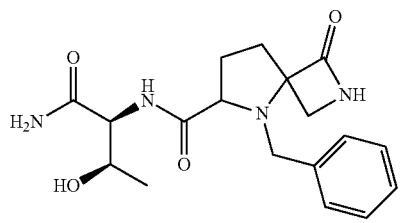 [SMILES: C[C@@H](O)[C@H](NC(=O)C1CCC2(CNC2=O)N1Cc1ccccc1)C(N)=O] |
| AQ-1 | 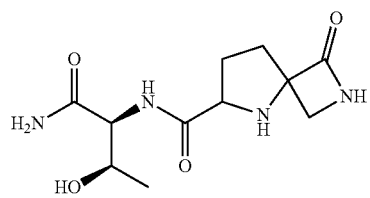 [SMILES: C[C@@H](O)[C@H](NC(=O)C1CCC2(CNC2=O)N1)C(N)=O] |
| AQ-2 | 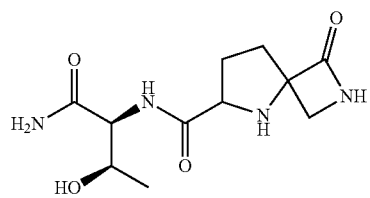 [SMILES: C[C@@H](O)[C@H](NC(=O)C1CCC2(CNC2=O)N1)C(N)=O] |
| DS | 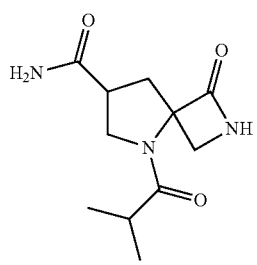 [SMILES: CC(C)C(=O)N1CC(C(N)=O)CC12CNC2=O] |
| AZ-1 | 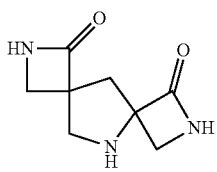 |
| AZ-2 | 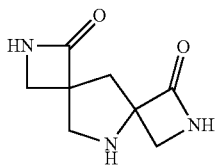 |

-continued

| Compound | Structure |
|---|---|
| AZ-3 | 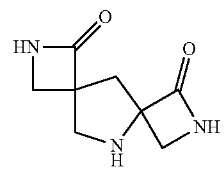 [SMILES: O=C1NCC12CNC1(CNC1=O)C2] |
| AZ-4 | 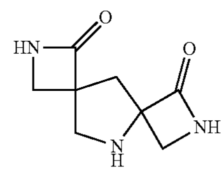 [SMILES: O=C1NCC12CNC1(CNC1=O)C2] |
| DT | 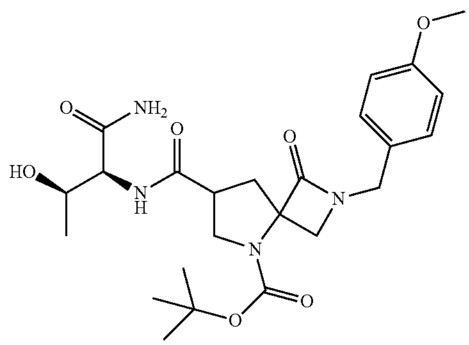 [SMILES: COc1ccc(CN2CC3(CC(C(=O)N[C@H](C(N)=O)[C@@H](C)O)CN3C(=O)OC(C)(C)C)C2=O)cc1] |
| DU | 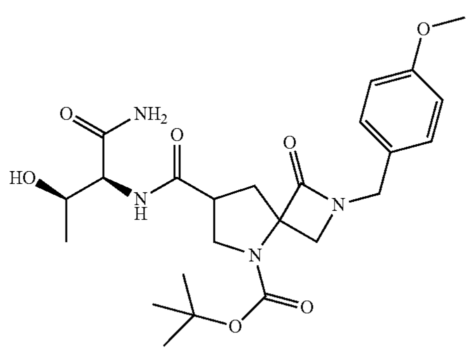 [SMILES: COc1ccc(CN2CC3(CC(C(=O)N[C@H](C(N)=O)[C@@H](C)O)CN3C(=O)OC(C)(C)C)C2=O)cc1] |
| DV | 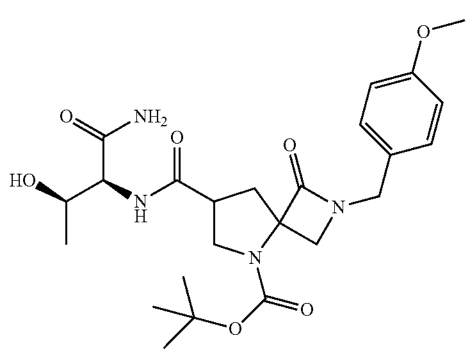 [SMILES: COc1ccc(CN2CC3(CC(C(=O)N[C@H](C(N)=O)[C@@H](C)O)CN3C(=O)OC(C)(C)C)C2=O)cc1] |

-continued
| Compound | Structure |
|---|---|
| DW | 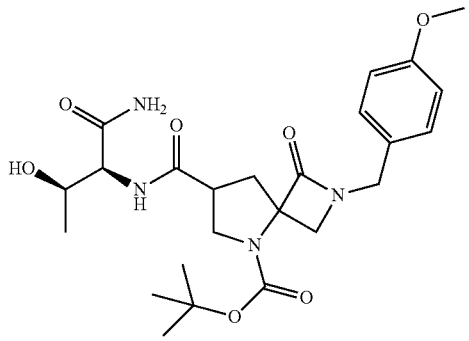 [SMILES: COc1ccc(CN2CC3(CC(C(=O)N[C@H](C(N)=O)[C@@H](C)O)CN3C(=O)OC(C)(C)C)C2=O)cc1] |
| DX | 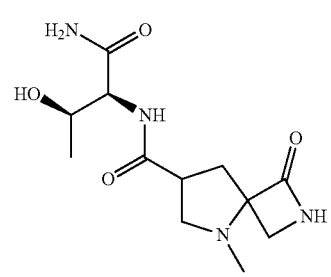 [SMILES: C[C@@H](O)[C@H](NC(=O)C1CN(C)C2(CNC2=O)C1)C(N)=O] |
| DY | 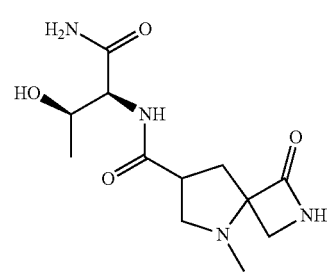 |
| DZ | 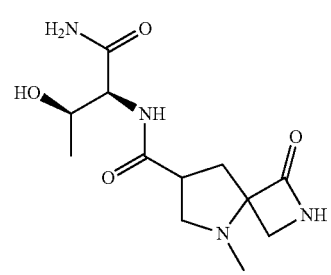 |
| EA | 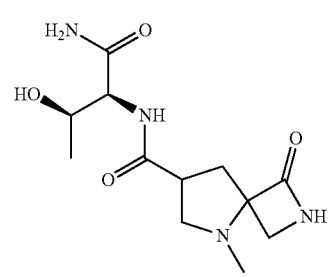 |

-continued

| Compound | Structure |
|---|---|
| EB | (chemical structure: threoninamide-NH-C(O)-[pyrrolidine-azetidinone spirocycle, N-isobutyl]) |
| EC | (chemical structure: threoninamide-NH-C(O)-[pyrrolidine-azetidinone spirocycle, N-isobutyl]) |
| ED | (chemical structure: threoninamide-NH-C(O)-[pyrrolidine-azetidinone spirocycle, N-isobutyl]) |
| EE | (chemical structure: threoninamide-NH-C(O)-[pyrrolidine-azetidinone spirocycle, N-isobutyl]) |
| EF | (chemical structure: threoninamide-NH-C(O)-[pyrrolidine-azetidinone spirocycle, N-Bn]) |

-continued

| Compound | Structure |
|---|---|
| EG | (structure) |
| EH | (structure) |
| EI | (structure) |
| EJ | (structure) |
| EK | (structure) |

-continued
| Compound | Structure |
|---|---|
| EL | 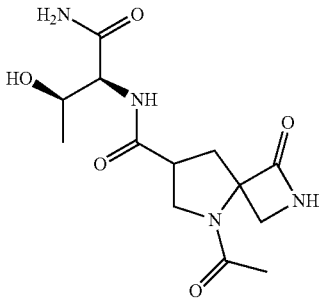 [SMILES: CC(=O)N1CC(C(=O)N[C@H](C(N)=O)[C@@H](C)O)CC12CNC2=O] |
| EM | 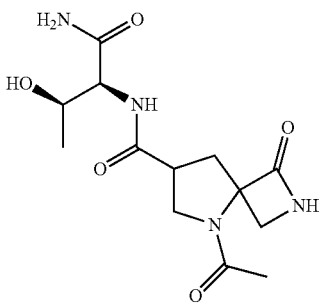 [SMILES: CC(=O)N1CC(C(=O)N[C@H](C(N)=O)[C@@H](C)O)CC12CNC2=O] |
| EN | 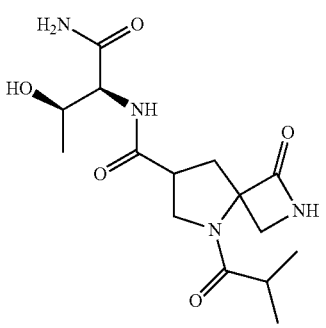 [SMILES: CC(C)C(=O)N1CC(C(=O)N[C@H](C(N)=O)[C@@H](C)O)CC12CNC2=O] |
| EO | 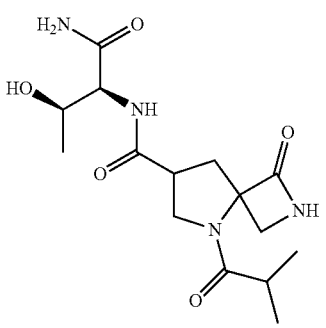 [SMILES: CC(C)C(=O)N1CC(C(=O)N[C@H](C(N)=O)[C@@H](C)O)CC12CNC2=O] |
| EP | 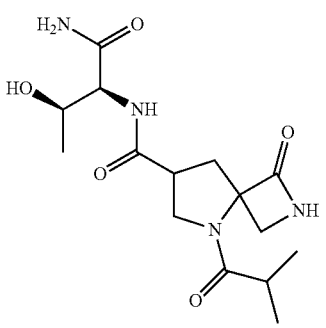 [SMILES: CC(C)C(=O)N1CC(C(=O)N[C@H](C(N)=O)[C@@H](C)O)CC12CNC2=O] |

-continued
| Compound | Structure |
|---|---|
| EQ | 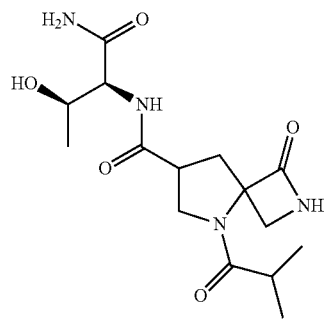 [SMILES: CC(C)C(=O)N1CC(C(=O)N[C@H](C(N)=O)[C@@H](C)O)CC12CNC2=O] |
| ER | 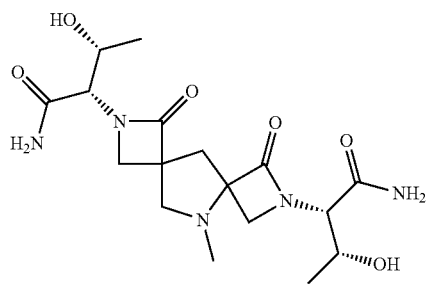 [SMILES: C[C@@H](O)[C@@H](C(N)=O)N1CC2(CN(C)C3(CN([C@H](C(N)=O)[C@@H](C)O)C3=O)C2)C1=O] |
| ES | 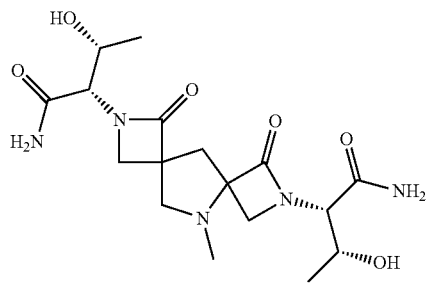 [SMILES: C[C@@H](O)[C@@H](C(N)=O)N1CC2(CN(C)C3(CN([C@H](C(N)=O)[C@@H](C)O)C3=O)C2)C1=O] |
| ET | 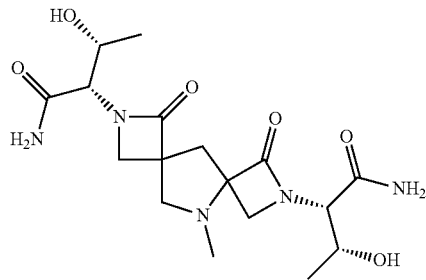 [SMILES: C[C@@H](O)[C@@H](C(N)=O)N1CC2(CN(C)C3(CN([C@H](C(N)=O)[C@@H](C)O)C3=O)C2)C1=O] |
| EU | 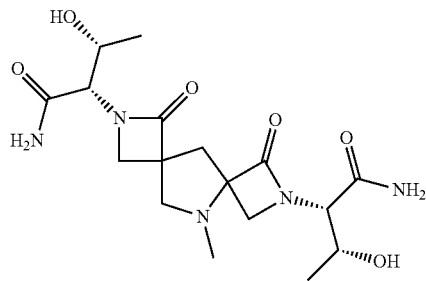 [SMILES: C[C@@H](O)[C@@H](C(N)=O)N1CC2(CN(C)C3(CN([C@H](C(N)=O)[C@@H](C)O)C3=O)C2)C1=O] |

-continued
| Compound | Structure |
|---|---|
| EV | 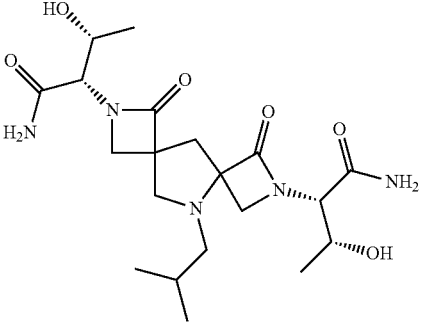 |
| EW | 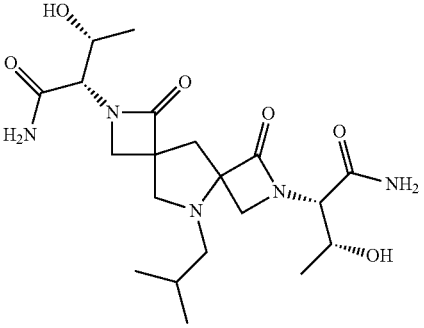 [SMILES: CC(C)CN1CC2(CN([C@H](C(N)=O)[C@@H](C)O)C2=O)CC12CN([C@H](C(N)=O)[C@@H](C)O)C2=O] |
| EX | 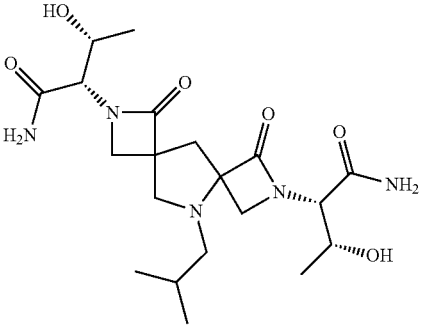 [SMILES: CC(C)CN1CC2(CN([C@H](C(N)=O)[C@@H](C)O)C2=O)CC12CN([C@H](C(N)=O)[C@@H](C)O)C2=O] |
| EY | 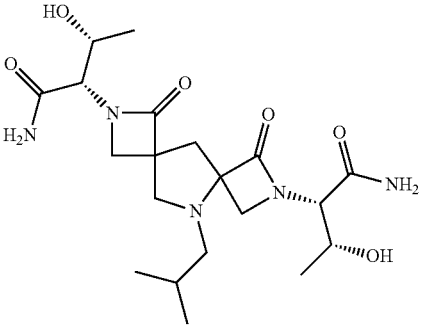 [SMILES: CC(C)CN1CC2(CN([C@H](C(N)=O)[C@@H](C)O)C2=O)CC12CN([C@H](C(N)=O)[C@@H](C)O)C2=O] |

-continued
| Compound | Structure |
|---|---|
| EZ | 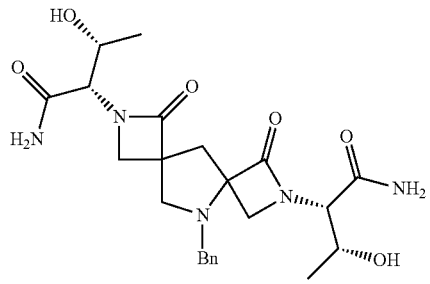 [SMILES: C[C@@H](O)[C@@H](C(N)=O)N1CC2(CN(Cc3ccccc3)C3(CN([C@H](C(N)=O)[C@@H](C)O)C3=O)C2)C1=O] |
| FA | 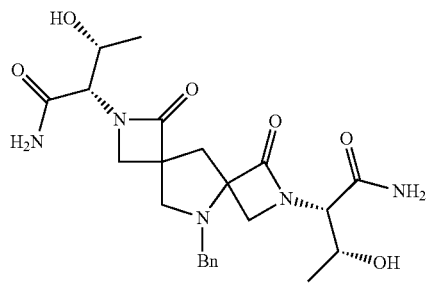 [SMILES: C[C@@H](O)[C@@H](C(N)=O)N1CC2(CN(Cc3ccccc3)C3(CN([C@H](C(N)=O)[C@@H](C)O)C3=O)C2)C1=O] |
| FB | 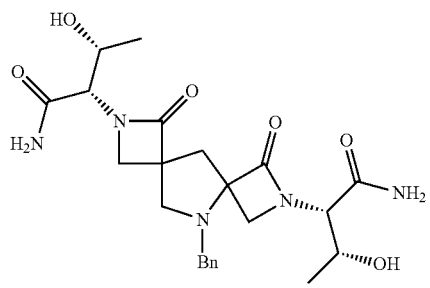 [SMILES: C[C@@H](O)[C@@H](C(N)=O)N1CC2(CN(Cc3ccccc3)C3(CN([C@H](C(N)=O)[C@@H](C)O)C3=O)C2)C1=O] |
| FC | 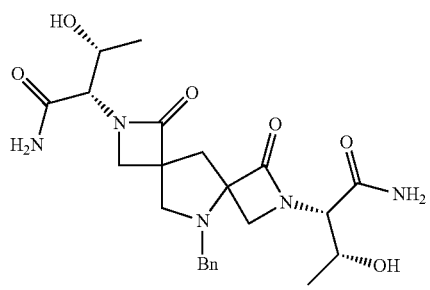 [SMILES: C[C@@H](O)[C@@H](C(N)=O)N1CC2(CN(Cc3ccccc3)C3(CN([C@H](C(N)=O)[C@@H](C)O)C3=O)C2)C1=O] |
| FD | 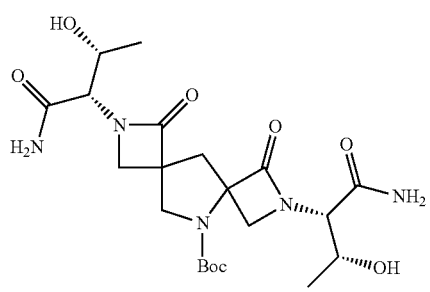 [SMILES: C[C@@H](O)[C@@H](C(N)=O)N1CC2(CN(C(=O)OC(C)(C)C)C3(CN([C@H](C(N)=O)[C@@H](C)O)C3=O)C2)C1=O] |

-continued
| Compound | Structure |
|---|---|
| FE | 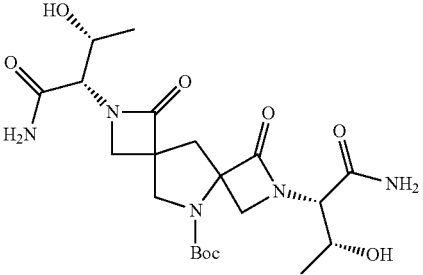 [SMILES: C[C@@H](O)[C@@H](C(N)=O)N1CC2(CN(C(=O)OC(C)(C)C)C3(CN([C@H](C(N)=O)[C@@H](C)O)C3=O)C2)C1=O] |
| FF | 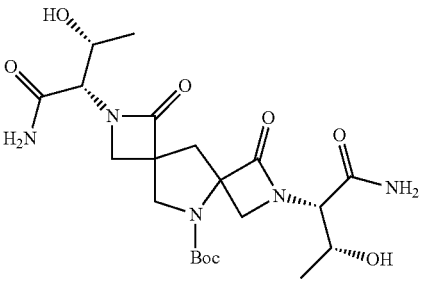 [SMILES: C[C@@H](O)[C@@H](C(N)=O)N1CC2(CN(C(=O)OC(C)(C)C)C3(CN([C@H](C(N)=O)[C@@H](C)O)C3=O)C2)C1=O] |
| FG | 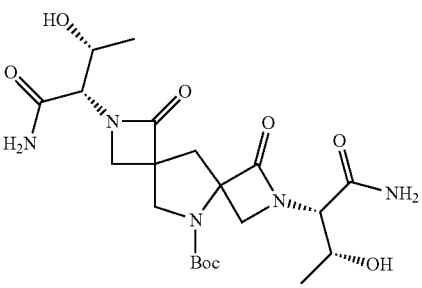 [SMILES: C[C@@H](O)[C@@H](C(N)=O)N1CC2(CN(C(=O)OC(C)(C)C)C3(CN([C@H](C(N)=O)[C@@H](C)O)C3=O)C2)C1=O] |
| FH | 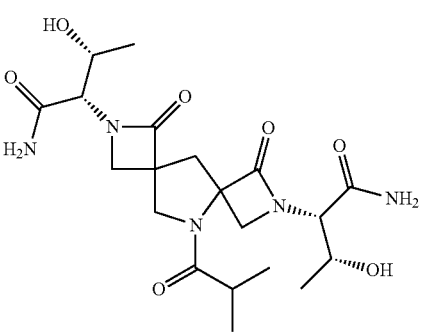 [SMILES: CC(C)C(=O)N1CC2(CN([C@H](C(N)=O)[C@@H](C)O)C2=O)CC12CN([C@H](C(N)=O)[C@@H](C)O)C2=O] |
| FI | 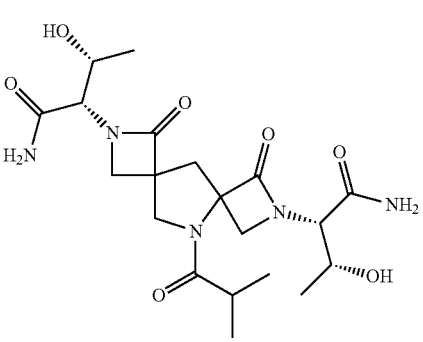 |

| Compound | Structure |
|---|---|
| FJ | 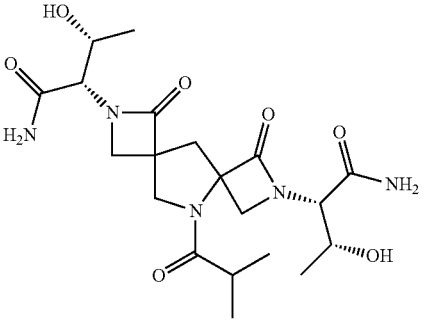 [SMILES: CC(C)C(=O)N1CC2(CN([C@H](C(N)=O)[C@@H](C)O)C2=O)CC12CN([C@H](C(N)=O)[C@@H](C)O)C2=O] |
| FK | 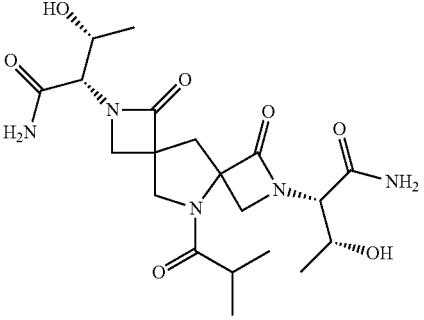 [SMILES: CC(C)C(=O)N1CC2(CN([C@H](C(N)=O)[C@@H](C)O)C2=O)CC12CN([C@H](C(N)=O)[C@@H](C)O)C2=O] |
| FL | 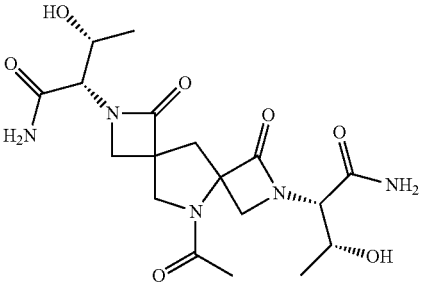 [SMILES: CC(=O)N1CC2(CN([C@H](C(N)=O)[C@@H](C)O)C2=O)CC12CN([C@H](C(N)=O)[C@@H](C)O)C2=O] |
| FM | 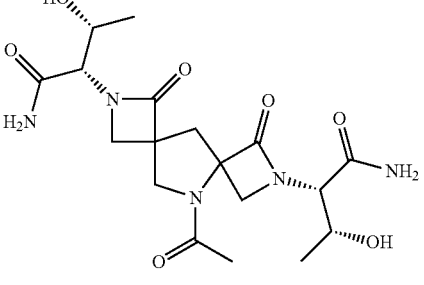 |
| FN | 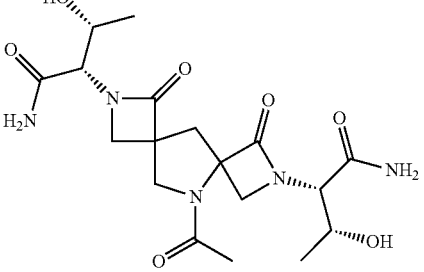 |

-continued
| Compound | Structure |
|---|---|
| FO | 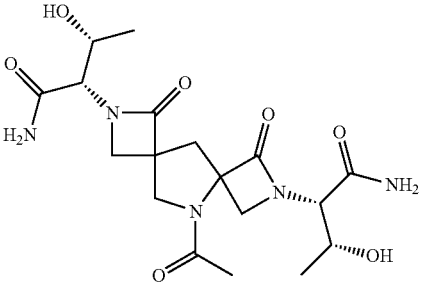 [SMILES: CC(=O)N1CC2(CN([C@H](C(N)=O)[C@@H](C)O)C2=O)CC12CN([C@H](C(N)=O)[C@@H](C)O)C2=O] |
| FP | 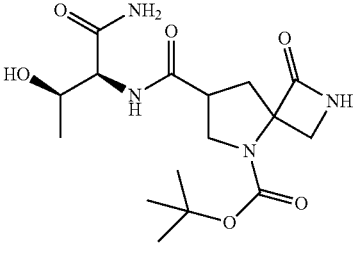 [SMILES: C[C@@H](O)[C@H](NC(=O)C1CN(C(=O)OC(C)(C)C)C2(CNC2=O)C1)C(N)=O] |
| FQ | 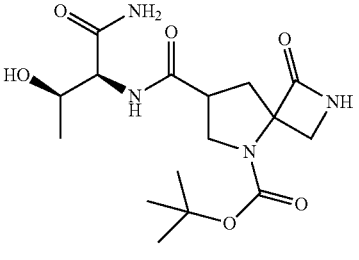 [SMILES: C[C@@H](O)[C@H](NC(=O)C1CN(C(=O)OC(C)(C)C)C2(CNC2=O)C1)C(N)=O] |
| FR | 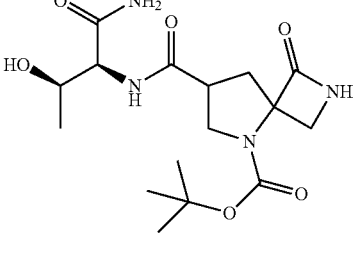 |
| FS | 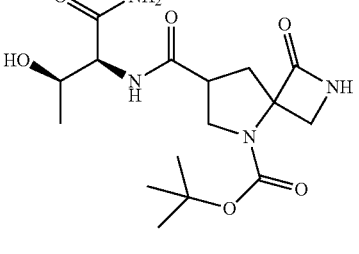 |
| CG | 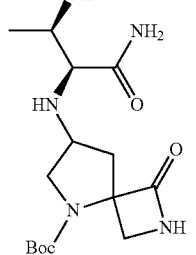 |

-continued
| Compound | Structure |
|---|---|
| CH | 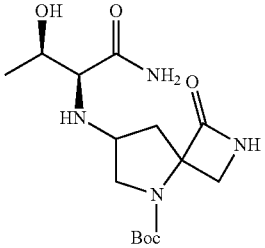 [SMILES: C[C@@H](O)[C@H](NC1CN(C(=O)OC(C)(C)C)C2(CNC2=O)C1)C(N)=O] |
| FT | 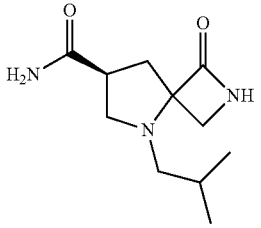 [SMILES: CC(C)CN1C[C@@H](C(N)=O)CC12CNC2=O] |
| FU | 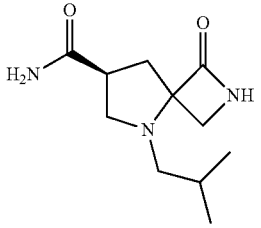 [SMILES: CC(C)CN1C[C@@H](C(N)=O)CC12CNC2=O] |
| FV | 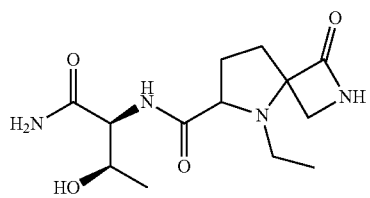 [SMILES: CCN1C(C(=O)N[C@H](C(N)=O)[C@@H](C)O)CCC12CNC2=O] |
| FW | 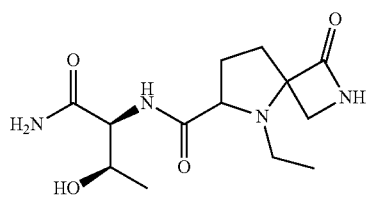 [SMILES: CCN1C(C(=O)N[C@H](C(N)=O)[C@@H](C)O)CCC12CNC2=O] |
| FX | 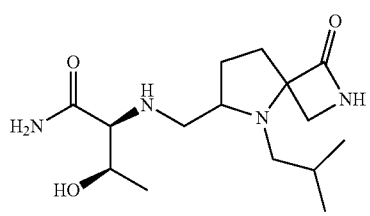 [SMILES: CC(C)CN1C(CN[C@H](C(N)=O)[C@@H](C)O)CCC12CNC2=O] |
| FY | 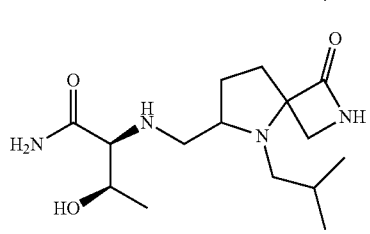 |

-continued
| Compound | Structure |
|---|---|
| FZ | 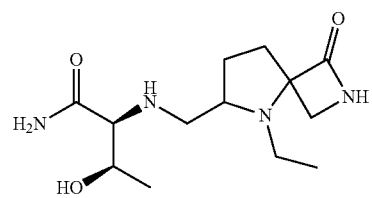 [SMILES: CCN1C(CN[C@H](C(N)=O)[C@@H](C)O)CCC12CNC2=O] |
| GA | 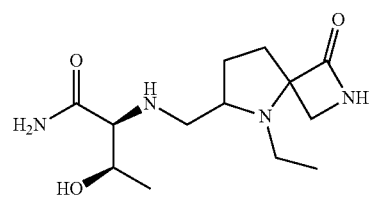 [SMILES: CCN1C(CN[C@H](C(N)=O)[C@@H](C)O)CCC12CNC2=O] |
| GB | 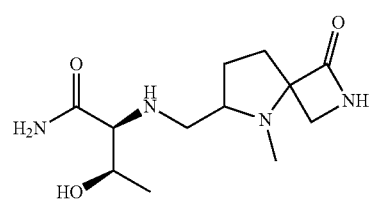 |
| GC | 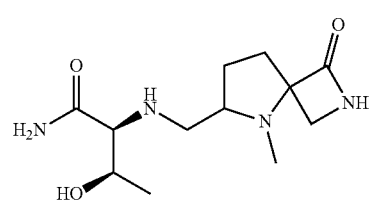 [SMILES: C[C@@H](O)[C@H](NCC1CCC2(CNC2=O)N1C)C(N)=O] |
| GD | 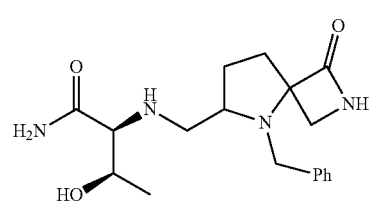 [SMILES: C[C@@H](O)[C@H](NCC1CCC2(CNC2=O)N1Cc1ccccc1)C(N)=O] |
| GE | 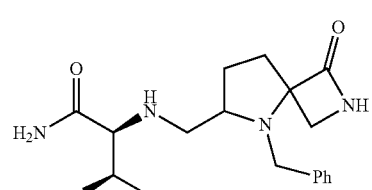 |
| GF | 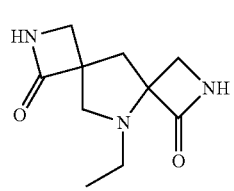 |
| GG | 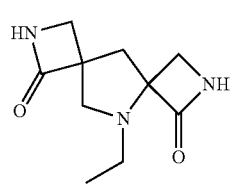 |

-continued

| Compound | Structure |
|---|---|
| GH | (structure) |
| GI | (structure) |
| GJ | (structure) |
| GK | (structure) |

B. Positive Emotional Learning (PEL) Test

This example demonstrates the positive emotional learning (PEL) test. Experiments were conducted as described in Burgdorf et al., "The effect of selective breeding for differential rates of 50-kHz ultrasonic vocalizations on emotional behavior in rats," Devel. Psychobiol., 51:34-46 (2009). Rat 50-kHz ultrasonic vocalization (hedonic USVs) is a validated model for the study of positive affective state and is best elicited by rough-and-tumble play. 50-kHz ultrasonic vocalizations have previously been shown to be positively correlated with reward and appetitive social behavior in rats, and to reflect a positive affective state.

The PEL assay measures the acquisition of positive (hedonic) 50-kHz ultrasonic vocalizations (USVs) to a social stimulus, heterospecific rough and tumble play stimulation. Heterospecific rough-and-tumble play stimulation was administered by the experimenter's right hand. One hour after administration of test compound or vehicle negative control (0.5% sodium carboxymethyl cellulose in 0.9% sterile saline vehicle), animals received 3 min of heterospecific rough-and-tumble play that consisted of alternating 15 sec blocks of heterospecific play and 15 sec of no-stimulation. High frequency ultrasonic vocalizations (USVs) were recorded and analyzed by sonogram with Avasoft SASlab Pro (Germany) as previously described by Burgdorf et al., "Positive emotional learning is regulated in the medial prefrontal cortex by GluN2B-containing NMDA receptors," Neuroscience, 192:515-523 (2011). Frequency modulated 50-kHz USVs that occurred during each of the no-stimulation periods were quantified to measure PEL. Animals were not habituated to play stimulation before testing. Positive emotional learning was measured during the conditioned stimulus (CS) trials preceding the tickle unconditioned stimulus (UCS) trials. Animals received 15 second trials consisting of 6 CS and 6 UCS trials each (3 min total).

The results are shown in the table below. As each experiment includes its own vehicle group, an example (typical) vehicle score is shown. Max effect (mean number of 50 kHz USVs per 15 seconds) is reported as ^: <6.0; *: 6-10.9; : 11-16.9; *: 17-22.

| Compound | Route | Dose (mg/kg) | Max Effect |
|---|---|---|---|
| Vehicle | PO | N/A | ^ |
| AB-2 | PO | 0.001-1 | ** |
| AC-1 | PO | 0.001-1 | * |
| AC-2 | PO | 0.001-1 | * |
| AQ-1 | PO | 0.1 | ** |
| AQ-2 | PO | 0.1 | * |
| AD | PO | 0.001-1 | ** |
| AF | PO | 0.001-1 | ** |
| AW | PO | 0.1 | ** |
| AM | PO | 0.1 | * |
| AN | PO | 0.1 | * |
| AH | PO | 0.1 | ** |
| AJ | PO | 0.1 | ** |
| BY | PO | 0.1 | ** |
| BH | PO | 0.1 | ** |

-continued

| Compound | Route | Dose (mg/kg) | Max Effect |
|---|---|---|---|
| AS | PO | 0.1 | ** |
| AO | PO | 0.1 | ** |

C. Microsomal Stability

Microsomal stability of disclosed compounds was investigated. The following table indicates the percent of compound remaining after 60 minutes.

| Compound | Microsomal (Human) | Microsomal (Rat) |
|---|---|---|
| AB-2 | 72% | 78% |
| AC-1 | 95% | 100% |
| AC-2 | 98% | 100% |
| AC-3 | 77% | 83% |
| AQ-1 | 100% | 84% |
| AQ-2 | 100% | 100% |
| AD | 100% | 100% |
| AF | 92% | 87% |
| AW | 2% | 0% |
| AM | 95% | 99% |
| AN | 88% | 87% |
| AH | 100% | 100% |
| AJ | 100% | 100% |
| BY | 100% | 81% |
| BH | 100% | 100% |
| AS | 84% | 100% |
| AO | 100% | 100% |

D. Plasma Stability

Plasma stability of disclosed compounds was investigated. The following table indicates the percent of compound remaining after 60 minutes.

| Compound | Plasma (Human) | Plasma (Rat) |
|---|---|---|
| AB-2 | 86% | 83% |
| AC-1 | 100% | 100% |
| AC-2 | 94% | 94% |
| AC-3 | 92% | 85% |
| AQ-1 | 100% | 100% |
| AQ-2 | 100% | 95% |
| AD | 83% | 88% |
| AF | 99% | 90% |
| AW | 90% | 0% |
| AM | 88% | 87% |
| AN | 88% | 87% |
| AH | 95% | 100% |
| AJ | 90% | 68% |
| BY | 81% | 82% |
| BH | 90% | 95% |
| AS | 100% | 100% |
| AO | 100% | 93% |

E. NMDAR Agonist Assays

Assays were conducted as described by Moskal et al., "GLYX-13: a monoclonal antibody-derived peptide that acts as an N-methyl-D-aspartate receptor modulator," Neuropharmacology, 49, 1077-87, 2005. These studies were designed to determine if the test compounds act to facilitate NMDAR activation in NMDAR2A, NMDAR2B, NMDAR2C or NMDAR2D expressing HEK cell membranes as measured by increases in [$^3$H]MK-801 binding.

In the assay, 300 μg of NMDAR expressing HEK cell membrane extract protein was preincubated for 15 minutes at 25° C. in the presence of saturating concentrations of glutamate (50 μM) and varying concentrations of test compound (1×10$^{-15}$M-1×10$^{-7}$M), or 1 mM glycine. Following the addition of 0.3 μCi of [$^3$H]MK-801 (22.5 Ci/mmol), reactions were again incubated for 15 minutes at 25° C. (nonequilibrium conditions). Bound and free [$^3$H]MK-801 were separated via rapid filtration using a Brandel apparatus.

In analyzing the data, the DPM (disintegrations per minute) of [$^3$H]MK-801 remaining on the filter were measured for each concentration of test compound or for 1 mM glycine. The DPM values for each concentration of a ligand (N=2) were averaged. The baseline value was determined from the best fit curve of the DPM values modeled using the GraphPad program and the log(agonist) vs. response(three parameters) algorithm was then subtracted from all points in the dataset. The % maximal [$^3$H]MK-801 binding was then calculated relative to that of 1 mM glycine: all baseline subtracted DPM values were divided by the average value for 1 mM glycine. The EC$_{50}$ and % maximal activity were then obtained from the best fit curve of the % maximal [$^3$H]MK-801 binding data modelled using the GraphPad program and the log(agonist) vs. response(three parameters) algorithm.

The tables below summarize the results for the wild type NMDAR agonists NMDAR2A, NMDAR2B, NMDAR2C, and NMDAR2D, and whether the compound is not an agonist (−), is an agonist (+), or is a strong agonist (++), where column A is based on the % maximal [$^3$H]MK-801 binding relative to 1 mM glycine (−=0; <100%=+; and >100%=++); and column B is based on log EC$_{50}$ values (0=−; ≥1×10$^{-9}$ M (e.g., −8)=+; and <1×10$^{-9}$ M (e.g., −10) =++)

| Compound | NMDAR2A | | NMDAR2B | |
|---|---|---|---|---|
| | A | B | A | B |
| AA-1 | − | − | − | − |
| AA-2 | + | + | − | − |
| AA-3 | − | − | − | − |
| AB-1 | + | ++ | − | − |
| AB-2 | − | − | + | ++ |
| AB-3 | − | − | − | − |
| AC-1 | + | + | + | ++ |
| AC-2 | + | ++ | + | ++ |
| AC-3 | + | ++ | + | ++ |
| AL-1 | + | ++ | − | − |
| AL-2 | + | + | − | − |
| AQ-1 | + | ++ | + | ++ |
| AQ-2 | + | ++ | + | ++ |
| AD | + | ++ | + | ++ |
| AE | − | − | − | − |
| AF | + | ++ | + | ++ |
| AT | + | + | − | − |
| AW | + | ++ | ++ | + |
| AX | + | ++ | − | − |
| AM | + | ++ | + | ++ |
| AN | + | ++ | + | ++ |
| AG | + | ++ | − | − |
| AH | + | ++ | + | ++ |
| AI | + | ++ | − | − |
| AJ | + | ++ | + | ++ |
| AK | − | − | − | − |
| AR | − | − | − | − |
| AS | + | ++ | + | ++ |
| AO | − | − | + | ++ |
| AP | − | − | + | ++ |
| AV | − | − | + | ++ |
| BY | − | − | ++ | ++ |
| BE | + | + | − | − |
| BF | + | ++ | + | ++ |
| BG | + | ++ | + | + |
| BH | − | − | + | ++ |
| BC | + | + | ++ | ++ |

-continued

| Compound | NMDAR2A A | NMDAR2A B | NMDAR2B A | NMDAR2B B |
|---|---|---|---|---|
| BD | + | ++ | + | ++ |
| BA | + | ++ | − | − |
| BB | + | + | + | ++ |
| AY-1 | − | − | + | ++ |
| AY-2 | − | − | + | ++ |
| AY-3 | + | ++ | + | ++ |
| AY-4 | + | ++ | + | + |
| CI | + | + | + | ++ |
| CJ | + | + | + | + |
| CA | − | − | − | − |
| CB | − | − | − | − |
| CC | + | + | − | − |
| CD | + | ++ | − | − |
| CE | − | − | ++ | ++ |
| CF | − | − | + | ++ |
| BI | − | − | − | − |
| BJ | − | − | − | − |
| BK | − | − | + | + |
| BL | − | − | + | ++ |
| BQ | − | − | + | ++ |
| BR | + | ++ | ++ | + |
| BM | − | − | − | − |
| BN | − | − | − | − |
| BO | + | + | ++ | ++ |
| BP | − | − | − | − |
| BS | − | − | + | ++ |
| BT | + | ++ | − | − |
| BU | + | ++ | + | ++ |
| BY | ++ | + | + | ++ |
| BW | + | ++ | ++ | ++ |
| BX | − | − | + | ++ |
| CG | + | ++ | − | − |
| CH | − | − | − | − |
| DO | + | ++ | − | − |
| DP | + | ++ | ++ | ++ |
| DQ | − | − | + | ++ |
| DR | + | ++ | + | ++ |
| CG | + | ++ | − | − |
| CH | − | − | − | − |
| DK | + | ++ | + | ++ |
| DL | − | − | + | ++ |
| DM | + | ++ | + | ++ |
| DN | + | ++ | + | ++ |
| DI | + | + | + | ++ |
| DJ | + | ++ | + | ++ |
| DC | + | ++ | ++ | ++ |
| DD | + | ++ | + | ++ |
| DE | + | ++ | + | ++ |
| DF | + | ++ | + | ++ |
| DG | + | ++ | + | + |
| DH | + | ++ | ++ | ++ |
| CY | + | ++ | + | ++ |
| CZ | + | ++ | + | + |
| DA | + | ++ | + | ++ |
| DB | + | + | + | ++ |
| CK | − | − | + | ++ |
| CL | + | ++ | + | ++ |
| CO | + | ++ | + | ++ |
| CP | + | ++ | + | ++ |
| CS | − | − | + | ++ |
| CT | + | ++ | + | ++ |
| CW | + | ++ | + | ++ |
| CX | + | ++ | ++ | ++ |
| CM | + | ++ | + | ++ |
| CN | ++ | ++ | + | ++ |
| CQ | − | − | ++ | ++ |
| CR | + | ++ | ++ | ++ |
| CU | − | − | ++ | + |
| CV | + | ++ | ++ | ++ |

| Compound | NMDAR2C A | NMDAR2C B | NMDAR2D A | NMDAR2D B |
|---|---|---|---|---|
| AB-2 | + | ++ | + | + |
| AC-1 | + | + | + | + |
| AC-2 | + | ++ | + | ++ |
| AC-3 | + | + | − | − |
| AQ-1 | + | + | + | ++ |
| AD | + | ++ | − | − |
| AF | ++ | + | + | + |
| AW | + | ++ | + | ++ |
| AM | − | − | + | ++ |
| AN | + | ++ | + | ++ |
| AH | + | ++ | + | ++ |
| AJ | + | ++ | + | ++ |
| BY | + | ++ | − | − |
| BE | NR | NR | + | ++ |
| BH | ++ | ++ | NR | NR |
| BA | NR | NR | + | ++ |
| AY-1 | + | ++ | + | ++ |
| AY-3 | − | − | + | ++ |

F. Pharmacokinetics Assays

Sprague Dawley rats were dosed intravenously using a normal saline formulation containing 2 mg/kg of the compounds identified in the below table. The table below summarizes the results of the IV pharmacokinetics.

| Compound | $C_0$ (ng/mL) | $AUC_{last}$ (hr*ng/mL) | $T_{1/2}$ (hr) | Cl (mL/min/kg) | $V_{ss}$ (L/kg) |
|---|---|---|---|---|---|
| AQ-1 | 6817.22 | 3334.15 | 0.36 | 9.84 | 0.28 |
| AQ-2 | 5143.2 | 2601.7 | 0.59 | 12.82 | 0.36 |
| AD | 2797.1 | 4709 | 2.27 | 7.01 | 0.92 |
| AF | 3902.8 | 6446.2 | 4.99 | 5.2 | 0.59 |
| AM | 3460.5 | 1004.02 | 2.38 | 33.32 | 1.21 |
| AN | 3209.4 | 727.7 | 4.67 | 45.98 | 2.45 |
| AH | 3870.5 | 3022.33 | 3.68 | 10.9 | 1.1 |
| AJ | 4862.9 | 2091.9 | 0.44 | 15.42 | 0.47 |
| BY | 10156.1 | 5963.3 | 0.64 | 5.6 | 0.15 |
| BH | 2387 | 655.54 | 0.34 | 50.53 | 0.82 |
| AS | 2233 | 2802 | 3.17 | 11.83 | 0.61 |
| AO | 11900 | 4432 | 2.17 | 7.59 | 0.22 |
| AY-3 | 3159.4 | 3552.4 | 6.11 | 9.4 | 1.03 |

In another experiment, Sprague Dawley rats were dosed per os using a normal saline formulation containing 10 mg/kg of the compounds identified in the table below. Plasma, brain, and CSF samples were analyzed at various time points over a 24 hour period. The table below summarizes the results of the oral pharmacokinetics.

| Compound | $T_{max}$ (hr) | $C_{max}$ (ng/mL) | $AUC_{last}$ (hr*ng/mL) | CSF $C_{max}$ (ng/mL) | Brain $C_{max}$ (ng/mL) | % F |
|---|---|---|---|---|---|---|
| AQ-1 | 0.83 | 132.9 | 349.73 | 0 | 0 | 2 |
| AQ-2 | 1.08 | 144.2 | 599.6 | 0 | 0 | 5 |
| AD | 0.33 | 8558.4 | 19310.9 | 1965.2 | 1143.2 | 82 |
| AF | 0.42 | 7253.4 | 16096.3 | 2781 | 1313.8 | 82 |
| AM | 0.33 | 34.22 | 97.64 | 0 | 0 | 2 |
| AN | 0.42 | 38.9 | 126.32 | 0 | 0 | 3 |
| AH | 1.67 | 655 | 2567.2 | 123 | 45.8 | 17 |
| AJ | 0.5 | 1163 | 2055.1 | 71.9 | 0 | 20 |
| BY | 0.83 | 155.9 | 486.3 | 0 | 0 | 2 |
| BH | 0.25 | 859.42 | 613.77 | 36.66 | 0 | 18 |
| AS | 0.83 | 75.37 | 366.75 | 0 | 0 | 3 |
| AO | 2.67 | 247.08 | 1316.03 | 17.89 | 0 | 6 |
| AY-3 | 0.83 | 2716 | 8863.3 | 277 | 125.3 | 50 |

G. Bennett Nerve Injury Assay

The Bennett model of mechanical analgesia is used to assess the analgesic effects of compounds as measured by paw withdrawal threshold. Bennett G J, Xie Y K, "A peripheral mononeuropathy in rat that produces disorders of pain sensation like those seen in man," Pain 33:87-107, 1988. Sciatic nerve chronic constriction nerve injury surgery is performed on animals with testing for analgesic response once animals have recovered from surgery but still exhibit a low threshold of paw withdrawal after application of von Frey filaments. Vehicle animals receive the surgery and then receive vehicle rather than test compound. Animals were tested 1 hr, 24 h and 1 wk post-test compound or vehicle administration.

Male 2-3 month old Sprague Dawley rats were used. Harlan was the supplier for all studies. Rats were housed in Lucite cages with aspen wood chip bedding, maintained on a 12:12 light:dark cycle (lights on at 5 AM), and given ad libitum access to Purina lab chow (USA) and tap water throughout the study.

Rats were anesthetized using inhaled isoflurane (2.5%). Sciatic nerve chronic constriction nerve injury surgery was performed as previously described (Bennett and Xie, 1988). An incision (~1.5 cm in length) was made with a scalpel blade dorsally through skin on the right hind limb, parallel and posterior to femur. Using a small pointed hemostat, the biceps femoris and gluteus superficialis muscles were separated. Using curved blunt forceps, the common sciatic nerve was isolated and exposed. For the mechanical analgesia studies, the whole sciatic nerve was ligated. Using hemostats/forceps and chromic gut (5-0), the nerve was loosely ligated with a square knot; 3 ligatures, 1 mm apart were placed on the nerve. The ligatures were tightened to the point that the suture did not slide up or down the nerve. This protocol resulted in a partial loss-of-function of the nerve. Testing occurred approximately 2 weeks post-surgery.

During testing, rats were acclimated to the surface of a suspended wire mesh grid (1 cm×1 cm, with the wire being 0.3 cm in diameter) for 15-20 min Starting from the smallest, each Von Frey filament was pressed perpendicularly to the plantar surface of the affected (ipsilateral) hind paw until slightly bent and then held for 6 second. If an obvious hind paw withdrawal or a flinching behavior immediately after the withdrawal of the filament was not observed, the next larger filament was used in the same manner. In case of a response, a lower filament was used. This was repeated until six responses were collected.

For all studies, animals were baselined prior to study start to test for allodynia (defined as a paw withdrawal threshold under 5). A subset of animals was tested with gabapentin (150 mg/kg, PO) to ensure at least 50% analgesia. Once it was confirmed animals were ready for study initiation, animals were balanced across groups. All study investigators were blind to treatment conditions. Animals were dosed with 0.1, 1 or 10 mg/kg of test compound via oral gavage (PO), control sets of animals were dosed with gabapentin (150 mg/kg, PO) or vehicle (0.5% Na-CMC in 0.9% sterile saline, PO). Testing occurred 1 h post-dosing with animals retested 24 hrs and 1 week post-dosing. The percent analgesia calculations for each animal were made using the following equation: % analgesia=[(log(x)−y)/((log (z)−y)]*100, where x=the paw withdrawal threshold for the drug-treated animal in grams, y=the average of the log(x) values for the vehicle treated group, and z=the paw withdrawal threshold for naïve animals in grams (historical value of 15 used). The results for Compound AD, where the percentage of analgesia is measured at 1 hour, 24 hours, and 1 week after compound administration are as follows: for 0.1 mg/kg dose: 37.8% at 1 h, 29.7% at 24 h, and 63.1% at 1 wk; for 1 mg/kg dose: 48.8% at 1 h, 20.6% at 24 h, and 19.8% at 1 wk; and for 10 mg/kg dose: 70.3% at 1 h, 38.8% at 24 h, and 11.3% at 1 wk. The study had a gabapentin control group, where example (typical) gabapentin control values for 150 mg/kg dose are 72% at 1 h, 16% at 24 h, and 0% at 1 wk. For the study, gabapentin was confirmed effective (demonstrating at least 50% analgesia at 1 h post-administration). Gabapentin was not different from vehicle and resulted in no analgesia (<5%) at 24 h and 1 week post-administration.

EQUIVALENTS

Those skilled in the art will recognize, or be able to ascertain using no more than routine experimentation, many equivalents to the specific embodiments of the disclosure described herein. Such equivalents are intended to be encompassed by the following claims.

INCORPORATION BY REFERENCE

The entire contents of all patents, published patent applications, websites, and other references cited herein are hereby expressly incorporated herein in their entireties by reference.

What is claimed is:

1. A compound represented by Formula I or Formula II:

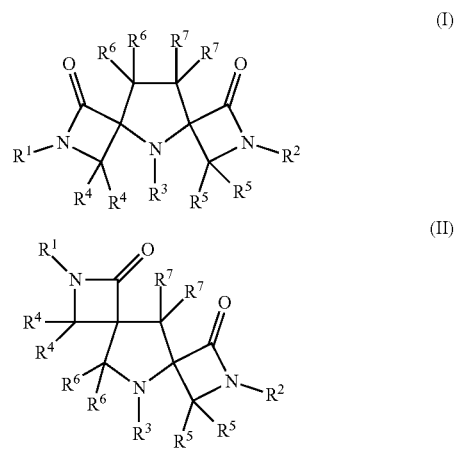

or a pharmaceutically acceptable salt, a stereoisomer, and/or an N-oxide thereof, wherein:

$R^1$ and $R^2$ are independently selected from the group consisting of hydrogen, —$C_1$-$C_6$alkyl, —C(O)—$C_1$-$C_6$alkyl, —C(O)—O—$C_1$-$C_6$alkyl, and —O—$CH_2$-phenyl;

$R^3$ is selected from the group consisting of hydrogen, —$C_1$-$C_6$alkyl, —C(O)—$R^{31}$, and —C(O)—O—$R^{32}$;

$R^{31}$ is selected from the group consisting of hydrogen, —$C_1$-$C_6$alkyl; —$C_1$-$C_6$haloalkyl, —$C_3$-$C_6$cycloalkyl, and phenyl;

$R^{32}$ is selected from the group consisting of hydrogen, —$C_1$-$C_6$alkyl; —$C_1$-$C_6$haloalkyl, —$C_3$-$C_6$cycloalkyl, and phenyl;

wherein any aforementioned $C_1$-$C_6$alkyl, independently for each occurrence, is optionally substituted by one, two or three substituents each independently selected from —C(O)$NR^aR^b$, —$NR^aR^b$, hydroxyl, —SH, phenyl, —O—$CH_2$-phenyl, and halogen; and any aforementioned phenyl, independently for each occurrence, is optionally substituted by one, two or three substituents each independently selected from —C(O)NR$^a$R$^b$, —NR$^a$R$^b$, —C$_1$-C$_3$alkoxy, hydroxyl, and halogen;

R$^a$ and R$^b$ are each independently for each occurrence selected from the group consisting of hydrogen, —C(O)—O—CH$_2$-phenyl, and —C$_1$-C$_3$alkyl; or R$^a$ and R$^b$ taken together with the nitrogen to which they are attached form a 4-6 membered heterocyclic ring;

R$^4$, R$^5$, R$^6$ and R$^7$ are each independently selected from the group consisting of hydrogen, halogen, hydroxyl, phenyl, amido, amino, C$_{1-4}$alkyl, C$_{2-4}$alkenyl, —NH—C(O)—C$_{1-6}$ alkyl, —NH—C(O)—C$_{1-6}$alkylene-phenyl, —NH—C(O)—O—C$_{1-6}$alkyl, and —NH—C(O)—O—C$_{1-6}$ alkylene-phenyl; wherein C$_{1-4}$alkyl, C$_{1-6}$alkylene, C$_{2-4}$alkenyl, and phenyl are optionally substituted by one or more substituents selected from R$^P$; or two R$^5$s taken together form an oxo moiety; or wherein for the compound of Formula I, R$^6$ and R$^7$ taken together with the adjacent carbons to which they are attached form a 3-membered carbocyclic ring which is optionally substituted by one or two substituents independently selected from the group consisting of halogen, hydroxyl, —C$_1$-C$_3$alkyl, —C$_1$-C$_3$alkoxy, —C(O)NR$^a$R$^b$, and —NR$^a$R$^b$; and R$^P$ is selected, independently for each occurrence, from the group consisting of carboxy, hydroxyl, halogen, amino, phenyl, C$_{1-6}$alkoxy, and C$_{1-6}$alkyl optionally substituted by one or more substituents independently selected from the group consisting of halogen, hydroxyl and amino.

2. The compound of claim 1, wherein R$^1$ and R$^2$ are hydrogen.

3. The compound of claim 1, wherein R$^1$ and R$^2$ are —C$_1$-C$_6$alkyl each independently and optionally substituted by one, two or three substituents independently selected from the group consisting of —C(O)NR$^a$R$^b$, hydroxyl, —SH, and halogen.

4. The compound of claim 1, wherein R$^3$ is hydrogen.

5. The compound of claim 1 wherein R$^3$ is —C$_1$-C$_6$alkyl.

6. The compound of claim 1, wherein R$^3$ is —C(O)—C$_1$-C$_6$alkyl.

7. The compound of claim 1, wherein R$^3$ is —C(O)—O—C$_1$-C$_6$alkyl.

8. The compound of claim 1, wherein R$^4$, R$^5$, R$^6$, and R$^7$ are hydrogen.

9. The compound of claim 1 represented by Formula III or Formula IV:

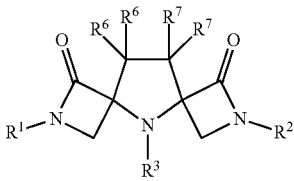

(III)

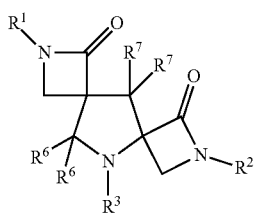

(IV)

or a pharmaceutically acceptable salt, a stereoisomer, and/or an N-oxide thereof, wherein:

R$^1$ and R$^2$ are independently selected from the group consisting of hydrogen, —C$_1$-C$_6$alkyl, —C(O)—C$_1$-C$_6$alkyl, —C(O)—O—C$_1$-C$_6$alkyl, and —O—H$_2$-phenyl;

R$^3$ is selected from the group consisting of hydrogen, —C$_1$-C$_6$alkyl, —C(O)—R$^{31}$, and —C(O)—O—R$^{32}$;

R$^{31}$ is selected from the group consisting of hydrogen, —C$_1$-C$_6$alkyl; —C$_1$-C$_6$haloalkyl, —C$_3$-C$_6$cycloalkyl, and phenyl;

R$^{32}$ is selected from the group consisting of hydrogen, —C$_1$-C$_6$alkyl; —C$_1$-C$_6$haloalkyl, —C$_3$-C$_6$cycloalkyl, and phenyl;

wherein any aforementioned C$_1$-C$_6$alkyl, independently for each occurrence, is optionally substituted by one, two or three substituents each independently selected from —C(O)NR$^a$R$^b$, —NR$^a$R$^b$, hydroxyl, —SH, phenyl, —O—CH$_2$-phenyl, and halogen; and any aforementioned phenyl, independently for each occurrence, is optionally substituted by one, two or three substituents each independently selected from —C(O)NR$^a$R$^b$, —NR$^a$R$^b$, —C$_1$-C$_3$alkoxy, hydroxyl, and halogen;

R$^a$ and R$^b$ are each independently for each occurrence selected from the group consisting of hydrogen, —C(O)—O—CH$_2$-phenyl, and —C$_1$-C$_3$alkyl; or R$^a$ and R$^b$ taken together with the nitrogen to which they are attached form a 4-6 membered heterocyclic ring;

R$^6$ and R$^7$ are each independently selected from the group consisting of hydrogen, halogen, hydroxyl, phenyl, amido, amino, C$_{1-4}$alkyl, C$_{2-4}$alkenyl, —NH—C(O)—C$_{1-6}$alkyl, —NH—C(O)—C$_{1-6}$alkylene-phenyl, —NH—C(O)—O—C$_{1-6}$alkyl, and —NH—C(O)—O—C$_{1-6}$ alkylene-phenyl; wherein C$_{1-4}$ alkyl, C$_{1-6}$alkylene, C$_{2-4}$alkenyl, and phenyl are optionally substituted by one or more substituents selected from R$^P$; or wherein for the compound of Formula III, R$^6$ and R$^7$ taken together with the adjacent carbons to which they are attached form a 3-membered carbocyclic ring which is optionally substituted by one or two substituents independently selected from the group consisting of halogen, hydroxyl, —C$_1$-C$_3$alkyl, —C$_1$-C$_3$alkoxy, —C(O)NR$^a$R$^b$, and —NR$^a$R$^b$; and R$^P$ is selected, independently for each occurrence, from the group consisting of carboxy, hydroxyl, halogen, amino, phenyl, C$_{1-6}$alkoxy, and C$_{1-6}$alkyl optionally substituted by one or more substituents independently selected from the group consisting of halogen, hydroxyl and amino.

10. The compound of claim 1 represented by Formula V or Formula VI:

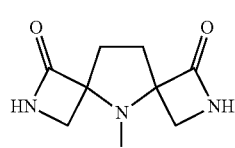

(V)

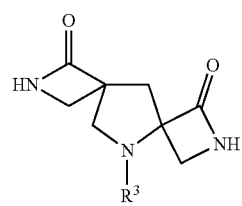

(VI)

or a pharmaceutically acceptable salt, a stereoisomer, and/or an N-oxide thereof, wherein:

$R^3$ is selected from the group consisting of hydrogen, —$C_1$-$C_6$alkyl, —C(O)—$R^{31}$, and —C(O)—O—$R^{32}$;

$R^{31}$ is selected from the group consisting of hydrogen, —$C_1$-$C_6$alkyl; —$C_1$-$C_6$haloalkyl, —$C_3$-$C_6$cycloalkyl, and phenyl;

$R^{32}$ is selected from the group consisting of hydrogen, —$C_1$-$C_6$alkyl; —$C_1$-$C_6$haloalkyl, —$C_3$-$C_6$cycloalkyl, and phenyl;

wherein any aforementioned $C_1$-$C_6$alkyl, independently for each occurrence, is optionally substituted by one, two or three substituents each independently selected from —C(O)$NR^aR^b$, —$NR^aR^b$, hydroxyl, —SH, phenyl, —O—$CH_2$-phenyl, and halogen; and any aforementioned phenyl, independently for each occurrence, is optionally substituted by one, two or three substituents each independently selected from —C(O)$NR^aR^b$, —$NR^aR^b$, —$C_1$-$C_3$alkoxy, hydroxyl, and halogen; and $R^a$ and $R^b$ are each independently for each occurrence selected from the group consisting of hydrogen, —C(O)—O—$CH_2$-phenyl, and —$C_1$-$C_3$alkyl; or $R^a$ and $R^b$ taken together with the nitrogen to which they are attached form a 4-6 membered heterocyclic ring.

11. A compound represented by Formula VI or Formula VII:

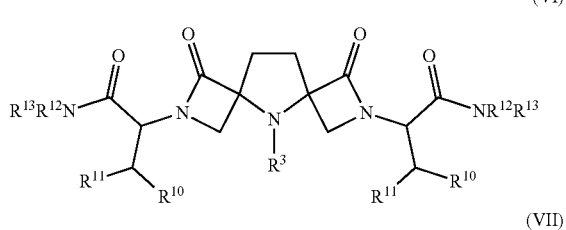

(VI)

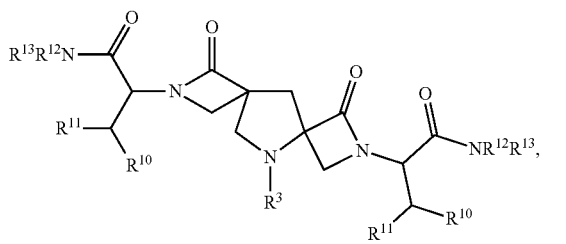

(VII)

or a pharmaceutically acceptable salt, a stereoisomer, and/or an N-oxide thereof, wherein:

$R^3$ is selected from the group consisting of hydrogen, —$C_1$-$C_6$alkyl, —C(O)—$R^{31}$, and —C(O)—O—$R^{32}$;

$R^{31}$ is selected from the group consisting of hydrogen, —$C_1$-$C_6$alkyl; —$C_1$-$C_6$haloalkyl, —$C_3$-$C_6$cycloalkyl, and phenyl;

$R^{32}$ is selected from the group consisting of hydrogen, —$C_1$-$C_6$alkyl; —$C_1$-$C_6$haloalkyl, —$C_3$-$C_6$cycloalkyl, and phenyl;

$R^{10}$ and $R^{11}$ for each occurrence are independently selected from the group consisting of hydrogen, halogen, —OH, —$C_1$-$C_6$alkyl, —$C_1$-$C_6$alkoxy, —$CO_2H$, or —NR'R', wherein R' for each occurrence is independently selected from hydrogen and, —$C_1$-$C_6$ alkyl; and $R^{12}$ and $R^{13}$ for each occurrence are independently selected from the group consisting of hydrogen and —$C_1$-$C_6$ alkyl; or $R_{13}$ and $R_{12}$ together with the nitrogen to which they are bound form a 4-6 membered heterocycle; and wherein $C_1$-$C_6$ alkyl is optionally for each occurrence substituted by one, two, or three substituents each selected from the group consisting of halogen, hydroxyl, and amino.

12. A compound represented by Formula IX or Formula X:

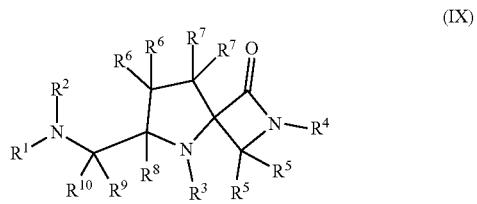

(IX)

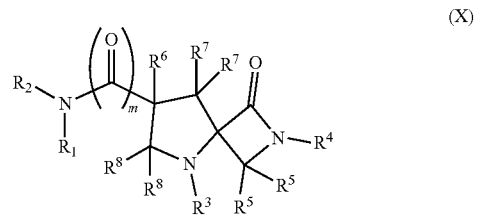

(X)

or a pharmaceutically acceptable salt, a stereoisomer, and/or an N-oxide thereof, wherein:

$R^1$ and $R^2$ are independently selected from the group consisting of hydrogen, —$C_1$-$C_6$alkyl, —C(O)—$C_1$-$C_6$alkyl, and —C(O)—O—$C_1$-$C_6$alkyl; or $R^1$ and $R^2$ taken together with the nitrogen to which they are attached form a 4-6 membered heterocyclic ring;

$R^3$ is selected from the group consisting of hydrogen, —$C_1$-$C_6$alkyl, —C(O)—$R^{31}$, and —C(O)—O—$R^{32}$;

$R^{31}$ is selected from the group consisting of hydrogen, —$C_1$-$C_6$alkyl; —$C_1$-$C_6$haloalkyl, —$C_3$-$C_6$cycloalkyl, and phenyl;

$R^{32}$ is selected from the group consisting of hydrogen, —$C_1$-$C_6$alkyl; —$C_1$-$C_6$haloalkyl, —$C_3$-$C_6$cycloalkyl, and phenyl;

$R^4$ is selected from the group consisting of hydrogen, —$C_1$-$C_6$alkyl, —C(O)—$C_1$-$C_6$alkyl, —C(O)—O—$C_1$-$C_6$alkyl, and —O—$CH_2$-phenyl;

wherein any aforementioned $C_1$-$C_6$alkyl, independently for each occurrence, is optionally substituted by one, two or three substituents each independently selected from —C(O)$NR^aR^b$, —$NR^aR^b$, hydroxyl, —SH, phenyl, —O—$CH_2$-phenyl, and halogen; and any aforementioned phenyl, independently for each occurrence, is optionally substituted by one, two or three substituents each independently selected from —C(O)$NR^aR^b$, —$NR^aR^b$, —$C_1$-$C_3$alkoxy, hydroxyl, and halogen;

$R^a$ and $R^b$ are each independently for each occurrence selected from the group consisting of hydrogen, —C(O)—O—$CH_2$-phenyl, and —$C_1$-$C_3$alkyl; or $R^a$ and $R^b$ taken together with the nitrogen to which they are attached form a 4-6 membered heterocyclic ring;

$R^5$, $R^6$, $R^7$ and $R^8$ are each independently selected from the group consisting of hydrogen, halogen, hydroxyl, phenyl, amido, amino, $C_{1-4}$alkyl, $C_{2-4}$alkenyl, —NH—C(O)—$C_{1-6}$alkyl, —NH—C(O)—$C_{1-6}$alkylene-phenyl, —NH—C(O)—O—$C_{1-6}$alkyl, and —NH—C(O)—O—$C_{1-6}$alkylene-phenyl; wherein $C_{1-4}$alkyl and phenyl are optionally substituted by one or more substituents selected from R$^P$; or R$^6$ and R$^7$ taken together with the adjacent carbons to which they are attached form a 3-membered carbocyclic ring which is optionally substituted by one or two substituents independently selected from the group consisting of halogen, hydroxyl, —C$_1$-C$_3$alkyl, —C$_1$-C$_3$alkoxy, —C(O)NR$^a$R$^b$, and —NR$^a$R$^b$;

R$^P$ is selected, independently for each occurrence, from the group consisting of carboxy, hydroxyl, halogen, amino, phenyl, C$_{1-6}$alkoxy, and C$_{1-3}$alkyl optionally substituted by one or more substituents independently selected from the group consisting of halogen, hydroxyl and amino;

R$^9$ and R$^{10}$ are each independently selected from the group consisting of hydrogen and —C$_1$-C$_3$alkyl, or R$^9$ and R$^{10}$ taken together form an oxo moiety; and m is 0 or 1.

13. The compound of claim 12, wherein R$^1$ and R$^2$ are hydrogen.

14. The compound of claim 12, wherein R$^1$ is hydrogen and R$^2$ is —C$_1$-C$_6$alkyl optionally substituted by one, two or three substituents independently selected from the group consisting of —C(O)NR$^a$R$^b$, hydroxyl, —SH, and halogen.

15. The compound of claim 12, wherein R$^3$ is hydrogen.

16. The compound of claim 12, wherein R$^4$, R$^5$, R$^6$, and R$^7$ are hydrogen.

17. A compound selected from the group consisting of

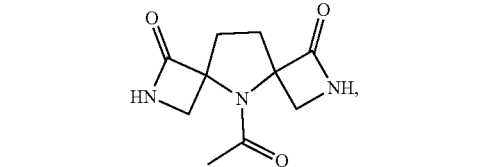

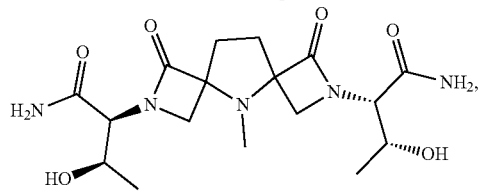

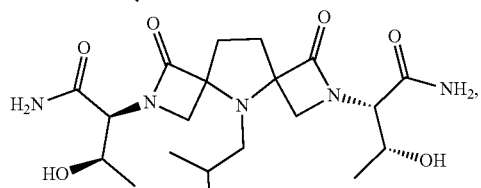

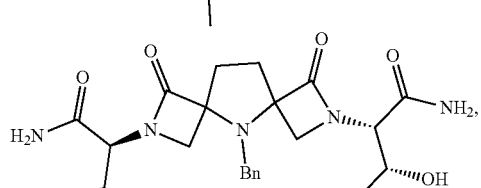

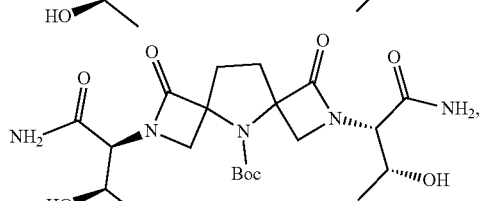

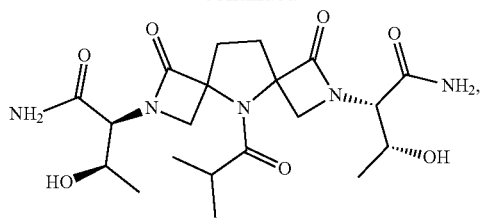

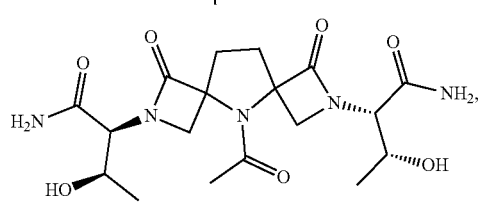

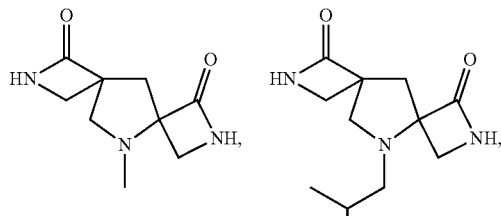

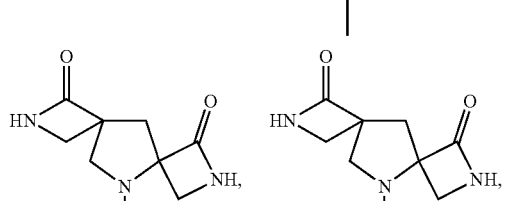

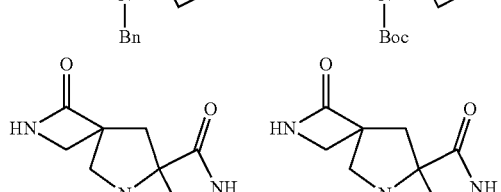

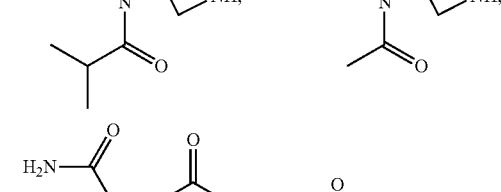

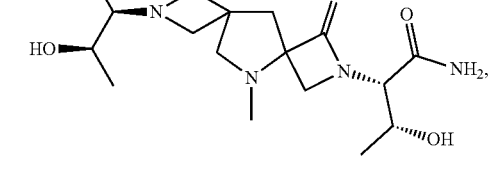

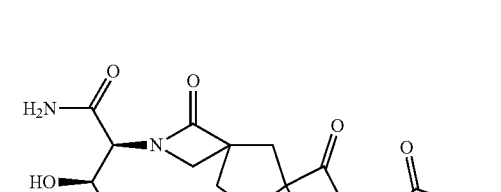

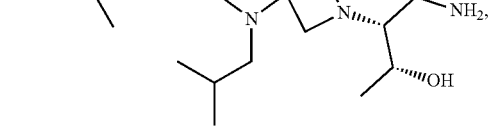

211
-continued
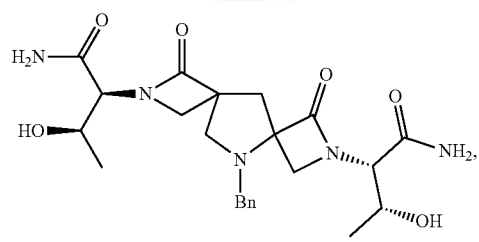
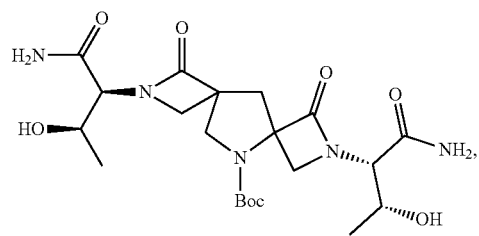
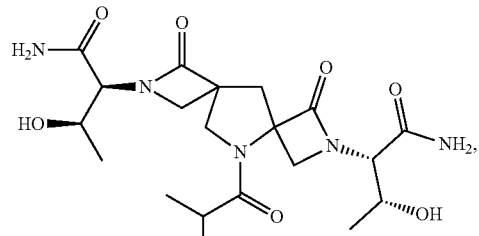
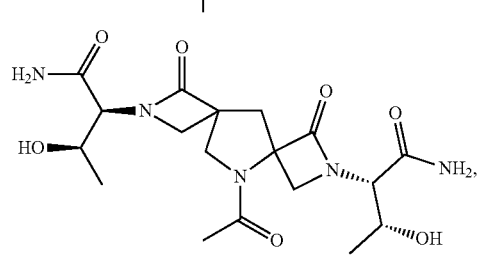
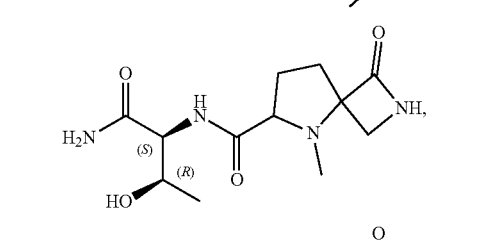
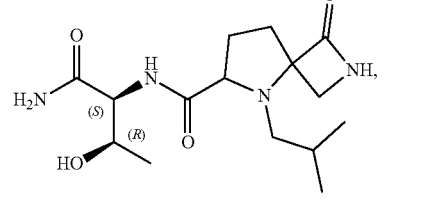
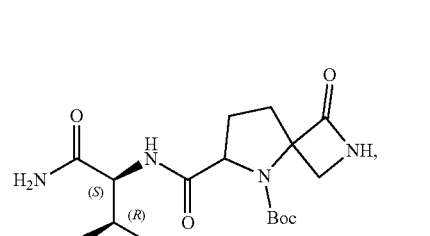
212
-continued
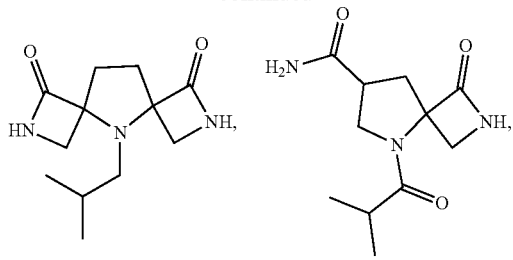
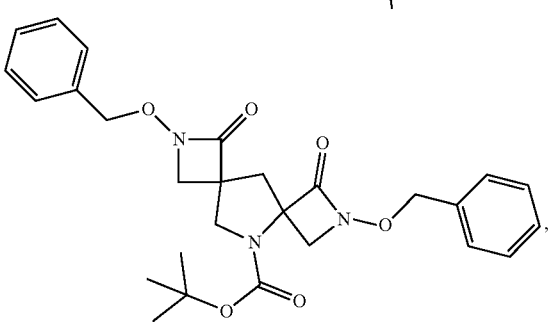
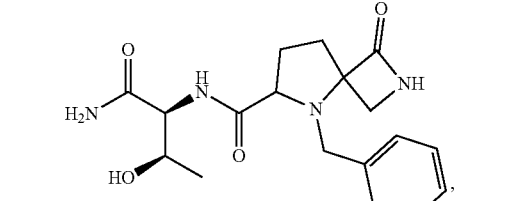
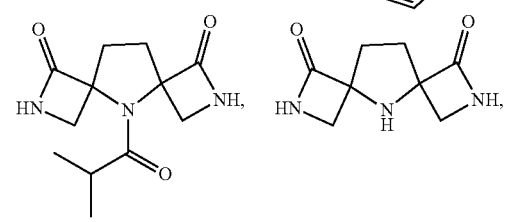
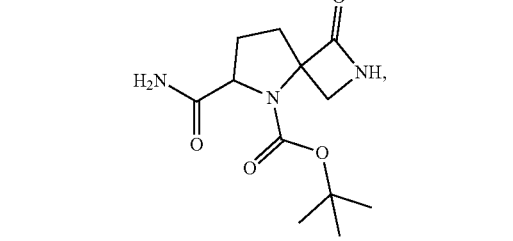
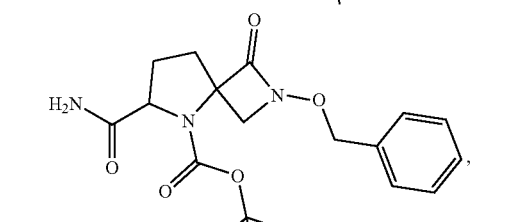
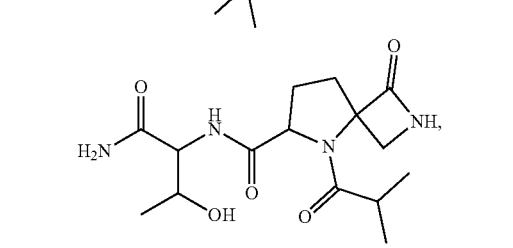

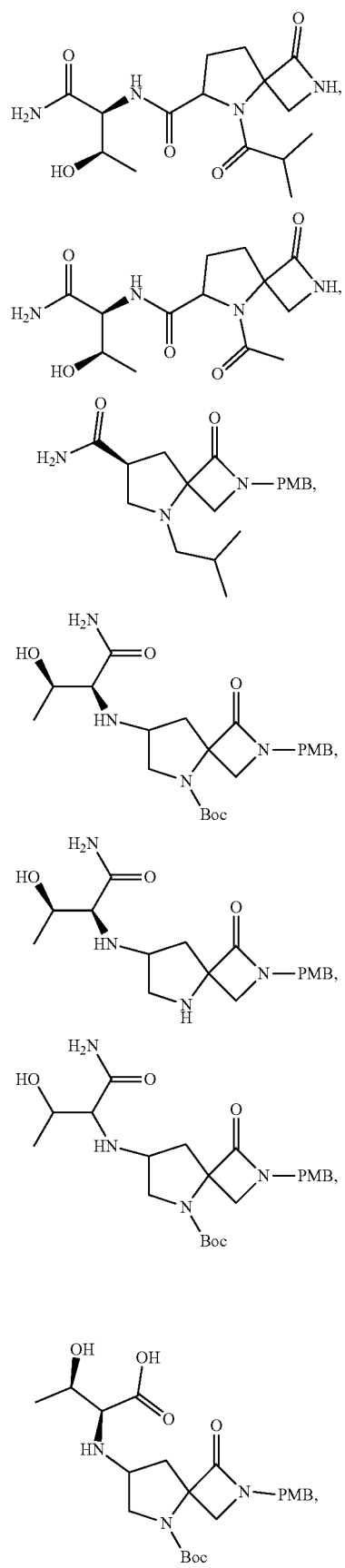
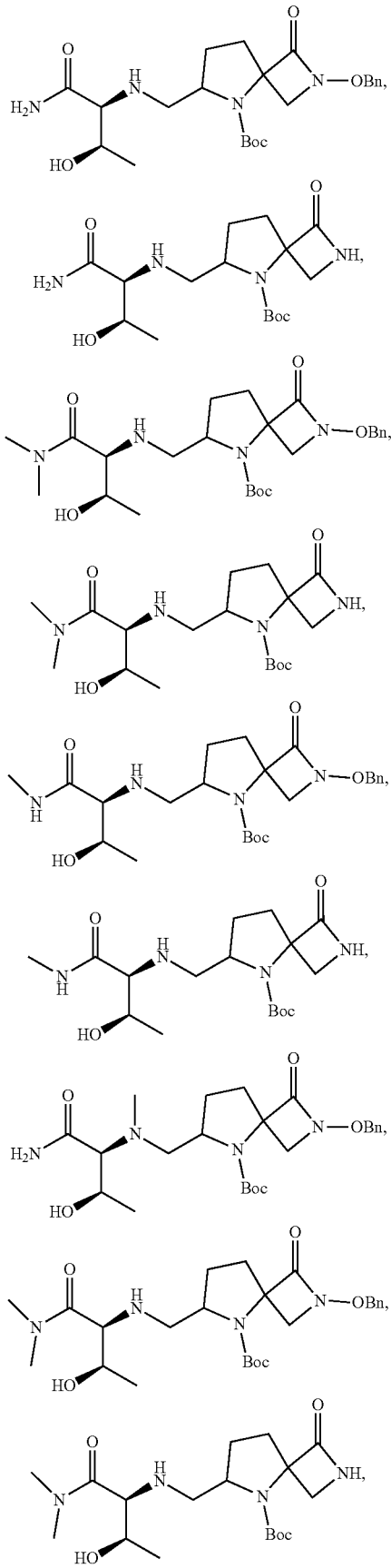

215
-continued
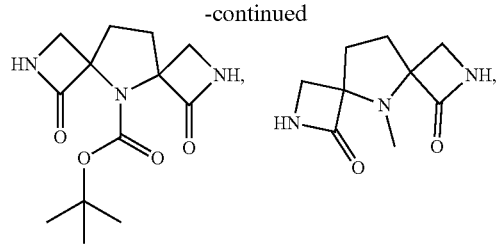
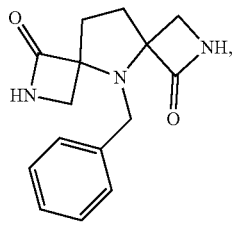
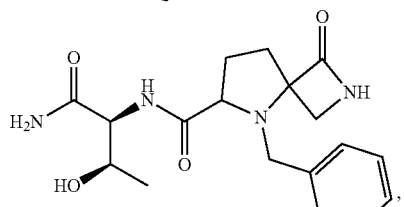
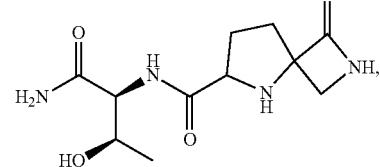
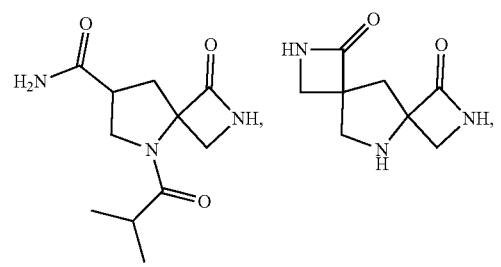
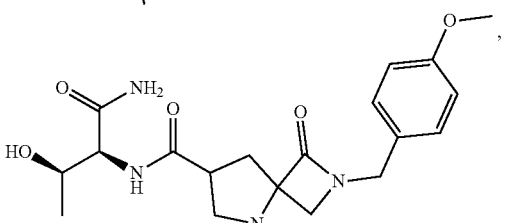
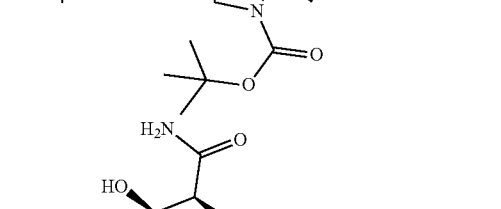
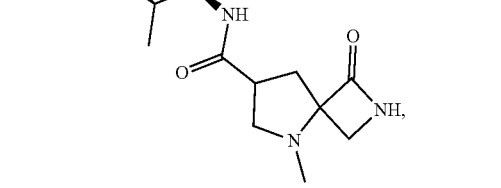
216
-continued
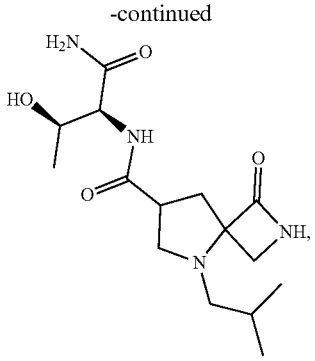
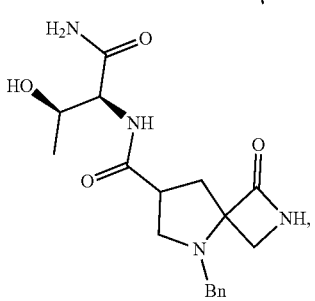
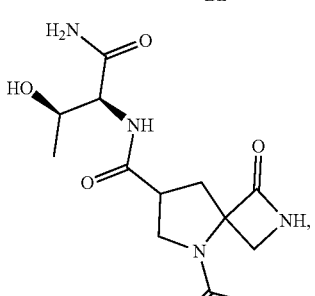
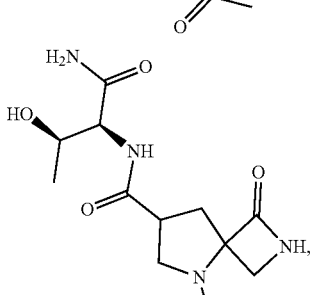
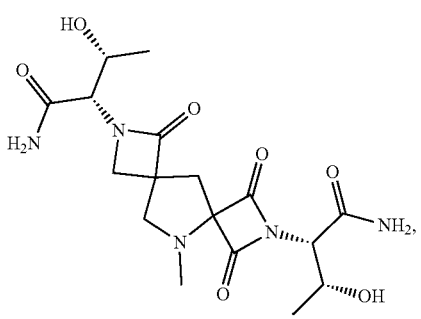

217
-continued
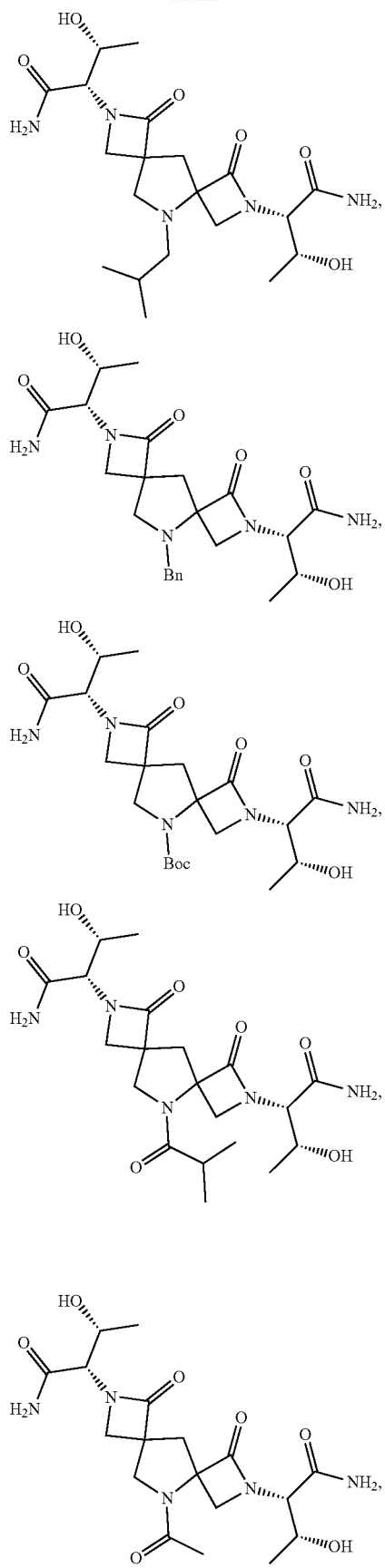
218
-continued
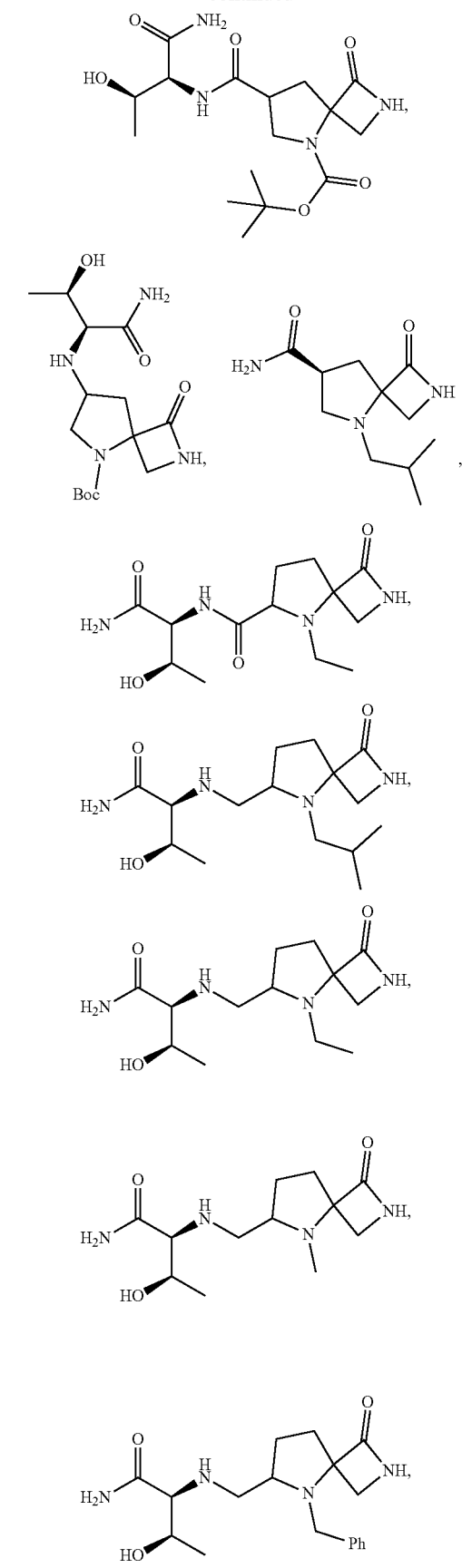

-continued

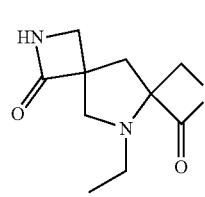 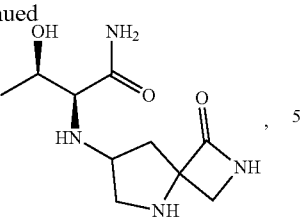, and and pharmaceutically acceptable salts, stereoisomers, and/or N-oxides thereof.

18. A pharmaceutical composition comprising the compound of claim 1, and a pharmaceutically acceptable excipient.

19. A method of lessening or reducing one or more symptoms of depression, Alzheimer's disease, attention deficit disorder, schizophrenia, or anxiety, in a patient in need thereof, the method comprising administering to the patient a therapeutically effective amount of the compound of claim 1.

20. A method of lessening or reducing one or more symptoms of a migraine, neuropathic pain, or traumatic brain injury in a patient in need thereof, the method comprising administering to the patient a therapeutically effective amount of the compound of claim 1.

* * * * *